US009068192B2

(12) United States Patent
Zeng et al.

(10) Patent No.: US 9,068,192 B2
(45) Date of Patent: Jun. 30, 2015

(54) COMPOSITIONS AND METHODS FOR CONVERSION OF ALDEHYDES TO ALKANES

(75) Inventors: Weiqing Zeng, Okemos, MI (US); Sheng Yang He, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1173 days.

(21) Appl. No.: 12/695,605

(22) Filed: Jan. 28, 2010

(65) Prior Publication Data

US 2010/0251428 A1   Sep. 30, 2010

Related U.S. Application Data

(60) Provisional application No. 61/147,869, filed on Jan. 28, 2009.

(51) Int. Cl.
| | |
|---|---|
| *C12N 15/82* | (2006.01) |
| *C07K 14/415* | (2006.01) |
| *C12N 9/02* | (2006.01) |
| *C12P 7/64* | (2006.01) |

(52) U.S. Cl.
CPC .......... *C12N 15/8247* (2013.01); *C07K 14/415* (2013.01); *C12N 9/0008* (2013.01); *C12P 7/6463* (2013.01); *C12P 7/6481* (2013.01)

(58) Field of Classification Search
None
See application file for complete search history.

(56) References Cited

FOREIGN PATENT DOCUMENTS

WO    WO 02/16655    *  2/2002  ............... C12Q 1/68

OTHER PUBLICATIONS

Aarts, M. G. M., et al., "Molecular Characterization of the CER1 Gene of *Arabidopsis* Involved in Epicuticular Wax Biosynthesis and Pollen Fertility", *Plant Cell*, 7, (1995), 2116-2127.
Back, K., et al., "Identifying functional domains with terpene cyclases using a domain-swapping strategy", *Proc. Natl. Acad. Sci.*, 93, (1996), 6841-6845.
Bessire, M., et al., "A permeable cuticle in *Arabidopsis* leads to a strong resistance to *Botrytis cinerea*", *The EMBO Journal*, 26, (2007), 2158-2168.
Cervantes, D. E., et al., "Oviposition responses by hessian fly, *Mayetiola destructor*, to wheats varying in surfaces waxes.", *J. Chem. Ecol.*, 28(1), (2002), 193-210.
Chassot, C., et al., "Cuticular defects lead to full immunity to a major plant pathogen", *The Plant J.*, 49(6), (2007), 972-980.
Cheesbrough, T. M., et al., "Alkane biosynthesis by decarbonylation of aldehydes catalyzed by a particulate preparation from *Pisum sativum*", *Proc. Natl. Acad. Sci. USA*, 81(21), (1984), 6613-6617.
Dennis, M. W., et al., "Alkane Biosynthesis by Decarbonylation of Aldehyde Catalyzed by a Microsomal Preparation from *Botryococcus braunii*", *Arch. Biochem. Biophys*., 287(2), (1991), 268-275.

Eigenbrode, S. D., et al., "Effects of Plant Epicuticular Lipids on Insect Herbivores", *Ann. Rev. Entomol.*, 40, (1995), 171-194.
Hansen, J. D., et al., "The *glossy1* Locus of Maize and an Epidermis-Specific cDNA from *Kleinia odora* Define a Class of Receptor-Like Proteins Required for the Normal Accumulation of Cuticular Waxes", *Plant Physiol.*, 113(4), (1997), 1091-1100.
Jenks, M. A., et al., "Leaf Epicuticular Waxes of the *Eceriferum* Mutants in *Arabidopsis*", *Plant Physiol.*, 108(1), (1995), 369-377.
Jetter, R., et al., "Plant surface lipid biosynthetic pathways and their utility for metabolic engineering of waxes and hydrocarbon biofuels", *The Plant. J.*, 54(4), (2008), 670-683.
Koornneef, M., et al., "A Genetic and Phenotypic Description of *Eceriferum (cer)* Mutants in *Arabidopsis thaliana*", *J. Heredity*, 80(2), (1989), 118-122.
Kunst, L., et al., "Biosynthesis and secretion of plant cuticular wax", *Prog. Lipid Res.*, 42(1), (2003), 51-80.
Li, Y., et al., "Identification of acyltransferases required for cutin biosynthesis and production of cutin with suberin-like monomers", *Proc. Natl. Acad. Sci. USA*, 104(46), (2007), 18339-18344.
Li, Y., et al., "Monoacylglycerols Are Components of Root Waxes and Can Be Produced in the Aerial Cuticle by Ectopic Expression of a Suberin-Associated Acyltransferase", *Plant Physiol.*, 144(3), (2007), 1267-1277.
McNevin, J. P., et al., "Isolation and characterization of *eceriferum (cer)* mutants induced by T-DNA insertions in *Arabidopsis thaliana*", *Genome*, 36(3), (1993), 610-618.
Meriot, S., et al., "Use of infrared thermal imaging to isolate *Arabidopsis* mutants defective in stomatal regulation", *The Plant J.*, 30(5), (2002), 601-609.
Morris, B. D., et al., "Identification of 1-octacosanal and 6-methoxy-2-benzoxazolinone from wheat as ovipositional stimulants for Hessian fly, *Mayetiola destructor*", *J. Chem. Ecol.*, 26(10), (2000), 859-867.
Pogson, B., et al., "*Arabidopsis* Carotenoid Mutants Demonstrate That Lutein Is Not Essential for Photosynthesis in Higher Plants", *The Plant Cell*, 8(9), (1996), 1627-1639.
Rashotte, A. M., et al., "Cuticular waxes on *eceriferum* mutants of *Arabidopsis thaliana*", *Phytochemistry*, 57(1), (2001), 115-123.
Samuels, L., et al., "Sealing Plant Surfaces: Cuticular Wax Formation by Epidermal Cells", *Annu. Rev. Plant Biol.*, 59, (2008), 683-707.
Scheider-Belhaddad, F., et al., "Solubilization, partial purification, and characterization of a fatty aldehyde decarbonylase from a higher plant, *Pisum sativum*", *Arch. Biochem. Biophy.*, 377(2), (2000), 341-349.

(Continued)

*Primary Examiner* — Russell Kallis
(74) *Attorney, Agent, or Firm* — Schwegman Lundberg & Woessner, P.A.

(57) ABSTRACT

The invention provides the discovery that SCD2 (Susceptible to Coronatine-Deficient Pst DC3118-2) protein converts aldehydes to alkanes, thereby changing the composition and/or amount of synthesized waxes. The invention additionally provides homologs, orthologs and paralogs of SCD2 protein, and nucleotide sequences encoding these proteins. Also provided are expression vectors, transgenic cells, transgenic plants, transgenic seeds, methods for altering alkane production in cells, methods for identifying the function of a nucleotide sequence in the synthesis of plant surface wax, and methods for identifying plant tissue that has an altered surface wax composition. The invention's compositions and methods are useful for altering the amount and/or composition of wax produced by cells, including plants and seeds, that have been transformed with the invention's sequences.

5 Claims, 14 Drawing Sheets

(56) References Cited

OTHER PUBLICATIONS

Stoner, K. A., "Glossy Leaf Wax and Plant Resistance to Insects in *Brassica oleracea* Under Natural Infestation", *Environ. Entomol.*, 19(3), (1990), 730-739.

Vioque, J., et al., "Resolution and Purification of an Aldehyde-Generating and an Alcohol-Generating Fatty Acyl-CoA Reductase from Pea Leaves (*Pisum sativum* L.)", *Arch. Biochem. Biophys.*, 340(1), (1997), 64-72.

White, C., et al., "Effects of Surface Wax Variation in *Pisum sativum* on Herbivorous and Entomophagous Insects in the Field", *Environ. Entomol.*, 29(4), (2000), 773-780.

Xie, X., et al., "The Identification of Genes Involved in the Stomatal Response to Reduced Atmospheric Relative Humidity", *Curr. Biol.*, 16(9), (2006), 882-887.

\* cited by examiner

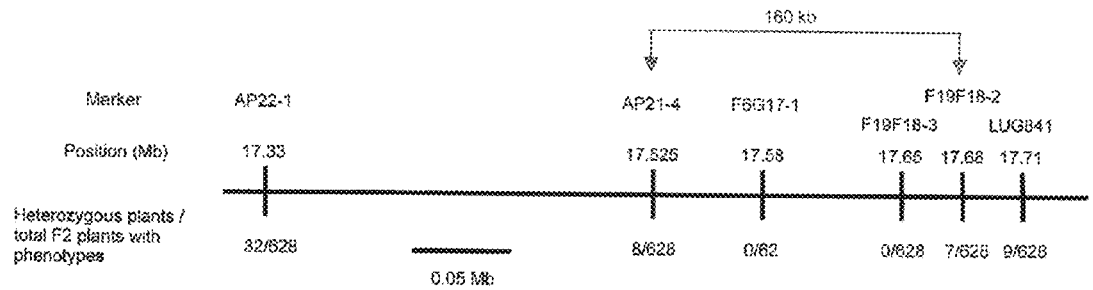

FIG. 6A

```
  1   M  G  V  V  E  E  A  H  N  V  K  V  I  G  S  G  E  A  T  I
  1   ATGGGTGTGGTAGAAGAAGCTCACAACGTGAAGGTGATTGGTTCAGGAGAAGCCACGATC

21   V  L  G  H  G  F  G  T  Q  S  V  W  K  H  L  V  P  H  L
 61   GTGTTAGGTCACGGCTTCGGCACGGACCAGTCAGTATGGAAACACTTGGTTCCACATCTG

41   V  D  D  Y  R  V  V  L  Y  D  N  M  G  A  G  T  T  N  P  D
121   GTCGACGATTACCGCGTCGTCCTCTACGACAACATGGGAGCCGGTACGACCAACCCTGAC

61   Y  F  D  F  D  R  Y  S  N  L  E  G  Y  S  F  D  L  I  A  I
181   TATTTCGACTTCGATCGTTACTCAAATCTCGAAGGCTACTCTTTCGATTTGATTGCAATC

81   L  E  D  L  K  I  E  S  C  I  F  V  G  H  S  V  S  A  M  I
241   TTGGAAGATCTCAAGATTGAGTCTTGTATCTTTGTTGGCCACTCTGTTTCTGCCATGATT

101   G  V  L  A  S  L  N  R  P  D  L  F  S  K  I  V  M  I  S  A
301   GGTGTCTTGGCTTCTCTTAACCGTCCTGATCTCTTCTCCAAAATCGTCATGATCTCTGCT

121   S  P  R  Y  V  N  D  V  D  Y  Q  G  G  F  E  Q  E  D  L  N
361   TCTCCGAGATACGTAAACGATGTTGATTACCAAGGTGGATTCGAACAAGAAGACTTAAAC

141   Q  L  F  E  A  I  R  S  N  Y  K  A  W  C  L  G  F  A  P  L
421   CAACTATTCGAAGCCATCCGAAGCAACTACAAAGCGTGGTGCTTAGGTTTCGCTCCACTC

161   A  V  G  G  D  M  D  S  I  A  V  Q  E  P  S  R  T  L  F  N
481   GCCGTCGGTGGCGACATGGACTCCATCGCCGTTCAAGAATTCAGCAGAACACTCTTCAAT

181   M  R  P  D  I  A  L  S  V  G  Q  T  I  F  Q  S  D  M  R  Q
541   ATGCGTCCCGACATAGCTCTCTCCGTCGGCCAGACCATTTTCCAAAGTGACATGAGACAG

201   I  L  P  F  V  T  V  P  C  K  I  L  Q  S  V  K  D  L  A  V
601   ATCTTACCTTTTGTCACTGTTCCGTGTCACATTCTCCAAAGTGTTAAGGACTTAGCTGTA

221   P  V  V  S  E  Y  L  H  A  N  L  G  C  E  S  V  V  E  V
661   CCAGTCGTTGTCTCCGAGTATCTTCACGCCAATCTTGGCTGTGAATCCGTCGTCGAGGTT

241   I  P  S  D  G  H  L  P  Q  L  S  S  P  D  S  V  I  P  V  I
721   ATTCCTTCTGATGGTCATCTTCCTCAGCTTAGCTCACCAGATTCTGTTATTCCTGTCATC
```

```
  1 ataagaataatacgtaacactctaaaacaacacaaatatcataatttctccacgaactg
 61 actaagagaggtaccaagaagaaaaccagagaagaatcttctttagagag
                                                    ATGGGTGTGG
  1                                                  M  G  V
121 TAGAAGAAGCTCACAACGTGAAGGTGATTGGTTCAGGAGAAGCCACGATCGTGTTAGGTC
  4  V  E  E  A  H  N  V  K  V  I  G  S  G  E  A  T  I  V  L  G
181 ACGGGTTCGGCACGGACCAGTCAGTATGGAAACACTTGGTTCCACATCTGGTCGACGATT
 24  H  G  F  G  T  D  Q  S  V  W  K  H  L  V  P  H  L  V  D  D
241 ACCGCGTCGTCCTCTACGACAACATGGGAGCCGGTACGACCAACCCTGACTATTTCGACT
 44  Y  R  V  V  L  Y  D  N  M  G  A  G  T  T  N  P  D  Y  F  D
301 TCGATCGTTACTCAAATCTCGAAGGCTACTCTTTCGATTTGATTGCAATCTTGGAAGATC
 64  F  D  R  Y  S  N  L  E  G  Y  S  F  D  L  I  A  I  L  E  D
361 TCAAGATTGAGTCTTGTATCTTTGTTGGCCACTCTGTTTCTGCCATGATTGGTGTCTTGG
 84  L  K  I  E  S  C  I  F  V  G  H  S  V  S  A  M  I  G  V  L
421 CTTCTCTTAACCGTCCTGATCTCTTCTCCAAAATCGTCATGATCTCTGCTTCTCCGAG
104  A  S  L  N  R  P  D  L  F  S  K  I  V  M  I  S  A  S  P  R
                                                              gt
481 ataactttttcacaagttgtacatagaaatatgttttgcttttatctcatcctgacata
541 gtttagacaaaagggcttctctgttccttctcttgtctgatttcataaaaactattaaac
601 attacaatttaaataaaaaaaatcatcttaagtccttaaatttacacaattatctatta
661 tttcgaaatatttatttctcattctgacataatttcgacaaagtgcctctttgtttatcc
721 tcttgtctgaattatcctatttctcaaaatcagtgaagcatttcattatatatttcaata
781 aaaatccgtaaattatgaacaaaaaatcatgaaatacccatttgtttattttgttttttt
841 tatttggttttactgaggtgttacttacactttttttaaaaaaaattgttgaaacggtgc
901 tcacacagtatattatatattttaattttcttctgacaaaagaaacatatataatcaaat
961 tatattgttttggtacgtttatag
                                   ATACGTAAACGATGTTGATTACCAAGGTGGATTCGA
124                                 Y  V  N  D  V  D  Y  Q  G  G  F  E
1021 ACAAGAAGACTTAAACCAACTATTCGAAGCCATCCGAAGCAACTACAAAGCGTGGTGCTT
136   Q  E  D  L  N  Q  L  F  E  A  I  R  S  N  Y  K  A  W  C  L
1081 AGGTTTCGCTCCACTCGCCGTCGGTGGCGACATGGACTCCATCGCCGTTCAAGAATTCAG
156   G  F  A  P  L  A  V  G  G  D  M  D  S  I  A  V  Q  E  F  S
1141 CAGAACACTCTTCAATATGCGTCCCGACATAGCTCTCTCCGTCGGCCAGACCATTTTCCA
176   R  T  L  F  N  M  R  P  D  I  A  L  S  V  G  Q  T  I  F  Q
1201 AAGTGACATGAGACAGATCTTACCTTTTGTCACTGTTCCGTGTCACATTCTCCAAAGTGT
196   S  D  M  R  Q  I  L  P  F  V  T  V  P  C  H  I  L  Q  S  V
1261 TAAGGACTTAGCTGTACCAGTCGTTGTCTCCGAGTATCTTCACGCCAATCTTGGCTGTGA
216   K  D  L  A  V  P  V  V  V  S  E  Y  L  H  A  N  L  G  C  E
1321 ATCCGTCGTCGAGGTTATTCCTTCTGATGGTCATCTTCCTCAGCTTAGCTCACCAGATTC
236   S  V  V  E  V  I  P  S  D  G  H  L  P  Q  L  S  P  D  S
1381 TGTTATTCCTGTCATCCTCCGTCACATTCGTAATGACATTGCTATGTGA
256   V  I  P  V  I  L  R  H  I  R  N  D  I  A  M  -
                                                   ttgtaagagat
1441 taattagttaattattaaacgatgtaagaaaagttgaaaaaaaatatctgatgtgatat
1501 gtctgtctagtctattgagaacattatttcgttgtcgtttggttctgattcgtttatctt
1561 gagtatcttgatctttgttgttcttatcttgtttaacgaaaagtctctgtcttttgtcca
1621 cagctttgctcagagctcattattgctgatgtaatagtgatgttcgtaattgatggtcc
1681 atagtgaattattgcaactttgcaagagtgcttgtgctatactgtgtgaagagtaattaa
1741 catgtgatactaggaattagcattgagtttgcatttatggatgggtaatccaaaccataa
1801 aacatacatattgtg
```

FIG. 10

```
                                                          ATGGGTGTGG
     1                                                    M  G  V

121  TAGAAGAAGCTCACAACGTGAAGGTGATTGGTTCAGGAGAAGCCACGATCGTGTTAGGTC
     4   V  E  E  A  H  N  V  K  V  I  G  S  G  E  A  T  I  V  L  G

181  ACGGGTTCGGCACGGACCAGTCAGTATGGAAACACTTGGTTCCACATCTGGTCGACGATT
    24   H  G  F  G  T  D  Q  S  V  W  K  H  L  V  P  H  L  V  D  D

241  ACCGCGTCGTCCTCTACGACAACATGGGAGCCGGTACGACCAACCCTGACTATTTCGACT
    44   Y  R  V  V  L  Y  D  N  M  G  A  G  T  T  N  P  D  Y  F  D

301  TCGATCGTTACTCAAATCTCGAAGGCTACTCTTTCGATTTGATTGCAATCTTGGAAGATC
    64   F  D  R  Y  S  N  L  E  G  Y  S  F  D  L  I  A  I  L  E  D

361  TCAAGATTGAGTCTTGTATCTTTGTTGGCCACTCTGTTTCTGCCATGATTGGTGTCTTGG
    84   L  K  I  E  S  C  I  F  V  G  H  S  V  S  A  M  I  G  V  L

421  CTTCTCTTAACCGTCCTGATCTCTTCTCCAAAATCGTCATGATCTCTGCTTCTCCGAG
   104   A  S  L  N  R  P  D  L  F  S  K  I  V  M  I  S  A  S  P  R

ATACGTAAACGATGTTGATTACCAAGGTGGATTCGA
   124                 Y  V  N  D  V  D  Y  Q  G  G  F  E

1021  ACAAGAAGACTTAAACCAACTATTCGAAGCCATCCGAAGCAACTACAAAGCGTGGTGCTT
   136   Q  E  D  L  N  Q  L  F  E  A  I  R  S  N  Y  K  A  W  C  L

1081  AGGTTTCGCTCCACTCGCCGTCGGTGGCGACATGGACTCCATCGCCGTTCAAGAATTCAG
   156   G  F  A  P  L  A  V  G  G  D  M  D  S  I  A  V  Q  E  F  S

1141  CAGAACACTCTTCAATATGCGTCCCGACATAGCTCTCTCCGTCGGCCAGACCATTTTCCA
   176   R  T  L  F  N  M  R  P  D  I  A  L  S  V  G  Q  T  I  F  Q

1201  AAGTGACATGAGACAGATCTTACCTTTTGTCACTGTTCCGTGTCACATTCTCCAAAGTGT
   196   S  D  M  R  Q  I  L  P  F  V  T  V  P  C  H  I  L  Q  S  V

1261  TAAGGACTTAGCTGTACCAGTCGTTGTCTCCGAGTATCTTCACGCCAATCTTGGCTGTGA
   216   K  D  L  A  V  P  V  V  V  S  E  Y  L  H  A  N  L  G  C  E

1321  ATCCGTCGTCGAGGTTATTCCTTCTGATGGTCATCTTCCTCAGCTTAGCTCACCAGATTC
   236   S  V  V  E  V  I  P  S  D  G  H  L  P  Q  L  S  S  P  D  S

1381  TGTTATTCCTGTCATCCTCCGTCACATTCGTAATGACATTGCTATGTGA
   256   V  I  P  V  I  L  R  H  I  R  N  D  I  A  M  -
```

*FIG. 11*

# COMPOSITIONS AND METHODS FOR CONVERSION OF ALDEHYDES TO ALKANES

This application claims the benefit of U.S. Provisional Application 61/147,869 filed Jan. 28, 2009.

This invention was made with government support under grant No. AI068718-01A1 awarded by the National Institutes of Health. The government has certain rights in the invention.

FIELD OF INVENTION

The invention provides the discovery that SCD2 (Susceptible to Coronatine-Deficient Pst DC3118-2) protein converts aldehydes to alkanes, thereby changing the composition and/or amount of synthesized waxes. The invention additionally provides homologs, orthologs and paralogs of SCD2 protein, and nucleotide sequences encoding these proteins. Also provided are expression vectors, transgenic cells, transgenic plants, transgenic seeds, methods for altering alkane production in cells, methods for identifying the function of a nucleotide sequence in the synthesis of plant surface wax, and methods for identifying plant tissue that has an altered surface wax composition. The invention's compositions and methods are useful for altering the amount and/or composition of wax produced by cells, including plants and seeds, that have been transformed with the inventions' sequences.

BACKGROUND

Plant waxes have a multitude of functions including increasing plant resistance to biotic stress (e.g., pathogens, etc.) and abiotic stress (e.g., temperature changes, drought, etc.). Plant waxes also have beneficial dietary effects, and have additionally been used commercially as lubricants, adhesives, coatings, sealants, impregnation materials and adjuvants in formulations of (bio)active compounds. In addition, they are high in caloric content as compared to fossil fuel, thus providing an alternative and renewable hydrocarbon energy resource.

Despite intensive efforts, the gene encoding the putative aldehyde decarbonylase that converts aldehydes to alkanes in the plant wax synthetic pathway has not yet been identified (Kunst et al. (2003) Prog Lipid Res 42:51-80; Jetter et al. (2008) Plant J 54:670-683). Accordingly, there remains a need for identification of compositions and methods for altering the level and/or composition of alkanes in plants.

SUMMARY OF THE INVENTION

The invention provides the discovery that SCD2 (Susceptible to Coronatine-Deficient Pst DC3118-2) protein is the decarbonylase that converts aldehydes to alkanes, thereby changing the composition and/or amount of synthesized alkanes (i.e., waxes). The invention additionally provides homologs, orthologs and paralogs of SCD2 protein, and nucleotide sequences encoding these proteins. Also provided are expression vectors, transgenic cells, transgenic plants, transgenic seeds, methods for altering alkane production in cells, methods for identifying the function of a nucleotide sequence in the synthesis of plant surface wax, and methods for identifying plant tissue that has an altered surface wax composition. The invention's compositions and methods are useful for altering the amount and/or composition of wax produced by cells, including plants and seeds, that have been transformed with the invention's sequences.

Data herein demonstrates the development of a novel screening strategy with the aid of bacteria pathogens to identify mutant plants in *Arabidopsis* with defects in leaf epicuticular wax layer. Using this strategy, the inventors identified a mutant plant scd2 that has decreased amount of alkanes and higher accumulation of aldehydes in leaves but not in stem, suggesting the SCD2 protein is involved specifically in the conversion of aldehyde to alkanes in leaves. This high-aldehyde and low-alkane phenotype of scd2 also confirmed the existence of aldehydes as the intermediate for VLCFA-to-alkane conversion, and that SCD2 is the decarbonylase leading to the formation of alkanes. Physical mapping identified SCD2 gene as encoding for a thioesterase/hydrolase, and the expression of a genomic fragment containing SCD2 complemented all the phenotypes of the scd2 plants. Furthermore, data herein shows that expression of SCD2 under CaMV:35S promoter increased the epicuticular alkane levels in some *Arabidopsis* transgenic plants by more than 25%. In one embodiment, the present invention contemplates a method wherein the alkane in the transgeneic plant is extracted (or otherwise isolated free of the transgeneic plant) and used for biofuel.

In particular, the invention provides an expression vector, comprising a nucleic acid sequence encoding a polypeptide at least 40% (and more preferably, at least 80% identity, or at least 85% identity, or at least 90% identity, or at least 95% identity, or at least 99% identity) identical to SCD2 protein listed as SEQ ID NO:2, wherein the polypeptide has activity that comprises converting an aldehyde to an alkane. While not intending to limit the invention to any particular nucleotide sequence, in one embodiment, the nucleic acid sequence comprises SEQ ID NO:1 (FIG. 11).

The invention further contemplates homologs of the SCD2 protein, such as those from *Arabidopsis thaliana* as exemplified by the group of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 (FIG. 6D). Also contemplated are orthologs of the SCD2 protein as exemplified by those disclosed in Table 1 (SEQ ID NO:12-107, that include *Arabidopsis thaliana* homologs).

In one embodiment, the expression vector is exemplified by a eukaryotic vector, including plant vector and yeast vector. In an alternative embodiment, the expression vector is a prokaryotic vector exemplified by an *Escherichia coli* vector.

While not intending to limit the type of promoter that drives expression of the invention's nucleotide sequences, in one embodiment, the nucleic acid sequence is operably linked to a heterologous promoter, exemplified by a eukaryotic promoter. In a preferred embodiment, the eukaryotic promoter is active in a plant cell and/or in a yeast cell. In another embodiment, the heterologous promoter is a prokaryotic promoter, such as one active in *Escherichia coli*.

Further provided is an antibody that specifically binds to SCD2 protein and/or its homologs. The antibody is selected from the group of monoclonal antibody and polyclonal antibody.

The invention additionally provides a transgenic cell comprising a heterologous nucleic acid sequence encoding a polypeptide at least 40% identical (and more preferably, at least 80% identity, or at least 85% identity, or at least 90% identity, or at least 95% identity, or at least 99% identity) to SCD2 protein listed as SEQ ID NO:2, wherein the polypeptide has activity that comprises converting an aldehyde to an alkane. In one embodiment, the transgenic is a eukaryotic cell, preferably a plant cell, and more preferably a plant cell that is comprised in a tissue selected from the group of seed and leaf. In an alternative embodiment, the eukaryotic cell is a yeast cell. In a further embodiment, the transgenic cell is a prokaryotic cell exemplified by *Escherichia coli*. In one embodiment, the present invention contemplates a method wherein the alkane in the transgeneic cell is extracted (or otherwise isolated free of the transgeneic cell) and used for biofuel.

Also provided herein is a transgenic plant comprising a heterologous nucleic acid sequence encoding a polypeptide at least 40% identical (and more preferably, at least 80% identity, or at least 85% identity, or at least 90% identity, or at least 95% identity, or at least 99% identity) to SCD2 protein listed as SEQ ID NO:2, wherein the polypeptide has activity that comprises converting an aldehyde to an alkane. While not intending to limit the phenotype of the transgenic plant, in one embodiment, the transgenic plant comprises an altered level of an alkane compared to a plant that lacks the heterologous nucleic acid sequence. In another embodiment, the transgenic plant comprises an altered level of an aldehyde compared to a plant that lacks the heterologous nucleic acid sequence. In a further embodiment, the transgenic plant has increased drought tolerance compared to a plant lacking the heterologous nucleic acid sequence. In yet another embodiment, the transgenic plant has increased temperature tolerance compared to a plant lacking the heterologous nucleic acid sequence. In a more preferred embodiment, the temperature tolerance is selected from cold tolerance and heat tolerance. In an alternative embodiment, the transgenic plant has increased resistance to a pathogen compared to a plant lacking the heterologous nucleic acid sequence. In a particular embodiment, the pathogen is selected from the group of virus, bacteria, fungus, insect, and nematode.

The invention additionally provides a transgenic plant seed comprising a heterologous nucleic acid sequence encoding a polypeptide at least 40% identical (and more preferably, at least 80% identity, or at least 85% identity, or at least 90% identity, or at least 95% identity, or at least 99% identity) to SCD2 protein listed as SEQ ID NO:2, wherein the polypeptide has activity that comprises converting an aldehyde to an alkane. In one embodiment, the present invention contemplates protein variants wherein conservative amino acid substitutions are introduced resulting in a protein that is at least 90% identical to SEQ ID NO:2.

Also provided herein is a method for altering alkane production in a cell, comprising a) providing i) an expression vector comprising any one or more of the nucleotide sequences described herein, and ii) a host cell, b) introducing the expression vector into the host to produce a transgenic cell that expresses the polypeptide, and culturing the transgenic cell under conditions such that the polypeptide alters the level of an alkane produced by the transgenic cell compared to the host cell. In some embodiments, e.g., when using *E. coli* and yeast cells, the expressed polypeptide is purified. The purified polypeptide may then be used in vitro to produce lipids and/or wax. In one embodiment, the method further comprises: c) extracting (or otherwise isolating) the alkane produced by the transgenic cell to produce purified alkane. In one embodiment, the method further comprises: d) using said purified alkane as a biofuel (e.g. for heat, or to run a machine, including a vehicle).

The invention also provides a method for identifying a function of a nucleotide sequence in synthesis of plant surface wax, comprising a) providing i) a first plant tissue (e.g., wild type) comprising the nucleotide sequence, ii) a second plant tissue (e.g., mutant) comprising one or more mutation in the nucleotide sequence, and iii) a surfactant, b) contacting the first plant tissue with the surfactant to produce a contacted first tissue, c) contacting the second plant tissue with the surfactant to produce a contacted second tissue, and d) detecting an alteration in one or more disease-like symptoms in the contacted first tissue compared to the contacted second tissue, thereby identifying a function of the nucleotide sequence in synthesis of plant surface wax. In one embodiment, step b) further comprises contacting the first plant tissue with a microorganism, and step c) further comprises contacting the second plant tissue with the microorganism. In a particular embodiment, the surfactant is Silwet L-77®.

Without intending to limit the microorganism to any particular type or source, in one embodiment, the microorganism is selected from the group of virus, bacteria, fungus, insect, and nematode. In another embodiment, the microorganism is selected from a pathogenic microorganism, and non-pathogenic microorganism. In a particular embodiment, the tissue is *Arabidopsis thaliana* leaf tissue, and the microorganism is selected from the group of *Pseudomonas syringae* pv. *tomato* (Pst) DC3118, Ps pv. *phaseonicola*, and Pst DC3000 (hrpH$^-$).

The invention additionally provides a method for identifying plant tissue that has an altered surface wax composition, comprising a) providing i) tissue from a first plant, ii) corresponding tissue from a second plant, and iii) a surfactant, b) contacting the tissue from the first plant with the surfactant to produce a contacted first tissue, b) contacting the tissue from the second plant with the surfactant to produce a contacted second tissue, and c) identifying an increase in one or more disease-like symptoms in the contacted first tissue compared to the contacted second tissue, thereby identifying the tissue from the first plant as having an altered surface wax composition compared the tissue from the second plant.

BRIEF DESCRIPTION OF THE DRAWINGS

FIG. 10: Genomic sequence of SCD2/At4g37470 [SEQ ID NO: 147] and encoded protein SCD2 [SEQ ID NO: 2]. Sequences of 5'UTR and 3'UTR are in lower case, exons are in upper case, intron is in lower case and underlined, and encoded amino acids are represented in single upper case letters. Sequence information is based on the *Arabidopsis* Genome Initiative database: SCD2 (At4g37470) and on annotation from The *Arabidopsis* Information Resource (TAIR, world wide web at arabidopsis.org).

FIG. 11: DNA sequence of SCD2 (SEQ ID NO:1) that encodes protein SCD2 (SEQ ID NO:2). Sequence information is based on the *Arabidopsis* Genome Initiative database: SCD2 (At4g37470) and on annotation from The *Arabidopsis* Information Resource (TAIR, world wide web at arabidopsis.org).

DEFINITIONS

Figure 1A:
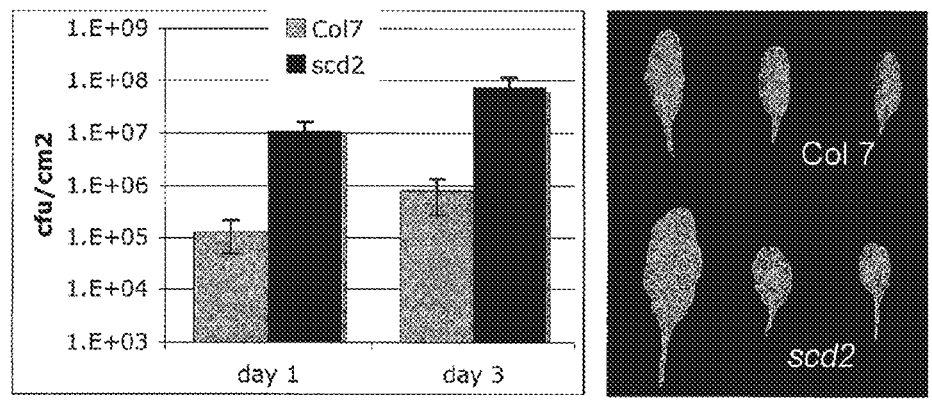
FIG. 1: Identification of scd2 through leaf surface inoculation of non-pathogenic bacteria, showing bacteria population at 1 dpi and 3 dpi after dip-inoculation at $10^8$ cfu/ml and leaf appearances at 3 dpi. A. Pst DC3118, B. Ps pv. *phaseolicola*, C. Pst DC3000 (hrpH$^-$).

To facilitate understanding of the invention, a number of terms are defined below.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed using a recombinant DNA molecule.

The term "recombinant mutation" refers to a mutation that is introduced by means of molecular biological techniques. This is in contrast to mutations that occur in nature.

A peptide sequence and nucleotide sequence may be "endogenous" or "heterologous" (i.e., "foreign"). The terms "endogenous" and "wild type" refer to a sequence that is naturally found in the cell or virus into which it is introduced so long as it does not contain some modification relative to the naturally occurring sequence. The term "heterologous" refers to a sequence that is not endogenous to the cell or virus into which it is introduced. For example, heterologous DNA includes a nucleotide sequence that is ligated to, or is manipulated to become ligated to, a nucleic acid sequence to which it is not ligated in nature, or to which it is ligated at a different location in nature. Heterologous DNA also includes a nucleotide sequence that is naturally found in the cell or virus into which it is introduced and which contains some modification relative to the naturally occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc.

The term "transgenic" when used in reference to a cell refers to a cell which contains a transgene, or whose genome has been altered by the introduction of a "transgene" i.e., any nucleic acid sequence which is introduced into the cell by experimental manipulations.

The terms "purified" and "isolated" and grammatical equivalents thereof as used herein, refer to the reduction in the amount of at least one undesirable contaminant (such as protein and/or nucleic acid sequence) from a sample. Thus, purification results in an "enrichment," i.e., an increase in the amount of a desirable composition, such as a virus, protein and/or nucleic acid sequence in the sample. For example, wax and/or alkanes that are produced by cells that have been transformed by the invention's sequences may be purified using methods known in the art.

The terms "operable combination" and "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest resulting in an mRNA that directs the synthesis of a polypeptide encoded by the nucleotide sequence of interest. The term also refers to the linkage of amino acid sequences in such a manner so that a functional protein is produced.

The term "altering" and grammatical equivalents as used herein in reference to the level of any molecule (e.g., amino acid sequence such as SCD2 protein and/or its homologs, and nucleic acid sequence such as those encoding any of the polypeptides described herein, alkane, aldehyde, wax, etc.), and/or phenomenon (e.g., drought tolerance, temperature tolerance, resistance to a pathogen, disease symptoms, disease-like symptoms, shape of a plant tissue, size of a plant tissue, cell death, cell apoptosis, cell viability, cell survival, binding to a molecule, expression of a nucleic acid sequence, transcription of a nucleic acid sequence, enzyme activity, etc.) refers to an increase and/or decrease in the quantity of the molecule and/or phenomenon, regardless of whether the quantity is determined objectively and/or subjectively.

The term "increase" when in reference to the level of any molecule (e.g., amino acid sequence such as SCD2 protein and/or its homologs, and nucleic acid sequence such as those encoding any of the polypeptides described herein, alkane, aldehyde, wax, etc.), and/or phenomenon (e.g., drought tolerance, temperature tolerance, resistance to a pathogen, disease symptoms, disease-like symptoms, shape of a plant tissue, size of a plant tissue, cell death, cell apoptosis, cell viability, cell survival, binding to a molecule, expression of a nucleic acid sequence, transcription of a nucleic acid sequence, enzyme activity, etc.) in a first sample relative to a second sample, mean that the quantity of the molecule and/or phenomenon in the first sample is higher than in the second sample by any amount that is statistically significant using any art-accepted statistical method of analysis. In one embodiment, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

The term "reduce" when in reference to the level of any molecule (e.g., amino acid sequence such as SCD2 protein and/or its homologs, and nucleic acid sequence such as those encoding any of the polypeptides described herein, alkane, aldehyde, wax, etc.), and/or phenomenon (e.g., drought tolerance, temperature tolerance, resistance to a pathogen, disease symptoms, disease-like symptoms, shape of a plant tissue, size of a plant tissue, cell death, cell apoptosis, cell viability, cell survival, binding to a molecule, expression of a nucleic acid sequence, transcription of a nucleic acid sequence, enzyme activity, etc.) in a first sample relative to a second sample, mean that the quantity of molecule and/or phenomenon in the first sample is lower than in the second sample by any amount that is statistically significant using any art-accepted statistical method of analysis. In another embodiment, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample.

"Plant wax" includes epicuticular wax and cuticular wax. The terms "epicuticular wax" and "surface wax" interchangeably refer to wax that covers the outside of the plant cuticle. This is in contrast to "cuticular wax" that is embedded in the cuticle. Epicuticular wax mainly consists of straight-chain aliphatic hydrocarbons with a variety of substituted groups. Common examples are paraffins in leaves of peas and cabbages, alkyl esters in leaves of carnauba palm and banana, the asymmetrical secondary alcohol 10-nonacosanol in most conifers such as Ginkgo biloba and Sitka spruce, symmetrical secondary alcohols in Brassicaceae including *Arabidopsis thaliana*, primary alcohols (mostly octacosan-1-ol) in most grasses, β-diketones in many grasses, aldehydes in young beech leaves, and triterpenes in fruit waxes of apple, plum and grape. Epicuticular wax is mostly soluble in organic solvents such as chloroform and hexane. Solvent extracts of cuticle waxes contain both epicuticular and cuticular waxes, often contaminated with cell membrane lipids of underlying cells. Epicuticular wax can be isolated by mechanical methods (Ensikat et al. (2000) Int. J. Plant Sci. 161:143-148), which distinguish the epicuticular wax from the cuticular wax.

"Alkane" and "paraffin" refer to a chemical compound that consist of the elements carbon (C) and hydrogen (H) (i.e., hydrocarbons), wherein these atoms are linked together exclusively by single bonds (i.e., they are saturated compounds) without any cyclic structure (i.e., loops). Alkanes belong to a homologous series of organic compounds in which the members differ by a constant relative atomic mass of 14. Each carbon atom has 4 bonds (either C—H or C—C bonds), and each hydrogen atom is joined to a carbon atom (H—C bonds). A series of linked carbon atoms is known as the carbon skeleton or carbon backbone. In general, the number of carbon atoms is often used to define the size of the alkane (e.g., C2-alkane).

"Aldehyde" refers to an organic compound containing a terminal carbonyl group. This functional group, which consists of a carbon atom bonded to a hydrogen atom and double-bonded to an oxygen atom (chemical formula O═CH—), is called the aldehyde group (also referred to as formyl group or methanoyl group).

"Lipid" refers to a fat-soluble (lipophilic) molecule, such as fat, oil, waxe, cholesterol, sterol, fat-soluble vitamin (such as vitamins A, D, E and K), monoglyceride, diglyceride, phospholipid, and others. Lipid catergories include fatty acyls, glycerolipids, glycerophospholipids, sphingolipids, sterol lipids, prenol lipids, saccharolipids, and polyketides.

"Drought tolerance" refers to the level to which a plant is adapted to arid or drought conditions, and may be measured by determining the level of wilting, change in leaf color, change in leaf curling, change in leaf size, change in plant survival, etc., under conditions of reduced availability of water to the plant. Desiccation tolerance is an extreme degree of drought tolerance. Plants naturally adapted to dry conditions are called xerophytes.

"Pathogen" refers to a first organism that causes a disease in a second organism. A "non-pathogen" refers to a first organism that does not cause a disease in a second organism.

A "fungus" is a eukaryotic organism that is a member of the kingdom Fungi. Fungi are heterotrophic organisms possessing a chitinous cell wall. The majority of species grow as multicellular filaments called hyphae forming a mycelium. Some fungal species also grow as single cells. Fungi include "mold," which are microscopic fungi that grow in the form of multicellular filaments, called hyphae. Fungi that infect plants include flagellated fungi and non-flagellated fungi. Flagellated fungi include Plasmodiophoromycetes, Chytridiomycota and Oomycetes. Plasmodiophoromycetes include *Plasmodiophora brassicae* that causes club root of cabbage, and *Spongospora subterranean* that causes powdery scab of potatoes. Chytridiomycota include *Olpidium* spp. that infect pollen, *Physoderma maydis* that causes brown spot of corn leaves, and *Synchytrium* spp. that cause wart of potatoes. The Peronosporales group is exemplified by the late blight of potato fungus *Phytophthora infestans*, *Peronospora*, *Bremia*, *Plasmopara* and others that cause "downy mildews", the "damping off" fungi, *Pythium* spp., and the white rust fungi, *Albugo* spp. Non-flagellated Fungi include Zygomycota, Ascomycota, Deuteromycetes and Basidiomycetes. Zygomycota include the Mucorales that are exemplified by members of the bread mold genus *Rhizopus*, and *Hoanephora* that causes blossom blight and decay of squash. Ascomycota include *Taphrina deformans* that causes peach leaf curl, and *Nematospora* that causes seed decay and root rot on cotton, Plectomycetes such as *Ophiostoma* (*Ceratocystis*), and *O. ulmi* that causes Dutch elm disease, Pyrenomycetes such as powdery mildews of the genus *Erysiphe* that is common on grasses, *Phyllactinia* on oaks and other trees, and *Uncinula* on grapes and other shrubs, Discomycetes such as *Sclerotinia* that causes stromatic rot of vegetables, and *Monilinia*, the cause of brown rot of peaches, and Loculoascomycetes such as Myriangiales that include *Elsinoe* species that cause citrus scab, and Dothideales that include *Capnodium* species that cause sooty molds of plants. Deuteromycetes include Ascomycetes such as species of *Alternaria, Bipolaris, Botrytis, Cercospora, Diplodia, Dreschlera, Exerohilum, Fusarium, Phoma, Phomopsis, Rhizoctonia*, and *Verticillium* that cause molds, blights, cankers, leaf spots, and root rots. Basidiomycetes include Uredinales, Exobasidiales, and Aphyllophorales that cause rusts, smuts, felt fungi, root rots, heart rots, and thread-blights.

"Virus" refers to an obligate intracellular parasite that does not have the molecular machinery to replicate without the host. Plant viruses are usually transmitted by a vector, most often insects such as leafhoppers, and include, without limitation, Agropyron mosaic rymovirus, alstroemeria carlavirus, Arabis mosaic nepovirus, banana infectious chlorosis virus, cabbage mosaic virus, Cassia ringspot virus, citrus psorosis virus complex, Dutch plum line pattern virus, grapevine Reisigkrankheit virus, maize chlorotic stripe virus, Oak ringspot virus, peanut severe mosaic virus, potato calico virus, Rice stripe tenuivirus, and Tobacco stunt varicosavirus "Bacteria" refers to all prokaryotic organisms, including those within all of the phyla in the Kingdom Procaryotae. Bacteria that are pathogenic to plants include *Acetobacter, Accidovorax, Bacillus, Brenneria, Burkholderia, Clavibacter, Clostridium, Curtobacterium, Enterobacter, Erwinia, Leifsonia, Nocardia, Pantoea, Pectobacterium, Pseudomonas, Ralstonia, Rhizobium, Streptomyces*, and *Xanthomonas* species.

"Insect" refers to a member of the class Insecta, which is a major group of arthoropods. Insects that feed on plants include, beetles, scales, mites, midges, aphids, etc.

"Nematode" and "roundworm" interchangeably refer to a multicellular organism that is a member of the Phylum Nematoda. Exemplary nematodes that are agricultural pests include corn pests such as *Belonolaimus* (Sting Nematode), *Criconemoides* (Ring nematode), *Helicotylenchus* (Spiral Nematode), *Heterodera zeae* (Corn Cyst Nematode), *Hoplolaimus* (Lance Nematode), *Xiphinema* (Dagger Nematode), *Longidorus* (Needle Nematode), *Meloidogyne* (Root-Knot Nematode), *Pratylenchus* (Lesion Nematode), *Paratrichodorus* (Stubby-Root Nematode), *Tylenchorhynchus* (Stunt Nematode); potato pests such as *Meloidogyne chitwoodi* (Columbia Root-knot Nematode), *Globodera rostochiensis* (Golden Nematode), *Meloidogyne hapla* (Northern Root Knot Nematode), *Ditylenchus destructor* (Potato Rot Nematode), *Globodera pallida* (Pale Potato Cyst Nematode); soybean pests such as *Heterodera glycines* (Soybean cyst nematode) and *Belonolaimus* spp. (Sting nematode); sugar beet pests such as *Heterodera schachtii* (Sugar beet cyst nematode) and *Nacobbus aberrans* (False root-knot nematode); turf pests such as *Belonolaimus* species (Sting Nematode), *Hoplolaimus galeatus* (Lance Nematode), *Meloidogyne* species (Root-knot Nematodes) and *Criconemoides* species (Ring Nematode); trees and vines pests such as *Bursaphelenchus xylophilus* (Pine wilt nematode), *Tylenchulus semipenetrans* (Citrus nematode), *Radopholus similis* (Burrowing nematode), *Belonolaimus longicaudatus* (Sting nematode), *Xiphinema americanum* (Dagger nematode), *Mesocriconema xenoplax* (Ring nematode), *Meloidogyne hapla* (Root-knot nematode), *Tylenchorhynchus* spp. (Stunt nematode), *Rotylenchulus* spp. (Reniform nematode) and *Pratylenchus* spp. (Lesion nematode); ornamentals and garden vegetables pests such as *Aphelenchoides* spp. (Foliar nematodes), *Meloidogyne* spp. (Root-knot nematodes), *Ditylenchus dipsaci* (Stem and bulb nematode), and *Belonolaimus longicaudatus* (Sting nematode).

"Disease-like symptom" refers to a manifestation of disease, such as those observed by the naked eye (e.g., change in color, appearance, and/or texture of a plant tissue such as change in leaf color, leaf curling, water soaking-like appearance of leaves (FIG. 2A), wilting, change in plant survival, etc.) or detected using biochemical assays (e.g., using antibodies, nucleic acid sequences, etc.).

The term "plant" as used herein refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, or cell culture.

"Plant cell" is the structural and physiological unit of plants, consisting of a protoplast and the cell wall, and may be derived from a plant, plantlet, seed, tissue, organ, callus, protocorm-like body, suspension culture, protoplasts, and the like. "Plant cell suspension culture" refers to plant cells in liquid medium.

"Plant tissue" is a group of plant cells organized into a structural and functional unit.

"Plant organ" is a collection of tissues that performs a particular function or set of functions in a plant's body. The leaf, stem, and root are exemplary organs found in many plants. Organs are composed of tissues.

The term "totipotent body" as used herein refers to a collection of cells (e.g., a cell aggregate) comprising undifferentiated plant cells capable of differentiation into a plant. A totipotent body may also contain some differentiated cells. A "totipotent body" includes, but is not limited to, a protocorm-like body, a callus, and the like. The ability of a totipotent body to differentiate into a plant is determined using methods known in the art as well as methods described herein. For example, differentiation into shoots may be accomplished by culturing a totipotent body on agar-solidified hormone-free modified MS medium, or on agar-solidified PM2 medium. Differentiation into roots may be accomplished by culture of a totipotent body in liquid modified MS medium containing 1 mg/L NAA.

"Plant callus" is a cluster of undifferentiated plant cells that have the capacity to regenerate a whole plant.

"Protocorm-like body," "plb," and "nodular body" when made in reference to pineapple refer to a totipotent body which is generally, though not necessarily, creamy yellow and globular shaped. A plb derived form pineapple tissue is morphologically distinguishable from a callus derived from pineapple. For example, a plb that is derived from pineapple tissue is characterized by having a partially organized morphology with a pre-determined apical meristematic region covered by a distinctive epidermal layer but lacking vascular tissue; a callus derived from pineapple tissue is a disorganized mass of undifferentiated plant cells lacking apical meristem, epidermis, and vascular tissue. Additionally, in vitro culture conditions for the generation of a plb are different from those for the generation of a callus. For example, pineapple plbs may be generated as previously described (Wakasa et al. (1978) Japan. J. Breed. 28:113-121, Mapes (1973) Proc. Intl. Plant Propagation Soc. 23:47-55) and using methods described herein. Pineapple callus may be produced as described by (Mathews et al. (1981) Scientia Horiculturae 14:227-234).

The term "embryonic cell" as used herein in reference to a plant cell refers to a plant cell (whether differentiated or un-differentiated) that is capable of differentiation into a plant tissue or plant. Embryonic cells include, without limitation, protoplasts such as those derived from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*. Also included are embryos such as those from sorghum, from maize (U.S. Pat. No. 5,593,874), and from banana, embryonic meristems such as those from soybean (U.S. Pat. No. 5,015,580), embryogenic callus such as from sugarcane, protocorm-like bodies such as from pineapple, and embryogenic cells as exemplified by those from garlic. The ability of an embryonic cell to differentiate into a plant is determined using methods known in the art as well as methods described herein. For example, differentiation of pineapple protocorm-like bodies into shoots may be accomplished by culturing the protocorm-like body on agar-solidified hormone-free modified Murashige & Skoog (MS) medium or on agar-solidified PM2 medium (U.S. Pat. No. 6,091,003). Differentiation into pineapple roots may be accomplished by culture of protocorm-like bodies in liquid modified MS medium containing 1 mg/L NAA.

"Biofuel" is a fuel derived from a biological carbon source, such as plant cell, yeast cell, *E. coli* cell, etc. Biofuel may be used directly, e.g., by burning to provide heat. Biofuel may also be processed to produce other energy sources such as biodiesel. "Biodiesel," also referred to as "fatty acid methyl ester," "FAME," and "fatty acid ethyl ester," is a liquid similar in composition to fossil/mineral diesel. It is produced from oils, fats, etc. using transesterification. Oils are mixed with sodium hydroxide and methanol (or ethanol) and the chemical reaction produces biodiesel (FAME) and glycerol. Biodiesel can be used in any diesel engine when mixed with mineral diesel.

DESCRIPTION OF THE INVENTION

The invention provides the discovery that SCD2 (Susceptible to Coronatine-Deficient Pst DC3118-2) protein converts aldehydes to alkanes, thereby changing the composition and/or amount of synthesized waxes. The invention additionally provides homologs, orthologs and paralogs of SCD2 protein, and nucleotide sequences encoding these proteins. Also provided are expression vectors, transgenic cells, transgenic plants, transgenic seeds, methods for altering alkane production in cells, methods for identifying the function of a nucleotide sequence in the synthesis of plant surface wax, and methods for identifying plant tissue that has an altered surface wax composition. The invention's compositions and methods are useful for altering the amount and/or composition of wax produced by cells, including plants and seeds, that have been transformed with the invention's sequences.

In particular, the invention discloses the discovery that altering expression of the SCD2/At4g37470 gene results in alteration of the composition of plant epicuticular wax, and that this gene encodes a protein (SEQ ID NO:2) that is involved in the biosynthesis of alkanes in epicuticular wax.

The epicuticular wax is essential for the protection of plants from both biotic and abiotic stresses. The biosynthesis of wax includes the de novo synthesis of C16 and C18 free fatty acids (FFAs), the elongation of C16 and C18 FFAs into C20-C34 very long chain fatty acids (VLCFAs), and the modification of VLCFAs into primary alcohols and esters through the primary alcohol/acyl reduction pathway or into aldehydes, alkanes, secondary alcohols and ketones through the alkane pathway. While many genes involved in the wax biosynthesis have been identified and characterized, the gene responsible for the formation of alkanes remained elusive, until the discovery of the present invention.

Data herein demonstrate the identification of an *Arabidopsis* mutant scd2, Susceptible to Coronatine-Deficient Pst DC3118-2 (Example 2) with 70-80% less alkanes and a 2-fold to 3-fold more aldehydes in rosette leaves compared to wild type Col7 (Example 3). Compared to wild type Col7, scd2 plants also showed altered morphological phenotype, including slightly wrinkled leaves, slightly elongated petioles, and longer hypercotyls during the early growth (Example 4). Contrary to many cer mutants, the wax composition phenotype of scd2 was not observed in the stems. Therefore it was the inventors' view that SCD2 was one of the enzymes and/or part of an enzyme complex that is involved in the conversion of VLCFAs to alkanes, specifically in leaves.

The gene SCD2 was identified herein through physical mapping and was found to encode a putative thioesterase/hydrolase. The mutant allele scd2 was found by the inventors to bear a single nucleotide deletion in the second exon that generated an earlier stop codon (Example 5). Another mutant allele scd2-2 in Ler background with a Ds element inserted into this gene showed similar morphological and wax compositional phenotypes (Example 6).

Data herein show that a 2.8 kb genomic fragment containing the SCD2 region was able to rescue both the morphological and wax phenotypes of the scd2 plants (Example 7). In addition, when SCD2 was expressed in wild type Col7 plants under control of CaMV $^{35}$S promoter, a large proportion of transgenic plants showed more than 25% increase of total alkanes (Example 8). In addition, the scd2 mutant plants were sensitive to drought stress (Example 4), indicating that not only the amount of epicuticular wax, as indicated before, but also the composition of the epicuticular wax affects water loss in leaves.

The invention's compositions and sequences are useful for altering the amount and/or composition of wax produced by cells that have been transformed with the invention's sequences. For example, plants transformed with the invention's sequences have increased tolerance to abiotic stress (such as drought, low and/or high temperatures, UV radiation, etc.) and biotic stress (such as from pathogenic bacteria, fungi, insects, nematodes, etc.). In addition, transformed plants may be used as a food source for animals, including humans. Plant waxes in human diet have been reported to lower total cholesterol and low-density lipoprotein cholesterol consistently (Gouni-Berthold et al. (2002) Am Heart J 143:356-365). Moreover, plant wax has also been widely used commercially as lubricants, adhesives, coatings, sealants, impregnation materials and adjuvants in formulations of (bio)active compounds.

In addition, cells (e.g., prokaryotic and/or eukaryotic cells) transformed with the invention's sequences may be used to produce wax for multiple utilities. In the industry, waxes are used in the manufacture of commercial products such as automobiles, textiles, pesticides, plastics, furniture, shoe polish, cosmetics, dental treatment products, drugs and food items (Jetter et al. (2008) Plant J 54:670-683).

Furthermore, cells (including plants) expressing waxes may also be used as biofuel. This is because alkanes, also known as hydrocarbons, hold the highest energy per molecule compared to other energy molecules. Alkanes are also the main component of gasoline, constituting more than 60% of its content. The invention's discovery provides sequences that are involved in hydrocarbon assembly, thus aiding in genetic engineering efforts for the production of bio-gasoline. Thus, alkanes expressed by cells (including plants) in accordance with the invention's methods have longer carbon numbers than gasoline and mostly are straight chains. These alkanes could either be extracted from the genetically modified cells (including plants) as waxes, or those plants could be used directly as fuel.

The invention is further described under A) Plant Wax, B) SCD2 Protein, Nucleotide Sequences Encoding SCD2, And Homologous Amino Acid And Nucleotide Sequences, C) Expression Vectors, D) Methods For Altering Alkane Production, E) Transgenic Cells, F) Transgenic Plants, G) Regeneration of Transgenic Plants, H) Methods For Identifying The Function Of A Gene In Synthesis Of Plant Surface Wax, and I) Methods For Identifying Plants With Altered Surface Wax Composition.

A. Plant Wax

The primary aerial parts of most vascular plants are covered with a layer of hydrophobic cuticle, which contains mostly cutin and wax (Bargel et al. (2006) Funct Plant Biol 33: 893-910). This cuticle layer serves as a physical barrier to protect the plants against abiotic stresses such as drought and the UV radiation, and biotic stressed from bacteria, fungi and insect attacks. The cuticular wax's essential function of regulating the non-stomatal water loss is also regarded as a key adaptation in the evolution process of land plants (Raven et al. "Physiological evolution of lower embryophytes: adaptations to the terrestrial environment;" in *The Evolution of Plant Physiology: From Whole Plants to Ecosystems*, A. Hemsley and I. Poole, eds (Amsterdam: Elsevier), 2004, pp. 17-41).

The cuticular wax is mainly composed of long chain aliphatic compounds derived from very-long-chain-fatty-acids (VLCFA). The biosynthesis of the epicuticular wax starts with the synthesis of C16 and C18 fatty acids in the chloroplast starting with short acyl chain precursors that are activated by the Acyl Carier Protein (ACP). The acyl chains are elongated by the Fatty Acid Synthetase (FAS) complex that adds the 2-carbon moiety from the malonyl-ACP onto the growing chain in each cycle. Once synthesized, the C16 and C18 free fatty acids are liberated from ACP by an acyl-ACP thioesterase and released into the cytoplasm. Over there, the C16 and C18 acids are activated by a Long-chain Acyl-CoA synthetase (LACS) into CoA thioesters and transferred into the ER. These long-chain fatty acids are then converted into VLCFAs by the Fatty Acid Elongases (FAEs) residing on the ER membranes, which use malonyl-CoA as C2 donor instead of malonyl-ACP. VLCFAs are converted into epicuticular waxes by either deactivation by acyl-CoA thioesterases to release the free fatty acids, or conjugation with primary alcohols to form aliphatic esters, or reduced to primary alcohols of the same chain length through the primary alcohol/acyl reduction pathway, or reduced to aldehydes and then alkanes of one-carbon-less chains through the decarbonylation/alkane pathway, which could be further converted into secondary alcohols and ketones. While the primary alcohols mostly have even numbered carbons, the alkanes, secondary alcohols and ketones mostly have odd numbered carbons (Jenks et al. (2002) "Cuticular Waxes of *Arabidopsis*;" in *The Arabidopsis Book* (Rockville, Md.: American Society of Plant Biologists; Samuels et al. (2008) Annu Rev Plant Biol 59:683-707).

In some plants, e.g., *Arabidopsis*, alkanes and primary alcohols are the main wax fractions of leaves and stems, while stems and siliques also have large amount of ketones and secondary alcohols that constitute only a very small fraction in leaves (Jenks et al. (2002) "Cuticular Waxes of *Arabidopsis*;" in The *Arabidopsis* Book (Rockville, Md.: American Society of Plant Biologists). Although alkanes are commonly found in plants and their various organs, and often accumulate to high concentrations, the conversion from VLCFAs to alkanes remains the least known step in the biosynthesis of the epicuticular waxes, even though the VLCFA elongation precedes the decarbonylation step and the acyl-CoA derivatives are the precursors for this step based on mutant characterizations (Jenks et al. (1995) Plant Physiol 108:369-377; Rashotte et al. (2001) Phytochemistry 57:115-123; Samuels et al. (2008) Annu Rev Plant Biol 59:683-707). Although there are two possible routes for the conversion of VLCFA acyl-CoA into alkanes, a direct decarboxylation step to generate the odd-chain length hydrocarbons is not very likely (Samuels et al. (2008) Annu Rev Plant Biol 59:683-707). A reduction step to form the aldehyde intermediates is required before the decarbonylation step, which releases CO instead of $CO_2$ that is predicted for the direct decarboxylation reaction (Cheesbrough et al. (1984) Proc Natl Acad Sci USA 81:6613-6617; Dennis et al. (1991) Arch Biochem Biophys 287:268-275; Vioque et al. (1997) Arch Biochem Biophys 340:64-72; Schneider-Belhaddad et al. (2000) Arch Biochem Biophys 377:341-349). Most of the knowledge about the final step of alkane formation only came out of some very early in vitro biochemical studies using microsomal protein preparations (Cheesbrough et al. (1984) Proc Natl Acad Sci USA 81:6613-6617; Dennis et al. (1991) Arch Biochem Biophys 287:268-275; Schneider-Belhaddad et al. (2000) Arch Biochem Biophys 377:341-349), and the characterization of the wax mutants cer1 (McNevin et al. (1993) Genome 36:610-618; Aarts et al. (1995) Plant Cell 7:2115-2127) from *Arabidopsis* and gl1 from maize (Hansen et al. (1997) Plant Physiol 113: 1091-1100). Despite intensive efforts, the gene encoding the putative aldehyde decarbonylase has not yet been identified and confirmed with biochemical activity assays (Kunst et al. (2003) Prog Lipid Res 42:51-80; Jetter et al. (2008) Plant J 54:670-683).

Wax-deficient mutants have been isolated from barley (*Hordeum vulgare*), maize (*Zea mays*), and *Brassica napus*. Current genetic studies in wax biosynthesis have focused on *Arabidopsis* cer mutants that were identified through visual observation of stem wax defects (Koornneef et al. (1989) Heredity 80:118-122). Even though wax compositional analysis of mutant plants have yielded much information about the structure and synthesis pathway of the epicuticular waxes (McNevin et al. (1993) Genome 36:610-618; Jenks et al. (1995) Plant Physiol 108:369-377), one drawback is that most of the mutants do not cause accumulation of intermediate chemicals that are indicative of the functions of the corresponding genes (Kunst et al. (2003) Prog Lipid Res 42:51-80). Moreover, much of the current studies focus on the wax synthesis in stems since the cer mutants were identified with stem phenotypes.

B. SCD2 Protein, Nucleotide Sequences Encoding SCD2, and Homologous Amino Acid and Nucleotide Sequences The invention is not limited to SEQ ID NOs:1 and 2, but rather expressly contemplates homologs of the invention's SCD2 protein (SEQ ID NO:2) and homologs of the nucleic acid sequences (SEQ ID NO:1) that encodes the SCD2 protein. In one embodiment, homologs of SCD2 protein (SEQ ID NO:2) comprise, without limitation, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11 (FIG. 6D) that are derived from *Arabidopsis thaliana*. In another embodiment, homologs of SCD2 protein (SEQ ID NO:2) are encoded by orthologs of nucleotide sequence SEQ ID NO:1, and are exemplified by those disclosed in Table 1 SEQ ID NO:12-107, that include *Arabidopsis thaliana* homologs.

Homologs of the SCD2 protein may be engineered for a variety of reasons, including but not limited to, altering the amount of aldehydes, amount of alkanes, ratio of aldehydes to alkanes, ratio of different alkanes to each other, and/or composition of wax.

In addition, homologs of the nucleotide sequences that encode SCD2 protein may be used to alter the efficiency of cloning, processing and/or expression of the gene product by, for example, insertion of new restriction sites and/or changing codon preference. Homologs of the nucleotide sequences that encode SCD2 protein may additionally be used to alter the activity and/or function of the encoded protein (e.g., altering binding kinetics of nucleic acid/protein complexes and/or of protein/protein complexes, altering reaction kinetics, altering subcellular localization, altering protein processing, and/or altering protein stability).

A "variant" or "homolog" of a polypeptide sequence of interest (e.g., SCD2 protein) or nucleotide sequence of interest (e.g., sequence encoding SCD2 protein) refers to a sequence that has at least 40% identity (including, for example, at least 98% identity, at least 95% identity, at least 90% identity, at least 85% identity, at least 80% identity, at least 75% identity, at least 70% identity, at least 65% identity, at least 60% identity, at least 55% identity, at least 50% identity, and/or at least 45% identity) with the an amino acid sequence of interest or nucleotide sequence of interest, respectively. Exemplary homologs of SCD2 protein (SEQ ID NO:2) are illustrated in Table 1.

TABLE 1

SCD2 Protein and Exemplary Homologs

| SEQ ID NO. | Reference No. | Source | Identity to SEQ ID NO: 2 |
|---|---|---|---|
| SEQ ID NO: 12 | emb\|BX841527.1\|CNS09YH1 | Arabidopsis thaliana | 269/270 (99%) |
| SEQ ID NO: 13 | emb\|BX826902.1\|CNS0A4L8 | Arabidopsis thaliana | 263/270 (97%) |
| SEQ ID NO: 14 | gb\|EF148499.1\| | Populus trichocarpa x Populus deltoides clone | 216/269 (80%) |
| SEQ ID NO: 15 | dbj\|AK104400.1\| | Oryza sativa Japonica | 207/271 (76%) |
| SEQ ID NO: 16 | dbj\|AK104138.1 | Oryza sativa Japonica | 207/271 (76%) |
| SEQ ID NO: 17 | ref\|NM_001056980.1 | Oryza sativa | 207/271 (76%) |
| SEQ ID NO: 18 | dbj\|AK251587.1 | Hordeum vulgare | 207/271 (76%) |
| SEQ ID NO: 19 | dbj\|AK061303.1 | Oryza sativa Japonica | 207/271 (76%) |
| SEQ ID NO: 20 | gb\|BT052459.1 | Medicago truncatula | 206/268 (76%) |
| SEQ ID NO: 21 | dbj\|AK073355.1 | Oryza sativa Japonica | 206/271 (76%) |
| SEQ ID NO: 22 | gb\|EU966829.1 | Zea mays | 206/271 (76%) |
| SEQ ID NO: 23 | gb\|BT036691.1 | Zea mays | 206/271 (76%) |
| SEQ ID NO: 24 | ref\|NM_001139253.1 | Zea mays | 206/271 (76%) |
| SEQ ID NO: 25 | gb\|EU970360.1 | Zea mays | 203/271 (74%) |
| SEQ ID NO: 26 | gb\|EF678591.1 | Picea sitchensis | 192/265 (72%) |
| SEQ ID NO: 27 | gb\|EF469908.1 | Helianthus annuus | 202/270 (74%) |
| SEQ ID NO: 28 | ref\|XM_001766787.1 | Physcomitrella patens | 188/263 (71%) |
| SEQ ID NO: 29 | ref\|XM_001769265.1 | Physcomitrella patens | 185/263 (70%) |
| SEQ ID NO: 30 | ref\|XM_001769512.1 | Physcomitrella patens | 182/263 (69%) |
| SEQ ID NO: 31 | ref\|XM_001772432.1 | Physcomitrella patens | 182/263 (69%) |
| SEQ ID NO: 32 | emb\|CT832000.1 | Oryza sativa | 168/219 (76%) |
| SEQ ID NO: 33 | ref\|XM_001782820.1\| | Physcomitrella patens | 167/265 (63%) |
| SEQ ID NO: 34 | gb\|DQ442381.1 | Striga asiatica clone | 159/268 (59%) |
| SEQ ID NO: 35 | ref\|XM_001760431.1 | Physcomitrella patens | 150/256 (58%) |
| SEQ ID NO: 36 | ref\|XM_001765180.1 | Physcomitrella patens | 156/260 (60%) |
| SEQ ID NO: 37 | dbj\|AK070827.1 | Oryza sativa Japonica | 146/254 (57%) |
| SEQ ID NO: 38 | ref\|NM_001055841.1 | Oryza sativa | 146/254 (57%) |
| SEQ ID NO: 39 | gb\|AY105548.1 | Zea mays | 146/202 (72%) |
| SEQ ID NO: 40 | ref\|XM_001767246.1 | Physcomitrella patens | 149/271 (54%) |
| SEQ ID NO: 41 | dbj\|AK248305.1 | Hordeum vulgare | 141/245 (57%) |
| SEQ ID NO: 42 | ref\|XM_001767598.1\| | Physcomitrella patens | 136/257 (52%) |
| SEQ ID NO: 43 | emb\|AL161591.2\|ATCHRIV87 | Arabidopsis thaliana | 150/166 (90%) |
| SEQ ID NO: 44 | emb\|AL035601.1\|ATF6G17 | Arabidopsis thaliana | 150/166 (99%) |
| SEQ ID NO: 45 | gb\|AC231507.1 | Oryza minuta | 76/123 (61%) |
| SEQ ID NO: 46 | dbj\|AP008209.1 | Oryza sativa | 73/142 (51%) |
| SEQ ID NO: 47 | gb\|AC146702.1 | Oryza sativa | 75/118 (63%) |
| SEQ ID NO: 48 | gb\|AC104429.2 | Oryza sativa Japonica | 75/118 (63%) |
| SEQ ID NO: 49 | emb\|BX828964.1\|CNS0A2KH | Arabidopsis thaliana | 148/166 (89%) |
| SEQ ID NO: 50 | gb\|EU968933.1 | Zea mays | 140/254 (55%) |
| SEQ ID NO: 51 | gb\|EU967732.1 | Zea mays | 140/254 (55%) |
| SEQ ID NO: 52 | gb\|AY088353.1 | Arabidopsis thaliana | 138/257 (53%) |
| SEQ ID NO: 53 | gb\|AY064145.1 | Arabidopsis thaliana | 137/257 (53%) |
| SEQ ID NO: 54 | ref\|NM_111270.2 | Arabidopsis thaliana | 137/257 (53%) |
| SEQ ID NO: 55 | gb\|AC011698.6\|ATAC011698 | Arabidopsis thaliana | 137/259 (53%) |
| SEQ ID NO: 56 | gb\|AY097402.1 | Arabidopsis thaliana | 137/259 (52%) |
| SEQ ID NO: 57 | dbj\|AK229798.1 | Arabidopsis thaliana | 135/256 (52%) |
| SEQ ID NO: 58 | ref\|XM_001780853.1 | Physcomitrella patens | 134/258 (51%) |
| SEQ ID NO: 59 | ref\|XM_001775159.1 | Physcomitrella patens | 134/258 (51%) |
| SEQ ID NO: 60 | dbj\|AK245636.1 | Glycine max | 134/251 (53%) |
| SEQ ID NO: 61 | emb\|AM260506.1 | Platanus acerifolia | 133/220 (60%) |
| SEQ ID NO: 62 | gb\|EF087543.1 | Picea sitchensis | 135/266 (50%) |
| SEQ ID NO: 63 | gb\|EF082227.1 | Picea sitchensis | 130/255 (50%) |
| SEQ ID NO: 64 | gb\|EF083105.1 | Picea sitchensis | 127/253 (50%) |
| SEQ ID NO: 65 | gb\|EF083085.1 | Picea sitchensis | 131/250 (52%) |
| SEQ ID NO: 66 | dbj\|AK245973.1 | Glycine max | 134/280 (47%) |
| SEQ ID NO: 67 | gb\|AE010300.1 | Leptospira interrogans | 132/253 (52%) |
| SEQ ID NO: 68 | gb\|AE016823.1 | Leptospira interrogans | 132/253 (52%) |
| SEQ ID NO: 69 | ref\|XM_001776083.1 | Physcomitrella patens | 129/261 (49%) |
| SEQ ID NO: 70 | gb\|EF677295.1 | Picea sitchensis | 128/246 (52%) |
| SEQ ID NO: 71 | gb\|EF147255.1 | Populus trichocarpa | 125/221 (56%) |
| SEQ ID NO: 72 | gb\|EU956365.1 | Zea mays | 123/227 (54%) |
| SEQ ID NO: 73 | gb\|EF084241.1 | Picea sitchensis | 123/253 (48%) |
| SEQ ID NO: 74 | gb\|AC215398.2 | Solanum lycopersicum | 121/148 (81%) |
| SEQ ID NO: 75 | emb\|CU457813.5 | Solanum lycopersicum | 121/148 (81%) |
| SEQ ID NO: 76 | emb\|AM483191.2 | Vitis vinifera | 123/146 (84%) |
| SEQ ID NO: 77 | emb\|AM449154.1 | Vitis vinifera | 123/146 (84%) |

TABLE 1-continued

SCD2 Protein and Exemplary Homologs

| SEQ ID NO. | Reference No. | Source | Identity to SEQ ID NO: 2 |
|---|---|---|---|
| SEQ ID NO: 78 | gb\|AC106887.3 | Oryza sativa | 119/150 (79%) |
| SEQ ID NO: 79 | gb\|AC144765.19 | Medicago truncatula | 116/147 (78%) |
| SEQ ID NO: 80 | gb\|AC146561.22 | Medicago truncatula | 114/146 (78%) |
| SEQ ID NO: 81 | gb\|EF461558.1 | Helianthus annuus | 114/141 (80%) |
| SEQ ID NO: 82 | emb\|BX826027.1\|CNS0A587 | Arabidopsis thaliana | 94/179 (52%) |
| SEQ ID NO: 83 | gb\|EF461565.1 | Helianthus annuus | 113/141 (80%) |
| SEQ ID NO: 84 | gb\|EF461563.1 | Helianthus annuus | 112/141 (79%) |
| SEQ ID NO: 85 | gb\|EF461555.1 | Helianthus annuus | 118/165 (71%) |
| SEQ ID NO: 86 | gb\|EF461560.1 | Helianthus annuus | 112/139 (80%) |
| SEQ ID NO: 87 | gb\|EF461562.1 | Helianthus annuus | 112/139 (80%) |
| SEQ ID NO: 88 | gb\|EF461559.1 | Helianthus annuus | 112/139 (80%) |
| SEQ ID NO: 89 | gb\|EF461561.1 | Helianthus annuus | 111/139 (79%) |
| SEQ ID NO: 90 | gb\|EF461564.1 | Helianthus annuus | 111/139 (79%) |
| SEQ ID NO: 91 | gb\|BT015839.1 | Arabidopsis thaliana | 110/258 (42%) |
| SEQ ID NO: 92 | dbj\|AK229212.1 | Arabidopsis thaliana | 110/258 (42%) |
| SEQ ID NO: 93 | gb\|BT015329.1 | Arabidopsis thaliana | 110/258 (42%) |
| SEQ ID NO: 94 | ref\|NM_113349.3 | Arabidopsis thaliana | 110/258 (42%) |
| SEQ ID NO: 95 | gb\|EF461557.1 | Helianthus annuus | 109/135 (80%) |
| SEQ ID NO: 96 | gb\|EF461566.1 | Helianthus annuus | 101/126 (80%) |
| SEQ ID NO: 97 | gb\|EF461567.1 | Helianthus annuus | 101/126 (80%) |
| SEQ ID NO: 98 | gb\|EF461571.1 | Helianthus annuus | 101/126 (80%) |
| SEQ ID NO: 99 | gb\|EF461568.1 | Helianthus annuus | 101/125 (80%) |
| SEQ ID NO: 100 | gb\|EF461575.1 | Helianthus annuus | 101/125 (80%) |
| SEQ ID NO: 101 | gb\|EF461576.1 | Helianthus annuus | 101/126 (80%) |
| SEQ ID NO: 102 | gb\|EF461574.1 | Helianthus annuus | 101/126 (80%) |
| SEQ ID NO: 103 | gb\|EF461573.1 | Helianthus annuus | 101/126 (80%) |
| SEQ ID NO: 104 | gb\|EF461570.1 | Helianthus annuus | 101/126 (80%) |
| SEQ ID NO: 105 | gb\|EF461569.1 | Helianthus annuus | 101/125 (80%) |
| SEQ ID NO: 106 | gb\|CP000817.1 | Lysinibacillus sphaericus | 101/260 (38%) |
| SEQ ID NO: 107 | gb\|EF147690.1 | Populus trichocarpa | 105/256 (41%) |

Homologous nucleotide sequences to the invention's SEQ ID NO:1 include those from *Arabidopsis thaliana*, as well as orthologs and paralogs of the SCD2 gene. The term "ortholog" refers to a gene in different species that evolved from a common ancestral gene by speciation. In some embodiments, orthologs retain the same function. The term "paralog" refers to genes related by duplication within a genome. In some embodiments, paralogs evolve new functions. In further embodiments, a new function of a paralog is related to the original function.

Variant nucleotide sequences may include codons that are preferred by a particular prokaryotic or eukaryotic host (Murray et al., Nucl. Acids Res., 17 (1989)) in order to increase the rate of SCD2 expression and/or to produce recombinant RNA transcripts having desirable properties, such as a longer half-life, than transcripts produced from naturally occurring sequence.

Homologs of a polypeptide sequence of interest and/or of a nucleotide sequence of interest may contain a mutation. The terms "mutation" and "modification" refer to a deletion, insertion, or substitution. A "deletion" is defined as a change in a nucleic acid sequence or amino acid sequence in which one or more nucleotides or amino acids, respectively, is absent. An "insertion" or "addition" is that change in a nucleic acid sequence or amino acid sequence that has resulted in the addition of one or more nucleotides or amino acids, respectively. An insertion also refers to the addition of any synthetic chemical group, such as those for increasing solubility, dimerization, binding to receptors, binding to substrates, resistance to proteolysis, and/or biological activity of the amino acid sequence. A "substitution" in a nucleic acid sequence or an amino acid sequence results from the replacement of one or more nucleotides or amino acids, respectively, by a molecule that is a different molecule from the replaced one or more nucleotides or amino acids. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. Substitution of an amino acid may be conservative or non-conservative.

A "conservative substitution" of an amino acid refers to the replacement of that amino acid with another amino acid that has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains that may be conservatively substituted one for the other include phenylalanine, tyrosine, and tryptophan. Cysteine and methionine are sulphur-containing amino acids that may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid.

"Non-conservative substitution" is a substitution other than a conservative substitution. Guidance in determining which and how many amino acid residues may be substituted, inserted or deleted without abolishing biological and/or immunological activity may be found using computer programs well known in the art, for example, DNAStar™ software.

Figure 8A:
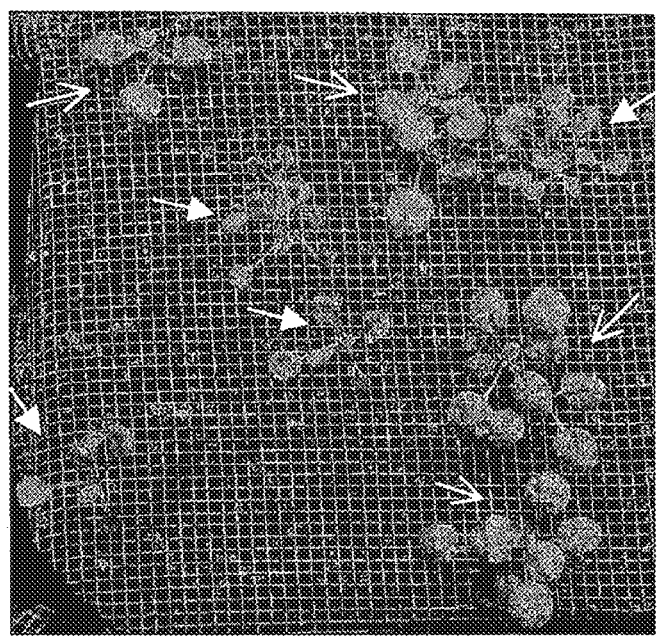
FIG. 8: scd2 phenotypes are complemented by a 2.8 kb genomic fragment containing SCD2 under the endogenous promoter. A. Segregating population of T2 plants: open arrows are complemented plants showing wild type Col7 appearance, closed arrows are plants with scd2 morphologies, B. Amount of epicuticular alkanes and aldehydes in T2 plants with or without scd2 phenotypes, "mu" are plants with scd2 appearance while "wt" are plants with wild type appearances.
Figure 8B:
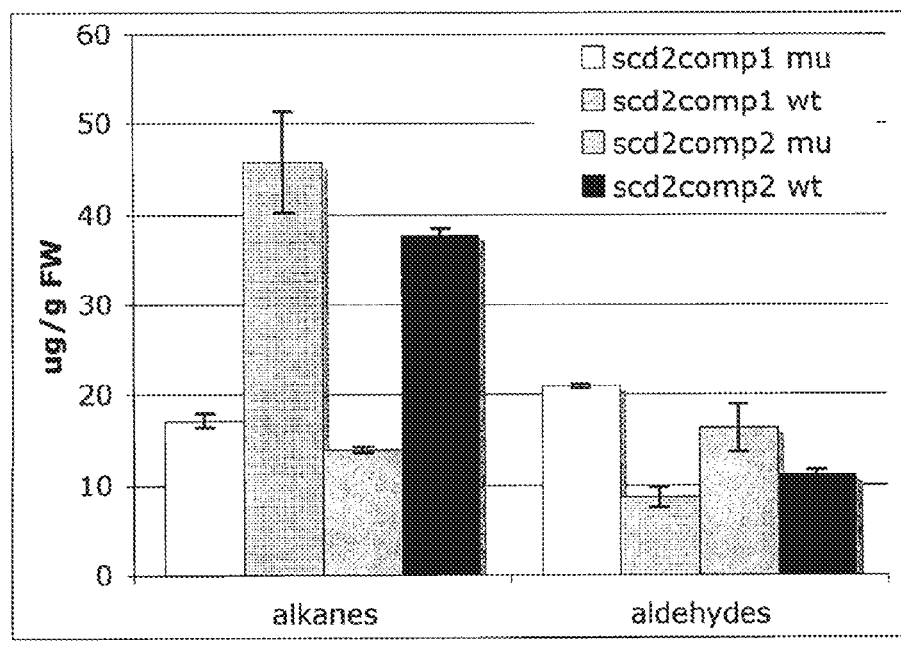
Figure 9:
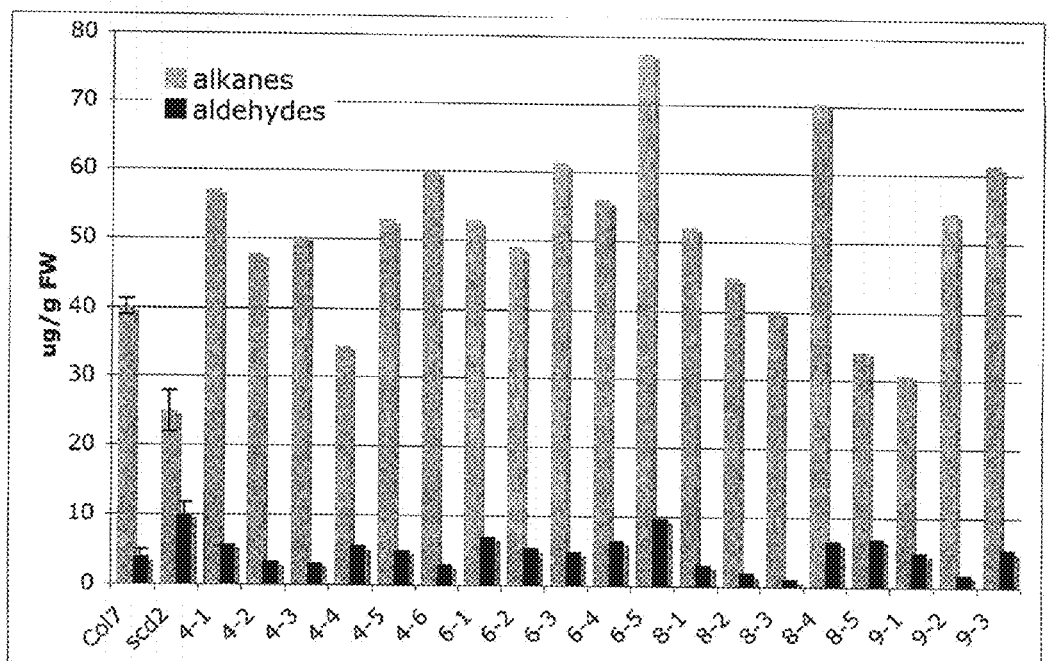
FIG. 9: analysis of alkanes and aldehydes from 19 T1 plants transformed with a SCD2 cDNA under CaMV:35S promoter.

Homologs can be tested in functional assays of conversion of aldehyde to alkane in vitro, as well as in vivo by determining changes in the levels of alkanes and/or aldehydes in transgenic plant tissue that expresses the homolog (FIGS. 7-9). Preferred homologs of the nucleotide sequence SEQ ID NO:1 have at least 90%, preferably at least 95%, and still more preferably at least 98% homology to SEQ ID NO:1.

Homologs of the nucleotide sequences that encode SCD2 protein can be generated by any suitable method well known in the art, including but not limited to EMS induced mutagenesis, site-directed mutagenesis, randomized "point" mutagenesis, and domain-swap mutagenesis in which portions of the scd2 cDNA are "swapped" with the analogous portion of other scd2-encoding cDNAs (Back and Chappell, PNAS 93: 6841-6845, (1996)). For example, mutants of scd2 are provided by EMS induced mutations (Pogson, et al. Plant Cell 8, 1627-1639 (1996)).

Homologs of the nucleotide sequences that encode SCD2 protein may also be produced by directed evolution, or other techniques for producing combinatorial libraries of homologs, by using nucleotide sequences that encode SCD2 protein as starting material. These techniques can be utilized to develop encoded SCD2 protein.

C. Expression Vectors

The invention provides expression vectors comprising a nucleic acid sequence encoding a polypeptide that is at least 40% identical (and more preferably, at least 80% identity, or at least 85% identity, or at least 90% identity, or at least 95% identity, or at least 99% identity) to SCD2 protein, "Susceptible to Coronatine-Deficient Pst DC3118-2," that is listed as SEQ ID NO:2, and that has is capable of converting an aldehyde to an alkane.

The invention's vectors are useful for altering the amount and/or composition of wax produced by cells that have been transformed with the vectors.

A protein's activity in "converting an aldehyde to an alkane" may be determined using assays known in the art, such as by in vitro enzyme assays and/or by determining the amounts of aldehydes and alkanes (FIGS. 3, 7C, 8B, 9).

The term "expression vector" as used herein refers to a recombinant DNA molecule containing a desired coding sequence and appropriate nucleic acid sequences necessary for the expression (i.e., transcription and/or translation) of the operably linked coding sequence in a particular host organism. Expression vectors are exemplified by, but not limited to, plasmid (including "bacterial artificial chromosomes," phagemid, shuttle vector, cosmid, virus, chromosome, mitochondrial DNA, plastid DNA, derivatives of plant tumor sequences, T-DNA sequences, and nucleic acid fragment. Expression vectors include "eukaryotic vectors," i.e., vectors that are capable of replicating in a eukaryotic cell (e.g., plant cell, yeast cell, mammalian cells, etc.) and "prokaryotic vectors," i.e., vectors that are capable of replicating in a prokaryotic cell (e.g., E. coli). Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals.

Large numbers of suitable vectors that function is prokaryotic, eukaryotic cells, and insect cells are known to those of skill in the art, and are commercially available. Prokaryotic bacterial vectors are exemplified by pBR322, pUC, pYeDP60, pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia). Eukaryotic vectors are exemplified by pMLBART, pSV2CAT, pOG44, PXT1, pSG (Stratagene) pSVK3, pBPV, pMSG, pSVL (Pharmacia), pGEMTeasy plasmid, pCambia1302 (for plant cell transformation using the exemplary Agrobacteria tumefaciens strain GV3101), and transcription-translation (TNT®) coupled wheat germ extract systems (Promega). Baculovirus vectors for expression in insect cells are also commercially available (e.g., Invitrogen). Any other vector may be used as long as it is replicable in the host.

Expression vectors contemplated within the scope of the invention include plant vectors. Plant expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences for expression in plants. In other embodiments, DNA sequences derived from the SV40 splice, and polyadenylation sites may be used to provide the required non-transcribed genetic elements.

In certain embodiments of the present invention, the nucleic acid sequence that is sought to be expressed by the expression vector is operatively linked to an appropriate expression control sequence(s) (promoter) to direct mRNA synthesis.

Numerous transformation vectors are available for plant transformation (see U.S. Pat. Nos. 7,365,182 and 7,446,188). The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18: 1062; Spencer et al. (1990) Theor. Appl. Genet. 79: 625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an Agrobacterium mediated transfection process (See for example, U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA 1-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Generally, the inserted plant polynucleotide of the present invention can be expressed from these vectors as a fusion protein (for example, coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785.

In some embodiments of the present invention, the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters useful for expression in plant cells include, but are not limited to, constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (for example, phaseolin, napin, oleosin, and a promoter for soybean beta conglycin (Beachy et al. (1985) EMBO J. 4: 3047-3053)).

Additional exemplary promoters include PEPCK promoter, MT promoter, SRα promoter, P450 family promoters, GALT promoter, K11 promoter, heat shock protein promoter, phage promoters (e.g., from phage lambda $P_L$ and $P_R$, T3 phage, T5 phage, T7 phage, SP6 phage), LTR or SV40 promoter, *E. coli* lac or trp promoter, cytomegalovirus (CMV) promoter, herpes simplex virus (HSV) thymidine kinase promoter, and mouse metallothionein-I promoters and other promoters known to control expression of gene in prokaryotic or eukaryotic cells or their viruses. "Prokaryotic promoters" include those carrying optimal −35 and −10 (Pribnow box) sequences for transcription by a prokaryotic (e.g. *E. coli*) RNA polymerase. Prokaryotic genes from which suitable promoters sequences may be obtained include the *E. coli* lac, ara and trp genes.

The term "promoter" also encompasses a single promoter sequence as well as to a plurality (i.e., one or more) of promoter sequences that are operably linked to each other and to at least one DNA sequence of interest. For example, one of skill in the art knows that it may be desirable to use a double promoter sequence (i.e., a DNA sequence containing two promoter sequences) or a triple promoter sequence (i.e., a DNA sequence containing three promoter sequences) to control expression of a DNA sequence of interest. Double promoters are exemplified, but not limited to, T7-T3, T3-T7, T7-SP6, SP6-T7, T3-SP6, vaRNA I-tRNA, vaRNA I-CMV, vaRNA I-RSV, vaRNA I-SV40, vaRNA I-PEPCK, vaRNA I-MT, vaRNA I-SRα, vaRNA I-P450 family, vaRNA I-GAL7, $T_7$-vaRNA I, $T_3$-vaRNA, vaRNA I-SP6, vaRNA I-K11, and vaRNA I-heat shock protein double promoters. Triple promoters are exemplified, but not limited to, the CMV-T7-vaRNA I triple promoter.

In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

D. Methods for Altering Alkane Production

The invention's vectors may be used in methods for altering alkane production in a cell, comprising a) providing i) any of the expression vectors described herein, and ii) a host cell, b) introducing the expression vector into the host to produce a transgenic cell that expresses the polypeptide, and culturing the transgenic cell under conditions such that the polypeptide alters the level of an alkane produced by the transgenic cell compared to the host cell. These methods are further described below.

a. Cell Transformation

The vectors of the invention may be introduced into cells using techniques well known in the art to produce a transformed cell. Methods of introducing nucleic acid sequences into cells are well known in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus.

The terms "transform" and "transfect" as used herein, interchangeably refer to any mechanism by which a vector may be incorporated into a host cell. A successful transfection results in the capability of the host cell to express any operative genes carried by the vector.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA), which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell that has transiently incorporated one or more nucleotide sequences of interest.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the cell with nucleic acid sequences that are capable of binding to one or more of the nucleotide sequences of interest. Alternatively, stable transformation of a cell may also be detected by the polymerase chain reaction of genomic DNA of the cell to amplify the nucleotide sequence of interest.

b. Reducing Expression of SCD2 and its Homologs

In some embodiments, the present invention provides methods for decreasing expression of the invention's SCD2 protein sequences and their homologs in plants. This may be accomplished by, for example, using antisense, short interfering RNA (siRNA), RNA interference (RNAi), and post-transcriptional gene silencing (PTGS) (see U.S. Pat. Nos. 7,365,182 and 7,446,188).

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression.

"Ribozyme" refers to a catalytic RNA and includes sequence-specific endoribonucleases. Methods for designing and using ribozymes are know (e.g., Wagner et al. U.S. Pat. No. 6,355,415). "Antisense inhibition" refers to the production of antisense RNA transcripts capable of preventing the expression of the target protein The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, which link the two strands of the double strand, as well as stem and other folded structures, which may be present within the linking sequence. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector which is not integrated into the genome. The expression of the gene is either completely or partially inhibited. RNAi may also be considered to inhibit the function of a target RNA; the function of the target RNA may be complete or partial.

The term "posttranscriptional gene silencing" or "PTGS" refers to silencing of gene expression in plants after transcription, and appears to involve the specific degradation of mRNAs synthesized from gene repeats.

c. Transformation Techniques

For example, with respect to "plant expression vectors," i.e., vectors that are capable of replicating in a plant cell, transformation of a plant cell may be accomplished by a variety of means known in the art including particle mediated gene transfer (see, e.g., U.S. Pat. No. 5,584,807); infection with an *Agrobacterium* strain containing the foreign DNA for random integration (U.S. Pat. No. 4,940,838) or targeted integration (U.S. Pat. No. 5,501,967) of the foreign DNA into the plant cell genome; electroinjection; fusion with liposomes, lysosomes, cells, minicells or other fusible lipid-surfaced bodies; chemicals that increase free DNA uptake; transformation using virus, and the like.

Further, the invention's sequences may be introduced using direct transformation in the plastid genome (U.S. Pat. Nos. 5,451,513; 5,545,817; 5,545,818; PCT application WO 95/16783), microinjected directly into plant cells by use of micropipettes (Crossway (1985) Mol. Gen. Genet, 202:179), using polyethylene glycol (Krens et al. (1982) Nature, 296: 72; Crossway et al. (1986) BioTechniques, 4:320), fusion of protoplasts with minicells, with cells, with lysosomes an/or or other fusible lipid-surfaced bodies (Fraley et al. (1982) Proc. Natl. Acad. Sci., USA, 79:1859), protoplast transformation (EP 0 292 435), direct gene transfer (Paszkowskii et al. (1984) EMBO J., 3:2717; Hayashimoto et al. (1990) Plant Physiol. 93:857), electroporation. (Fromm, et al. (1985) Pro. Natl Acad. Sci. USA 82:5824; Riggs et al. (1986) Proc. Natl. Acad. Sci. USA 83:5602), ballistic particle acceleration (U.S. Pat. No. 4,945,050; McCabe et al. (1988) Biotechnology 6:923), Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat), as well as using *Agrobacterium*-mediated transformation (Ishida et al. (1996) Nature Biotechnology 14:745). See also U.S. Pat. Nos. 7,365,182 and 7,446,188.

d. Antibodies

Expression levels of the encoded SCD2 protein and/or its homologs may be determined using antibodies that specifically bind to the expressed SCD2 protein and/or its homologs. Such antibodies may be employed in "sandwich" immunoassays such as ELISA (enzyme-linked immunosorbant assay), and ELISpot (enzyme-linked immunosorbent spot assay), immunoradiometric assays, gel diffusion precipitin reactions, immunodiffusion assays, in situ immunoassays (using colloidal gold, enzyme or radioisotope labels, for example), Western Blots, etc.), complement fixation assays, immunofluorescence assays, protein A assays, and immunoelectrophoresis assays, etc.

The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule. For example, if a second molecule is specific for structure "A" that is on or within a first molecule, the presence of a third nucleic acid sequence containing structure A will reduce the amount of the second molecule which is bound to the first molecule.

The term "antibody" encompasses any immunoglobulin (e.g., IgG, IgM, IgA, IgE, IgD, etc.) obtained from any source (e.g., humans, rodents, non-human primates, caprines, bovines, equines, ovines, etc.). Included within this definition are polyclonal antibody, monoclonal antibody, and chimeric antibody.

"Polyclonal antibody" refers to an immunoglobulin produced from more than a single clone of plasma cells; in contrast "monoclonal antibody" refers to an immunoglobulin produced from a single clone of plasma cells. Monoclonal and polyclonal antibodies may or may not be purified. For example, polyclonal antibodies contained in crude antiserum may be used in this unpurified state. Those skilled in the art know how to make polyclonal and monoclonal antibodies which are specific to a desirable polypeptide. For the production of monoclonal and polyclonal antibodies, various host animals can be immunized by injection with the peptide corresponding to any molecule of interest in the present invention, including but not limited to rabbits, mice, rats, sheep, goats, etc. For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 (1975)), techniques using germ-free animals and utilizing technology such as that described in PCT/US90/02545, as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

A "chimeric antibody" contains portions of two different antibodies, typically of two different species. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al.

E. Transgenic Cells

The invention provides transgenic cells comprising a heterologous nucleic acid sequence encoding a polypeptide that is at least 40% identical (and more preferably, at least 80% identity, or at least 85% identity, or at least 90% identity, or at least 95% identity, or at least 99% identity) to SCD2 protein listed as SEQ ID NO:2, and that has activity that comprises converting an aldehyde to an alkane (e.g., in plant cells) and/or lipid (e.g., in *E. coli* and yeast cells).

The invention's transgenic cells are useful for expressing the invention's sequences, thereby producing altered amounts and/or compositions of wax compared to in the absence of the invention's sequences. In another embodiment, the invention's transgenic cells may be used to express SCD2 protein and/or its homologs, for the purpose of purifying these proteins and subsequently using them in an vitro system to produce waxes and/or lipids.

The term "cell" refers to a single cell that may be comprised in a population of cells in vitro and/or in vivo.

Any type of cell into which the invention's vectors may be introduced is expressly included within the scope of this invention, including "eukaryotic cell" and "prokaryotic cell.

"Prokaryotic cell" includes bacteria, virus (including bacteriophage), blue-green algae, archaebacteria, actinomycetes and mycoplasma etc.).

"Eukaryotic cell" includes cells from protists (including nematodes), yeast, animals, algae, diatom, fungi, and plants.

Eukaryotic plant cells are exemplified by protocorm-like body cells, callus cells, leaf cells, stem cells, etc.).

Eukaryotic animal cells are exemplified by human cells such as U937 cells (macrophage), ATCC# crl 1593.2; A-375 cells (melanoma/melanocyte), ATCC# crl-1619; KLE cells (uterine endometrium), ATCC# crl-1622; T98G cells (glioblastoma), ATCC# crl-1690; CCF-STTG1 cells (astrocytoma), ATCC# crl-1718; HUV-EC-C cells (vascular endothelium), ATCC# CRL-1730; UM-UC-3 cells (bladder), ATCC# crl-1749; CCD841-CoN cells (colon, ATCC# er1-1790; SNU-423 cells (hepatocellular carcinoma), ATCC# crl-2238; WI38 cells (lung, normal), ATCC# crl-75; Raji cells (lymphoblastoid), ATCC# ccl-86; BeWo cells (placenta, choriocarcinoma), ATCC# ccl-98; HT1080 cells (fibrosarcoma), ATCC# ccl-121; MIA PaCa2 cells (pancreas), ATCC# crl-1420; CCD-25SK cells (skin fibroblast), ATCC# crl-1474; ZR75-30 cells (mammary gland), ATCC# crl-1504; HOS cells (bone osteosarcoma), ATCC# er1-1543; 293-SF cells (kidney), ATCC# er1-1573; LL47 (MaDo) cells (normal lymphoblast), ATCC# ccl-135; and HeLa cells (cervical carcinoma), ATCC# ccl-2.

Eukaryotic animal cells also include non-human cells and are exemplified, but not limited to, yeast cells (AH109), LM cells (mouse fibroblast), ATCC# ccl-1.2; NCTC 3526 cells (rhesus monkey kidney), ATCC# ccl-7.2; BHK-21 cells (golden hamster kidney), ATCC# ccl-10; MDBK cells (bovine kidney), ATCC# ccl-22; PK 15 cells (pig kidney), ATCC# ccl-33; MDCK cells (dog kidney), ATCC# ccl-34; PtK1 cells (kangaroo rat kidney), ATCC# ccl-35; Rk 13 cells (rabbit kidney), ATCC# ccl-37; Dede cells (Chinese hamster lung fibroblast), ATCC# ccl-39; Bu (IMR31) cells (bison lung fibroblast), ATCC# ccl-40; FHM cells (minnow epithelial), ATCC# ccl-42; LC-540 cells (rat Leydig cell tumor), ATCC# ccl-43; TH-1 cells (turtle heart epithelial), ATCC# ccl-50; E. Derm (NBL-6) cells (horse fibroblast), ATCC# ccl-57; MvLn cells (mink epithelial), ATCC# ccl-64; Ch1 Es cells (goat fibroblast), ATCC# ccl-73; P1 I Nt cells (raccoon fibroblast), ATCC# ccl-74; Sp I k cells (dolphin epithelial), ATCC# ccl-78; CRFK cells (cat epithelial), ATCC# ccl-94; Gekko Lung 1 cells (lizard-gekko epithelial), ATCC# ccl-111; Aedes Aegypti cells (mosquito epithelial), ATCC# ccl-125; ICR 134 cells (frog epithelial), ATCC# ccl-128; Duck embryo cells (duck fibroblast), ATCC# ccl-141; DBS Fcl-1 cells (monkey lung fibroblast), ATCC# ccl-161.

F. Transgenic Plants

The invention further provides transgenic plants comprising a heterologous nucleic acid sequence encoding a polypeptide that is at least 40% identical (and more preferably, at least 80% identity, or at least 85% identity, or at least 90% identity, or at least 95% identity, or at least 99% identity) to SCD2 protein listed as SEQ ID NO:2, and that has activity that comprises converting an aldehyde to an alkane.

The transgenic plants of the invention are useful since the altering amounts and/or composition of wax that is expressed by these plants may be used. The invention's transgenic plants are also useful as a source of transgenic seeds that may be used to propagate additional transgenic plants.

a. Alkanes as Biofuel

In one embodiment, transgenic plant comprises an altered level of an alkane compared to a plant that lacks the heterologous nucleic acid sequence. For example, data herein show that twelve out of the nineteen plants tested over expressing the SCD2 cDNA showed at least 25% higher content of alkanes compared to the wild types plants (FIG. 9). Interestingly also, plant 4-3, 4-6, 8-1 and 9-2 also had lower contents of aldehydes in addition to the increased yield of alkanes, and therefore are likely have elevated abilities to convert aldehydes to alkanes.

In another embodiment, the transgenic plant comprises an altered level of an aldehyde compared to a plant that lacks the heterologous nucleic acid sequence (FIG. 9). In one embodiment, the present invention contemplates a method wherein the alkane in the transgeneic plant is extracted and used for biofuel.

b. Drought Tolerant Phenotype

In particularly preferred embodiments, the transgenic plants that express the invention's sequences exhibit increased drought tolerance compared to a control plant lacking those sequences. For example, data herein demonstrate that mutant scd2 plants were more drought sensitive than the wild type (Example 4, FIG. 5). This observation was surprising to the inventors since the overall wax load did not change much. While not intending to limit the invention to any particular mechanism, this observation suggests that the different components of the epicuticular waxes might contribute differently for the control of non-stomatal water loss through cuticles. This is likely due to the different chemical characteristics of these molecules. This observation points to a new direction for bioengineering for more drought-tolerant plants by engineering individual components of the waxes instead of pursuing only the increase of the total waxes. It is worth noting that alkanes, together with alcohols, ketones and esters, were found to have more ability to repel water interactions compared with other wax components (Holloway (1969) J. Sci. Fd. Agri. 20:124-128; Peter et al. (1987) Pestic. Sci. 19:265-281).

Furthermore, data herein show that complementation of mutant scd2 plants with wild type SCD2 (SEQ ID NO:2) under control of its endogenous promoter restored both wild type plant morphology (FIG. 8A) and wild type alkane and aldehyde phenotype (FIG. 8B) (Example 7).

Additionally, complementation of the scd2 plants with the genomic copy of SCD2 driven by its endogenous promoter is direct evidence that SCD2 is very likely responsible for the direct conversion of aldehydes to alkanes (FIG. 8). This supports the notion that a decarbonylation step is involved in the VLCFA-to-alkane conversion.

In addition, 15 out of 19 wild type plants that had been transformed with wild type SCD2 (SEQ ID NO:2) under control of CaMV:35S promoter exhibited higher levels of an alkane compared to the untransfected wild type plants (FIG. 9, Example 8), thus demonstrating the utility of the invention's sequences in altering the levels of alkanes, levels of aldehydes, and/or ratio of alkane to aldehyde.

c. Temperature Tolerant Phenotype

In yet other particularly preferred embodiments, the transgenic plants that express the invention's sequences exhibit increased temperature tolerance (including cold tolerance and heat tolerance) compared to a control plant lacking those sequence. "Temperature tolerance" refers to the level to which a plant is adapted to temperature alterations (i.e., increased or decreased temperatures), and may be measured by determining the level of wilting, change in leaf color, change in leaf curling, change in plant survival, ion leakage, etc., under different temperatures.

In this regard, it is well established that plant tolerance for drought is always associated with their tolerance for cold (including freezing stress). Thus, data herein that demonstrate drought tolerance of the invention's transgenic plants (Example 4, FIG. 5) may also be extrapolated to conference of temperature tolerance by the invention's sequences.

d. Resistance to Pathogens Phenotype

In a further particularly preferred embodiments, the transgenic plants that express the invention's sequences exhibit increased resistance to a pathogen (such as virus, bacteria, fungus, insect, and nematode) compared to a control plant lacking those sequences.

In this regards, it is well established that the epicuticular waxes contribute to, and are essential for, the plant defense against pathogenic fungi and insects. For example, with respect to pathogenic fungi, recent studies showed that the altered cuticle structures brought about by the loss-of-function of genes involved in the cuticle biosynthesis actually elevated the resistance of *Arabidopsis* plants to *Botrytis* and *Sclerotinia* (Bessire et al. (2007) Embo J 26:2158-2168; Chassot et al. (2007) Plant J 49:972-980).

With respect to pathogenic insects, insect activity and interactions with plants are known to be affected by the cuticle structures. Some cer mutants in *Brassica* and *Pisum* with reduced waxes made the plants more vulnerable to beetle damages (Stoner (1990) Environ. Entomol. 19:730-739; White et al. (2000) Environ. Entomol. 29:773-780). The chemical composition of plant wax can also influence the feeding and oviposition of insect herbivores (Eigenbrode et al. (1995) Ann. Rev. Entomol. 40:171-194; Morris et al. (2000) J. Chem. Ecol. 26:859-867; Cervantes et al. (2002) J Chem Ecol 28:193-210). A very good example in *Arabidopsis* comes from the studies on the cer3 mutant. The cabbage aphid *Brevicoryne brassicae* L. was found to probe less and walk more on the stems of cer3 mutant plants (Rashotte (1999) "Epicuticular wax in *Arabidopsis thaliana*: a study of the genetics, chemistry, structure, and interactions with insects," in *Plant Science*, Tucson: University of Arizona). Similar behavior was recorded when the waxes from cer3 plants were extracted and applied onto wild type plants (Rashotte (1999) "Epicuticular wax in *Arabidopsis thaliana*: a study of the genetics, chemistry, structure, and interactions with insects," in *Plant Science*, Tucson: University of Arizona).

e. Exemplary Plants Useful in the Invention

Plants that may be useful in the invention's methods include, without limitation, any plant that is capable of being transformed by a nucleic acid sequence using any method. In one embodiment, the plant has an agronomic, horticultural, ornamental, economic, and/or commercial value. Exemplary plants include acacia, alfalfa, aneth, apple, apricot, artichoke, arugula, asparagus, avocado, banana, barley and other cereal grains, beans, beet, blackberry, blueberry, loganberry, currants, gooseberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower and other oilseed crops, sweet potato, sweetgum, tangerine, tea, tobacco, tomato, triticale, turf, turnip, a vine, watermelon, wheat, yams, zucchini, grasses and other forage crops.

Plant cells that may be manipulated using the invention's compositions and methods include cells from a totipotent body, an embryo, protoplast, callus, protocorm-like body, etc.

Transformation of a plant cell with the invention's nucleotide sequences and/or vectors may be accomplished by a variety of means known in the art including particle mediated gene transfer (see, e.g., U.S. Pat. No. 5,584,807), infection with an *Agrobacterium* strain containing the foreign DNA for random integration (U.S. Pat. No. 4,940,838) or targeted integration (U.S. Pat. No. 5,501,967) of the foreign DNA into the plant cell genome, electroinjection (Nan et al. (1995) In "Biotechnology in Agriculture and Forestry," Ed. Y. P. S. Bajaj, Springer-Verlag Berlin Heidelberg, Vol 34:145-155, Griesbach (1992) HortScience 27:620), fusion with liposomes, lysosomes, cells, minicells or other fusible lipid-surfaced bodies (Fraley et al. (1982) Proc. Natl. Acad. Sci. USA 79:1859-1863, polyethylene glycol (Krens et al. (1982) nature 296:72-74), chemicals that increase free DNA uptake, transformation using virus, and the like.

G. Regeneration of Transgenic Plants

Transformed cells may be used to regenerate plant tissue and/or a whole plant. The term "regeneration" as used herein, means growing a plant tissue and/or whole plant from a plant cell, a group of plant cells, a plant part or a plant piece (e.g., from a protoplast, callus, protocorm-like body, or tissue part). Methods for regenerating plant tissue and/or a whole plant from a totipotent body, an embryo, protoplast, callus, protocorm-like body, etc. are known in the art.

For example, plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots (for example, the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos geminate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

H. Methods for Identifying the Function of a Gene in Synthesis of Plant Surface Wax Since their identification, the studies on the more than 20 cer mutants have become one of the most important approaches to dissect the wax biosynthesis pathway and to explore the structure of the cuticles. The cer mutants were identified through a convenient genetic approach by observing *Arabidopsis* stems for the glaucousness appearance. However, a different screening strategy seems necessary considering most cer mutants have more dramatic wax accumulation phenotypes since subtle compositional change that do not affect the overall amount of waxes might not be readily seen by the naked eye. In addition, most of our knowledge about wax synthesis is focusing on the stems. Data herein shows successful development of a novel genetic approach to identify leaf wax mutants that bear phenotypes with more subtle compositional alterations.

Thus, in one embodiment, the invention provides methods for identifying a function of a nucleotide sequence in synthesis of plant surface wax, comprising a) providing i) a first plant tissue (e.g., a wild type plant) comprising the nucleotide sequence, ii) a second plant tissue (e.g., a transgenic plant) comprising one or more mutation in the nucleotide sequence, and iii) a surfactant, b) contacting the first plant tissue with the surfactant to produce a contacted first tissue, c) contacting the second plant tissue with the surfactant to produce a contacted second tissue, and d) detecting an alteration (i.e., increase an/or decrease) in one or more disease-like symptoms (e.g., those shown in FIG. 2C) in the contacted first tissue compared to the contacted second tissue, thereby identifying a function of the nucleotide sequence in synthesis of plant surface wax. In a further embodiment, step b) further comprises contacting the first plant tissue with a microorganism, and step c) further comprises contacting the second plant tissue with the microorganism.

The invention's methods are useful for screening whether one or more genes, and/or their expression products, that are present in a mutant plant and that contain one or more mutations compared to the corresponding genes in another plant (e.g., a wild type plant) are involved in the biosynthesis of surface wax. Indeed, this method was used herein to identity that SCD2 is essential for the aldehyde-to-alkane conversion of epicuticular wax (Example 2). These genes may then be expressed in cells (e.g., prokaryotic and eukaryotic cells) to produce wax that may be used as biofuel. Where this expression is in a plant and/or plant tissue, such expression may also be used to alter drought tolerance, temperature tolerance and/or pathogen resistance.

Figure 1B:
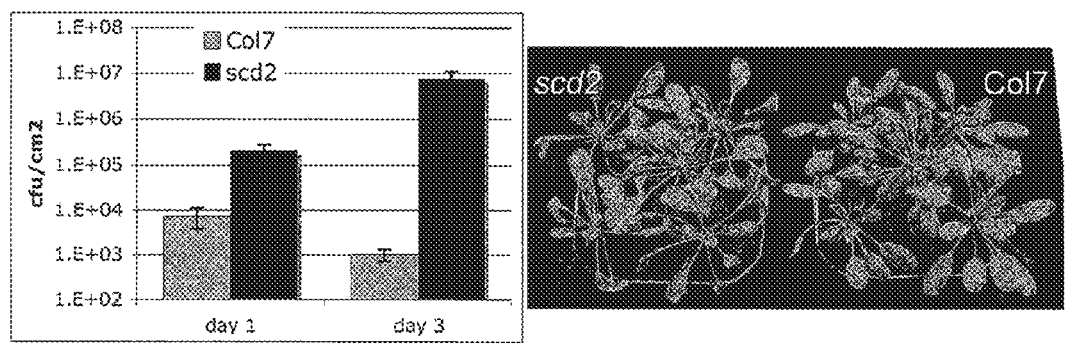
Figure 1C:
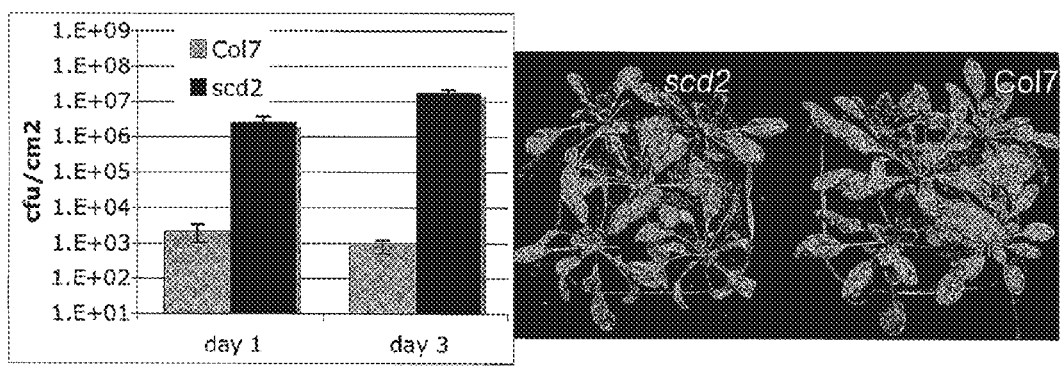

One of the main functions of the plant surface cuticle is to increase the surface tension so that water droplets would not be able to stay on the leaves so not to offer the opportunity for fungi or bacteria pathogens to infect. The inventors were of the opinion that if the wax layer is defected and weakened in its function as the physical barrier, then the surfactant that normally is harmless now might disrupt the wax layer and cause damages of the leaf cells. The inventors took advantage of this and used Silwet L-77® to screen for *Arabidopsis* mutants with altered leaf wax layers (FIG. 2C). In addition, Pst DC3118 was used to aid the mutant screen since normally DC3118 is not able to penetrate the leaf surface unless the stomata closure response to bacteria is impaired or the leaf surface epidermal cells are damaged and broken already, such as caused by the surfactant on wax-deficient mutant plants. The use of DC3118 amplified the leaf surface damage signal and made the leaf surface damage more visually noticeable. Further test for stomata response with bacteria and using other non-pathogenic bacteria, such as Ps pv. *phaseolicola* and Pst DC3000 (hrpH⁻), for surface inoculation could rather easily distinguish the possible cause between stomata and cuticle (FIG. 1). So far we have identified two wax related scd mutants during this pilot screen, scd2 and scd5.

The invention's methods utilize one or more surfactant. A "surfactant" is a chemical compound that lowers the surface tension of a liquid, allowing easier spreading of the liquid, and thereby acting as a wetting agent. In one embodiment, a surfactant is an organic compound that is amphiphilic, meaning that it contains one or more hydrophobic groups ("tails") and one or more hydrophilic groups ("heads"). Surfactants may be anionic, neutral or cationic. "Anionic surfactants" are surfactants that dissolve in water to release an anion, and include, for example, sodium lauryl ether sulfate, also referred to as sodium lauryl sulfate (CAS 009004-82-4), ammonium lauryl sulfate (CAS 2235-54-3), alkylbenzene sulfonic acid (CAS 27176-87-0), sodium 2-ethylhexyl sulfate (CAS 126-92-1), and dioctyl sodium sulfosuccinate (Andrews et al., U.S. Pat. No. 5,490,992). "Neutral surfactants" are surfactants that dissolve in water without releasing an anion or cation, and include, without limitation, octyl phenol ethoxylate (CAS 9002-93-1), glyceryl monostearate (CAS 31566-31-1), polyglyceryl-10 decaoleate (CAS 011094-60-3), and lauryl lactyl lactate (CAS 910661-93-7). "Cationic surfactants" are surfactants that dissolve in water to release a cation, and include the exemplary cetrimonium bromide (CAS 57-09-0), cetylpyridinium chloride (CAS 123-03-5), benzalkonium chloride (CAS 8001-54-5), and cocamidopropyl betaine (CAS 86438-79-1). Additional examples of surfactants include those that contain ethylene oxide moieties and/or propylene oxide moieties. Yet more examples of surfactants include linear alkylbenzene sulfonates, alcohol sulfates, alpha-olefin sulfonates, alcohol ethoxylates, nonylphenyl ethoxylates, alkylpolyglucosides, fatty alkanoamides, fatty amine oxides, sodium dioctylsulfosuccinate, dodecylbenzene sulfonic acid and salts thereof, the sodium salt of sulfonated oleic acid, sodium dodecylbenzene sulfonate, dodecyldiphenyloxidedisulfonic acid and salts thereof (Koefod et al., U.S. Pat. No. 7,090,882, Andrews et al., U.S. Pat. No. 5,490,992), and Silwet L-77® (Helena Chemical Co., Fresno, Calif.).

The microorganism that is used in the invention's methods includes, without limitation, virus, bacteria, fungus, insect, and nematode. The microorganism may be a pathogenic microorganism or a non-pathogenic microorganism. For example, data herein demonstrates the use *Pseudomonas syringae* pv. *tomato* (Pst) DC3118 that lacks coronatine phytotoxin, Ps pv. *phaseonicola*, and Pst DC3000 (hrpH⁻) to infect *Arabidopsis thaliana* leaf tissue. The microorganisms may be contacted with the plant tissue using any method, such as by surface inoculation or injections inside the leaves using a syringe (Example 1).

I. Methods for Identifying Plants with Altered Surface Wax Composition

The invention provides methods for identifying plant tissue that has an altered surface wax composition, comprising a) providing i) tissue from a first plant (e.g. a mutant plant), ii) corresponding tissue from a second plant (e.g., a wild type plant), and iii) a surfactant, b) contacting the tissue from the first plant with the surfactant to produce a contacted first tissue, c) contacting the tissue from the second plant with the surfactant to produce a contacted second tissue, and d) identifying an increase in one or more disease-like symptoms (e.g., FIG. 2C) in the contacted first tissue compared to the contacted second tissue, thereby identifying the tissue from the first plant as having an altered surface wax composition compared the tissue from the second plant. The term "corresponding tissue" means that tissue is from the same anatomical location on the plant. For example, leaf tissue from a first plant corresponds to leaf tissue from the second plant.

The invention's methods are useful for screening whether one or more genes, and/or their expression products, that are present in the first plant (e.g., a mutant plant) and that contain one or more mutations compared to the corresponding genes in the second plant (e.g., a wild type plant) are involved in the biosynthesis of surface wax. Indeed, this method was used herein to identity that SCD2 is essential for the aldehyde-to-alkane conversion of epicuticular wax (Example 2). These genes may then be expressed in cells (e.g., prokaryotic and eukaryotic cells) to produce wax that may be used as biofuel. Where this expression is in a plant and/or plant tissue, such expression may also be used to alter drought tolerance, temperature tolerance, and pathogen resistance.

EXPERIMENTAL

The following examples serve to illustrate certain embodiments and aspects of the present invention and are not to be construed as limiting the scope thereof.

Example 1

Exemplary Materials and Methods

A. *Arabidopsis* Materials

The collection of T-DNA enhancer lines CS23153 were purchased from ABRC (*Arabidopsis* Biological Research Center, Ohio State Univesity, Ohio, USA) with Col7 as the wild type. The Ds insertion line CS100282 was purchased through ABRC with Ler as the wild type.

B. Bacterial Infection Assays

Bacteria were started from fresh plates in 10 ml small cultures for 10 hours before being diluted 1:100 for over night culture until $OD_{600}$ reached 0.6-1.0. Bacteria were spun down and re-suspended in water to $OD_{600}$ of 0.2, which is equivalent of $10^8$ cfu/ml. Silwet L-77® was added in to a concentration of 0.02-0.08%. *Arabidopsis* plants grown under long day condition for 5-6 weeks were dipped in the bacteria solution for a few seconds and put back for further growth for the surface inoculation. For infiltration, bacteria concentration was adjusted to $OD_{600}$ 0.002, equivalent of $10^6$ cfu/ml, and hand infiltrated into leaves using 1 ml blunt-end syringes. When sampled for bacteria growth, leaves were detached and briefly washed in 70% ethanol and then in $ddH_2O$ before leaf discs were collected and grinded. Bacteria counting were conducted with a serial dilution of the leaf extracts.

C. Drought Tolerance Assays

Plants of 5-week-old were held without water for 10 days before photos were taken. For leaf assays, leaves from 5-weeks-old plants were detached and left on the bench and weighed at the indicated time points. Dry weights were measured when leaves are completely dried after two days on the bench.

D. Molecular Biology

Genomic DNA from *Arabidopsis* plants were isolated using the Sigma PlantExtract kit according to the instruction.

The primers for marker AP21-4 were: FP (5'-GGTTAAC-GAAAGAATTTTGTCG-3') [SEQ. ID NO. 133] and RP (5'-TGGCAAAAAGTTCTTATTTGGG-3') [SEQ. ID NO: 134]. The primers for marker F19F18-2 are: FP (5'-GACATCT-TCAGGGACAGTGTAGTC-3') [SEQ. ID NO: 135] and RP (5'-TGGTGAGTTTATATGTGATCAAAGTTGC-3') [SEQ ID NO: 136].

The primers used to confirm the existence of Ds element in CS100282 plants are as follows: Ds5'-1a (5'-GGTCGG-GAAACTAGCTCTAC-3') [SEQ ID NO: 137] Ds3'-3a (5'-TCGTTTCCGTCCCGCAAGT-3') [SEQ ID NO: 138], At4g37470genoseq2 (5'-CGTTTACGTATCTATAAACG-TAC-3') [SEQ ID NO: 139], and At4g37470genoDN (5'-ATACGTAACACTCTAAAACAAAC-3') [SEQ ID NO: 140].

The 2.8 kb genomic region of SCD2 used for complementation starts at about 800 by upstream of the start codon and stops at about 680 by downstream of the stop codon, and was amplified with primer At4g37479CompUP (5'-CACGACT-GCAGACTTTATTGGT-3') [SEQ ID NO: 141] and AT4G37470CompDN (5'-AATTTGGTAACCATCA-CAATATGTA-3') [SEQ ID NO: 142] The fragment was cloned onto pGEMTeasy and released by PstI and BstEII for the cloning into pCambia1302. For overexpression of SCD2, the coding region was amplified using primers At4g374700Eup (5'-TAGAGCCATGGGTGTGGTAGA-3') [SEQ ID NO: 143] and AT4G374700Edn (5'-AAATCGGT-TACCATCACATAG-3') [SEQ ID NO: 144]. Again, the fragment was cloned into pGEMTeasy first' and released with NcoI and BstEII for the cloning into pCambia1302. Constructs on pCambia1302 were electroporated into *Agrobacteria* GV3101 (pMP90) for plant transformation, and positive plants were identified on MS agar plates containing 50 µg/ml hygromycin.

E. Bioinformatics

Sequence homology search for At4g37470 was carried out using the Blastp program at NCBI with default parameters. The protein sequences with E values of 0.001 and lower were fetched from the NCBI database (December, 2008), and the duplicate sequences with same TAIR ID were removed before further analysis. The multiple sequence alignment was performed with Jalview 2.4 (Clamp et al. (2004) Bioinformatics 20:426-427) with option of "Muscle multiple protein alignment", and the phylogenetic tree was constructed using "Neighbor joining tree using BLOSUM6" method with the same program.

F. GC-MS Analysis

GC-MS analysis of wax and cutin followed previous protocols (Li et al. (2007b) Proc Natl Acad Sci USA 104:18339-18344; Li et al. (2007a) Plant Physiol 144:1267-1277)

Example 2

Identification of scd2

*Pseudomonas syringae* pv. *tomato* (Pst) DC3118 is a mutant form of Pst DC3000 that has lost its ability to synthesize the phytotoxin coronatine, and therefore cannot reopen the stomata to gain entry into the leaf apoplast when surface inoculated. We reasoned that when the leaf wax layer was defected, the surfactant used in the bacteria surface inoculation would very easily break the physical barrier and allow DC3118 to access the nutrients released from the broken cells. DC3118 then would be able to multiply and cause disease symptoms that could be visually observed.

From a collection of T-DNA insertion lines, we identified a mutant scd2 using this approach. When surface inoculated, scd2 plant allowed the multiplication of DC3118 to much higher level than wild type Col7 plants even at 1 dpi (FIG. 1A). By 3 dpi, the disease symptoms on scd2 leaves are prominent while the wild type leaves remain disease-free (FIG. 1A). Because DC3118 is pathogenic to *Arabidopsis* once inside the apoplast, we tested another two bacteria pathogens to confirm the unusual susceptibility of scd2 to bacteria. One is Ps pv. *phaseonicola*, a non-host pathogen of *Arabidopsis*, and therefore normally it would not be able to induce disease in *Arabidopsis* regardless whether it is inoculated on the surface or inside the leaves. Another one is Pst DC3000 (hrpH⁻), a DC3000 derivative that is deficient in the type III secretion system (TTSS) and has totally lost its ability to secrete effector proteins to cause disease. In similar surface inoculation assays, both Ps pv. *phaseonicola* and Pst DC3000 (hrpH⁻) were able to multiply to very high level and caused dramatic disease symptoms on scd2 leaves (FIG. 1B, C). Therefore, it was our opinion that scd2 leaves must have some unusual features that have enabled the growth of non-pathogenic bacteria that normally have difficulty to gain nutrients from the host cells.

Figure 2A:
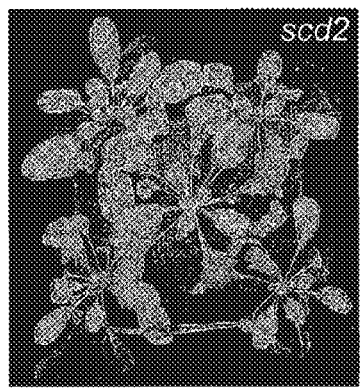
FIG. 2: Leaf surface of scd2 allowed the penetration of surfactant. A. Leaf appearance at 1 dpi after dip-inoculation with Pst DC3000 (hrpH$^-$), B. bacteria population at 0 dpi and 3 dpi when hand infiltrated with Pst DC3000 (hrpH$^-$) at $10^6$ cfu/ml, C. scd2 leaves are susceptible to Silwet L-77® solution. Plant appearances are recorded 3 days after dipping.
Figure 2A:
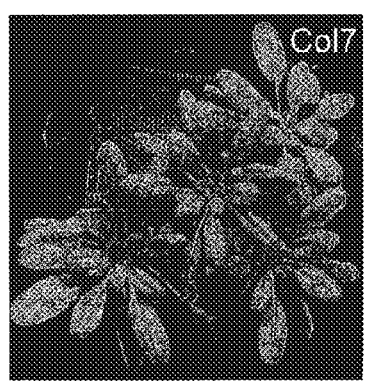
Figure 2B:
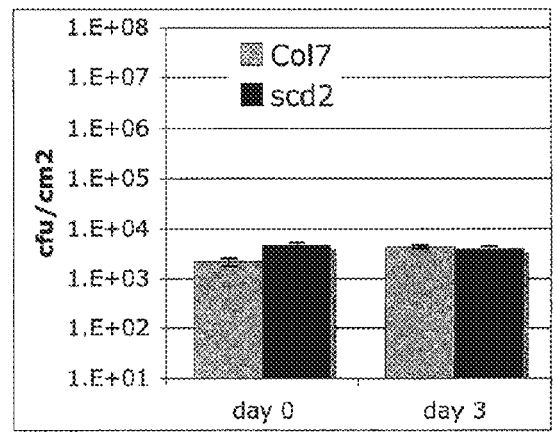
Figure 2C:
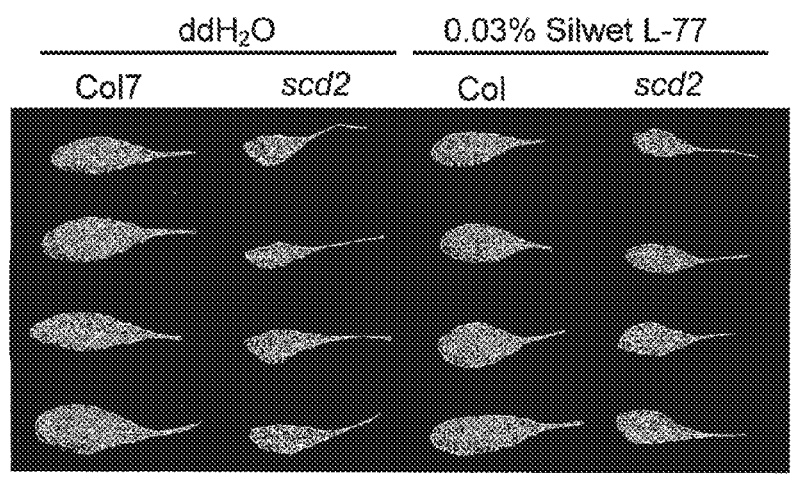

We noticed that even at day 1, when surface inoculated with Pst DC3000 (hrpH−), the leaves of scd2 plants showed some water soaking-like symptoms (FIG. 2A). This symptom is similar to that at the early moment of chloroform soaking of leaves during epicuticular wax extraction, indicating there might be defects in the cuticles of scd2 leaves, which would allow the surfactants included in the inoculation buffer to break the cuticule layer more easily. Therefore Pst DC3000 (hrpH−) was hand infiltrated into scd2 and wild type Col7 leaves without the surfactant. No growth of Pst DC3000 (hrpH−) was observed (FIG. 2B). Finally the inoculation buffer itself containing surfactant was used to test the leaf responses, and scd2 leaves showed yellowing and disease-like symptoms even though it was at a much lower extent compared to when inoculated with bacteria (FIG. 2C). Therefore, we conclude that some type of defect in leaf surface cuticle of scd2 might have allowed the penetration of surfactant and the phenotype was amplified by the bacteria growth leading to disease symptoms when the scd2 cells are more readily to be broken and nutrients are released to the bacteria's access.

Example 3

Figure 3A:
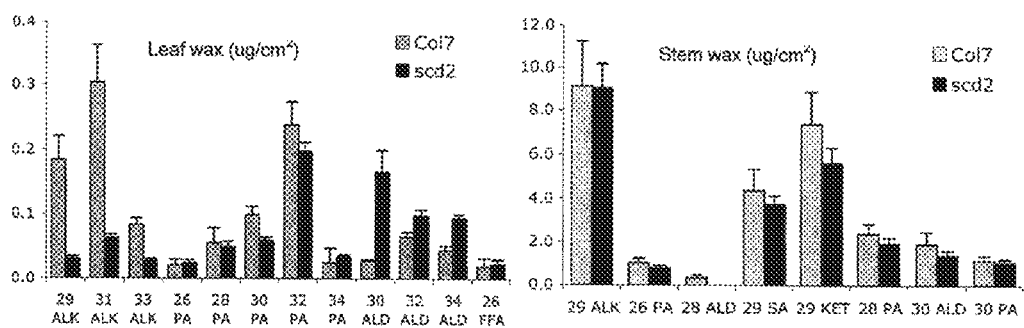
FIG. 3: Wax and cutin analysis for rosette leaves and stems of scd2 and Col7 plants. A. wax composition analysis for leaves and stems, B. cutin composition analysis for leaves and stems.

SDC2 is Essential for the Aldehyde-to-Alkane Conversion, and Leaves but not Stems of Scd2 have Less Alkanes and More Aldehydes in the Epicuticular Wax Epicuticular waxes and cutins were isolated from both rosette leaves and stems of scd2 and wild type Col7 plants. We found that leaf waxes of scd2 contain much less alkanes, including all the three main ones, at C29, C31 and C33 (FIG. 3A). Meanwhile, all three main aldehydes accumulated to much higher level in scd2 epicuticular waxes accordingly, with the C29 alkane and C30 aldehyde are the most dramatically affected (FIG. 3A). The epicuticular wax of scd2 plants have less alkanes and more aldehydes accumulated (FIG. 3A, 9). However, the extent of changes varied from experiment to experiment, which might have been partially caused by the difference on growth conditions.

Figure 3B:
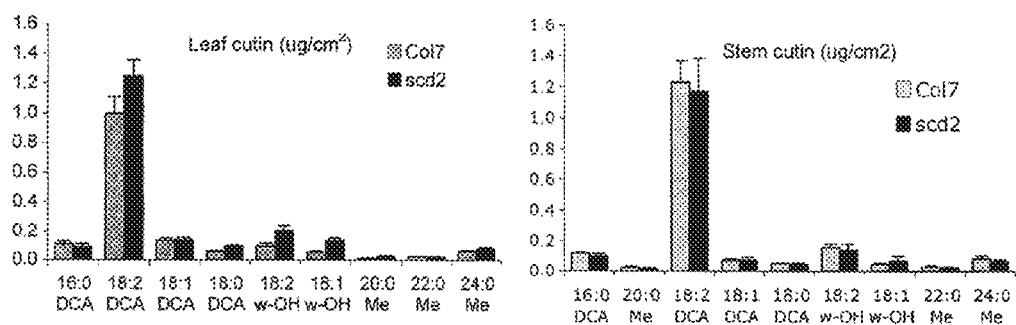

Intriguingly, the composition of epicuticular waxes from scd2 stems is very similar to the wild types plants. On the other hand, not much difference was detected in the cutin composition between scd2 and wild type Col7 plants from either the leaves or the stems (FIG. 3B). Therefore, this demonstrates that SCD2 is a gene that is involved in the aldehyde-to-alkane conversion, particularly in leaves. In particular, the SCD2/At4g37470 gene was identified to be responsible for the phenotype displayed by the scd2 mutant plants that showed 2-3 times higher accumulation of aldehydes and 70-80% lower amounts of alkanes in the leaf epicuticular wax compared to the wild type plants.

Example 4

Figure 4A:
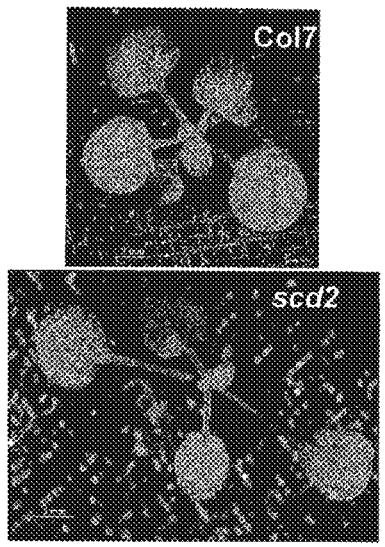
FIG. 4: Morphological phenotypes of scd2 plants. A. 3-weeks-old plants, B. 5-weeks-old plants, C. SEM of 5-weeks-old leaves.
Figure 4B:
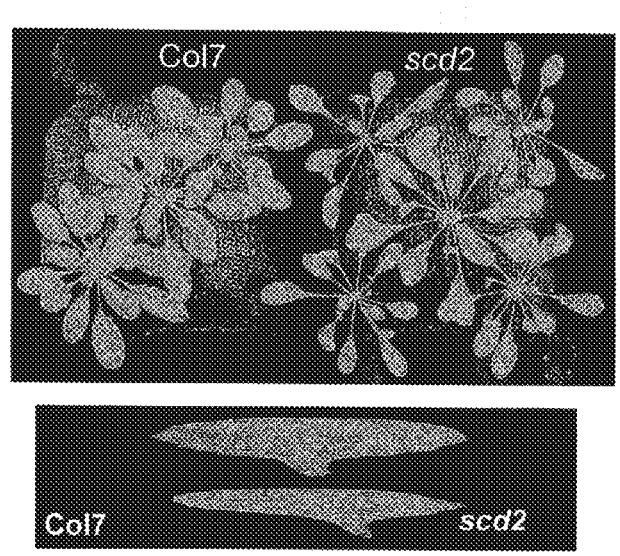
Figure 4C:
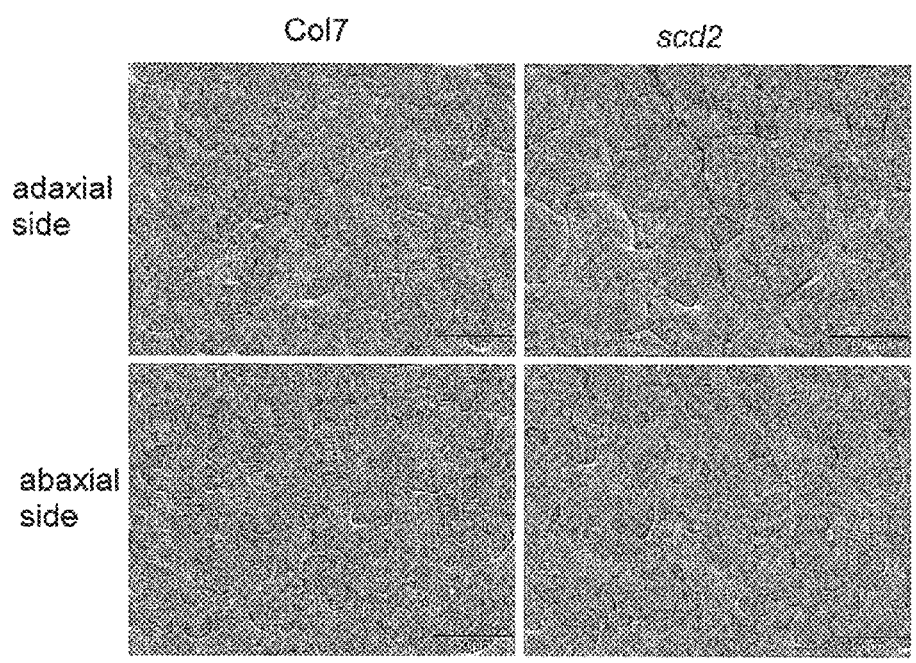

Scd2 Plants have Altered Phenotype Including Altered Leaf Morphology and Drought Sensitivity Under normal growth conditions, scd2 plants have longer petioles and longer hypocotyls (FIG. 4A). Leaves from scd2 plants are slightly curly and wrinkled, and look a little thinner and drier than wild type Col7 leaves (FIG. 4A). The epidermal cells of scd2 leaves are larger than that of wild type Col7 when observed under SEM (FIG. 4B). However, the stomata morphology and stomata index of scd2 are similar to wild type Col7 plants (FIG. 4B).

Figure 5A:
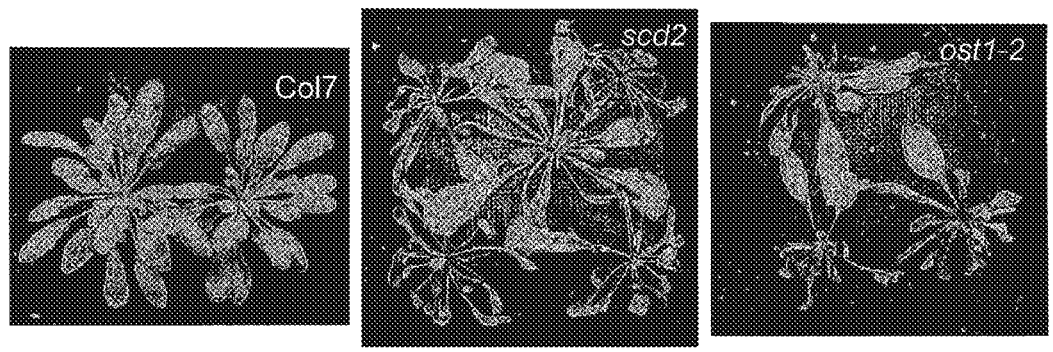
FIG. 5: scd2 plants are drought sensitive. A. after holding water from 5-weeks-old plants for 10 days, B. water-loss rate of detached leaves.
Figure 5B:
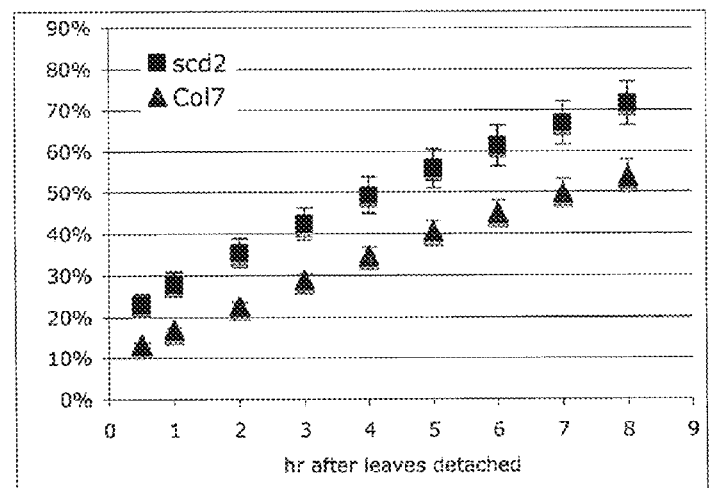

Mutant scd2 plants are also drought sensitive. After holding water from 5-week-old plants for 10 days, scd2 plants wilted while the wild type Col7 plants still looked normal (FIG. 5A). Another drought sensitive mutant ost1-2 (Merlot et al. (2002) Plant J 30:601-609; Xie et al. (2006) Curr Biol 16:882-887) was used as a control here and behaved very similar to scd2. In addition, the detached leaves of scd2 lost water faster than the wild type plants (FIG. 5B).

Example 5

Physical Mapping of scd2 Mutation

Since scd2 was identified from a T-DNA enhancer collection, we first cloned a T-DNA flanking fragment by plasmid rescue. While the T-DNA insertion in this particular position could be confirmed in the scd2 genome, neither the loss-of-function of that particular gene nor the overexpression of the immediate downstream gene seemed to contribute to the phenotypes observed for scd2, based on the characterization of independent loss-of-function and gain-of-function mutant plants. Therefore, we resorted to a map based cloning strategy. Backcrossing of scd2 with wild type Col7 plants showed that the phenotypes of scd2 were caused by a single recessive mutation. To identify the mutation locus, scd2 was crossed with Ler, and a pool of 628 F2 plants with scd2 phenotypes were identified and selected. These plants were used to map the mutation locus on chromosomal 4 between indel markers AP21-4 and F19F18-2 encompassing a region of 160 kb (FIG. 6A). From one of the four candidate genes that we amplified from scd2 genome and sequenced, a single nucleotide deletion was identified on the second exon of At4g37470 that led to an early stop codon (FIG. 6B). To make sure this deletion was really from the scd2 mutation, the same region was amplified from Co10, Col7, and 12 recombinant F2 plants. While the sequences from Col0 and Col7 both matched with the GenBank database, the deletion was found from all the 12 recombinant F2 plants.

Figure 6C:
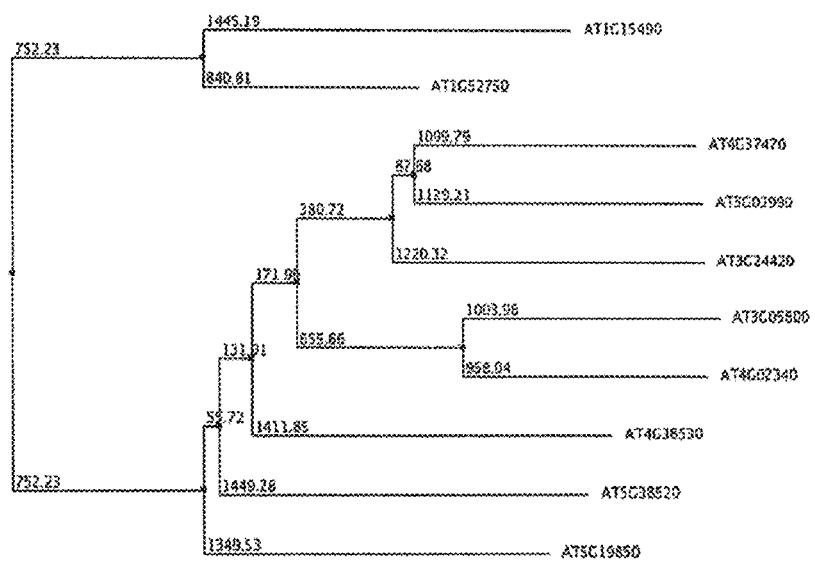
FIG. 6: Physical mapping of scd2 mutation and sequence analysis of SCD2. A. Primers used for fine mapping and their chromosomal positions, B. Coding region and amino acid sequence of SCD2, A376 is missing from scd2 mutant plants, and the early stop codon is underlined, C. Phylogenetic tree of SCD2 protein and its close homologs in *Arabidopsis*, D. sequence alignment of SCD2 (AT4G37470/1-270) and its homologs AT3G03990/1-267 (SEQ ID NO:3), AT3G24420/1-273 (SEQ ID NO:4), AT5G19850/1-359 (SEQ ID NO:5), AT4G36530/1-321 (SEQ ID NO:6), AT3G05600/1-331 (SEQ ID NO:7), AT1G15490/1-648 (SEQ ID NO:8), AT1G52750/1-523 (SEQ ID NO:9), AT5G38520/1-362 (SEQ ID NO:10), and AT4G02340/1-324 (SEQ ID NO:11).
Figure 6D:
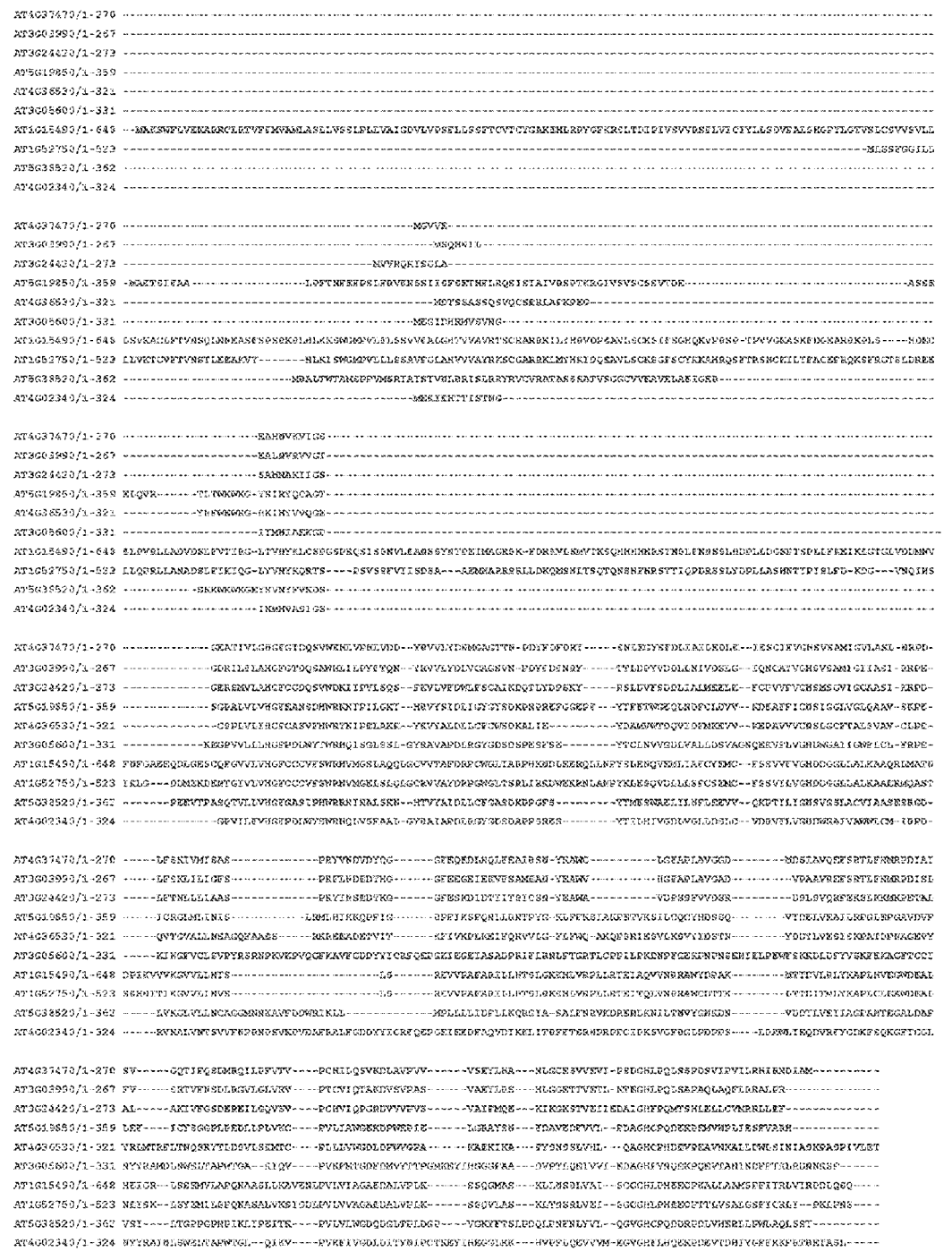

SCD2 was predicted by the inventors to encode a thioesterase/hydrolase of 270 aa. A BlastP search against the GenBank database revealed that SCD2 protein belongs to a very large family of hydrolases. A phytogenetic tree was constructed with the sequence of SCD2 and its closest 9 homologs (FIG. 6C). The protein alignment showed that there are a few conserved domains across all the 10 members (FIG. 6D).

Example 6 scd2-2 is a Different Allele of scd2

Figure 7A:
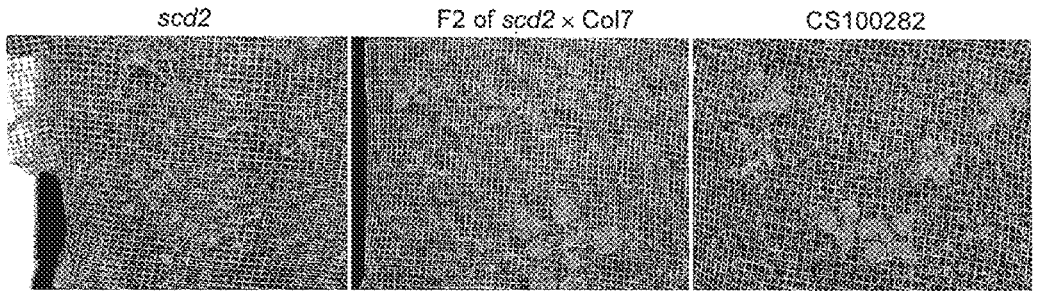
FIG. 7: CS100282 is another allele of scd2. A. Plants from CS100282 showed segregation of morphological phenotypes that is similar to the F2 plant population from scd2×7 backcrossing. Plants with or without scd2 morphological phenotypes were selected for further PCR reactions and wax analysis, B. Insertion position of Ds in CS100282 plants, and the positions of primers used for PCR reactions, and PCR reactions showing the presence of the Ds insertion, C. Amounts of alkanes and aldehydes in these 20 plants.
Figure 7B:
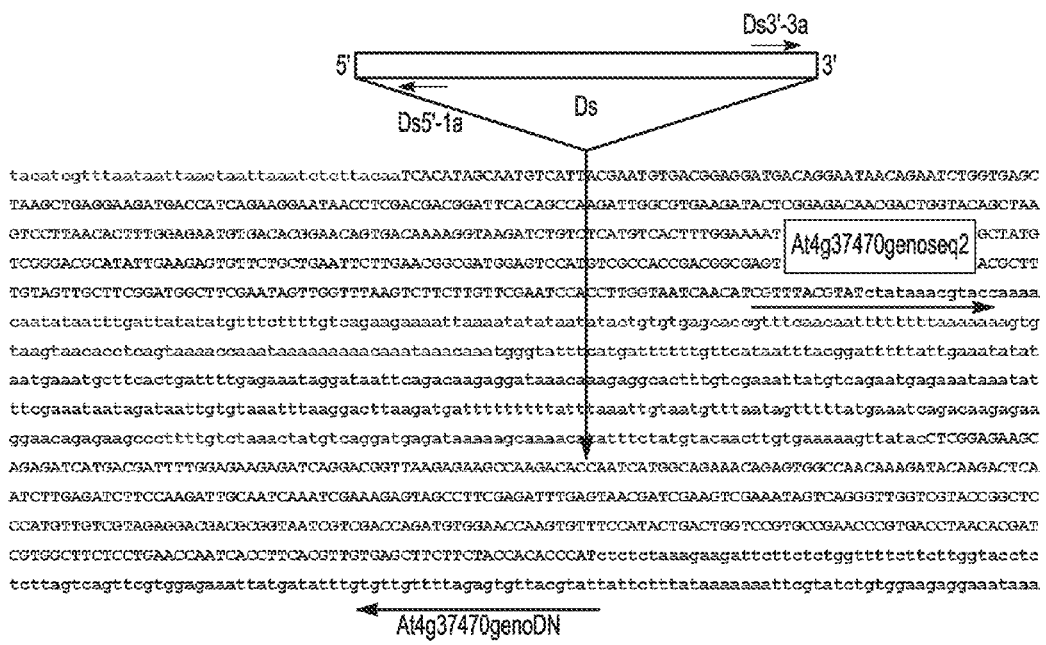
Figure 7B:
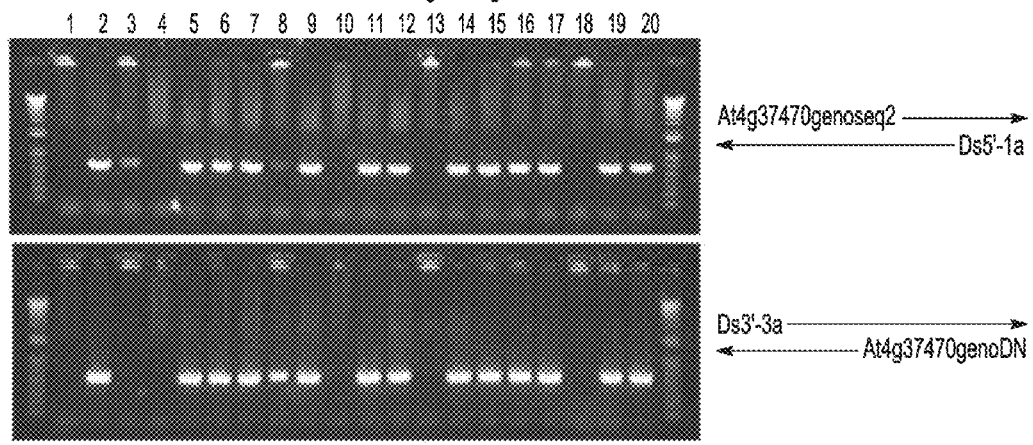
Figure 7C:
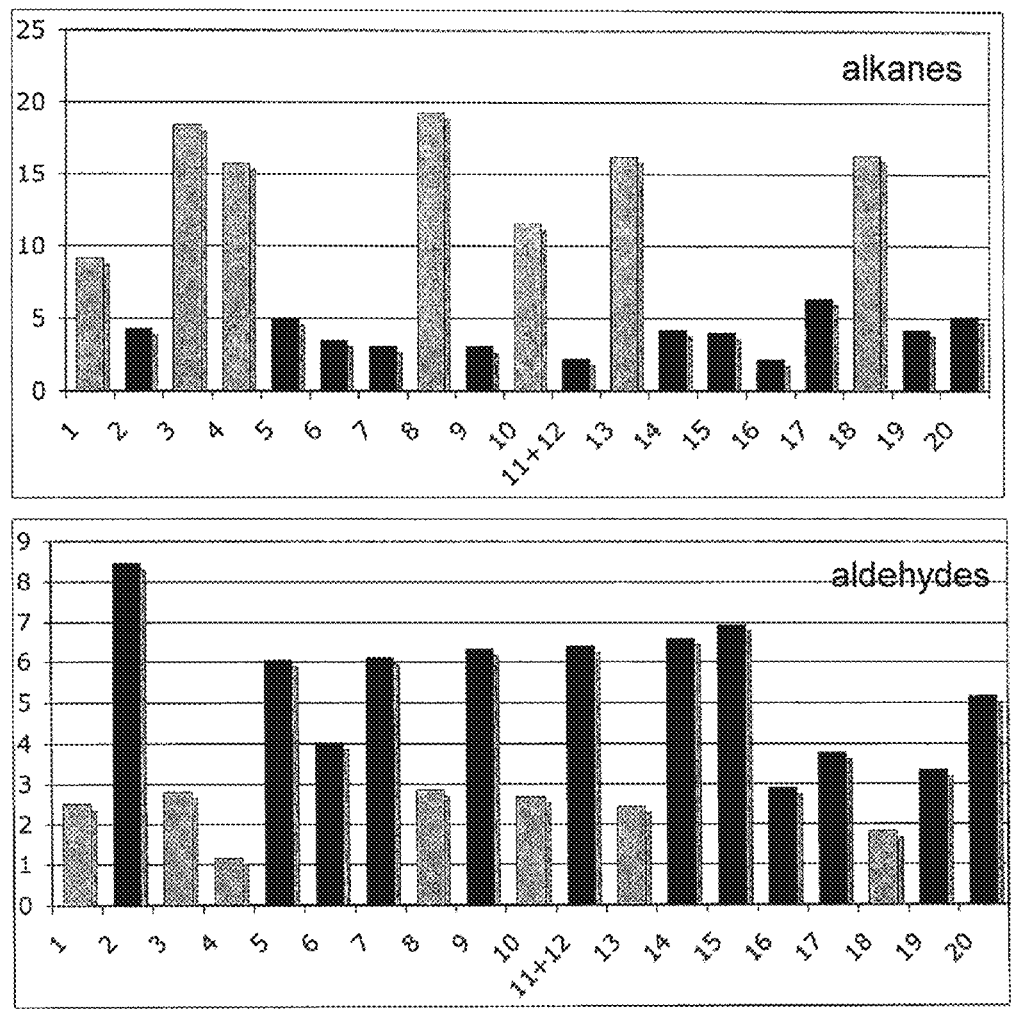

To confirm the gene identity of At4g37470 as SCD2, a different mutant line CS100282 with a Ds element insertion was obtained from ABRC. The same morphological phenotypes as scd2 (for example, altered leaf morphology; see Example 4) was observed for some of the plants derived from this mutant (FIG. 7A). Twenty plants from this mutant line with or without scd2 phenotypes were randomly selected and the existence of the Ds insertion was confirmed (FIG. 7B). In both sets of PCR reactions using primers specific for each end of the Ds element and the flanking sequences, plants number 2, 5, 6, 7, 9, 11, 12, 14, 15, 16, 17, 19 and 20 showed consistent heavy PCR products, and are likely homozygous for the Ds insertion (FIG. 7B). Indeed, all these plants had morphological phenotypes like scd2. Plants 3, 8, 13 and 18 looked like wild type plants, but showed a weak band from those PCR reactions (FIG. 7B), and thus likely to be heterozygous for the Ds insertion. We further analyzed these plants for the amount of alkanes and aldehydes from the epicuticular waxes (FIG. 7C). Plants with scd2 morphologies all had much less amount of alkanes in their epicuticular wax but more aldehydes, compared to the other plants that showed wild type-like morphologies (FIG. 7C). Therefore we concluded that this mutant in Ler background with a Ds insertion in At4g37470 indeed is another allele of scd2, and named it as scd2-2.

Example 7

Scd2 Phenotypes are Complemented by the Expression of SCD2 Genomic Fragment

A fragment of 2.8 kb containing the whole genomic structure of SCD2 including the endogenous promoter was amplified from wild type Col7 genome and introduced into the scd2 mutant plants. In the T2 generation, segregation of morphological phenotypes was observed with some plants showed normal appearance just like wild type Col7 plants, and the others maintained their scd2 morphologies (e.g., altered leaf morphology described in Example 4) (FIG. 8A). A few plants with either morphology were selected from the T2 population derived from two different T1 lines representing different complementation transformation events, and analyzed for their epicuticular wax compositions. As expected, all plants with scd2 morphologies showed lower-alkane and higher-aldehyde phenotypes just as scd2, and the plants with wild type Col7-like appearances showed much higher amount of alkanes and less aldehydes (FIG. 8B). Therefore, SCD2 under its own promoter is fully functional to convert the aldehydes to alkanes in leaf epicuticular wax.

Example 8

Overexpression of SCD2 Produce More Alkanes in *Arabidopsis*

To further assess the function of SCD2, we introduced SCD2 into wild type Col7 plants behind the CaMV:35S promoter. From four different transformation experiments, 19 T1 plants were randomly selected for wax analysis (FIG. 9). All the T1 plants showed higher alkane content and lower aldehyde content compared to the scd2 plants (FIG. 9). Furthermore, most of the plants (15/19) showed higher amounts of alkanes compared to the wild type Col7 plants. Plants 6-3, 6-5, 8-4 and 9-3 had much higher levels of alkanes and higher levels of aldehydes than wild type plants. Plants 4-6, 8-1 and 9-2 had higher alkane contents and lower amounts of aldehydes than wild type plants. This data demonstrates that the plant wax compositions may be manipulated by genetically engineering the SCD2 gene into cells.

Each and every publication and patent mentioned in the above specification is herein incorporated by reference. Various modifications and variations of the described compositions and methods of the invention will be apparent to those skilled in the art without departing from the scope and spirit of the invention. Although the invention has been described in connection with specific preferred embodiment, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A transgenic cell comprising a heterologous nucleic acid encoding a polypeptide with a sequence that is at least 95% identical to SEQ ID NO:2, wherein the cell converts 10% more aldehyde to alkane than a cell without the heterologous nucleic acid.

2. The transgenic cell of claim 1, wherein the cell is a eukaryotic cell.

3. The transgenic cell of claim 1, wherein the cell is a prokaryotic cell.

4. A transgenic plant comprising a heterologous nucleic acid encoding a polypeptide with a sequence that is at least 95% identical to SEQ ID NO:2, wherein the plant converts 10% more aldehyde to an alkane than a plant that lacks the heterologous nucleic acid.

5. A transgenic plant seed comprising a heterologous nucleic acid encoding a polypeptide with a sequence that is at least 95% identical to SEQ ID NO:2, wherein a plant grown from the seed converts 10% more aldehyde to alkane than a plant without the heterologous nucleic acid.

* * * * *

SEQUENCE LISTING

```
<160> NUMBER OF SEQ ID NOS: 147

<210> SEQ ID NO 1
<211> LENGTH: 813
<212> TYPE: DNA
<213> ORGANISM: Arabidopsis thaliana

<400> SEQUENCE: 1
atgggtgtgg tagaagaagc tcacaacgtg aaggtgattg gttcaggaga agccacgatc      60
gtgttaggtc acgggttcgg cacggaccag tcagtatgga aacacttggt tccacatctg     120
gtcgacgatt accgcgtcgt cctctacgac aacatgggag ccggtacgac caaccctgac     180
tatttcgact tcgatcgtta ctcaaatctc gaaggctact ctttcgattt gattgcaatc     240
ttggaagatc tcaagattga gtcttgtatc tttgttggcc actctgtttc tgccatgatt     300
ggtgtcttgg cttctcttaa ccgtcctgat ctcttctcca aaatcgtcat gatctctgct     360
tctccgagat acgtaaacga tgttgattac caaggtggat cgaacaaga agacttaaac      420 caactattcg aagccatccg aagcaactac aaagcgtggt gcttaggttt cgctccactc     480
gccgtcggtg gcgacatgga ctccatcgcc gttcaagaat tcagcagaac actcttcaat     540
atgcgtcccg acatagctct ctccgtcggc cagaccattt tccaaagtga catgagacag     600
atcttacctt ttgtcactgt tccgtgtcac attctccaaa gtgttaagga cttagctgta     660
ccagtcgttg tctccgagta tcttcacgcc aatcttggct gtgaatccgt cgtcgaggtt     720
attccttctg atggtcatct tcctcagctt agctcaccag attctgttat tcctgtcatc     780
ctccgtcaca ttcgtaatga cattgctatg tga                                  813
```

```
<210> SEQ ID NO 2
<211> LENGTH: 270
<212> TYPE: PRT
<213> ORGANISM: Arabidopsis thaliana

<400> SEQUENCE: 2

Met Gly Val Val Glu Ala His Asn Val Lys Val Ile Gly Ser Gly
  1               5                  10                  15

Glu Ala Thr Ile Val Leu Gly His Gly Phe Gly Thr Asp Gln Ser Val
             20                  25                  30

Trp Lys His Leu Val Pro His Leu Val Asp Asp Tyr Arg Val Val Leu
         35                  40                  45

Tyr Asp Asn Met Gly Ala Gly Thr Thr Asn Pro Asp Tyr Phe Asp Phe
 50                  55                  60

Asp Arg Tyr Ser Asn Leu Glu Gly Tyr Ser Phe Asp Leu Ile Ala Ile
 65                  70                  75                  80

Leu Glu Asp Leu Lys Ile Glu Ser Cys Ile Phe Val Gly His Ser Val
                 85                  90                  95

Ser Ala Met Ile Gly Val Leu Ala Ser Leu Asn Arg Pro Asp Leu Phe
            100                 105                 110

Ser Lys Ile Val Met Ile Ser Ala Ser Pro Arg Tyr Val Asn Asp Val
        115                 120                 125

Asp Tyr Gln Gly Gly Phe Glu Gln Glu Asp Leu Asn Gln Leu Phe Glu
130                 135                 140

Ala Ile Arg Ser Asn Tyr Lys Ala Trp Cys Leu Gly Phe Ala Pro Leu
145                 150                 155                 160

Ala Val Gly Gly Asp Met Asp Ser Ile Ala Val Gln Glu Phe Ser Arg
                165                 170                 175

Thr Leu Phe Asn Met Arg Pro Asp Ile Ala Leu Ser Val Gly Gln Thr
            180                 185                 190

Ile Phe Gln Ser Asp Met Arg Gln Ile Leu Pro Phe Val Thr Val Pro
        195                 200                 205

Cys His Ile Leu Gln Ser Val Lys Asp Leu Ala Val Pro Val Val Val
    210                 215                 220

Ser Glu Tyr Leu His Ala Asn Leu Gly Cys Glu Ser Val Val Glu Val
225                 230                 235                 240

Ile Pro Ser Asp Gly His Leu Pro Gln Leu Ser Ser Pro Asp Ser Val
                245                 250                 255

Ile Pro Val Ile Leu Arg His Ile Arg Asn Asp Ile Ala Met
            260                 265                 270

<210> SEQ ID NO 3
<211> LENGTH: 267
<212> TYPE: PRT
<213> ORGANISM: Arabidopsis thaliana

<400> SEQUENCE: 3

Met Ser Gln His Asn Ile Leu Glu Ala Leu Asn Val Arg Val Val Gly
  1               5                  10                  15

Thr Gly Asp Arg Ile Leu Phe Leu Ala His Gly Phe Gly Thr Asp Gln
             20                  25                  30

Ser Ala Trp His Leu Ile Leu Pro Tyr Phe Thr Gln Asn Tyr Arg Val
         35                  40                  45

Val Leu Tyr Asp Leu Val Cys Ala Gly Ser Val Asn Pro Asp Tyr Phe
 50                  55                  60
```

```
Asp Phe Asn Arg Tyr Thr Thr Leu Asp Pro Tyr Val Asp Leu Leu
 65                  70                  75                  80

Asn Ile Val Asp Ser Leu Gly Ile Gln Asn Cys Ala Tyr Val Gly His
                 85                  90                  95

Ser Val Ser Ala Met Ile Gly Ile Ile Ala Ser Ile Arg Arg Pro Glu
            100                 105                 110

Leu Phe Ser Lys Leu Ile Leu Ile Gly Phe Ser Pro Arg Phe Leu Asn
        115                 120                 125

Asp Glu Asp Tyr His Gly Gly Phe Glu Glu Gly Ile Glu Lys Val
    130                 135                 140

Phe Ser Ala Met Glu Ala Asn Tyr Glu Ala Trp Val His Gly Phe Ala
145                 150                 155                 160

Pro Leu Ala Val Gly Ala Asp Val Pro Ala Ala Val Arg Glu Phe Ser
                165                 170                 175

Arg Thr Leu Phe Asn Met Arg Pro Asp Ile Ser Leu Phe Val Ser Arg
            180                 185                 190

Thr Val Phe Asn Ser Asp Leu Arg Gly Val Leu Gly Leu Val Arg Val
        195                 200                 205

Pro Thr Cys Val Ile Gln Thr Ala Lys Asp Val Ser Val Pro Ala Ser
    210                 215                 220

Val Ala Glu Tyr Leu Arg Ser His Leu Gly Gly Asp Thr Thr Val Glu
225                 230                 235                 240

Thr Leu Lys Thr Glu Gly His Leu Pro Gln Leu Ser Ala Pro Ala Gln
                245                 250                 255

Leu Ala Gln Phe Leu Arg Arg Ala Leu Pro Arg
            260                 265

<210> SEQ ID NO 4
<211> LENGTH: 273
<212> TYPE: PRT
<213> ORGANISM: Arabidopsis thaliana

<400> SEQUENCE: 4

Met Val Val Asn Gln Lys Ile Ser Gly Leu Ala Ser Ala Met Asn Ala
 1                   5                  10                  15

Lys Ile Ile Gly Ser Gly Glu Arg Ser Met Val Leu Ala His Gly Phe
             20                  25                  30

Gly Gly Asp Gln Ser Val Trp Asp Lys Ile Ile Pro Val Leu Ser Gln
         35                  40                  45

Ser Phe Lys Val Leu Val Phe Asp Trp Leu Phe Ser Gly Ala Ile Lys
     50                  55                  60

Asp Gln Thr Leu Tyr Asp Pro Ser Lys Tyr Asn Ser Leu Asp Val Phe
 65                  70                  75                  80

Ser Asp Asp Leu Ile Ala Leu Met Glu Glu Leu Lys Phe Gly Pro Val
                 85                  90                  95

Val Phe Val Gly His Ser Met Ser Gly Val Ile Gly Cys Ala Ala Ser
            100                 105                 110

Ile Lys Arg Pro Asp Leu Phe Thr Asn Leu Leu Leu Ile Ala Ala Ser
        115                 120                 125

Pro Arg Tyr Ile Asn Ser Glu Asp Tyr Lys Gly Gly Phe Glu Ser Lys
    130                 135                 140

Asp Ile Asp Thr Ile Ile Thr Ser Ile Gly Ser Asn Tyr Glu Ala Trp
145                 150                 155                 160

Ala Val Asp Phe Ser Ser Phe Val Val Asp Ser Arg Asp Ser Leu Ser
                165                 170                 175
```

```
Val Gln Arg Phe Glu Lys Ser Leu Lys Lys Met Lys Pro Glu Thr Ala
            180                 185                 190

Leu Ala Leu Ala Lys Ile Val Phe Gly Ser Asp Glu Arg Glu Ile Leu
        195                 200                 205

Gly Gln Val Ser Val Pro Cys His Val Ile Gln Pro Gly Asn Asp Val
    210                 215                 220

Val Val Pro Val Ser Val Ala Tyr Phe Met Gln Glu Lys Ile Lys Gly
225                 230                 235                 240

Lys Ser Thr Val Glu Ile Ile Glu Asp Ala Ile Gly His Phe Pro Gln
                245                 250                 255

Met Thr Ser His Leu Glu Leu Leu Gly Val Met Arg Arg Leu Leu Glu
            260                 265                 270

Phe

<210> SEQ ID NO 5
<211> LENGTH: 359
<212> TYPE: PRT
<213> ORGANISM: Arabidopsis thaliana

<400> SEQUENCE: 5

Met Ala Lys Thr Ser Ile Phe Ala Ala Leu Pro Phe Thr Asn Phe Glu
1               5                   10                  15

Phe Pro Ser Leu Phe Arg Val Lys Asn Ser Ser Ile Ile Ser Phe Ser
            20                  25                  30

Glu Thr His Phe Leu Arg Gln Ser Ile Ser Thr Ala Ile Val Arg Ser
        35                  40                  45

Pro Thr Lys Arg Gly Ile Val Ser Val Ser Cys Ser Ser Val Thr Asp
    50                  55                  60

Glu Ala Ser Ser Glu Glu Leu Gln Val Arg Thr Leu Thr Trp Lys Trp
65                  70                  75                  80

Lys Gly Tyr Ser Ile Arg Tyr Gln Cys Ala Gly Thr Ser Gly Pro Ala
                85                  90                  95

Leu Val Leu Val His Gly Phe Gly Ala Asn Ser Asp His Trp Arg Lys
            100                 105                 110

Asn Thr Pro Ile Leu Gly Lys Thr His Arg Val Tyr Ser Ile Asp Leu
        115                 120                 125

Ile Gly Tyr Gly Tyr Ser Asp Lys Pro Asn Pro Arg Glu Phe Gly Gly
    130                 135                 140

Glu Pro Phe Tyr Thr Phe Glu Thr Trp Gly Glu Gln Leu Asn Asp Phe
145                 150                 155                 160

Cys Leu Asp Val Val Lys Asp Glu Ala Phe Phe Ile Cys Asn Ser Ile
                165                 170                 175

Gly Gly Leu Val Gly Leu Gln Ala Ala Val Ser Lys Pro Glu Ile Cys
            180                 185                 190

Arg Gly Leu Met Leu Ile Asn Ile Ser Leu Arg Met Leu His Ile Lys
        195                 200                 205

Lys Gln Pro Phe Ile Gly Arg Pro Phe Ile Lys Ser Phe Gln Asn Leu
    210                 215                 220

Leu Arg Asn Thr Pro Val Gly Lys Leu Phe Phe Lys Ser Ile Ala Lys
225                 230                 235                 240

Pro Glu Thr Val Lys Ser Ile Leu Cys Gln Cys Tyr His Asp Ser Ser
                245                 250                 255

Gln Val Thr Asp Glu Leu Val Glu Ala Ile Leu Arg Pro Gly Leu Glu
            260                 265                 270
```

```
Pro Gly Ala Val Asp Val Phe Leu Glu Phe Ile Cys Tyr Ser Gly Gly
        275                 280                 285

Pro Leu Pro Glu Asp Leu Leu Pro Leu Val Lys Cys Pro Val Leu Ile
290                 295                 300

Ala Trp Gly Glu Lys Asp Pro Trp Glu Pro Ile Glu Leu Gly Arg Ala
305                 310                 315                 320

Tyr Ser Asn Phe Asp Ala Val Glu Asp Phe Val Val Leu Pro Asp Ala
                325                 330                 335

Gly His Cys Pro Gln Asp Glu Lys Pro Glu Met Val Asn Pro Leu Ile
                340                 345                 350

Glu Ser Phe Val Ala Arg His
                355

<210> SEQ ID NO 6
<211> LENGTH: 321
<212> TYPE: PRT
<213> ORGANISM: Arabidopsis thaliana

<400> SEQUENCE: 6

Met Asp Thr Ser Ser Ala Ser Ser Gln Ser Val Gln Gly Ser Glu Arg
1               5                   10                  15

Leu Ala Phe Lys Pro Glu Gly Tyr Asn Phe Trp Glu Trp Arg Gly His
                20                  25                  30

Lys Ile His Tyr Val Val Gln Gly Glu Gly Ser Pro Leu Val Leu Ile
                35                  40                  45

His Gly Phe Gly Ala Ser Val Phe His Trp Arg Tyr Asn Ile Pro Glu
        50                  55                  60

Leu Ala Lys Lys Tyr Lys Val Tyr Ala Leu Asp Leu Leu Gly Phe Gly
65                  70                  75                  80

Trp Ser Asp Lys Ala Leu Ile Glu Tyr Asp Ala Met Val Trp Thr Asp
                85                  90                  95

Gln Val Ile Asp Phe Met Lys Glu Val Val Lys Glu Pro Ala Val Val
                100                 105                 110

Val Gly Asn Ser Leu Gly Gly Phe Thr Ala Leu Ser Val Ala Val Gly
                115                 120                 125

Leu Pro Glu Gln Val Thr Gly Val Ala Leu Leu Asn Ser Ala Gly Gln
        130                 135                 140

Phe Ala Ala Glu Ser Arg Lys Arg Glu Glu Ala Asp Glu Thr Val Ile
145                 150                 155                 160

Thr Lys Phe Ile Val Lys Pro Leu Lys Glu Ile Phe Gln Arg Val Val
                165                 170                 175

Leu Gly Phe Leu Phe Trp Gln Ala Lys Gln Pro Ser Arg Ile Glu Ser
                180                 185                 190

Val Leu Lys Ser Val Tyr Ile Asp Ser Thr Asn Val Asp Asp Tyr Leu
        195                 200                 205

Val Glu Ser Ile Ser Lys Pro Ala Thr Asp Pro Asn Ala Gly Glu Val
        210                 215                 220

Tyr Tyr Arg Leu Met Thr Arg Phe Leu Thr Asn Gln Ser Arg Tyr Thr
225                 230                 235                 240

Leu Asp Ser Val Leu Ser Lys Met Thr Cys Pro Leu Leu Leu Val Trp
                245                 250                 255

Gly Asp Leu Asp Pro Trp Val Gly Pro Ala Lys Ala Glu Lys Ile Lys
                260                 265                 270

Ala Phe Tyr Ser Asn Ser Ser Leu Val His Leu Gln Ala Gly His Cys
```

```
            275                 280                 285
Pro His Asp Glu Val Pro Glu Ala Val Asn Lys Ala Leu Leu Asp Trp
    290                 295                 300

Leu Ser Ile Asn Ile Ala Ser Lys Pro Ala Ser Pro Ile Val Leu Glu
305                 310                 315                 320

Thr

<210> SEQ ID NO 7
<211> LENGTH: 331
<212> TYPE: PRT
<213> ORGANISM: Arabidopsis thaliana

<400> SEQUENCE: 7

Met Glu Gly Ile Asp His Arg Met Val Ser Val Asn Gly Ile Thr Met
1               5                   10                  15

His Ile Ala Glu Lys Gly Pro Lys Glu Gly Pro Val Val Leu Leu Leu
            20                  25                  30

His Gly Phe Pro Asp Leu Trp Tyr Thr Trp Arg His Gln Ile Ser Gly
        35                  40                  45

Leu Ser Ser Leu Gly Tyr Arg Ala Val Ala Pro Asp Leu Arg Gly Tyr
    50                  55                  60

Gly Asp Ser Asp Ser Pro Glu Ser Phe Ser Glu Tyr Thr Cys Leu Asn
65                  70                  75                  80

Val Val Gly Asp Leu Val Ala Leu Leu Asp Ser Val Ala Gly Asn Gln
                85                  90                  95

Glu Lys Val Phe Leu Val Gly His Asp Trp Gly Ala Ile Ile Gly Trp
            100                 105                 110

Phe Leu Cys Leu Phe Arg Pro Glu Lys Ile Asn Gly Phe Val Cys Leu
        115                 120                 125

Ser Val Pro Tyr Arg Ser Arg Asn Pro Lys Val Lys Pro Val Gln Gly
    130                 135                 140

Phe Lys Ala Val Phe Gly Asp Asp Tyr Tyr Ile Cys Arg Phe Gln Glu
145                 150                 155                 160

Pro Gly Lys Ile Glu Gly Glu Ile Ala Ser Ala Asp Pro Arg Ile Phe
                165                 170                 175

Leu Arg Asn Leu Phe Thr Gly Arg Thr Leu Gly Pro Pro Ile Leu Pro
            180                 185                 190

Lys Asp Asn Pro Phe Gly Glu Lys Pro Asn Pro Asn Ser Glu Asn Ile
        195                 200                 205

Glu Leu Pro Glu Trp Phe Ser Lys Lys Asp Leu Asp Phe Tyr Val Ser
    210                 215                 220

Lys Phe Glu Lys Ala Gly Phe Thr Gly Gly Leu Asn Tyr Tyr Arg Ala
225                 230                 235                 240

Met Asp Leu Asn Trp Glu Leu Thr Ala Pro Trp Thr Gly Ala Lys Ile
                245                 250                 255

Gln Val Pro Val Lys Phe Met Thr Gly Asp Phe Asp Met Val Tyr Thr
            260                 265                 270

Thr Pro Gly Met Lys Glu Tyr Ile His Gly Gly Phe Ala Ala Asp
        275                 280                 285

Val Pro Thr Leu Gln Glu Ile Val Val Ile Glu Asp Ala Gly His Phe
    290                 295                 300

Val Asn Gln Glu Lys Pro Gln Glu Val Thr Ala His Ile Asn Asp Phe
305                 310                 315                 320

Phe Thr Lys Leu Arg Asp Asn Asn Lys Ser Phe
```

```
                    325                 330

<210> SEQ ID NO 8
<211> LENGTH: 648
<212> TYPE: PRT
<213> ORGANISM: Arabidopsis thaliana

<400> SEQUENCE: 8

Met Ala Lys Ser Trp Phe Leu Val Glu Lys Ala Arg Arg Cys Leu Arg
 1               5                   10                  15

Thr Val Phe Phe Met Val Ala Met Leu Ala Ser Leu Leu Val Ser Ser
                20                  25                  30

Leu Pro Leu Leu Val Ala Ile Gly Asp Val Leu Val Pro Ser Phe Leu
            35                  40                  45

Leu Ser Ser Phe Thr Cys Val Thr Cys Tyr Gly Ala Lys Glu His Leu
        50                  55                  60

Arg Arg Tyr Gly Phe Lys Arg Ser Leu Thr Asp Ile Pro Ile Val Ser
 65                  70                  75                  80

Val Val Arg Ser Phe Leu Val Ile Cys Ile Tyr Leu Leu Ser Asp Val
                 85                  90                  95

Pro Ala Leu Ser His Gly Pro Tyr Leu Gly Thr Val Ser Leu Cys Ser
            100                 105                 110

Val Val Ser Val Leu Leu Ser Val Lys Ala Cys Leu Phe Thr Val
        115                 120                 125

Asn Ser Gln Leu Asn Asn Glu Ala Ser Phe Ser Pro Ser Arg Lys Arg
130                 135                 140

Leu His Leu Lys Lys Ser Trp Gly Met Pro Val Leu Phe Leu Ser Ser
145                 150                 155                 160

Val Val Phe Ala Leu Gly His Thr Val Val Ala Tyr Arg Thr Ser Cys
                165                 170                 175

Arg Ala Arg Arg Lys Ile Leu Tyr His Arg Val Asp Pro Glu Ala Val
            180                 185                 190

Leu Ser Cys Lys Ser Ile Phe Ser Gly His Gln Lys Val Pro Arg Ser
        195                 200                 205

Pro Thr Pro Val Val Gly Lys Ala Ser Lys Phe Asp Gly Glu Ala Arg
    210                 215                 220

Arg Lys Pro Leu Ser His Asp Glu Gly Glu Leu Pro Val Arg Leu Leu
225                 230                 235                 240

Ala Asp Val Asp Ser Leu Phe Val Thr Ile Arg Gly Leu Thr Val His
                245                 250                 255

Tyr Lys Leu Cys Ser Pro Gly Ser Pro Arg Gln Ser Ile Ser Ser Asn
            260                 265                 270

Val Leu Glu Ala Asn Ser Ser Tyr Asn Thr Pro Glu Ile Met Ala Gly
        275                 280                 285

Arg Ser Lys Phe Asp Arg Lys Val Leu Ser Met Val Thr Lys Ser Gln
    290                 295                 300

His His His His Arg Ser Tyr Asn Ser Leu Phe Asn Asn Ser Ser
305                 310                 315                 320

Leu His Asp Pro Leu Leu Asp Gly Ser Pro Thr Ser Pro Leu Leu Phe
                325                 330                 335

Lys Glu Ile Lys Glu Gly Thr Gly Leu Val Asp Asp Met Asn Val Phe
            340                 345                 350

Asn Phe Gly Ala Glu Glu Gln Asp Leu Gly Glu Ser Gly Gln Phe Gly
        355                 360                 365
```

Val Val Leu Val His Gly Phe Gly Gly Gly Val Phe Ser Trp Arg His
370 375 380

Val Met Gly Ser Leu Ala Gln Gln Leu Gly Cys Val Val Thr Ala Phe
385 390 395 400

Asp Arg Pro Gly Trp Gly Leu Thr Ala Arg Pro His Lys Asn Asp Leu
405 410 415

Glu Glu Arg Gln Leu Leu Asn Pro Tyr Ser Leu Glu Asn Gln Val Glu
420 425 430

Met Leu Ile Ala Phe Cys Tyr Glu Met Gly Phe Ser Ser Val Val Phe
435 440 445

Val Gly His Asp Asp Gly Gly Leu Leu Ala Leu Lys Ala Ala Gln Arg
450 455 460

Leu Met Ala Thr Asn Asp Pro Ile Lys Val Val Lys Gly Val Val
465 470 475 480

Leu Leu Asn Thr Ser Leu Ser Arg Glu Val Val Pro Ala Phe Ala Arg
485 490 495

Ile Leu Leu His Thr Ser Leu Gly Lys Lys His Leu Val Arg Pro Leu
500 505 510

Leu Arg Thr Glu Ile Ala Gln Val Val Asn Arg Arg Ala Trp Tyr Asp
515 520 525

Pro Ala Lys Met Thr Thr Asp Val Leu Arg Leu Tyr Lys Ala Pro Leu
530 535 540

His Val Glu Gly Trp Asp Glu Ala Leu His Glu Ile Gly Arg Leu Ser
545 550 555 560

Ser Glu Met Val Leu Ala Pro Gln Asn Ala Ala Ser Leu Leu Lys Ala
565 570 575

Val Glu Asn Leu Pro Val Leu Val Ile Ala Gly Ala Glu Asp Ala Leu
580 585 590

Val Pro Leu Lys Ser Ser Gln Gly Met Ala Ser Lys Leu Leu Asn Ser
595 600 605

Arg Leu Val Ala Ile Ser Gly Cys Gly His Leu Pro His Glu Glu Cys
610 615 620

Pro Lys Ala Leu Leu Ala Ala Met Ser Pro Phe Ile Thr Arg Leu Val
625 630 635 640

Ile Arg Pro Asp Leu Gln Ser Gln
645

<210> SEQ ID NO 9
<211> LENGTH: 523
<212> TYPE: PRT
<213> ORGANISM: Arabidopsis thaliana

<400> SEQUENCE: 9

Met Leu Ser Ser Phe Gly Gly Ile Leu Leu Leu Val Lys Thr Cys
1 5 10 15

Val Phe Thr Val Asn Ser Thr Leu Glu Glu Ala Lys Val Tyr His Leu
20 25 30

Lys Ile Ser Trp Gly Met Pro Val Leu Leu Ser Ser Ala Val Phe
35 40 45

Gly Leu Ala His Val Val Ala Tyr Arg Lys Ser Cys Gly Ala Arg
50 55 60

Arg Lys Leu Met Tyr His Lys Ile Asp Gln Glu Ala Val Leu Ser Cys
65 70 75 80

Lys Ser Gly Phe Ser Gly Tyr Lys Lys Ala His Arg Gln Ser Phe Thr
85 90 95

```
Arg Ser Asn Cys Lys Ile Leu Thr Phe Ala Gly Glu Phe Arg Gln Lys
            100                 105                 110

Ser Phe Arg Gly Thr Ser Leu Asp Arg Glu Glu Leu Leu Gln Pro Arg
            115                 120                 125

Leu Leu Ala Asn Ala Asp Ser Leu Phe Ile Lys Ile Gln Gly Leu Tyr
            130                 135                 140

Val His Tyr Lys Gln Arg Thr Ser Pro Ser Val Ser Ser Phe Val Ile
145                 150                 155                 160

Ile Ser Asp Ser Ala Ala Glu Met Asn Ala Arg Arg Ser Arg Leu Leu
                165                 170                 175

Asp Lys Gln Met Ser Asn Leu Thr Ser Gln Thr Gln Asn Ser His Phe
            180                 185                 190

His Arg Ser Tyr Thr Ile Gln Pro Asp Arg Ser Ser Leu Tyr Asp Pro
            195                 200                 205

Leu Leu Ala Ser His Asn Thr Thr Pro Ile Ser Leu Phe Asp Lys Asp
            210                 215                 220

Gly Val Asn Gln Ile Asn Ser Ile Lys Leu Gly Asp Asp Met Glu Lys
225                 230                 235                 240

Asp Glu Asn Thr Gly Ile Val Leu Val His Gly Phe Gly Gly Val
                245                 250                 255

Phe Ser Trp Arg His Val Met Gly Glu Leu Ser Leu Gln Leu Gly Cys
            260                 265                 270

Arg Val Val Ala Tyr Asp Arg Pro Gly Trp Gly Leu Thr Ser Arg Leu
            275                 280                 285

Ile Arg Lys Asp Trp Glu Lys Arg Asn Leu Ala Asn Pro Tyr Lys Leu
            290                 295                 300

Glu Ser Gln Val Asp Leu Leu Ser Phe Cys Ser Glu Met Gly Phe
305                 310                 315                 320

Ser Ser Val Ile Leu Val Gly His Asp Asp Gly Gly Leu Leu Ala Leu
            325                 330                 335

Lys Ala Ala Glu Arg Met Gln Ala Ser Thr Ser Lys His Asn Ile Thr
            340                 345                 350

Ile Lys Gly Val Val Leu Ile Asn Val Ser Leu Ser Arg Glu Val Val
            355                 360                 365

Pro Ala Phe Ala Arg Ile Leu Leu His Thr Ser Leu Arg Lys Lys His
            370                 375                 380

Leu Val Arg Pro Leu Leu Arg Thr Glu Ile Thr Gln Leu Val Asn Arg
385                 390                 395                 400

Arg Ala Trp Cys Asp Thr Thr Lys Leu Thr Thr Asp Ile Thr Met Leu
            405                 410                 415

Tyr Lys Ala Pro Leu Cys Leu Glu Ala Trp Asp Glu Ala Leu Asn Glu
            420                 425                 430

Ile Ser Lys Leu Ser Tyr Glu Met Ile Leu Ser Pro Gln Asn Ala Ser
            435                 440                 445

Ala Leu Val Lys Ser Ile Gly Asp Leu Pro Val Leu Val Val Ala Gly
            450                 455                 460

Ala Glu Asp Ala Leu Val Pro Leu Lys Ser Ser Gln Val Leu Ala Ser
465                 470                 475                 480

Lys Leu Thr Asn Ser Arg Leu Val Glu Ile Ser Gly Cys Gly His Leu
            485                 490                 495

Pro His Glu Glu Cys Pro Thr Thr Leu Val Ser Ala Leu Gly Ser Phe
            500                 505                 510
```

```
Ile Cys Arg Leu Ile Pro Lys Leu Pro Asn Ser
        515                 520

<210> SEQ ID NO 10
<211> LENGTH: 362
<212> TYPE: PRT
<213> ORGANISM: Arabidopsis thaliana

<400> SEQUENCE: 10

Met Arg Ala Leu Thr Trp Thr Ala Met Ser Pro Val Met Ser Arg
 1               5                  10                  15

Thr Ala Thr Ser Thr Val Asn Leu Arg Arg Ile Ser Leu Arg Arg Asp
            20                  25                  30

Arg Val Cys Val Arg Ala Thr Ala Ser Ser Ser Ala Thr Val Ser Gly
        35                  40                  45

Gly Gly Val Val Glu Ala Val Glu Leu Ala Glu Ile Gly Glu Arg Ser
    50                  55                  60

Lys Lys Trp Lys Trp Lys Gly Glu Tyr Ser Val Asn Tyr Phe Val Lys
65                  70                  75                  80

Asp Ser Pro Glu Glu Val Thr Pro Ala Ser Gln Thr Val Leu Leu Val
                85                  90                  95

His Gly Phe Gly Ala Ser Ile Pro His Trp Arg Arg Asn Ile Asn Ala
            100                 105                 110

Leu Ser Lys Asn His Thr Val Tyr Ala Ile Asp Leu Leu Gly Phe Gly
        115                 120                 125

Ala Ser Asp Lys Pro Pro Gly Phe Ser Tyr Thr Met Glu Ser Trp Ala
    130                 135                 140

Glu Leu Ile Leu Asn Phe Leu Glu Glu Val Val Gln Lys Pro Thr Ile
145                 150                 155                 160

Leu Ile Gly Asn Ser Val Gly Ser Leu Ala Cys Val Ile Ala Ala Ser
                165                 170                 175

Glu Ser Arg Gly Asp Leu Val Lys Gly Leu Val Leu Leu Asn Cys Ala
            180                 185                 190

Gly Gly Met Asn Asn Lys Ala Val Phe Asp Asp Trp Arg Ile Lys Leu
        195                 200                 205

Leu Met Pro Leu Leu Leu Ile Asp Phe Leu Leu Lys Gln Arg Gly
    210                 215                 220

Ile Ala Ser Ala Leu Phe Asn Arg Val Lys Asp Arg Glu Asn Leu Lys
225                 230                 235                 240

Asn Ile Leu Thr Asn Val Tyr Gly Asn Lys Asp Asn Val Asp Asp Thr
                245                 250                 255

Leu Val Glu Ile Ile Ala Gly Pro Ala Asn Thr Glu Gly Ala Leu Asp
            260                 265                 270

Ala Phe Val Ser Ile Leu Thr Gly Pro Gly Pro Asn Pro Ile Lys
    275                 280                 285

Leu Ile Pro Glu Ile Thr Lys Pro Val Leu Val Leu Trp Gly Asp Gln
    290                 295                 300

Asp Gly Leu Thr Pro Leu Asp Gly Pro Val Gly Lys Tyr Phe Thr Ser
305                 310                 315                 320

Leu Pro Asp Gln Leu Pro Asn Phe Asn Leu Tyr Val Leu Gln Gly Val
                325                 330                 335

Gly His Cys Pro Gln Asp Asp Arg Pro Asp Leu Val His Glu Arg Leu
            340                 345                 350

Leu Pro Trp Leu Ala Gln Leu Ser Ser Thr
        355                 360
```

<210> SEQ ID NO 11
<211> LENGTH: 324
<212> TYPE: PRT
<213> ORGANISM: Arabidopsis thaliana

<400> SEQUENCE: 11

| Met | Glu | Lys | Ile | Glu | His | Thr | Thr | Ile | Ser | Thr | Asn | Gly | Ile | Asn | Met |
|---|---|---|---|---|---|---|---|---|---|---|---|---|---|---|---|
| 1 | | | | 5 | | | | | 10 | | | | | 15 | |

| His | Val | Ala | Ser | Ile | Gly | Ser | Gly | Pro | Val | Ile | Leu | Phe | Val | His | Gly |
| | | | 20 | | | | | 25 | | | | | 30 | | |

| Phe | Pro | Asp | Leu | Trp | Tyr | Ser | Trp | Arg | His | Gln | Leu | Val | Ser | Phe | Ala |
| | | 35 | | | | | 40 | | | | | 45 | | | |

| Ala | Leu | Gly | Tyr | Arg | Ala | Ile | Ala | Pro | Asp | Leu | Arg | Gly | Tyr | Gly | Asp |
| 50 | | | | | 55 | | | | | 60 | | | | | |

| Ser | Asp | Ala | Pro | Pro | Ser | Arg | Glu | Ser | Tyr | Thr | Ile | Leu | His | Ile | Val |
| 65 | | | | | 70 | | | | | 75 | | | | | 80 |

| Gly | Asp | Leu | Val | Gly | Leu | Leu | Asp | Ser | Leu | Gly | Val | Asp | Arg | Val | Phe |
| | | | | 85 | | | | | 90 | | | | | 95 | |

| Leu | Val | Gly | His | Asp | Trp | Gly | Ala | Ile | Val | Ala | Trp | Trp | Leu | Cys | Met |
| | | | 100 | | | | | 105 | | | | | 110 | | |

| Ile | Arg | Pro | Asp | Arg | Val | Asn | Ala | Leu | Val | Asn | Thr | Ser | Val | Val | Phe |
| | | 115 | | | | | 120 | | | | | 125 | | | |

| Asn | Pro | Arg | Asn | Pro | Ser | Val | Lys | Pro | Val | Asp | Ala | Phe | Arg | Ala | Leu |
| 130 | | | | | 135 | | | | | 140 | | | | | |

| Phe | Gly | Asp | Asp | Tyr | Tyr | Ile | Cys | Arg | Phe | Gln | Glu | Pro | Gly | Glu | Ile |
| 145 | | | | | 150 | | | | | 155 | | | | | 160 |

| Glu | Glu | Asp | Phe | Ala | Gln | Val | Asp | Thr | Lys | Lys | Leu | Ile | Thr | Arg | Phe |
| | | | | 165 | | | | | 170 | | | | | 175 | |

| Phe | Thr | Ser | Arg | Asn | Pro | Arg | Pro | Cys | Ile | Pro | Lys | Ser | Val | Gly |
| | | | 180 | | | | | 185 | | | | | 190 | | |

| Phe | Arg | Gly | Leu | Pro | Asp | Pro | Ser | Leu | Pro | Ala | Trp | Leu | Thr | Glu |
| | | | 195 | | | | | 200 | | | | | 205 | | |

| Gln | Asp | Val | Arg | Phe | Tyr | Gly | Asp | Lys | Phe | Ser | Gln | Lys | Gly | Phe | Thr |
| 210 | | | | | 215 | | | | | 220 | | | | | |

| Gly | Gly | Leu | Asn | Tyr | Tyr | Arg | Ala | Leu | Asn | Leu | Ser | Trp | Glu | Leu | Thr |
| 225 | | | | | 230 | | | | | 235 | | | | | 240 |

| Ala | Pro | Trp | Thr | Gly | Leu | Gln | Ile | Lys | Val | Pro | Val | Lys | Phe | Ile | Val |
| | | | | 245 | | | | | 250 | | | | | 255 | |

| Gly | Asp | Leu | Asp | Ile | Thr | Tyr | Asn | Ile | Pro | Gly | Thr | Lys | Glu | Tyr | Ile |
| | | | 260 | | | | | 265 | | | | | 270 | | |

| His | Glu | Gly | Gly | Leu | Lys | Lys | His | Val | Pro | Phe | Leu | Gln | Glu | Val | Val |
| | | | 275 | | | | | 280 | | | | | 285 | | |

| Val | Met | Glu | Gly | Val | Gly | His | Phe | Leu | His | Gln | Glu | Lys | Pro | Asp | Glu |
| | | | 290 | | | | | 295 | | | | | 300 | | |

| Val | Thr | Asp | His | Ile | Tyr | Gly | Phe | Phe | Lys | Lys | Phe | Arg | Thr | Arg | Glu |
| 305 | | | | | 310 | | | | | 315 | | | | | 320 |

| Thr | Ala | Ser | Leu |
|---|---|---|---|

<210> SEQ ID NO 12
<211> LENGTH: 270
<212> TYPE: PRT
<213> ORGANISM: Arabidopsis thaliana

<400> SEQUENCE: 12

Met Gly Val Val Glu Ala His Asn Val Lys Val Ile Gly Ser Gly
1               5                   10                  15

Glu Ala Thr Ile Val Leu Gly His Gly Phe Gly Thr Asp Gln Ser Val
            20                  25                  30

Trp Lys Asp Leu Val Pro His Leu Val Asp Asp Tyr Arg Val Val Leu
        35                  40                  45

Tyr Asp Asn Met Gly Ala Gly Thr Thr Asn Pro Asp Tyr Phe Asp Phe
50                  55                  60

Asp Arg Tyr Ser Asn Leu Glu Gly Tyr Ser Phe Asp Leu Ile Ala Ile
65                  70                  75                  80

Leu Glu Asp Leu Lys Ile Glu Ser Cys Ile Phe Val Gly His Ser Val
                85                  90                  95

Ser Ala Met Ile Gly Val Leu Ala Ser Leu Asn Arg Pro Asp Leu Phe
            100                 105                 110

Ser Lys Ile Val Met Ile Ser Ala Ser Pro Arg Tyr Val Asn Asp Val
        115                 120                 125

Asp Tyr Gln Gly Gly Phe Glu Gln Glu Asp Leu Asn Gln Leu Phe Glu
130                 135                 140

Ala Ile Arg Ser Asn Tyr Lys Ala Trp Cys Leu Gly Phe Ala Pro Leu
145                 150                 155                 160

Ala Val Gly Gly Asp Met Asp Ser Ile Ala Val Gln Glu Phe Ser Arg
                165                 170                 175

Thr Leu Phe Asn Met Arg Pro Asp Ile Ala Leu Ser Val Gly Gln Thr
            180                 185                 190

Ile Phe Gln Ser Asp Met Arg Gln Ile Leu Pro Phe Val Thr Val Pro
        195                 200                 205

Cys His Ile Leu Gln Ser Val Lys Asp Leu Ala Val Pro Val Val Val
210                 215                 220

Ser Glu Tyr Leu His Ala Asn Leu Gly Cys Glu Ser Val Val Glu Val
225                 230                 235                 240

Ile Pro Ser Asp Gly His Leu Pro Gln Leu Ser Ser Pro Asp Ser Val
                245                 250                 255

Ile Pro Val Ile Leu Arg His Ile Arg Asn Asp Ile Ala Met
            260                 265                 270

<210> SEQ ID NO 13
<211> LENGTH: 269
<212> TYPE: PRT
<213> ORGANISM: Arabidopsis thaliana

<400> SEQUENCE: 13

Met Gly Val Val Glu Ala His Asn Val Lys Val Ile Gly Ser Gly
1               5                   10                  15

Glu Ala Thr Ile Val Leu Gly His Gly Phe Gly Thr Asp Gln Val Trp
            20                  25                  30

Lys Asn Leu Val Pro His Leu Val Asp Asp Tyr Arg Val Val Leu Tyr
        35                  40                  45

Asp Asn Met Gly Ala Gly Thr Thr Asn Pro Asp Tyr Phe Asp Phe Asp
50                  55                  60

Arg Tyr Ser Asn Leu Glu Gly Tyr Ser Phe Asp Leu Ile Ala Met Leu
65                  70                  75                  80

Glu Asp Leu Lys Ile Glu Ser Cys Ile Phe Val Gly His Ser Val Ser
                85                  90                  95

Ala Ile Ile Gly Val Leu Ala Phe Leu Asn Arg Pro Asp Leu Phe Ser
            100                 105                 110

Lys Ile Val Met Ile Ser Ala Ser Pro Arg Tyr Val Asn Asp Val Asp
            115                 120                 125

Tyr Gln Gly Gly Phe Glu Gln Glu Asp Leu Asn Gln Leu Phe Glu Ala
130                 135                 140

Ile Arg Ser Asn Tyr Lys Ala Trp Cys Leu Gly Phe Ala Pro Leu Ala
145                 150                 155                 160

Val Gly Gly Asp Met Asp Ser Ile Ala Val Gln Glu Phe Ser Arg Thr
                165                 170                 175

Leu Phe Asn Met Arg Pro Asp Ile Ala Leu Ser Val Gly Gln Thr Ile
                180                 185                 190

Phe Gln Ser Asp Met Arg Lys Ile Leu Pro Phe Val Thr Val Pro Cys
            195                 200                 205

Tyr Ile Leu Gln Ser Val Lys Asp Leu Ala Val Pro Val Val Ser
            210                 215                 220

Glu Tyr Leu His Ala Asn Leu Gly Cys Glu Ser Val Val Glu Val Ile
225                 230                 235                 240

Pro Ser Asp Gly His Leu Pro Gln Leu Ser Ser Pro Asp Ser Val Ile
                245                 250                 255

Pro Val Ile Leu Arg His Ile Arg Asn Asp Ile Ala Met
                260                 265

<210> SEQ ID NO 14
<211> LENGTH: 269
<212> TYPE: PRT
<213> ORGANISM: Populus trichocarpa

<400> SEQUENCE: 14

Met Gly Ile Val Glu Glu Ala His Asn Ala Lys Ile Leu Gly Ser Gly
1               5                   10                  15

Glu Gln Val Ile Val Leu Ala His Gly Phe Gly Thr Asp Gln Ser Val
            20                  25                  30

Trp Lys His Leu Ile Pro His Ile Val Asp Glu Tyr Lys Val Ile Leu
        35                  40                  45

Tyr Asp Asn Met Gly Ala Gly Thr Thr Asn Pro Asp Tyr Phe Asp Phe
50                  55                  60

Asn Arg Tyr Ser Ser Leu Glu Gly Tyr Ala Tyr Asp Leu Leu Ala Ile
65                  70                  75                  80

Leu Glu Glu Leu Lys Val Glu Ser Cys Ile Leu Val Ala His Ser Val
                85                  90                  95

Ser Gly Ile Ile Gly Ala Ile Ala Ser Ile Ser Arg Pro Asp Leu Phe
            100                 105                 110

Ser Lys Ile Val Met Leu Ser Ala Ser Pro Arg Tyr Leu Asn Asp Val
            115                 120                 125

Asp Tyr Tyr Gly Gly Phe Glu Gln Glu Asp Leu Asp Gln Leu Phe Glu
130                 135                 140

Ala Met Gln Asn Asn Tyr Lys Ala Trp Cys Ser Gly Phe Ala Pro Leu
145                 150                 155                 160

Ala Val Gly Gly Asp Met Asp Ser Val Ala Val Gln Glu Phe Ser Arg
                165                 170                 175

Thr Leu Phe Asn Met Arg Pro Asp Ile Ala Leu Ser Val Ala Gln Thr
                180                 185                 190

Ile Phe Gln Ser Asp Met Arg Ser Ile Leu His Met Val Thr Val Pro
            195                 200                 205

Cys His Ile Leu Gln Ser Met Lys Asp Leu Ala Val Pro Val Val Ala

```
            210                 215                 220
Ala Glu Tyr Leu His Gln Asn Leu Gly Gly Glu Ser Ile Val Glu Val
225                 230                 235                 240

Met Ser Ser Asp Gly His Leu Pro Gln Leu Ser Ser Pro Asp Ile Val
                245                 250                 255

Ile Pro Val Leu Leu Lys His Ile Arg Tyr Asn Ile Ala
            260                 265

<210> SEQ ID NO 15
<211> LENGTH: 271
<212> TYPE: PRT
<213> ORGANISM: Oryza sativa

<400> SEQUENCE: 15

Met Gly Ile Val Glu Glu Ala His Asn Leu Arg Val Val Gly Glu Gly
 1               5                  10                  15

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65                  70                  75                  80

Ile Leu Gln Glu Leu Arg Val Ala Ser Cys Ile Tyr Val Gly His Ser
                85                  90                  95

Val Ser Ala Val Ile Gly Ala Ile Ala Ser Ile Ser Arg Pro Asp Leu
            100                 105                 110

Phe Ser Lys Leu Val Leu Leu Ser Ala Ser Pro Arg Tyr Leu Asn Asp
        115                 120                 125

Val Asp Tyr Tyr Gly Gly Phe Glu Gln Glu Asp Leu Asp Glu Leu Phe
    130                 135                 140

Glu Ala Met Gly Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro Leu Val Thr Val
        195                 200                 205

Pro Cys His Ile Val Gln Ser Thr Lys Asp Leu Ala Val Pro Val Val
    210                 215                 220

Val Ser Glu Tyr Leu His Lys His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Ile Pro Val Leu Leu Arg His Ile Gln His Asp Ile Ala Val
            260                 265                 270

<210> SEQ ID NO 16
<211> LENGTH: 271
<212> TYPE: PRT
<213> ORGANISM: Oryza sativa

<400> SEQUENCE: 16

Met Gly Ile Val Glu Glu Ala His Asn Leu Arg Val Val Gly Glu Gly
```

```
               1               5              10              15

Lys Arg Gly Val Ile Val Leu Ala His Gly Phe Gly Thr Asp Gln Ser
                        20                  25                  30

Val Trp Lys His Leu Val Pro His Leu Val Ala Asp Tyr Arg Val Val
                    35                  40                  45

Leu Phe Asp Thr Met Gly Ala Gly Pro Thr Asn Pro Asp Tyr Phe Asp
                50                  55                  60

Phe Ser Arg Tyr Ala Thr Leu Glu Gly Tyr Ala Leu Asp Leu Leu Ala
        65                  70                  75                  80

Ile Leu Gln Glu Leu Arg Val Ala Ser Cys Ile Tyr Val Gly His Ser
                        85                  90                  95

Val Ser Ala Val Ile Gly Ala Ile Ala Ser Ile Ser Arg Pro Asp Leu
                    100                 105                 110

Phe Ser Lys Leu Val Leu Leu Ser Ala Ser Pro Arg Tyr Leu Asn Asp
                115                 120                 125

Val Asp Tyr Tyr Gly Gly Phe Glu Gln Glu Asp Leu Asp Gly Leu Phe
            130                 135                 140

Glu Ala Met Gly Ser Asn Tyr Lys Ala Trp Cys Ser Gly Phe Ala Pro
        145                 150                 155                 160

Leu Cys Val Gly Gly Asp Met Glu Ser Val Ala Val Gln Glu Phe Ser
                        165                 170                 175

Arg Thr Leu Phe Asn Ile Arg Pro Asp Ile Ala Leu Ser Val Ala Gln
                    180                 185                 190

Thr Ile Phe Gln Ser Asp Val Arg Ser Leu Leu Pro Leu Val Thr Val
                195                 200                 205

Pro Cys His Ile Val Gln Ser Thr Lys Asp Leu Ala Val Pro Val Val
            210                 215                 220

Val Ser Glu Tyr Leu His Lys His Leu Gly Gly Asp Ser Ile Val Glu
        225                 230                 235                 240

Val Met Pro Ser Glu Gly His Leu Pro Gln Leu Ser Ser Pro Asp Ile
                        245                 250                 255

Val Ile Pro Val Leu Leu Arg His Ile Gln His Asp Ile Ala Val
                    260                 265                 270

<210> SEQ ID NO 17
<211> LENGTH: 271
<212> TYPE: PRT
<213> ORGANISM: Oryza sativa

<400> SEQUENCE: 17

Met Gly Ile Val Glu Glu Ala His Asn Leu Arg Val Val Gly Glu Gly
        1               5                  10                  15

Lys Arg Gly Val Ile Val Leu Ala His Gly Phe Gly Thr Asp Gln Ser
                        20                  25                  30

Val Trp Lys His Leu Val Pro His Leu Val Ala Asp Tyr Arg Val Val
                    35                  40                  45

Leu Phe Asp Thr Met Gly Ala Gly Pro Thr Asn Pro Asp Tyr Phe Asp
                50                  55                  60

Phe Ser Arg Tyr Ala Thr Leu Glu Gly Tyr Ala Leu Asp Leu Leu Ala
        65                  70                  75                  80

Ile Leu Gln Glu Leu Arg Val Ala Ser Cys Ile Tyr Val Gly His Ser
                        85                  90                  95

Val Ser Ala Val Ile Gly Ala Ile Ala Ser Ile Ser Arg Pro Asp Leu
                    100                 105                 110
```

```
Phe Ser Lys Leu Val Leu Leu Ser Ala Ser Pro Arg Tyr Leu Asn Asp
            115                 120                 125

Val Asp Tyr Tyr Gly Gly Phe Glu Gln Glu Asp Leu Asp Glu Leu Phe
        130                 135                 140

Glu Ala Met Gly Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro Leu Val Thr Val
        195                 200                 205

Pro Cys His Ile Val Gln Ser Thr Lys Asp Leu Ala Val Pro Val Val
    210                 215                 220

Val Ser Glu Tyr Leu His Lys His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Ile Pro Val Leu Arg His Ile Gln His Asp Ile Ala Val
            260                 265                 270

<210> SEQ ID NO 18
<211> LENGTH: 271
<212> TYPE: PRT
<213> ORGANISM: Hordeum vulgare

<400> SEQUENCE: 18

Met Gly Ile Val Glu Glu Ala His Asn Leu Arg Val Val Gly Glu Gly
1               5                   10                  15

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65                  70                  75                  80

Ile Leu Glu Glu Leu Gly Ile Ala Ser Cys Ile Tyr Val Gly His Ser
                85                  90                  95

Val Ser Ala Val Ile Gly Val Leu Ala Ser Ile Ser Arg Pro Asp Leu
            100                 105                 110

Phe Ser Lys Leu Val Leu Leu Ser Ala Ser Pro Arg Tyr Leu Asn Asp
        115                 120                 125

Val Asp Tyr Tyr Gly Gly Phe Glu Gln Glu Glu Leu Asp Glu Leu Phe
    130                 135                 140

Glu Ala Met Arg Ser Asn Tyr Lys Ala Trp Cys Ser Gly Phe Ala Pro
145                 150                 155                 160

Leu Cys Val Gly Gly Asp Leu Glu Ser Val Ser Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Thr Leu Leu Pro Leu Val Ser Val
        195                 200                 205

Pro Cys His Ile Val Gln Ser Thr Lys Asp Leu Ala Val Pro Val Val
    210                 215                 220
```

```
Val Ser Glu Tyr Leu His Lys His Leu Gly Ser Asp Ser Ile Val Glu
225                 230                 235                 240

Val Met Pro Ser Glu Gly His Leu Pro Gln Leu Ser Ser Pro Asp Ile
                245                 250                 255

Val Thr Pro Val Leu Leu Arg His Ile Gln His Asp Ile Ala Phe
            260                 265                 270
```

<210> SEQ ID NO 19
<211> LENGTH: 271
<212> TYPE: PRT
<213> ORGANISM: Oryza sativa

<400> SEQUENCE: 19

```
Met Gly Ile Val Glu Glu Ala His Asn Leu Arg Val Val Gly Glu Gly
1               5                   10                  15

Lys Arg Gly Val Ile Val Leu Ala His Gly Phe Gly Thr Asp Gln Ser
                20                  25                  30

Val Trp Lys His Leu Val Pro His Leu Ala Asp Tyr Arg Val Val
            35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65              70                  75                  80

Ile Leu Gln Glu Leu Arg Val Ala Ser Cys Ile Tyr Val Gly His Ser
                85                  90                  95

Val Ser Ala Val Ile Gly Ala Ile Ala Ser Ile Ser Arg Pro Asp Leu
            100                 105                 110

Phe Ser Lys Leu Val Leu Leu Ser Ala Ser Pro Arg Tyr Leu Asn Asp
        115                 120                 125

Val Asp Tyr Tyr Gly Gly Phe Glu Gln Glu Asp Leu Asp Glu Leu Phe
    130                 135                 140

Glu Ala Met Gly Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro Leu Val Thr Val
        195                 200                 205

Pro Cys His Ile Val Gln Ser Thr Lys Asp Leu Ala Val Pro Val Val
    210                 215                 220

Val Ser Glu Tyr Leu His Lys His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Ile Pro Val Leu Leu Arg His Ile Gln His Asp Ile Ala Val
            260                 265                 270
```

<210> SEQ ID NO 20
<211> LENGTH: 268
<212> TYPE: PRT
<213> ORGANISM: Medicago truncatula

<400> SEQUENCE: 20

```
Met Gly Ile Val Glu Glu Ala His Asn Val Lys Val Leu Gly Thr Gly
1               5                   10                  15
```

Asn Arg Tyr Ile Val Leu Ala His Gly Phe Gly Thr Asp Gln Ser Val
                 20                  25                  30

Trp Lys His Phe Val Pro Tyr Leu Val Asp Asp Phe Arg Val Val Leu
             35                  40                  45

Tyr Asp Asn Met Gly Ala Gly Thr Thr Asn Pro Glu Tyr Phe Asp Ser
 50                  55                  60

Glu Arg His Ser Ser Leu Glu Gly Tyr Ala Tyr Asp Leu Leu Ala Ile
 65                  70                  75                  80

Leu Glu Glu Leu Gln Ile Asp Ser Cys Ile Phe Val Gly His Ser Val
                 85                  90                  95

Ser Ala Met Ile Gly Ala Ile Ala Ser Ile Thr Arg Pro Asp Leu Phe
            100                 105                 110

Leu Lys Leu Ile Met Val Ser Ser Pro Arg Tyr Leu Asn Asp Val
            115                 120                 125

Asn Tyr Phe Gly Gly Phe Glu Gln Glu Asp Leu Asn Gln Leu Phe Asn
130                 135                 140

Ala Met Ala Glu Asn Tyr Lys Ala Trp Cys Tyr Gly Phe Ala Pro Leu
145                 150                 155                 160

Ala Val Gly Gly Asp Met Asp Ser Val Ala Val Gln Glu Phe Ser Arg
                165                 170                 175

Thr Leu Phe Asn Met Arg Pro Asp Ile Ala Leu Ile Val Ser Arg Thr
            180                 185                 190

Ile Phe Gln Ser Asp Met Arg Gln Ile Leu Asn Leu Val Thr Val Pro
            195                 200                 205

Cys His Ile Ile Gln Ala Glu Lys Asp Met Ala Val Pro Val Met Val
            210                 215                 220

Ser Glu Tyr Leu His Gln His Leu Gly Gly Gln Ser Ile Val Glu Val
225                 230                 235                 240

Met Thr Thr Asp Gly His Leu Pro Gln Leu Ser Ser Pro Asp Ile Val
                245                 250                 255

Ile Pro Val Leu Leu Arg His Ile Gln Leu Asn Ile
            260                 265

<210> SEQ ID NO 21
<211> LENGTH: 271
<212> TYPE: PRT
<213> ORGANISM: Oryza sativa

<400> SEQUENCE: 21

Met Gly Ile Val Glu Glu Ala His Asn Leu Arg Val Val Gly Glu Gly
 1               5                  10                  15

Lys Arg Gly Val Ile Val Leu Ala His Gly Phe Gly Thr Asp Gln Ser
                 20                  25                  30

Val Trp Lys His Leu Val Pro His Leu Val Ala Asp Tyr Arg Val Val
             35                  40                  45

Leu Phe Asp Thr Met Gly Ala Gly Pro Thr Asn Pro Asp Tyr Phe Asp
 50                  55                  60

Phe Ser Arg Tyr Ala Thr Leu Glu Gly Tyr Ala Leu Asp Leu Leu Ala
 65                  70                  75                  80

Ile Leu Gln Glu Leu Arg Val Ala Ser Cys Ile Tyr Val Gly His Ser
                 85                  90                  95

Val Ser Ala Val Ile Gly Ala Ile Ala Ser Ile Ser Arg Pro Asp Leu
            100                 105                 110

Phe Ser Lys Leu Val Leu Leu Ser Ala Ser Pro Arg Tyr Leu Asn Asp

```
            115                 120                 125
Val Asp Tyr Tyr Gly Gly Phe Glu Gln Glu Asp Leu Asp Glu Leu Phe
    130                 135                 140

Glu Ala Met Gly Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro Leu Val Thr Val
        195                 200                 205

Pro Cys His Ile Val Gln Ser Thr Lys Asp Leu Ala Val Ala Val Val
    210                 215                 220

Val Ser Glu Tyr Leu His Lys His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Ile Pro Val Leu Leu Arg His Ile Gln His Asp Ile Ala Val
            260                 265                 270

<210> SEQ ID NO 22
<211> LENGTH: 271
<212> TYPE: PRT
<213> ORGANISM: Zea mays

<400> SEQUENCE: 22

Met Gly Ile Val Glu Glu Ala His Asn Leu Arg Val Val Gly Glu Gly
1               5                   10                  15

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65                  70                  75                  80

Ile Leu Gln Glu Leu Gly Val Arg Ser Cys Ile Tyr Val Gly His Ser
                85                  90                  95

Val Ser Ala Val Ile Gly Ala Leu Ala Ser Ile Ser Arg Pro Asp Leu
            100                 105                 110

Phe Thr Lys Leu Val Leu Leu Ser Ala Ser Pro Arg Tyr Leu Asn Asp
        115                 120                 125

Val Asp Tyr Tyr Gly Gly Phe Glu Gln Asp Glu Leu Asp Glu Leu Phe
    130                 135                 140

Glu Ala Met Arg Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro His Val Thr Val
        195                 200                 205

Pro Cys His Ile Val Gln Ser Thr Lys Asp Leu Ala Val Pro Val Val
    210                 215                 220
```

```
Val Ser Glu Tyr Leu His Arg His Leu Gly Gly Asp Ser Ile Val Glu
225                 230                 235                 240

Val Met Pro Ser Glu Gly His Leu Pro Gln Leu Ser Ser Pro Asp Ile
            245                 250                 255

Val Ile Pro Val Leu Leu Arg His Ile Gln His Asp Ile Ala Val
        260                 265                 270
```

<210> SEQ ID NO 23
<211> LENGTH: 271
<212> TYPE: PRT
<213> ORGANISM: Zea mays

<400> SEQUENCE: 23

```
Met Gly Ile Val Glu Glu Ala His Asn Leu Arg Val Val Gly Glu Gly
1               5                   10                  15

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65                  70                  75                  80

Ile Leu Gln Glu Leu Gly Val Arg Ser Cys Ile Tyr Val Gly His Ser
                85                  90                  95

Val Ser Ala Val Ile Gly Ala Leu Ala Ser Ile Ser Arg Pro Asp Leu
            100                 105                 110

Phe Thr Lys Leu Val Leu Leu Ser Ala Ser Pro Arg Tyr Leu Asn Asp
        115                 120                 125

Val Asp Tyr Tyr Gly Gly Phe Glu Gln Asp Glu Leu Asp Glu Leu Phe
    130                 135                 140

Glu Ala Met Arg Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro His Val Thr Val
        195                 200                 205

Pro Cys His Ile Val Gln Ser Thr Lys Asp Leu Ala Val Pro Val Val
    210                 215                 220

Val Ser Glu Tyr Leu His Arg His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Ile Pro Val Leu Leu Arg His Ile Gln His Asp Ile Ala Val
            260                 265                 270
```

<210> SEQ ID NO 24
<211> LENGTH: 271
<212> TYPE: PRT
<213> ORGANISM: Zea mays

<400> SEQUENCE: 24

```
Met Gly Ile Val Glu Glu Ala His Asn Leu Arg Val Val Gly Glu Gly
1               5                   10                  15
```

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65                  70                  75                  80

Ile Leu Gln Glu Leu Gly Val Arg Ser Cys Ile Tyr Val Gly His Ser
                85                  90                  95

Val Ser Ala Val Ile Gly Ala Leu Ala Ser Ile Ser Arg Pro Asp Leu
            100                 105                 110

Phe Thr Lys Leu Val Leu Leu Ser Ala Ser Pro Arg Tyr Leu Asn Asp
        115                 120                 125

Val Asp Tyr Tyr Gly Gly Phe Glu Gln Asp Glu Leu Asp Glu Leu Phe
    130                 135                 140

Glu Ala Met Arg Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Thr Ile Phe Gln Ser Asp Val Arg Ser Leu Leu Pro His Val Thr Val
        195                 200                 205

Pro Cys His Ile Val Gln Ser Thr Lys Asp Leu Ala Val Pro Val Val
    210                 215                 220

Val Ser Glu Tyr Leu His Arg His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Ile Pro Val Leu Leu Arg His Ile Gln His Asp Ile Ala Val
            260                 265                 270

<210> SEQ ID NO 25
<211> LENGTH: 271
<212> TYPE: PRT
<213> ORGANISM: Zea mays

<400> SEQUENCE: 25

Met Gly Ile Val Glu Glu Ala His Asn Leu Arg Val Val Gly Glu Gly
1               5                   10                  15

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
    50                  55                  60

Phe Ser Arg Tyr Ala Thr Leu Glu Gly Tyr Ala Leu Asp Leu Leu Ala
65                  70                  75                  80

Ile Leu Gln Glu Leu Gly Val Gln Ser Cys Ile Tyr Val Gly His Ser
                85                  90                  95

Val Ser Ala Ile Ile Gly Ala Leu Ala Ser Ile Ser Arg Pro Asp Leu
            100                 105                 110

Phe Thr Lys Leu Val Leu Leu Ser Ala Ser Pro Arg Tyr Leu Asn Asp
        115                 120                 125

```
Val Asp Tyr Tyr Gly Gly Phe Glu Gln Asp Glu Leu Asp Glu Leu Phe
        130                 135                 140

Glu Ala Met Gln Ser Asn Tyr Lys Ala Trp Cys Leu Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Asn Val Ala Gln
                180                 185                 190

Thr Ile Phe Gln Ser Asp Val Arg Ser Leu Leu Pro His Val Ser Val
            195                 200                 205

Pro Cys His Ile Val Gln Ser Thr Lys Asp Leu Ala Val Pro Val Val
        210                 215                 220

Val Ser Glu Tyr Leu His Arg His Leu Gly Gly Asp Ser Ile Val Glu
225                 230                 235                 240

Val Met Pro Ser Glu Gly His Leu Pro Gln Leu Ser Ser Pro Asp Ile
                245                 250                 255

Val Thr Pro Val Leu Leu Arg His Ile Gln His Asp Ile Ala Ile
                260                 265                 270

<210> SEQ ID NO 26
<211> LENGTH: 265
<212> TYPE: PRT
<213> ORGANISM: Picea sitchensis

<400> SEQUENCE: 26

Leu Thr Asn Ala His Asn Val His Val Leu Gly Ser Gly His Glu Leu
 1               5                  10                  15

Ile Val Leu Ala His Gly Phe Gly Thr Asp Gln Ser Val Trp Lys His
             20                  25                  30

Val Val Pro Asn Leu Glu Asn Ser Tyr Arg Leu Ile Met Phe Asp Asn
         35                  40                  45

Met Gly Ala Gly Thr Thr Asn Pro Asp Phe Phe Asp Phe Glu Arg Tyr
     50                  55                  60

Ser Thr Leu His Gly Tyr Ala Tyr Asp Leu Leu Ala Ile Leu Glu Glu
65                  70                  75                  80

Leu His Val Asp Thr Cys Ile Phe Val Gly His Ser Val Ser Gly Leu
                 85                  90                  95

Val Gly Ile Leu Ala Ser Ile Glu Arg Pro Asp Leu Phe Ser Lys Ile
            100                 105                 110

Ile Thr Ile Ser Ala Ser Pro Arg Tyr Leu Asn Asp Ile Asp Tyr Phe
         115                 120                 125

Gly Gly Phe Glu Gln Glu Asp Leu Asn Gln Leu Phe Glu Ala Met Gln
    130                 135                 140

Ser Asn Phe Lys Ala Trp Val Ser Gly Phe Ala Pro Leu Ala Val Gly
145                 150                 155                 160

Ala Asp Leu Asp Ser Met Ala Val Gln Glu Phe Ser Arg Thr Leu Phe
                165                 170                 175

Asn Val Arg Pro Asp Ile Ala Leu Ser Val Ala Lys Thr Ile Phe Gln
            180                 185                 190

Ser Asp Met Arg Ser Met Leu Pro His Val Thr Val Pro Cys His Ile
         195                 200                 205

Leu Gln Ser Ser Lys Asp Leu Ala Val Pro Val Thr Val Ala Asp Tyr
    210                 215                 220

Ile His Gln Asn Leu Gly Ala Lys Ser Ile Val Glu Ile Leu Pro Ser
```

```
                225                 230                 235                 240

Glu Gly His Leu Pro Gln Leu Ser Ser Pro Ala Ile Val Ile Pro Val
                245                 250                 255

Leu Leu Arg His Ile Glu Gly Tyr Ile
            260                 265

<210> SEQ ID NO 27
<211> LENGTH: 269
<212> TYPE: PRT
<213> ORGANISM: Helianthus annuus
<220> FEATURE:
<221> NAME/KEY: misc_feature
<222> LOCATION: (15)..(15)
<223> OTHER INFORMATION: Xaa can be any naturally occurring amino acid

<400> SEQUENCE: 27

Met Gly Val Val Glu Ala Ala His Asn Val Lys Ile Leu Gly Xaa Gly
  1               5                  10                  15

Asp Arg Thr Ile Val Leu Ala His Gly Phe Gly Thr Asp Gln Ser Val
             20                  25                  30

Trp Lys His Leu Val Pro His Leu Val Asp Asp Tyr Lys Val Val Leu
         35                  40                  45

Tyr Asp Asn Met Gly Ala Gly Thr Thr Asn Pro Glu Tyr Phe Asp Phe
 50                  55                  60

Gly Arg Tyr Ala Thr Leu Glu Gly Tyr Ala Tyr Asp Val Ile Ser Ile
65                  70                  75                  80

Leu Glu Glu Leu Lys Ile Ser Ser Cys Val Phe Val Gly His Ser Val
                 85                  90                  95

Ser Val Trp Leu Val Arg Leu Leu Leu Leu Val Arg Ile Cys Phe
            100                 105                 110

Arg Lys Leu Leu Phe Arg Leu Pro Pro Arg Tyr Leu Asn Thr Lys Asp
            115                 120                 125

Tyr Phe Gly Gly Phe Glu Gln Glu Asp Leu Asp Gln Leu Phe Glu Ala
        130                 135                 140

Met Gln Ser Asn Tyr Lys Ala Trp Cys Ser Gly Phe Ala Pro Leu Ala
145                 150                 155                 160

Val Gly Gly Asp Met Asp Ser Val Ala Val Gln Glu Phe Ser Arg Thr
                165                 170                 175

Leu Phe Asn Met Arg Pro Asp Ile Ala Leu Ser Val Ala Gln Thr Ile
            180                 185                 190

Phe Gln Cys Asp Met Arg His Leu Leu Cys His Val Val Pro Cys
        195                 200                 205

His Ile Ile Gln Ser Met Lys Asp Leu Ala Val Pro Val Val Ala
210                 215                 220

Glu Tyr Leu His Gln Asn Leu Gly Gly Glu Ser Ile Val Glu Val Met
225                 230                 235                 240

Ser Thr Asp Gly His Leu Pro Gln Leu Ser Ser Pro Asp Ile Val Ile
                245                 250                 255

Pro Val Leu Leu Arg His Ile Arg Cys Asp Ile Ala Val
            260                 265

<210> SEQ ID NO 28
<211> LENGTH: 263
<212> TYPE: PRT
<213> ORGANISM: Physcomitrella patens

<400> SEQUENCE: 28
```

```
Glu Val His Asn Val Arg Ile Val Gly Met Gly Glu Leu Val Val
 1               5                  10                  15

Leu Ala His Gly Phe Gly Thr Asp Gln Ser Val Trp Lys His Val Ile
             20                  25                  30

Pro His Leu Val Asp Asp Tyr Arg Val Ile Leu Phe Asp Asn Met Gly
             35                  40                  45

Ala Gly Thr Thr Asp Pro Glu Tyr Phe Ser Phe Ser Arg Tyr Ser Thr
 50                  55                  60

Leu Tyr Gly Tyr Ala Asp Leu Leu Thr Ile Leu Asp Glu Leu Glu
 65                  70                  75                  80

Val Gln Ser Cys Ile Phe Val Gly His Ser Val Ser Gly Met Val Gly
             85                  90                  95

Cys Leu Ala Ser Leu Tyr Arg Pro Glu Ile Phe Ser Lys Ile Ile Thr
            100                 105                 110

Ile Ser Ala Ser Pro Arg Tyr Leu Asn Asp Met Asp Tyr Phe Gly Gly
            115                 120                 125

Phe Glu Gln Glu Asp Leu Asn Gln Leu Phe Glu Ala Met Gln Ser Asn
            130                 135                 140

Phe Lys Ala Trp Val Ser Gly Phe Ala Pro Leu Ala Val Gly Ala Asp
145                 150                 155                 160

Ile Asp Ser Met Ala Val Gln Glu Phe Gly Arg Thr Leu Phe Asn Ile
                165                 170                 175

Arg Pro Asp Ile Ala Phe Ser Val Ala Lys Thr Ile Phe Gln Ser Asp
                180                 185                 190

Leu Arg Ser Ile Leu Pro Lys Val Thr Val Pro Cys His Ile Leu Gln
                195                 200                 205

Ser Ser Lys Asp Leu Ala Val Pro Val Val Ala Asp Tyr Leu His
                210                 215                 220

Leu Thr Leu Gly Gly Pro Thr Ile Val Glu Val Leu Pro Thr Glu Gly
225                 230                 235                 240

His Leu Pro Gln Leu Ser Ser Pro Asp Ile Val Ile Pro Val Leu Lys
                245                 250                 255

Arg His Val Ala Gly Asn Leu
                260

<210> SEQ ID NO 29
<211> LENGTH: 263
<212> TYPE: PRT
<213> ORGANISM: Physcomitrella patens

<400> SEQUENCE: 29

Glu Ala His Asn Val Arg Ala Ile Gly Met Gly Glu Glu Val Val
 1               5                  10                  15

Leu Gly His Gly Phe Gly Thr Asp Gln Ser Val Trp Lys His Val Ile
             20                  25                  30

Pro His Leu Val Asp Glu Tyr Arg Val Ile Leu Phe Asp Asn Met Gly
             35                  40                  45

Ala Gly Thr Thr Asp Pro Glu Tyr Phe Ser Phe Ser Arg Tyr Ser Thr
 50                  55                  60

Leu His Gly Tyr Ala Asp Asp Leu Leu Ser Ile Leu Glu Glu Leu Glu
 65                  70                  75                  80

Val Glu Ser Cys Ile Tyr Val Gly His Ser Val Ser Gly Met Val Gly
             85                  90                  95

Phe Leu Ala Ser Leu Glu Arg Pro Glu Ile Phe Ser Lys Ile Ile Thr
            100                 105                 110
```

-continued

Ile Ser Ala Ser Pro Arg Tyr Leu Asn Asp Met Asp Tyr Phe Gly Gly
            115                 120                 125

Phe Glu Gln Asp Asp Leu Asn Gln Leu Phe Glu Ala Met Gln Ser Asn
130                 135                 140

Phe Glu Ala Trp Val Ser Gly Phe Ala Pro Leu Ala Val Gly Ala Asp
145                 150                 155                 160

Ile Asp Ser Met Ala Val Gln Glu Phe Gly Arg Thr Leu Phe Asn Ile
                165                 170                 175

Arg Pro Asp Ile Ala Phe Ser Val Ala Lys Thr Ile Phe Gln Ser Asp
            180                 185                 190

Leu Arg Ile Val Leu Pro Asn Val Thr Val Pro Cys His Ile Leu Gln
        195                 200                 205

Ser Ser Lys Asp Leu Ala Val Pro Ile Val Val Ala Asp Tyr Leu His
        210                 215                 220

His Thr Leu Gly Gly Pro Thr Ile Val Glu Val Leu Gln Thr Glu Gly
225                 230                 235                 240

His Leu Pro Gln Leu Ser Ser Pro Glu Ile Val Ile Pro Val Leu Lys
                245                 250                 255

Arg His Leu Ala Gly Ser Leu
            260

<210> SEQ ID NO 30
<211> LENGTH: 263
<212> TYPE: PRT
<213> ORGANISM: Physcomitrella patens

<400> SEQUENCE: 30

Asp Ala His Asn Val Arg Val Val Gly Met Gly Ser Glu Leu Val Val
1               5                   10                  15

Leu Gly His Gly Phe Gly Thr Asp Gln Ser Val Trp Lys His Val Ile
            20                  25                  30

Pro His Leu Val Asp Asp Tyr Arg Val Ile Leu Phe Asp Asn Met Gly
        35                  40                  45

Ala Gly Thr Thr Asp Pro Glu Phe Phe Ser Phe Ser Arg Tyr Ser Thr
50                  55                  60

Leu His Gly Tyr Ala Asp Asp Leu Leu Ser Ile Leu Glu Glu Leu Glu
65                  70                  75                  80

Val Glu Ser Cys Ile Tyr Val Gly His Ser Val Ala Gly Met Val Gly
                85                  90                  95

Cys Leu Ala Ser Leu Glu Arg Pro Glu Ile Phe Thr Lys Ile Ile Thr
            100                 105                 110

Leu Ser Ala Ser Pro Arg Tyr Leu Asn Asp Arg Asp Tyr Phe Gly Gly
        115                 120                 125

Phe Glu Gln Asp Asp Leu Asn Gln Leu Phe Glu Ala Met Gln Ser Asn
130                 135                 140

Phe Lys Ala Trp Val Ser Gly Phe Ala Pro Leu Ala Val Gly Ser Asp
145                 150                 155                 160

Ile Asp Ser Met Ala Val Gln Glu Phe Gly Arg Thr Leu Phe Asn Ile
                165                 170                 175

Arg Pro Asp Ile Ala Phe Ser Val Ala Lys Thr Ile Phe Gln Ser Asp
            180                 185                 190

Leu Arg Ile Met Leu Pro Lys Val Thr Val Pro Cys His Ile Leu Gln
        195                 200                 205

Ser Ser Lys Asp Leu Ala Val Pro Leu Val Val Ala Asp Tyr Leu His

His Ala Leu Gly Gly Pro Thr Ile Val Glu Val Pro Thr Glu Gly
225                 230                 235                 240

His Leu Pro Gln Leu Ser Ser Pro Asp Ile Ile Pro Val Leu Lys
                245                 250                 255

Arg His Leu Ala Gly Ser Leu
            260

<210> SEQ ID NO 31
<211> LENGTH: 263
<212> TYPE: PRT
<213> ORGANISM: Physcomitrella patens

<400> SEQUENCE: 31

Glu Ala His Asn Val His Val Val Gly His Gly Glu Glu Leu Val Val
1               5                   10                  15

Leu Ala His Gly Phe Gly Thr Asp Gln Ser Val Trp Lys His Val Leu
            20                  25                  30

Pro His Leu Ile Asp Glu Tyr Arg Leu Ile Leu Phe Asp Asn Met Gly
        35                  40                  45

Ala Gly Thr Thr Asp Pro Glu Tyr Tyr Cys Phe Gln Arg Tyr Ser Ser
    50                  55                  60

Leu Tyr Gly Tyr Ala Asp Asp Leu Leu Ala Ile Leu Asp Glu Leu Glu
65                  70                  75                  80

Ile Thr Ser Cys Ile Phe Val Gly His Ser Val Ser Gly Met Ile Gly
                85                  90                  95

Cys Leu Ala Ser Leu Ala Arg Pro Asn Phe Phe Thr Lys Ile Ile Thr
            100                 105                 110

Ile Ser Ala Ser Pro Arg Tyr Leu Asn Asp Ala Asp Tyr Phe Gly Gly
        115                 120                 125

Phe Glu Gln Asp Asp Leu Asn Gln Leu Phe Gln Ala Met Gln Ser Asn
    130                 135                 140

Phe Lys Ala Trp Val Ser Gly Phe Ala Pro Leu Ala Val Gly Ala Asp
145                 150                 155                 160

Ile Glu Ser Met Ala Val Gln Glu Phe Gly Arg Thr Leu Phe Asn Ile
                165                 170                 175

Arg Pro Asp Ile Ala Phe Ser Val Ala Lys Thr Ile Phe Gln Ser Asp
            180                 185                 190

Leu Arg Ser Ile Leu Pro Gln Val Thr Val Pro Cys His Ile Leu Gln
        195                 200                 205

Ser Ser Arg Asp Leu Ala Val Pro Val Ile Val Ser Asp Tyr Ile His
    210                 215                 220

Gln Arg Ile Ser Gly Ala Ser Ile Val Glu Val Leu His Thr Glu Gly
225                 230                 235                 240

His Leu Pro Gln Leu Ser Ser Pro Asp Val Val Ile Pro Val Leu Lys
                245                 250                 255

Arg His Leu Val Gly Asp Leu
            260

<210> SEQ ID NO 32
<211> LENGTH: 219
<212> TYPE: PRT
<213> ORGANISM: Oryza sativa

<400> SEQUENCE: 32

Met Gly Ala Gly Pro Thr Asn Pro Asp Tyr Phe Asp Phe Ser Arg Tyr

```
                1               5                      10                      15
             Ala Thr Leu Glu Gly Tyr Ala Leu Asp Leu Leu Ala Ile Leu Gln Glu
                              20                      25                      30

Leu Arg Val Ala Ser Cys Ile Tyr Val Gly His Ser Val Ser Ala Val
                              35                      40                      45

Ile Gly Ala Ile Ala Ser Ile Ser Arg Pro Asp Leu Phe Ser Lys Leu
                  50                          55                      60

Val Leu Ser Ala Ser Pro Arg Tyr Leu Asn Asp Val Asp Tyr Tyr
              65                  70                      75                      80

Gly Gly Phe Glu Gln Glu Asp Leu Asp Glu Leu Phe Glu Ala Met Gly
                                  85                      90                      95

Ser Asn Tyr Lys Ala Trp Cys Ser Gly Phe Ala Pro Leu Cys Val Gly
                              100                     105                     110

Gly Asp Met Glu Ser Val Ala Val Gln Glu Phe Ser Arg Thr Leu Phe
                              115                     120                     125

Asn Ile Arg Pro Asp Ile Ala Leu Ser Val Ala Gln Thr Ile Phe Gln
                  130                         135                     140

Ser Asp Val Arg Ser Leu Leu Pro Leu Val Thr Val Pro Cys His Ile
              145                     150                     155                     160

Val Gln Ser Thr Lys Asp Leu Ala Val Pro Val Val Ser Glu Tyr
                                  165                     170                     175

Leu His Lys His Leu Gly Gly Asp Ser Ile Val Glu Val Met Pro Ser
                              180                     185                     190

Glu Gly His Leu Pro Gln Leu Ser Ser Pro Asp Ile Val Ile Pro Val
                              195                     200                     205

Leu Leu Arg His Ile Gln His Asp Ile Ala Val
                              210                     215

<210> SEQ ID NO 33
<211> LENGTH: 258
<212> TYPE: PRT
<213> ORGANISM: Physcomitrella patens

<400> SEQUENCE: 33

Glu Ala His Asn Val Thr Ile Ser Gly Cys Gly Asp Glu Ile Val Val
              1                   5                       10                      15

Leu Gly His Gly Phe Gly Thr Asp Gln Ser Val Trp Lys His Val Val
                              20                      25                      30

Pro His Leu Val Asp Asp Tyr Lys Leu Val Leu Phe Asp Ser Met Gly
                              35                      40                      45

Ala Gly Thr Thr Asp Pro Glu Tyr Phe Ser Ala Gln Arg Tyr Ser Asn
                  50                          55                      60

Leu Tyr Gly Tyr Ala Asp Asp Leu Leu Ala Ile Leu Asp Glu Leu Lys
              65                  70                      75                      80

Ile Asp Ser Cys Ile Tyr Ile Gly His Ser Val Ala Gly Met Val Gly
                              85                      90                      95

Cys Leu Ala Ser Met Glu Arg Pro His Arg Ile Tyr Leu Cys Arg Tyr
                              100                     105                     110

Leu Asn Ala Ser Glu Tyr Phe Gly Gly Leu Asp Glu Glu Val Leu Asn
                              115                     120                     125

Gln Leu Phe Tyr Ala Met Gln Ser Asn Phe Lys Ala Trp Val Ser Gly
                  130                         135                     140

Phe Ala Pro Leu Ala Leu Gly Ala Asp Ile Asp Ser Met Ala Val Gln
              145                     150                     155                     160
```

```
Glu Phe Ser Arg Thr Leu Phe Asn Ile Arg Pro Asp Ile Ala Phe Thr
                165                 170                 175

Val Ala Lys Thr Ile Phe Gln Ser Asp Leu Arg Ser Val Leu His Gln
            180                 185                 190

Val Gln Val Pro Cys His Ile Leu Gln Ser Ser Lys Asp Leu Ala Val
        195                 200                 205

Pro Val Val Ala Ser Tyr Leu His His Ala Leu Gly Gly Pro Ser
    210                 215                 220

Ala Val Glu Ile Leu Gln Thr Glu Gly His Leu Pro Gln Leu Ser Ala
225                 230                 235                 240

Pro Asp Val Val Ile Pro Val Leu Lys Arg His Leu Val Cys Asp Val
                245                 250                 255

Cys Val

<210> SEQ ID NO 34
<211> LENGTH: 268
<212> TYPE: PRT
<213> ORGANISM: Striga asiatica

<400> SEQUENCE: 34

Met Ser Ser Ile Gly Leu Ala His Asn Val Ser Ile Leu Gly Ser Gly
 1               5                  10                  15

Glu Thr Thr Val Val Leu Ser His Gly Tyr Gly Thr Asp Gln Ser Val
             20                  25                  30

Trp Lys Leu Leu Val Pro His Leu Val Asp Asp Asn Lys Val Leu Leu
         35                  40                  45

Tyr Asp Asn Met Gly Ala Gly Thr Thr Asn Pro Asp Tyr Phe Asp Phe
     50                  55                  60

Glu Arg Tyr Ser Ser Leu Glu Gly Tyr Ser Tyr Asp Leu Ile Ala Ile
 65                  70                  75                  80

Leu Asp Glu Phe His Val Ser Lys Cys Ile Tyr Val Gly His Ser Met
                 85                  90                  95

Ser Ala Val Ala Gly Ala Val Ala Ser Ile Phe Arg Pro Asp Leu Phe
            100                 105                 110

His Lys Leu Ile Met Ile Ser Pro Ser Pro Arg Leu Ala Asn Thr Glu
        115                 120                 125

Asp Tyr Tyr Gly Gly Leu Glu Gln Lys Glu Ile Asp Glu Val Val Gly
    130                 135                 140

Ser Met Glu Glu Asn Tyr Lys Ser Met Ala Leu Gly Ser Ala Pro Leu
145                 150                 155                 160

Ile Leu Ala Cys Asp Leu Glu Ser Ala Ala Val Gln Glu Tyr Val Arg
                165                 170                 175

Thr Leu Phe Asn Met Arg Pro Asp Ile Ser Cys Cys Ile Ala Arg Met
            180                 185                 190

Ile Phe Gly Leu Asp Leu Arg Pro Tyr Ile Gly His Ile Lys Val Pro
        195                 200                 205

Cys His Ile Ile His Ser Ala Lys Asp Phe Met Val Pro Val Ala Val
    210                 215                 220

Gly Glu Tyr Leu Cys Lys His Leu Gly Gly Pro Ser Val Val Glu Val
225                 230                 235                 240

Met Pro Thr Glu Gly His Leu Pro His Leu Ser Ala Pro Glu Val Thr
                245                 250                 255

Ile Pro Val Val Leu Arg His Val Arg Gln Asp Ile
            260                 265
```

<210> SEQ ID NO 35
<211> LENGTH: 256
<212> TYPE: PRT
<213> ORGANISM: Physcomitrella patens

<400> SEQUENCE: 35

Ala His Asn Val Thr Ile Val Gly Asp Gly Asp Gln Tyr Val Val Leu
1               5                   10                  15

Ser His Gly Phe Gly Ser Asp Gln Thr Val Trp Lys Tyr Leu Leu Pro
            20                  25                  30

Tyr Leu Val Ser Asp Tyr Arg Val Leu Leu Tyr Asp Leu Met Gly Ala
        35                  40                  45

Gly Ser Thr Asn Pro Lys Asp Phe Ser Phe Ser Arg Tyr Ser Ser Leu
    50                  55                  60

His Ala Tyr Ala Asp Asp Leu Leu Ala Ile Leu Asp Glu Leu Glu Ile
65                  70                  75                  80

Glu Ser Cys Thr Phe Val Gly Ala Ser Val Ser Gly Met Ile Gly Cys
                85                  90                  95

Leu Ala Ser Ile Glu Arg Pro Glu Val Phe Thr Lys Leu Ile Leu Leu
            100                 105                 110

Ala Ser Ser Pro Arg Tyr Leu Asn Asp Val Gly Tyr Tyr Gly Gly Phe
        115                 120                 125

Asp Gln Lys Asp Leu Asp Gln Leu Tyr Gly Asp Met Lys Ser Asn Phe
    130                 135                 140

Arg Ser Trp Val Thr Gly Phe Gly Pro Leu Ala Ile Gly Ala Asp Leu
145                 150                 155                 160

Glu Ser Ser Ala Val Gln Glu Phe Ser Arg Thr Leu Tyr Ser Ile Arg
                165                 170                 175

Pro Asp Ile Ala Leu Asn Val Cys Lys Thr Ile Phe Gln Ser Asp Leu
            180                 185                 190

Arg Ser Ile Leu Pro Leu Val Thr Val Pro Val Tyr Val Val Gln Thr
        195                 200                 205

Arg Lys Asp Met Ala Val Pro Leu Gln Val Ala Asn Tyr Met Val Arg
    210                 215                 220

Asn Leu Gly Gly Trp Thr Met Met Glu Val Leu Asn Thr Gly Gly His
225                 230                 235                 240

Leu Pro His Leu Ser Asp Pro Asn Val Val Leu Pro Val Leu Leu Arg
                245                 250                 255

<210> SEQ ID NO 36
<211> LENGTH: 260
<212> TYPE: PRT
<213> ORGANISM: Physcomitrella patens

<400> SEQUENCE: 36

Thr His Asn Val Thr Val Leu Gly Asn Arg Ser Asp Pro Val Val Val
1               5                   10                  15

Leu Gly His Gly Leu Gly Thr Asp Gln Ser Val Trp Lys Tyr Thr Val
            20                  25                  30

Pro Ser Leu Val Asn Gln Asn Phe Gln Val Val Leu Tyr Asp Thr Met
        35                  40                  45

Gly Ala Gly Ser Thr Glu Thr Ser Asp Phe Asn Phe Lys Arg Tyr Ser
    50                  55                  60

Ser Leu Gln Gly His Val Asp Asp Leu Leu Ala Ile Leu Asp Glu Leu
65                  70                  75                  80

```
Glu Ile Glu Asn Cys Val Tyr Val Gly His Ser Met Ser Gly Met Ile
                85                  90                  95
Gly Val Leu Ala Ser Leu Glu Arg Pro Asp Leu Phe Lys Leu Ile
        100                 105                 110
Leu Leu Ser Ala Ser Pro Arg Tyr Leu Asn Asp Ser Ser Tyr Tyr Gly
            115                 120                 125
Gly Phe Glu Gln Glu Asp Leu Asp Gln Leu Phe Ser Ser Met Arg Ser
130                 135                 140
Asn Phe Ser Ala Trp Val Ser Gly Phe Ala Thr Ala Ala Val Gly Thr
145                 150                 155                 160
Asp Ile His Asp Glu Ala Val Gln Glu Phe Ser Ser Thr Phe Ile Ser
                165                 170                 175
Met Arg Pro Asp Val Ala Leu Arg Thr Ser Gln Phe Val Phe Gln Ser
            180                 185                 190
Asp Phe Arg Ser Ile Leu Ser Glu Val Thr Val Pro Cys His Ile Val
        195                 200                 205
Gln Ser Arg Lys Asp Ile Ala Val Pro Ile Glu Val Ala Glu Tyr Leu
    210                 215                 220
Arg Cys Asn Leu Gly Gly Trp Thr Ser Val Asp Ile Leu Gln Thr Asp
225                 230                 235                 240
Gly His Leu Pro Gln Leu Ser Cys Pro Glu Leu Val Val Pro Val Leu
                245                 250                 255
Leu His Cys Ile
            260

<210> SEQ ID NO 37
<211> LENGTH: 253
<212> TYPE: PRT
<213> ORGANISM: Oryza sativa

<400> SEQUENCE: 37

Asn Val Arg Val Val Gly Ser Gly Glu Arg Val Val Leu Ser His
  1               5                  10                  15
Gly Phe Gly Thr Asp Gln Ser Ala Trp Ser Arg Val Leu Pro Tyr Leu
            20                  25                  30
Thr Arg Asp His Arg Val Val Leu Tyr Asp Leu Val Cys Ala Gly Ser
        35                  40                  45
Val Asn Pro Asp His Phe Asp Phe Arg Arg Tyr Asp Asn Leu Asp Ala
    50                  55                  60
Tyr Val Asp Asp Leu Leu Ala Ile Leu Asp Ala Leu Arg Ile Pro Arg
65                  70                  75                  80
Cys Ala Phe Val Gly His Ser Val Ser Ala Met Ile Gly Ile Leu Ala
                85                  90                  95
Ser Ile Arg Arg Pro Asp Leu Phe Ala Lys Leu Val Leu Ile Gly Ala
            100                 105                 110
Ser Pro Arg Phe Leu Asn Asp Ser Asp Tyr His Gly Gly Phe Glu Leu
        115                 120                 125
Glu Glu Ile Gln Gln Val Phe Asp Ala Met Gly Ala Asn Tyr Ser Ala
    130                 135                 140
Trp Ala Thr Gly Tyr Ala Pro Leu Ala Val Gly Ala Asp Val Pro Ala
145                 150                 155                 160
Ala Val Gln Glu Phe Ser Arg Thr Leu Phe Asn Met Arg Pro Asp Ile
                165                 170                 175
Ser Leu His Val Cys Gln Thr Val Phe Lys Thr Asp Leu Arg Gly Val
            180                 185                 190
```

```
Leu Gly Met Val Arg Ala Pro Cys Val Val Gln Thr Thr Arg Asp
        195                 200                 205

Val Ser Val Pro Ala Ser Val Ala Ala Tyr Leu Lys Ala His Leu Gly
    210                 215                 220

Gly Arg Thr Thr Val Glu Phe Leu Gln Thr Glu Gly His Leu Pro His
225                 230                 235                 240

Leu Ser Ala Pro Ser Leu Leu Ala Gln Val Leu Arg Arg
                245                 250

<210> SEQ ID NO 38
<211> LENGTH: 253
<212> TYPE: PRT
<213> ORGANISM: Oryza sativa

<400> SEQUENCE: 38

Asn Val Arg Val Val Gly Ser Gly Glu Arg Val Val Leu Ser His
1               5                   10                  15

Gly Phe Gly Thr Asp Gln Ser Ala Trp Ser Arg Val Leu Pro Tyr Leu
            20                  25                  30

Thr Arg Asp His Arg Val Val Leu Tyr Asp Leu Val Cys Ala Gly Ser
        35                  40                  45

Val Asn Pro Asp His Phe Asp Phe Arg Arg Tyr Asp Asn Leu Asp Ala
    50                  55                  60

Tyr Val Asp Asp Leu Leu Ala Ile Leu Asp Ala Leu Arg Ile Pro Arg
65                  70                  75                  80

Cys Ala Phe Val Gly His Ser Val Ser Ala Met Ile Gly Ile Leu Ala
                85                  90                  95

Ser Ile Arg Arg Pro Asp Leu Phe Ala Lys Leu Val Leu Ile Gly Ala
            100                 105                 110

Ser Pro Arg Phe Leu Asn Asp Ser Asp Tyr His Gly Gly Phe Glu Leu
        115                 120                 125

Glu Glu Ile Gln Gln Val Phe Asp Ala Met Gly Ala Asn Tyr Ser Ala
    130                 135                 140

Trp Ala Thr Gly Tyr Ala Pro Leu Ala Val Gly Ala Asp Val Pro Ala
145                 150                 155                 160

Ala Val Gln Glu Phe Ser Arg Thr Leu Phe Asn Met Arg Pro Asp Ile
                165                 170                 175

Ser Leu His Val Cys Gln Thr Val Phe Lys Thr Asp Leu Arg Gly Val
            180                 185                 190

Leu Gly Met Val Arg Ala Pro Cys Val Val Gln Thr Thr Arg Asp
        195                 200                 205

Val Ser Val Pro Ala Ser Val Ala Ala Tyr Leu Lys Ala His Leu Gly
    210                 215                 220

Gly Arg Thr Thr Val Glu Phe Leu Gln Thr Glu Gly His Leu Pro His
225                 230                 235                 240

Leu Ser Ala Pro Ser Leu Leu Ala Gln Val Leu Arg Arg
                245                 250

<210> SEQ ID NO 39
<211> LENGTH: 202
<212> TYPE: PRT
<213> ORGANISM: Zea mays

<400> SEQUENCE: 39

Met Gly Ile Val Glu Glu Ala His Asn Leu Arg Val Val Gly Glu Gly
1               5                   10                  15
```

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
 50                  55                  60

Phe Ser Arg Tyr Ala Thr Leu Glu Gly Tyr Ala Leu Asp Leu Leu Ala
 65                  70                  75                  80

Ile Leu Gln Glu Leu Gly Val Arg Ser Cys Ile Tyr Val Gly His Ser
                85                  90                  95

Val Ser Ala Val Ile Gly Ala Leu Ala Ser Ile Ser Arg Pro Asp Leu
            100                 105                 110

Phe Thr Lys Leu Val Leu Leu Ser Ala Ser Pro Arg Tyr Leu Asn Asp
        115                 120                 125

Val Asp Tyr Tyr Gly Gly Phe Glu Gln Asp Glu Leu Asp Glu Leu Phe
130                 135                 140

Glu Ala Met Arg Ser Asn Tyr Lys Ala Trp Cys Ser Gly Phe Ala Pro
145                 150                 155                 160

Leu Cys Val Gly Gly Asp Met Glu Ser Val Ala Val Gln Glu Phe Ser
                165                 170                 175

Arg Thr Leu Phe Asn Ile Arg Pro Asp Ile Ala Leu Ser Val Ala Gln
            180                 185                 190

Lys Asn Leu Pro Glu Arg Arg Ala Gln Leu
        195                 200

<210> SEQ ID NO 40
<211> LENGTH: 271
<212> TYPE: PRT
<213> ORGANISM: Physcomitrella patens

<400> SEQUENCE: 40

Ser His Asn Val Arg Asp Leu Gly Asn Gly Asp Gln Val Val Val Leu
 1               5                  10                  15

Gly His Gly Phe Gly Ser Asp Gln Ser Met Trp Arg Tyr Ile Val Pro
            20                  25                  30

Ser Leu Leu Ser Asn Asn Leu Lys Ile Val Leu Phe Asp Ile Met Gly
        35                  40                  45

Ala Gly Thr Thr Asp Pro Glu His Phe Ser Ser Lys Ser Tyr Ser Ser
 50                  55                  60

Leu Gln Ala His Ala Asp Asp Leu Leu Ala Val Leu Arg Glu Leu Asp
 65                  70                  75                  80

Ile Val Ser Cys Val Tyr Val Gly His Ser Met Ser Gly Met Ile Gly
                85                  90                  95

Cys Leu Ala Ser Ile Gln Arg Pro Glu Ile Phe Arg Lys Leu Ile Leu
            100                 105                 110

Leu Ala Thr Ser Pro Arg Tyr Leu Asn Asp Arg Asn Tyr Tyr Gly Gly
        115                 120                 125

Phe Glu Gln His Asp Leu Asp Gln Leu Phe Ala Asn Ile Lys Phe Asp
130                 135                 140

Phe Lys Ser Trp Val Ser Val Phe Ala Pro Gly Ala Val Gly Gly Asp
145                 150                 155                 160

Ile Asp Asp Lys Ala Val Gln Glu Phe Phe Arg Thr Leu Leu Ser Met
                165                 170                 175

Arg Pro Asp Ile Val Leu Ser Thr Ser Lys Thr Ile Phe Gln Ser Asp

```
                180                 185                 190
Leu Arg Ser Ile Leu Pro Glu Ala Arg Lys Leu Gln Ser Cys Lys Ser
            195                 200                 205

Val Tyr Ile Val Thr Val Pro Cys His Ile Ile Gln Ser Arg Lys Asp
        210                 215                 220

Leu Ala Val Pro Val Glu Val Ala Glu Tyr Leu Ser Arg Asn Leu Gly
225                 230                 235                 240

Gly Trp Thr Ser Met Glu Ile Leu Gln Thr Glu Gly His Ile Pro Gln
                245                 250                 255

Leu Ser Ser Pro Glu Leu Val Ile Pro Val Leu Leu Arg Cys Ile
                260                 265                 270

<210> SEQ ID NO 41
<211> LENGTH: 244
<212> TYPE: PRT
<213> ORGANISM: Hordeum vulgare

<400> SEQUENCE: 41

Asn Val Arg Val Val Gly Thr Gly Glu Arg Val Val Leu Ser His
1               5                   10                  15

Gly Phe Gly Thr Asp Gln Ser Ala Trp Ser Arg Val Leu Pro Tyr Leu
            20                  25                  30

Thr Arg Asp His Arg Val Val Leu Tyr Asp Leu Val Cys Ala Gly Ser
        35                  40                  45

Val Asn Pro Asp His Phe Asp Phe Arg Arg Tyr Asn Asn Leu Asp Ala
    50                  55                  60

Tyr Val Asp Leu Leu Ser Ile Leu Asp Ala Leu Arg Ile Pro Arg
65                  70                  75                  80

Cys Ala Phe Val Gly His Ser Val Ser Ala Met Ile Gly Ile Leu Ala
                85                  90                  95

Ser Ile Arg Arg Pro Asp Leu Phe Ala Lys Leu Val Leu Ile Gly Ala
            100                 105                 110

Ser Pro Arg Phe Leu Asn Asp Ser Asp Tyr His Gly Gly Phe Glu Leu
        115                 120                 125

Glu Gln Ile Gln Gln Val Phe Asp Ala Met Ser Ala Asn Tyr Ala Ala
    130                 135                 140

Trp Ala Thr Gly Tyr Ala Pro Leu Ala Val Gly Ala Asp Val Pro Ala
145                 150                 155                 160

Ala Val Gln Glu Phe Ser Arg Thr Leu Phe Asn Met Arg Pro Asp Ile
                165                 170                 175

Ser Leu His Val Cys Gln Ser Val Phe Lys Thr Asp Leu Arg Gly Val
            180                 185                 190

Leu Gly Met Val Gln Ala Pro Cys Val Val Gln Thr Thr Arg Asp
    195                 200                 205

Val Ser Val Pro Ala Ser Val Ala Ala Tyr Leu Lys Ala His Leu Gly
    210                 215                 220

Gly Arg Thr Thr Ile Glu Pro Leu Pro Thr Glu Gly His Leu Pro His
225                 230                 235                 240

Leu Ser Ala Pro

<210> SEQ ID NO 42
<211> LENGTH: 257
<212> TYPE: PRT
<213> ORGANISM: Physcomitrella patens

<400> SEQUENCE: 42
```

Gln Ser His Asn Val Ile Ile Val Gly Asn Gly Asp Gln Tyr Val Val
1               5                   10                  15

Leu Ser His Gly Phe Gly Ser Asp Gln Thr Val Trp Lys Tyr Val Leu
            20                  25                  30

Pro Tyr Ile Met Asn Asp Tyr Lys Val Ile Leu Tyr Asp Leu Met Gly
            35                  40                  45

Ala Gly Ser Thr Ser Ala Asp Asp Phe Ser Phe Asn Arg Tyr Ser Ser
50                      55                  60

Leu His Ala Tyr Ala Asp Asp Leu Leu Thr Ile Leu Asp Glu Leu Glu
65                  70                  75                  80

Ile Lys Ser Cys Met Tyr Val Gly Ala Ser Val Ser Gly Met Ile Gly
                85                  90                  95

Cys Leu Ala Ser Ile Glu Arg Pro Glu Val Phe Lys Lys Leu Ile Leu
                100                 105                 110

Leu Gly Ser Ser Pro Arg Tyr Leu Asn Asp Val Asn Tyr Phe Gly Gly
            115                 120                 125

Phe Glu Gln Gln Asp Leu Glu Gln Ile Tyr Gly Asp Met Lys Ser Asn
130                 135                 140

Phe Arg Ser Trp Val Thr Gly Phe Gly Glu Leu Leu Val Ala Ala Asp
145                 150                 155                 160

Leu Gln Ser Arg Ala Val Gln Glu Phe Cys Arg Thr Phe Tyr Ser Ile
                165                 170                 175

Arg Pro Asp Ile Ala Leu Ser Ile Thr Arg Thr Ile Phe Gln Ser Asp
                180                 185                 190

Leu Arg Ser Thr Leu Pro Leu Val Lys Val Pro Val His Leu Leu Gln
                195                 200                 205

Thr Met Lys Asp Met Ala Val Pro Leu Gln Val Ala His Tyr Leu Gln
210                 215                 220

Gln Asn Leu Gly Gly Trp Thr Thr Met Glu Ile Leu Asp Thr Glu Gly
225                 230                 235                 240

His Leu Pro His Leu Ser Asp Pro Gly Val Val Ile Ala Ala Leu Leu
                245                 250                 255

Arg

<210> SEQ ID NO 43
<211> LENGTH: 166
<212> TYPE: PRT
<213> ORGANISM: Arabidopsis thaliana

<400> SEQUENCE: 43

Ser Ser Asp Lys Arg Asn Ile Tyr Asn Gln Ile Ile Leu Phe Trp Tyr
1               5                   10                  15

Val Tyr Arg Tyr Val Asn Asp Val Asp Tyr Gln Gly Gly Phe Glu Gln
            20                  25                  30

Glu Asp Leu Asn Gln Leu Phe Glu Ala Ile Arg Ser Asn Tyr Lys Ala
            35                  40                  45

Trp Cys Leu Gly Phe Ala Pro Leu Ala Val Gly Gly Asp Met Asp Ser
50                  55                  60

Ile Ala Val Gln Glu Phe Ser Arg Thr Leu Phe Asn Met Arg Pro Asp
65                  70                  75                  80

Ile Ala Leu Ser Val Gly Gln Thr Ile Phe Gln Ser Asp Met Arg Gln
                85                  90                  95

Ile Leu Pro Phe Val Thr Val Pro Cys His Ile Leu Gln Ser Val Lys
                100                 105                 110

Asp Leu Ala Val Pro Val Val Ser Glu Tyr Leu His Ala Asn Leu
            115                 120                 125

Gly Cys Glu Ser Val Val Glu Val Ile Pro Ser Asp Gly His Leu Pro
        130                 135                 140

Gln Leu Ser Ser Pro Asp Ser Val Ile Pro Val Ile Leu Arg His Ile
145                 150                 155                 160

Arg Asn Asp Ile Ala Met
                165

<210> SEQ ID NO 44
<211> LENGTH: 166
<212> TYPE: PRT
<213> ORGANISM: Arabidopsis thaliana

<400> SEQUENCE: 44

Ser Ser Asp Lys Arg Asn Ile Tyr Asn Gln Ile Ile Leu Phe Trp Tyr
1               5                   10                  15

Val Tyr Arg Tyr Val Asn Asp Val Asp Tyr Gln Gly Gly Phe Glu Gln
            20                  25                  30

Glu Asp Leu Asn Gln Leu Phe Glu Ala Ile Arg Ser Asn Tyr Lys Ala
        35                  40                  45

Trp Cys Leu Gly Phe Ala Pro Leu Ala Val Gly Gly Asp Met Asp Ser
    50                  55                  60

Ile Ala Val Gln Glu Phe Ser Arg Thr Leu Phe Asn Met Arg Pro Asp
65                  70                  75                  80

Ile Ala Leu Ser Val Gly Gln Thr Ile Phe Gln Ser Asp Met Arg Gln
                85                  90                  95

Ile Leu Pro Phe Val Thr Val Pro Cys His Ile Leu Gln Ser Val Lys
            100                 105                 110

Asp Leu Ala Val Pro Val Val Ser Glu Tyr Leu His Ala Asn Leu
        115                 120                 125

Gly Cys Glu Ser Val Val Glu Val Ile Pro Ser Asp Gly His Leu Pro
    130                 135                 140

Gln Leu Ser Ser Pro Asp Ser Val Ile Pro Val Ile Leu Arg His Ile
145                 150                 155                 160

Arg Asn Asp Ile Ala Met
                165

<210> SEQ ID NO 45
<211> LENGTH: 122
<212> TYPE: PRT
<213> ORGANISM: Oryza minuta

<400> SEQUENCE: 45

Asn Val Arg Val Val Gly Ser Gly Glu Arg Val Val Leu Ser His
1               5                   10                  15

Gly Phe Gly Thr Asp Gln Ser Ala Trp Ser Arg Val Leu Pro Tyr Leu
            20                  25                  30

Thr Arg Asp His Arg Val Val Leu Tyr Asp Leu Val Cys Ala Gly Ser
        35                  40                  45

Val Asn Pro Asp His Phe Asp Phe Arg Arg Tyr Asp Asn Leu Asp Ala
    50                  55                  60

Tyr Val Asp Asp Leu Leu Ala Ile Leu Asp Ala Leu Arg Ile Pro Arg
65                  70                  75                  80

Cys Ala Phe Val Gly His Ser Val Ser Ala Met Ile Gly Ile Leu Ala
                85                  90                  95

```
Ser Ile Arg Arg Pro Asp Leu Phe Ala Lys Leu Val Leu Ile Gly Ala
            100                 105                 110

Ser Pro Arg Tyr Ala Arg Ser Leu Phe Gln
            115                 120

<210> SEQ ID NO 46
<211> LENGTH: 141
<212> TYPE: PRT
<213> ORGANISM: Oryza sativa

<400> SEQUENCE: 46

Arg Phe Leu Asn Asp Ser Asp Tyr His Gly Gly Phe Glu Leu Glu Glu
  1               5                  10                  15

Ile Gln Gln Val Phe Asp Ala Met Gly Ala Asn Tyr Ser Ala Trp Ala
                 20                  25                  30

Thr Gly Tyr Ala Pro Leu Ala Val Gly Ala Asp Val Pro Ala Ala Val
             35                  40                  45

Gln Glu Phe Ser Arg Thr Leu Phe Asn Met Arg Pro Asp Ile Ser Leu
         50                  55                  60

His Val Cys Gln Thr Val Phe Lys Thr Asp Leu Arg Gly Val Leu Gly
 65                  70                  75                  80

Met Val Arg Ala Pro Cys Val Val Gln Thr Thr Arg Asp Val Ser
                 85                  90                  95

Val Pro Ala Ser Val Ala Ala Tyr Leu Lys Ala His Leu Gly Gly Arg
             100                 105                 110

Thr Thr Val Glu Phe Leu Gln Thr Glu Gly His Leu Pro His Leu Ser
         115                 120                 125

Ala Pro Ser Leu Leu Ala Gln Val Leu Arg Arg Ala Leu
     130                 135                 140

<210> SEQ ID NO 47
<211> LENGTH: 118
<212> TYPE: PRT
<213> ORGANISM: Oryza sativa

<400> SEQUENCE: 47

Asn Val Arg Val Val Gly Ser Gly Glu Arg Val Val Leu Ser His
  1               5                  10                  15

Gly Phe Gly Thr Asp Gln Ser Ala Trp Ser Arg Val Leu Pro Tyr Leu
                 20                  25                  30

Thr Arg Asp His Arg Val Val Leu Tyr Asp Leu Val Cys Ala Gly Ser
             35                  40                  45

Val Asn Pro Asp His Phe Asp Phe Arg Arg Tyr Asp Asn Leu Asp Ala
         50                  55                  60

Tyr Val Asp Asp Leu Leu Ala Ile Leu Asp Ala Leu Arg Ile Pro Arg
 65                  70                  75                  80

Cys Ala Phe Val Gly His Ser Val Ser Ala Met Ile Gly Ile Leu Ala
                 85                  90                  95

Ser Ile Arg Arg Pro Asp Leu Phe Ala Lys Leu Val Leu Ile Gly Ala
            100                 105                 110

Ser Pro Arg Tyr Ala Arg
            115

<210> SEQ ID NO 48
<211> LENGTH: 118
<212> TYPE: PRT
<213> ORGANISM: Oryza sativa
```

<400> SEQUENCE: 48

Asn Val Arg Val Val Gly Ser Gly Glu Arg Val Val Leu Ser His
1               5                   10                  15

Gly Phe Gly Thr Asp Gln Ser Ala Trp Ser Arg Val Leu Pro Tyr Leu
            20                  25                  30

Thr Arg Asp His Arg Val Val Leu Tyr Asp Leu Val Cys Ala Gly Ser
                35                  40                  45

Val Asn Pro Asp His Phe Asp Phe Arg Arg Tyr Asp Asn Leu Asp Ala
    50                  55                  60

Tyr Val Asp Asp Leu Leu Ala Ile Leu Asp Ala Leu Arg Ile Pro Arg
65                  70                  75                  80

Cys Ala Phe Val Gly His Ser Val Ser Ala Met Ile Gly Ile Leu Ala
                85                  90                  95

Ser Ile Arg Arg Pro Asp Leu Phe Ala Lys Leu Val Leu Ile Gly Ala
                100                 105                 110

Ser Pro Arg Tyr Ala Arg
            115

<210> SEQ ID NO 49
<211> LENGTH: 166
<212> TYPE: PRT
<213> ORGANISM: Arabidopsis thaliana

<400> SEQUENCE: 49

Ser Ser Asp Lys Arg Asn Ile Tyr Asn Gln Ile Ile Leu Phe Trp Tyr
1               5                   10                  15

Val Tyr Arg Tyr Val Asn Asp Val Asp Tyr Gln Gly Gly Phe Glu Gln
            20                  25                  30

Glu Asp Leu Asn Gln Leu Phe Glu Ala Ile Arg Ser Asn Tyr Lys Ala
        35                  40                  45

Trp Cys Leu Gly Phe Ala Pro Leu Ala Val Gly Gly Asp Met Asp Ser
    50                  55                  60

Ile Ala Val Gln Glu Phe Ser Arg Thr Leu Phe Asn Met Arg Pro Asp
65                  70                  75                  80

Ile Ala Leu Ser Val Gly Gln Thr Ile Phe Gln Ser Asp Met Arg Gln
                85                  90                  95

Phe Leu Pro Phe Val Thr Val Pro Cys Asn Ile Leu Gln Ser Val Lys
                100                 105                 110

Asp Leu Ala Val Pro Val Val Ser Glu Tyr Leu His Ala Asn Leu
            115                 120                 125

Gly Cys Glu Ser Val Val Glu Val Ile Pro Ser Asp Gly His Leu Pro
    130                 135                 140

Gln Leu Ser Ser Pro Asp Ser Val Ile Pro Val Ile Leu Arg His Ile
145                 150                 155                 160

Arg Asn Asp Ile Ala Met
            165

<210> SEQ ID NO 50
<211> LENGTH: 253
<212> TYPE: PRT
<213> ORGANISM: Zea mays

<400> SEQUENCE: 50

Asn Val Arg Val Val Gly Ser Gly Asp Arg Val Val Leu Ser His
1               5                   10                  15

```
Gly Phe Gly Thr Asp Gln Ser Ala Trp Ser Arg Val Leu Pro Tyr Leu
             20                  25                  30

Thr Arg Asp His Arg Val Val Leu Tyr Asp Leu Val Cys Ala Gly Ser
         35                  40                  45

Val Asn Pro Glu His Phe Asp Phe Arg Arg Tyr Asp Thr Leu Asp Ser
     50                  55                  60

Tyr Val Asp Asp Leu Leu Ala Ile Leu Asp Ala Leu Arg Ile Ala Arg
 65                  70                  75                  80

Cys Ala Phe Val Gly His Ser Val Ser Ala Met Ile Gly Ile Leu Ala
                 85                  90                  95

Ser Ile Arg Arg Pro Glu Leu Phe Ala Lys Leu Val Leu Ile Gly Ala
            100                 105                 110

Ser Pro Arg Phe Leu Asn Asp His Asp Tyr His Gly Gly Phe Glu Leu
        115                 120                 125

Pro Glu Ile Gln Gln Val Phe Asp Ala Met Ala Ala Asn Tyr Ser Ala
    130                 135                 140

Trp Ala Thr Gly Tyr Ala Pro Leu Ala Val Gly Ala Asp Val Pro Ala
145                 150                 155                 160

Ala Val Gln Glu Phe Ser Arg Thr Leu Phe Asn Met Arg Pro Asp Ile
                165                 170                 175

Ser Leu His Val Cys Arg Thr Val Phe Asn Thr Asp Leu Arg Gly Val
            180                 185                 190

Leu Gly Met Val Arg Ser Pro Cys Val Val Gln Thr Thr Arg Asp
        195                 200                 205

Val Ser Val Pro Ala Ser Val Ala Ala Tyr Leu Lys Ala His Leu Gly
    210                 215                 220

Gly Arg Thr Ala Val Glu Phe Leu Gln Thr Glu Gly His Leu Pro His
225                 230                 235                 240

Leu Ser Ala Pro Gly Leu Leu Ala Gln Val Leu Arg Arg
                245                 250

<210> SEQ ID NO 51
<211> LENGTH: 253
<212> TYPE: PRT
<213> ORGANISM: Zea mays

<400> SEQUENCE: 51

Asn Val Arg Val Val Gly Ser Gly Asp Arg Val Val Leu Ser His
 1               5                  10                  15

Gly Phe Gly Thr Asp Gln Ser Ala Trp Ser Arg Val Leu Pro Tyr Leu
             20                  25                  30

Thr Arg Asp His Arg Val Val Leu Tyr Asp Leu Val Cys Ala Gly Ser
         35                  40                  45

Val Asn Pro Glu His Phe Asp Phe Arg Arg Tyr Asp Thr Leu Asp Ser
     50                  55                  60

Tyr Val Asp Asp Leu Leu Ala Ile Leu Asp Ala Leu Arg Ile Ala Arg
 65                  70                  75                  80

Cys Ala Phe Val Gly His Ser Val Ser Ala Met Ile Gly Ile Leu Ala
                 85                  90                  95

Ser Ile Arg Arg Pro Glu Leu Phe Ala Lys Leu Val Leu Ile Gly Ala
            100                 105                 110

Ser Pro Arg Phe Leu Asn Asp His Asp Tyr His Gly Gly Phe Glu Leu
        115                 120                 125

Pro Glu Ile Gln Gln Val Phe Asp Ala Met Ala Ala Asn Tyr Ser Ala
    130                 135                 140
```

```
Trp Ala Thr Gly Tyr Ala Pro Leu Ala Val Gly Ala Asp Val Pro Ala
145                 150                 155                 160

Ala Val Gln Glu Phe Ser Arg Thr Leu Phe Asn Met Arg Pro Asp Ile
                165                 170                 175

Ser Leu His Val Cys Arg Thr Val Phe Asn Thr Asp Leu Arg Gly Val
            180                 185                 190

Leu Gly Met Val Arg Ser Pro Cys Val Val Gln Thr Thr Arg Asp
        195                 200                 205

Val Ser Val Pro Ala Ser Val Ala Ala Tyr Leu Lys Ala His Leu Gly
    210                 215                 220

Gly Arg Thr Ala Val Glu Phe Leu Gln Thr Gly His Leu Pro His
225                 230                 235                 240

Leu Ser Ala Pro Gly Leu Leu Ala Gln Val Leu Arg Arg
                245                 250
```

<210> SEQ ID NO 52
<211> LENGTH: 256
<212> TYPE: PRT
<213> ORGANISM: Arabidopsis thaliana

<400> SEQUENCE: 52

```
Glu Ala Leu Asn Val Arg Val Val Gly Thr Gly Asp Arg Ile Leu Phe
1               5                   10                  15

Leu Ala His Gly Phe Gly Thr Asp Gln Ser Ala Trp His Leu Ile Leu
                20                  25                  30

Pro Tyr Phe Thr Gln Asn Tyr Arg Val Val Leu Tyr Asp Leu Val Cys
            35                  40                  45

Ala Gly Ser Val Asn Pro Asp Tyr Phe Asp Phe Asn Arg Tyr Thr Thr
    50                  55                  60

Leu Asp Pro Tyr Val Asp Asp Leu Leu Asn Ile Val Asp Ser Leu Gly
65                  70                  75                  80

Ile Gln Asn Cys Ala Tyr Val Gly His Ser Val Ser Ala Met Ile Gly
                85                  90                  95

Ile Ile Ala Ser Ile Arg Arg Pro Glu Leu Phe Ser Lys Leu Ile Leu
            100                 105                 110

Ile Gly Phe Ser Pro Arg Phe Leu Asn Asp Glu Asp Tyr His Gly Gly
        115                 120                 125

Phe Glu Glu Gly Glu Ile Glu Lys Val Phe Ser Ala Met Glu Ala Asn
130                 135                 140

Tyr Glu Ala Trp Val His Gly Phe Ala Pro Leu Ala Val Gly Ala Asp
145                 150                 155                 160

Val Pro Ala Ala Val Arg Glu Phe Ser Arg Thr Leu Phe Asn Met Arg
                165                 170                 175

Pro Asp Ile Ser Leu Phe Val Ser Arg Thr Val Phe Asn Ser Asp Leu
            180                 185                 190

Arg Gly Val Leu Gly Leu Val Arg Val Pro Thr Cys Val Ile Gln Thr
        195                 200                 205

Ala Lys Asp Val Ser Val Pro Ala Ser Val Ala Glu Tyr Leu Arg Ser
    210                 215                 220

His Leu Gly Gly Glu Thr Thr Val Glu Thr Leu Lys Thr Glu Gly His
225                 230                 235                 240

Leu Pro Gln Leu Ser Ala Pro Ala Gln Leu Ala Gln Phe Leu Arg Arg
                245                 250                 255
```

```
<210> SEQ ID NO 53
<211> LENGTH: 256
<212> TYPE: PRT
<213> ORGANISM: Arabidopsis thaliana

<400> SEQUENCE: 53

Glu Ala Leu Asn Val Arg Val Val Gly Thr Gly Asp Arg Ile Leu Phe
  1               5                  10                  15

Leu Ala His Gly Phe Gly Thr Asp Gln Ser Ala Trp His Leu Ile Leu
             20                  25                  30

Pro Tyr Phe Thr Gln Asn Tyr Arg Val Val Leu Tyr Asp Leu Val Cys
         35                  40                  45

Ala Gly Ser Val Asn Pro Asp Tyr Phe Asp Phe Asn Arg Tyr Thr Thr
     50                  55                  60

Leu Asp Pro Tyr Val Asp Asp Leu Leu Asn Ile Val Asp Ser Leu Gly
 65                  70                  75                  80

Ile Gln Asn Cys Ala Tyr Val Gly His Ser Val Ser Ala Met Ile Gly
                 85                  90                  95

Ile Ile Ala Ser Ile Arg Arg Pro Glu Leu Phe Ser Lys Leu Ile Leu
                100                 105                 110

Ile Gly Phe Ser Pro Arg Phe Leu Asn Asp Glu Asp Tyr His Gly Gly
            115                 120                 125

Phe Glu Glu Gly Glu Ile Glu Lys Val Phe Ser Ala Met Glu Ala Asn
130                 135                 140

Tyr Glu Ala Trp Val His Gly Phe Ala Pro Leu Ala Val Gly Ala Asp
145                 150                 155                 160

Val Pro Ala Ala Val Arg Glu Phe Ser Arg Thr Leu Phe Asn Met Arg
                165                 170                 175

Pro Asp Ile Ser Leu Phe Val Ser Arg Thr Val Phe Asn Ser Asp Leu
            180                 185                 190

Arg Gly Val Leu Gly Leu Val Arg Val Pro Thr Cys Val Ile Gln Thr
        195                 200                 205

Ala Lys Asp Val Ser Val Pro Ala Ser Val Ala Glu Tyr Leu Arg Ser
210                 215                 220

His Leu Gly Gly Asp Thr Thr Val Glu Thr Leu Lys Thr Glu Gly His
225                 230                 235                 240

Leu Pro Gln Leu Ser Ala Pro Ala Gln Leu Ala Gln Phe Leu Arg Arg
                245                 250                 255

<210> SEQ ID NO 54
<211> LENGTH: 256
<212> TYPE: PRT
<213> ORGANISM: Arabidopsis thaliana

<400> SEQUENCE: 54

Glu Ala Leu Asn Val Arg Val Val Gly Thr Gly Asp Arg Ile Leu Phe
  1               5                  10                  15

Leu Ala His Gly Phe Gly Thr Asp Gln Ser Ala Trp His Leu Ile Leu
             20                  25                  30

Pro Tyr Phe Thr Gln Asn Tyr Arg Val Val Leu Tyr Asp Leu Val Cys
         35                  40                  45

Ala Gly Ser Val Asn Pro Asp Tyr Phe Asp Phe Asn Arg Tyr Thr Thr
     50                  55                  60

Leu Asp Pro Tyr Val Asp Asp Leu Leu Asn Ile Val Asp Ser Leu Gly
 65                  70                  75                  80

Ile Gln Asn Cys Ala Tyr Val Gly His Ser Val Ser Ala Met Ile Gly
```

```
                     85                  90                  95
Ile Ile Ala Ser Ile Arg Arg Pro Glu Leu Phe Ser Lys Leu Ile Leu
            100                 105                 110

Ile Gly Phe Ser Pro Arg Phe Leu Asn Asp Glu Asp Tyr His Gly Gly
            115                 120                 125

Phe Glu Glu Gly Glu Ile Glu Lys Val Phe Ser Ala Met Glu Ala Asn
            130                 135                 140

Tyr Glu Ala Trp Val His Gly Phe Ala Pro Leu Ala Val Gly Ala Asp
145                 150                 155                 160

Val Pro Ala Ala Val Arg Glu Phe Ser Arg Thr Leu Phe Asn Met Arg
                165                 170                 175

Pro Asp Ile Ser Leu Phe Val Ser Arg Thr Val Phe Asn Ser Asp Leu
            180                 185                 190

Arg Gly Val Leu Gly Leu Val Arg Val Pro Thr Cys Val Ile Gln Thr
            195                 200                 205

Ala Lys Asp Val Ser Val Pro Ala Ser Val Ala Glu Tyr Leu Arg Ser
            210                 215                 220

His Leu Gly Gly Asp Thr Thr Val Glu Thr Leu Lys Thr Glu Gly His
225                 230                 235                 240

Leu Pro Gln Leu Ser Ala Pro Ala Gln Leu Ala Gln Phe Leu Arg Arg
                245                 250                 255

<210> SEQ ID NO 55
<211> LENGTH: 258
<212> TYPE: PRT
<213> ORGANISM: Arabidopsis thaliana

<400> SEQUENCE: 55

Glu Ala Leu Asn Val Arg Val Val Gly Thr Gly Asp Arg Ile Leu Phe
1               5                   10                  15

Leu Ala His Gly Phe Gly Thr Asp Gln Ser Ala Trp His Leu Ile Leu
            20                  25                  30

Pro Tyr Phe Thr Gln Asn Tyr Arg Val Val Leu Tyr Asp Leu Val Cys
            35                  40                  45

Ala Gly Ser Val Asn Pro Asp Tyr Phe Asp Phe Asn Arg Tyr Thr Thr
        50                  55                  60

Leu Asp Pro Tyr Val Asp Asp Leu Leu Asn Ile Val Asp Ser Leu Gly
65                  70                  75                  80

Ile Gln Asn Cys Ala Tyr Val Gly His Ser Val Ser Ala Met Ile Gly
                85                  90                  95

Ile Ile Ala Ser Ile Arg Arg Pro Glu Leu Phe Ser Lys Leu Ile Leu
            100                 105                 110

Ile Gly Phe Ser Pro Arg Phe Leu Asn Asp Glu Asp Tyr His Gly Gly
            115                 120                 125

Phe Glu Glu Gly Glu Ile Glu Lys Val Phe Ser Ala Met Glu Ala Asn
            130                 135                 140

Tyr Glu Ala Trp Val His Gly Phe Ala Pro Leu Ala Val Gly Ala Asp
145                 150                 155                 160

Val Pro Ala Ala Val Arg Glu Phe Ser Arg Thr Leu Phe Asn Met Arg
                165                 170                 175

Pro Asp Ile Ser Leu Phe Val Ser Arg Thr Val Phe Asn Ser Asp Leu
            180                 185                 190

Arg Gly Val Leu Gly Leu Val Arg Val Pro Thr Cys Val Ile Gln Thr
            195                 200                 205
```

```
Ala Lys Asp Val Ser Val Pro Ala Ser Val Ala Glu Tyr Leu Arg Ser
    210                 215                 220

His Leu Gly Gly Asp Thr Thr Val Glu Thr Leu Lys Thr Glu Gly His
225                 230                 235                 240

Leu Pro Gln Leu Ser Ala Pro Ala Gln Leu Ala Gln Phe Leu Arg Arg
                245                 250                 255

Ala Leu
```

<210> SEQ ID NO 56
<211> LENGTH: 258
<212> TYPE: PRT
<213> ORGANISM: Arabidopsis thaliana

<400> SEQUENCE: 56

```
Glu Ala Leu Asn Val Arg Val Val Gly Thr Gly Asp Arg Ile Leu Phe
1               5                   10                  15

Leu Ala His Gly Phe Gly Thr Asp Gln Ser Ala Trp His Leu Ile Leu
                20                  25                  30

Pro Tyr Phe Thr Gln Asn Tyr Arg Val Val Leu Tyr Asp Leu Val Cys
            35                  40                  45

Ala Gly Ser Val Asn Pro Asp Tyr Phe Asp Phe Asn Arg Tyr Thr Thr
50                  55                  60

Leu Asp Pro Tyr Val Asp Leu Leu Asn Ile Val Asp Ser Leu Gly
65                  70                  75                  80

Ile Gln Asn Cys Ala Tyr Val Gly His Ser Val Ser Ala Met Ile Gly
                85                  90                  95

Ile Ile Ala Ser Ile Arg Arg Pro Glu Leu Phe Ser Lys Leu Ile Leu
            100                 105                 110

Ile Gly Phe Ser Pro Arg Phe Leu Asn Asp Glu Asp Tyr His Gly Gly
        115                 120                 125

Phe Glu Glu Gly Glu Ile Glu Lys Val Phe Ser Ala Met Glu Ala Asn
130                 135                 140

Tyr Glu Ala Trp Val His Gly Phe Ala Pro Leu Ala Val Gly Ala Asp
145                 150                 155                 160

Val Pro Ala Ala Val Arg Glu Phe Ser Arg Thr Leu Phe Asn Met Arg
                165                 170                 175

Pro Asp Ile Ser Leu Phe Val Ser Arg Thr Val Phe Asn Ser Asp Leu
            180                 185                 190

Arg Gly Val Leu Gly Leu Val Arg Val Pro Thr Cys Val Ile Gln Thr
        195                 200                 205

Ala Lys Asp Val Ser Val Pro Ala Ser Val Ala Glu Tyr Leu Arg Ser
    210                 215                 220

His Leu Gly Gly Asp Thr Thr Val Glu Thr Leu Lys Thr Glu Gly His
225                 230                 235                 240

Leu Pro Gln Leu Ser Ala Pro Ala Gln Leu Ala Gln Phe Leu Arg Arg
                245                 250                 255

Ala Leu
```

<210> SEQ ID NO 57
<211> LENGTH: 256
<212> TYPE: PRT
<213> ORGANISM: Arabidopsis thaliana

<400> SEQUENCE: 57

```
Asn Val Arg Val Val Gly Thr Gly Asp Arg Ile Leu Phe Leu Ala His
1               5                   10                  15
```

Gly Phe Gly Thr Asp Gln Ser Ala Trp His Leu Ile Leu Pro Tyr Phe
            20                  25                  30

Thr Gln Asn Tyr Arg Val Val Leu Tyr Asp Leu Val Cys Ala Gly Ser
        35                  40                  45

Val Asn Pro Asp Tyr Phe Asp Phe Asn Arg Tyr Thr Thr Leu Asp Pro
 50                  55                  60

Tyr Val Asp Asp Leu Leu Asn Ile Val Asp Ser Leu Gly Ile Gln Asn
 65                  70                  75                  80

Cys Ala Tyr Val Gly His Ser Val Ser Ala Met Ile Gly Ile Ile Ala
            85                  90                  95

Ser Ile Arg Arg Pro Glu Leu Phe Ser Lys Leu Ile Leu Ile Gly Phe
            100                 105                 110

Ser Pro Arg Phe Leu Asn Asp Glu Asp Tyr His Gly Gly Phe Glu Glu
            115                 120                 125

Gly Glu Ile Glu Ile Lys Val Phe Ser Ala Met Glu Ala Asn Tyr Glu
130                 135                 140

Ala Trp Val His Gly Phe Ala Pro Leu Ala Val Gly Ala Asp Val Pro
145                 150                 155                 160

Ala Ala Val Arg Glu Phe Ser Arg Thr Leu Phe Asn Met Arg Pro Asp
                165                 170                 175

Ile Ser Leu Phe Val Ser Arg Thr Val Phe Asn Ser Asp Leu Arg Gly
            180                 185                 190

Val Leu Gly Leu Val Arg Val Pro Thr Cys Val Ile Gln Thr Ala Lys
            195                 200                 205

Asp Val Ser Val Pro Ala Ser Val Ala Glu Tyr Leu Arg Ser His Leu
    210                 215                 220

Gly Gly Asp Thr Thr Val Glu Thr Leu Lys Thr Glu Gly His Leu Pro
225                 230                 235                 240

Gln Leu Ser Ala Pro Ala Gln Leu Ala Gln Phe Leu Arg Arg Ala Leu
                245                 250                 255

<210> SEQ ID NO 58
<211> LENGTH: 258
<212> TYPE: PRT
<213> ORGANISM: Physcomitrella patens

<400> SEQUENCE: 58

Lys Ala His Asn Val Ser Val Phe Gly Asn Gly Asp Gln Trp Leu Val
 1               5                  10                  15

Phe Gly His Gly Phe Gly Ser Asp Gln Ser Val Trp Gln Leu Val Ala
            20                  25                  30

Pro His Phe Ser Lys Thr Tyr Lys Val Leu Leu Phe Asp Leu Met Gly
            35                  40                  45

Ala Gly Ser Thr Asn Ser His Ser Phe Thr Phe Ser Arg Tyr Asn Thr
 50                  55                  60

Leu His Ala Tyr Ala Asp Asp Leu Leu Ala Ile Leu Glu Glu Met Asp
 65                  70                  75                  80

Ile Gln Ser Cys Thr Tyr Val Gly His Ser Met Ser Gly Met Ile Gly
            85                  90                  95

Cys Ile Ala Ser Ile Glu Arg Pro Ser Val Phe Lys Lys Leu Ile Leu
            100                 105                 110

Met Ala Ala Ser Pro Arg Tyr Ile Asn Asp Asp Asn Tyr Ile Gly Gly
            115                 120                 125

Phe Glu Leu Glu Asp Leu Leu Glu Val Phe Ala Ala Met Gln Ser Asn

```
            130                 135                 140
Phe Arg Ala Trp Ala Thr Gly Phe Val Pro Lys Ala Met Gly Ala Asp
145                 150                 155                 160

Ile Gln Ser Trp Pro Val Arg Glu Phe Thr Arg Thr Leu Phe Asn Met
                165                 170                 175

Arg Pro Asp Ile Ala Leu Gly Val Ser Lys Thr Cys Phe Glu Ser Asp
            180                 185                 190

Leu Arg Pro Ile Leu Pro Gln Val Thr Val Pro Cys Tyr Leu Met Gln
        195                 200                 205

Thr Gly Met Asp Ile Ser Val Ser Ile Glu Val Val Lys Tyr Met Ala
    210                 215                 220

Ala His Leu Gly Gly Lys Thr Glu Val Glu Ile Leu His Asp Leu Glu
225                 230                 235                 240

Gly His Leu Pro His Leu Thr His Pro Ala Glu Val Thr Ala Met Leu
                245                 250                 255

Gln Arg

<210> SEQ ID NO 59
<211> LENGTH: 258
<212> TYPE: PRT
<213> ORGANISM: Physcomitrella patens

<400> SEQUENCE: 59

Lys Ser His Asn Val Arg Ile Leu Gly Ser Gly Asp Glu Trp Leu Val
1               5                   10                  15

Phe Gly His Gly Phe Gly Ser Asp Gln Ser Val Trp Gln Leu Ile Val
            20                  25                  30

Pro His Phe Ala Lys Ser Tyr Lys Ile Leu Leu Phe Asp Leu Met Gly
        35                  40                  45

Ala Gly Ser Thr Asn Pro His Ser Phe Thr Phe Ser Arg Tyr Asn Thr
    50                  55                  60

Leu Tyr Ala His Ala Asp Asp Leu Leu Thr Ile Leu Asp Glu Leu Gly
65                  70                  75                  80

Ile Val Ser Cys Thr Tyr Ile Gly His Ser Met Ser Gly Met Ile Gly
                85                  90                  95

Cys Ile Ala Ser Ile Glu Arg Pro Ser Val Phe Lys Lys Leu Val Leu
            100                 105                 110

Ile Ala Thr Ser Pro Arg Tyr Ser Asn Asp Gly Asp Tyr Ile Gly Gly
        115                 120                 125

Phe Glu Met Glu Glu Leu His Glu Leu Phe Ala Ala Met Arg Ser Asn
    130                 135                 140

Phe Ile Ala Trp Ile Thr Gly Phe Ser Pro Lys Ala Val Gly Ser Asp
145                 150                 155                 160

Ile Gln Ser Trp Pro Val Gln Glu Phe Ser Arg Thr Phe Phe Asn Met
                165                 170                 175

Arg Pro Asp Ile Ala Leu Ser Ile Cys Lys Thr Cys Phe Ala Ser Asp
            180                 185                 190

Leu Arg Pro Leu Ile Pro Gln Val Met Ile Pro Cys Tyr Leu Val Gln
        195                 200                 205

Ser Gly Val Asp Ala Ser Leu Ser Ile Lys Val Val Lys Tyr Met Ala
    210                 215                 220

Ala Asn Leu Gly Gly Met Ser His Val Asp Ile Leu Gln Asp Ile Gln
225                 230                 235                 240

Gly His Leu Pro His Leu Ala His Pro Glu Ala Val Ile Ala Met Leu
```

-continued

```
                245                 250                 255
Gln Arg

<210> SEQ ID NO 60
<211> LENGTH: 250
<212> TYPE: PRT
<213> ORGANISM: Glycine max

<400> SEQUENCE: 60

Asp Ala Leu Asn Val Arg Val Glu Gly Ser Gly Asp Lys Tyr Leu Val
  1               5                  10                  15

Leu Ala His Gly Phe Gly Thr Asp Gln Ser Ala Trp Gln Arg Val Leu
             20                  25                  30

Pro Tyr Phe Thr Arg Asn Tyr Ser Val Ile Leu Tyr Asp Leu Val Cys
         35                  40                  45

Ala Gly Ser Val Asn Pro Asp His Phe Asp Tyr Arg Arg Tyr Thr Thr
     50                  55                  60

Leu Asp Ala Tyr Val Asp Leu Leu Asn Ile Leu Asp Ala Leu Arg
 65                  70                  75                  80

Val Pro Arg Cys Ala Tyr Val Gly His Ser Ile Ser Ala Met Ile Gly
                 85                  90                  95

Met Leu Ala Ser Ile Arg Arg Pro Asp Leu Phe Ser Lys Leu Ile Leu
             100                 105                 110

Ile Gly Ala Ser Pro Arg Tyr Asn Lys Phe Leu Asn Asp Lys Asp Tyr
         115                 120                 125

His Gly Gly Phe Glu Gln Gly Glu Ile Glu Gln Val Phe Ser Ala Met
     130                 135                 140

Glu Ala Asn Tyr Glu Ala Trp Val Asn Gly Phe Ala Pro Leu Ala Val
145                 150                 155                 160

Gly Ala Asp Val Pro Ala Ala Val Arg Glu Phe Ser Arg Thr Leu Phe
                165                 170                 175

Asn Met Arg Pro Asp Ile Ser Leu Phe Val Ser Arg Thr Val Phe Asn
            180                 185                 190

Ser Asp Leu Arg Gly Ile Leu Gly Leu Val Asn Val Pro Cys Cys Ile
        195                 200                 205

Met Gln Thr Ala Arg Asp Met Ser Val Pro Ala Ser Val Ala Thr Tyr
    210                 215                 220

Met Arg Asp His Ile Ala Gly Lys Ser Thr Ile Gln Trp Leu Asp Thr
225                 230                 235                 240

Glu Gly His Leu Pro His Leu Ser Ala Pro
                245                 250

<210> SEQ ID NO 61
<211> LENGTH: 219
<212> TYPE: PRT
<213> ORGANISM: Platanus acerifolia

<400> SEQUENCE: 61

Glu Ala Leu Asn Val Arg Val Val Gly Thr Gly Glu Arg Thr Leu Val
  1               5                  10                  15

Leu Ala His Gly Phe Gly Thr Asp Gln Ser Ala Trp Gln Arg Val Leu
             20                  25                  30

Pro Tyr Phe Val Pro His Tyr Arg Ile Val Leu Tyr Asp Leu Val Cys
         35                  40                  45

Ala Gly Ser Val Asn Pro Asp His Phe Asp Phe Arg Arg Tyr Thr Ser
     50                  55                  60
```

```
Leu Tyr Ala Tyr Val Glu Asp Leu Leu His Ile Leu Glu Ala Leu Gly
 65                  70                  75                  80

Ile Glu Lys Cys Ala Tyr Val Gly His Ser Ile Ser Ala Met Ile Gly
                 85                  90                  95

Ile Leu Ala Ser Ile Arg Arg Pro Asp Leu Phe Thr Lys Leu Val Leu
            100                 105                 110

Ile Gly Ala Ser Pro Arg Phe Leu Asn Asp Arg Asp Tyr His Gly Gly
            115                 120                 125

Phe Glu Arg Glu Glu Ile Glu Lys Leu Phe Ser Ala Met Glu Ala Asn
130                 135                 140

Tyr Glu Ala Trp Val Asn Gly Phe Ala Pro Leu Ala Val Gly Ala Asp
145                 150                 155                 160

Val Pro Ala Val Val Arg Glu Phe Ser Arg Thr Leu Phe Asn Met Arg
                165                 170                 175

Pro Asp Ile Ser Leu Phe Val Ser Arg Thr Val Phe Asn Ser Asp Phe
            180                 185                 190

Arg Gly Val Leu Gly Leu Val Lys Val Pro Cys Cys Ile Ile Gln Ser
            195                 200                 205

Val Arg Asp Val Ser Val Pro Val Ser Val Ala
    210                 215

<210> SEQ ID NO 62
<211> LENGTH: 265
<212> TYPE: PRT
<213> ORGANISM: Picea sitchensis

<400> SEQUENCE: 62

Met Gly Val Glu Ser Glu Leu Leu Gly Val Leu Asn Val Lys Val Ile
  1               5                  10                  15

Gly Ser Gly Gln Arg Ile Leu Val Leu Ala His Gly Phe Gly Ala Asp
                 20                  25                  30

Gln Ser Val Trp Gln Tyr Ile Leu Pro Tyr Leu Val Ala His Tyr Lys
             35                  40                  45

Val Ile Val Phe Asp Met Val Phe Ser Gly Asn Val Asp Pro Lys His
 50                  55                  60

Phe Asp Phe Asp Arg Tyr Thr Ser Leu Ser Ala Tyr Thr Ala Asp Leu
 65                  70                  75                  80

Leu Gly Ile Leu Asp Glu Leu Lys Val Asp Lys Cys Leu Tyr Val Gly
                 85                  90                  95

His Ser Val Ser Gly Met Val Gly Cys Leu Ala Ser Ile Glu Arg Pro
            100                 105                 110

Glu Leu Phe Glu Lys Leu Ile Leu Leu Cys Ala Ser Pro Arg Tyr Leu
            115                 120                 125

Asn Asp Glu Ser Tyr His Gly Gly Phe Glu Arg Gly Glu Ile Asp Arg
130                 135                 140

Leu Tyr Cys Ala Met Lys Ser Asp Tyr Ala Ala Trp Val Ser Gly Phe
145                 150                 155                 160

Ala Pro Leu Ala Val Gly Val Asp Glu Pro Ser Val Val Lys Glu Phe
                165                 170                 175

Ser Arg Thr Met Met Asn Met Arg Pro Glu Ile Ala Leu Leu Val Ala
            180                 185                 190

Arg Thr Ile Phe Glu Ser Asp Met Arg Ser Ile Leu Ser Asp Val Lys
            195                 200                 205

Thr Pro Cys Ser Ile Ile Gln Thr Ala Lys Asp Ile Val Val Pro Met
```

```
            210                 215                 220
Ala Val Pro Tyr His Met Gln Gly Ser Leu Gly Gly Lys Met Asn Ser
225                 230                 235                 240

Val Asp Ile Leu Asp Glu Asp Gly His Leu Pro Gln Leu Thr Asn Pro
                245                 250                 255

Gly Leu Leu Leu His Ala Phe Lys Arg
            260                 265

<210> SEQ ID NO 63
<211> LENGTH: 254
<212> TYPE: PRT
<213> ORGANISM: Picea sitchensis

<400> SEQUENCE: 63

Asn Val Lys Val Ile Gly Ser Gly His Arg Ile Leu Val Leu Ala His
1               5                   10                  15

Gly Phe Gly Ala Asp Gln Ser Val Trp Gln Tyr Ile Leu Pro Tyr Leu
            20                  25                  30

Val Gly His Tyr Lys Val Ile Phe Asp Met Val Phe Ser Gly His
        35                  40                  45

Val Asp Pro Lys His Phe Asp Phe Asp Arg Tyr Thr Ser Leu Ser Ala
    50                  55                  60

Tyr Ala Ala Asp Leu Leu Gly Ile Leu Asp Glu Leu Lys Val Asp Lys
65                  70                  75                  80

Cys Leu Tyr Val Gly His Ser Val Ser Gly Met Val Gly Cys Leu Ala
                85                  90                  95

Ser Ile Glu Arg Pro Glu Leu Phe Glu Arg Leu Ile Leu Leu Cys Ala
            100                 105                 110

Ser Pro Arg Tyr Leu Asn Asp Glu Ser Tyr His Gly Gly Phe Glu Arg
        115                 120                 125

Gly Glu Ile Asp Arg Leu Tyr Cys Ala Met Lys Ser Asp Tyr Ala Ala
    130                 135                 140

Trp Val Ser Gly Phe Ala Pro Leu Ala Val Gly Val Asp Glu Pro Ser
145                 150                 155                 160

Val Val Lys Glu Phe Ser Arg Thr Met Met Asn Met Arg Pro Glu Ile
                165                 170                 175

Ala Leu Ala Val Ala Arg Thr Ile Phe Glu Ser Asp Met Arg Ser Ile
            180                 185                 190

Leu Ser Asp Val Lys Thr Pro Cys Ser Ile Ile Gln Thr Ala Lys Asp
        195                 200                 205

Ile Val Val Pro Met Ala Val Pro Tyr His Met Gln Gly Ser Leu Gly
    210                 215                 220

Gly Lys Met Asn Ser Val Asp Leu Leu Asp Glu Asp Gly His Leu Pro
225                 230                 235                 240

Gln Leu Thr His Pro Gly Leu Leu Leu Gln Ala Phe Lys Arg
                245                 250

<210> SEQ ID NO 64
<211> LENGTH: 252
<212> TYPE: PRT
<213> ORGANISM: Picea sitchensis

<400> SEQUENCE: 64

Asn Val Lys Ile Ile Gly Ser Gly Lys Pro Thr Leu Val Leu Ala His
1               5                   10                  15

Gly Phe Gly Ser Asp Gln Ser Val Trp Gln Tyr Ile Leu Pro Tyr Leu
```

```
            20                  25                  30
Val Ala His Tyr Lys Val Ile Val Phe Asp Met Val Phe Ser Gly Lys
                35                  40                  45
Val Asp Pro Lys Asn Phe Asp Phe Asp Arg Tyr Thr Ser Leu Ser Ala
 50                  55                  60
Tyr Ala Ala Asp Leu Leu Ser Ile Leu Asp Glu Leu Lys Ile Asp Lys
 65                  70                  75                  80
Cys Leu Tyr Val Gly His Ser Val Ser Gly Met Val Gly Cys Leu Ala
                85                  90                  95
Ser Ile Glu Arg Pro Glu Leu Phe Arg Leu Ile Leu Leu Cys Ala
                100                 105                 110
Ser Pro Arg Tyr Leu Asn Glu Glu Ser Tyr His Gly Gly Phe Glu Arg
                115                 120                 125
Gly Glu Val Asp Ser Leu Tyr Tyr Ala Lys Lys Ser His Tyr Ala Ala
                130                 135                 140
Trp Ala Ser Gly Phe Ala Pro Leu Ala Val Gly Val Asp Glu Pro Ser
145                 150                 155                 160
Val Val Glu Glu Phe Arg Arg Thr Met Met Asn Met Lys Pro Glu Ile
                165                 170                 175
Ala Leu Ala Val Ala Lys Thr Ile Phe Glu Ser Asp Met Arg Ser Ile
                180                 185                 190
Leu Cys Asp Val Lys Thr Pro Cys Ser Ile Ile Gln Thr Ala Lys Asp
                195                 200                 205
Ile Val Val Pro Met Ala Val Pro Tyr His Met Gln Gly Asn Leu Gly
                210                 215                 220
Gly Lys Met Asn Ser Val Ile Ile Leu Asp Ala Glu Gly His Leu Pro
225                 230                 235                 240
Gln Leu Thr Ala Gln Asp Leu Leu Gln Ala Val
                245                 250

<210> SEQ ID NO 65
<211> LENGTH: 249
<212> TYPE: PRT
<213> ORGANISM: Picea sitchensis

<400> SEQUENCE: 65

Asp Ala Leu Asn Val Thr Val Asn Gly Ser Gly Glu Arg Ile Leu Val
 1                   5                  10                  15
Leu Ser His Gly Phe Gly Gly Asp Gln Ser Met Trp Lys His Ile Leu
                20                  25                  30
Pro Tyr Leu Leu Pro Asp Phe Lys Val Ile Val Phe Asp Met Val Phe
                35                  40                  45
Ser Gly Ser Val Asp Pro Lys His Phe Asp Phe Asp Arg Tyr Thr Asp
 50                  55                  60
Ser Leu Ser Ala Tyr Ala Asp Asp Leu Leu Ala Ile Leu Asp Glu Leu
 65                  70                  75                  80
Lys Ala Asp Lys Cys Val Tyr Val Gly His Ser Val Ser Ala Met Val
                85                  90                  95
Gly Cys Leu Ala Ser Ile Lys Arg Pro Gly Leu Phe Glu Arg Leu Ile
                100                 105                 110
Leu Leu Cys Ala Ser Pro Arg Tyr Leu Asn Asn Glu Ser Tyr Glu Gly
                115                 120                 125
Gly Phe Glu Arg Gly Asp Ile Asp Gly Ile Phe Ser Ala Ile Lys Ser
                130                 135                 140
```

```
Asn Tyr Ser Ala Trp Val Ser Gly Phe Val Pro Leu Leu Ile Gly Val
145                 150                 155                 160

Asp Glu Pro Ser Leu Val Lys Glu Phe Ser Lys Lys Leu Met Asn Met
                165                 170                 175

Lys Pro Glu Ile Ala Leu Val Ala Lys Ala Ile Phe Gln Ser Asp
            180                 185                 190

Val Arg Asn Ile Leu Cys Asp Val Lys Thr Pro Cys Ser Ile Ile Gln
            195                 200                 205

Thr Arg Lys Asp Ile Ala Val Pro Leu Ser Val Pro Tyr Tyr Met Gln
            210                 215                 220

Arg Asn Leu Gly Gly Glu Lys Asn Ser Val His Ile Leu Asp Thr Asp
225                 230                 235                 240

Gly His Ile Pro Gln Leu Thr Ser Pro
                245
```

```
<210> SEQ ID NO 66
<211> LENGTH: 277
<212> TYPE: PRT
<213> ORGANISM: Glycine max

<400> SEQUENCE: 66

Asp Ala Leu Asn Val Arg Val Glu Gly Ser Gly Asp Lys Tyr Leu Val
1               5                   10                  15

Leu Ala His Gly Phe Gly Thr Asp Gln Ser Ala Trp Gln Arg Val Leu
            20                  25                  30

Pro Tyr Phe Thr Arg Asn Tyr Ser Val Ile Leu Tyr Asp Leu Val Cys
            35                  40                  45

Ala Gly Ser Val Asn Pro Asp His Phe Asp Tyr Arg Arg Tyr Thr Thr
    50                  55                  60

Leu Asp Ala Tyr Val Asp Asp Leu Leu Asn Ile Leu Asp Ala Leu Arg
65                  70                  75                  80

Val Pro Arg Cys Ala Tyr Val Gly His Ser Ile Ser Ala Met Ile Gly
                85                  90                  95

Met Leu Ala Ser Thr Arg Arg Pro Asp Leu Phe Ser Lys Leu Ile Leu
            100                 105                 110

Ile Gly Ala Ser Pro Arg Tyr Asn Lys Phe Ser Ser Pro Ser Ser Ile
            115                 120                 125

Leu Phe Tyr Ser Ile Leu Phe Tyr Ala Ser Lys Glu Gln Leu Ala Leu
        130                 135                 140

Glu Phe Leu Arg Phe Leu Asn Asp Lys Asp Tyr His Gly Gly Phe Glu
145                 150                 155                 160

Gln Gly Glu Ile Glu Gln Val Phe Ser Ala Met Glu Ala Asn Tyr Glu
                165                 170                 175

Ala Trp Val Asn Gly Phe Ala Pro Leu Ala Val Gly Ala Asp Val Pro
            180                 185                 190

Ala Ala Val Arg Glu Phe Ser Arg Thr Leu Phe Asn Met Arg Pro Asp
            195                 200                 205

Ile Ser Leu Phe Val Ser Arg Thr Val Phe Asn Ser Asp Leu Arg Gly
        210                 215                 220

Ile Leu Gly Leu Val Asn Val Pro Cys Cys Ile Met Gln Thr Ala Arg
225                 230                 235                 240

Asp Met Ser Val Pro Ala Ser Val Ala Thr Tyr Met Arg Asp His Ile
                245                 250                 255

Ala Gly Lys Ser Thr Ile Gln Trp Leu Asp Thr Glu Gly His Leu Pro
            260                 265                 270
```

His Leu Ser Ala Pro
        275

<210> SEQ ID NO 67
<211> LENGTH: 252
<212> TYPE: PRT
<213> ORGANISM: Leptospira interrogans

<400> SEQUENCE: 67

His Asn Leu Lys Ile Ile Gly Ser Glu Lys Glu Thr Ile Val Phe Ser
 1               5                  10                  15

His Gly Phe Gly Cys Asp Gln Ser Thr Trp Asn Lys Leu Ile Pro Asn
            20                  25                  30

Leu Lys Asp His Tyr Arg Leu Val Leu Phe Asp Thr Ile Gly Ser Gly
        35                  40                  45

Lys Thr Asp Pro Ser Leu Phe Ser Ala Asp Arg Tyr Ser Asn Leu Tyr
    50                  55                  60

Ser Tyr Ala Glu Asp Leu Ile Leu Met Asp Glu Leu Lys Ile Arg
65                  70                  75                  80

Asn Ser Leu Tyr Val Gly His Ser Val Ser Gly Met Ile Gly Leu Ile
                85                  90                  95

Thr Ser Ile Arg Arg Pro Glu Leu Phe Ser Lys Leu Ala Phe Ile Ser
            100                 105                 110

Ala Ser Pro Arg Tyr Leu Asn Asp Thr Asn Tyr Lys Gly Gly Phe Glu
        115                 120                 125

Gln Thr Asp Leu Asp Gln Leu Phe Ala Ala Met Glu Thr Asn Phe Phe
    130                 135                 140

Ser Trp Ala Gly Gly Phe Ala Pro Leu Ala Met Gly Asn Pro Asp Arg
145                 150                 155                 160

Pro Glu Leu Ala Gln Ser Phe Ala Glu Ser Leu Arg Glu Ile Arg Pro
                165                 170                 175

Asp Ile Gly Leu Thr Val Ser Arg Thr Ile Phe Gln Ser Asp His Arg
            180                 185                 190

Lys Asp Leu Asn Gln Cys Lys Gln Pro Val Leu Ile Leu Gln Pro Ser
        195                 200                 205

Ser Asp Ile Ala Val Pro Ile Glu Val Gly Lys Tyr Leu Ser Ala Asn
    210                 215                 220

Ile Pro Gln Ala Ile Phe Lys Ser Ile Pro Ala Thr Gly His Leu Pro
225                 230                 235                 240

His Phe Ser Ser Pro Glu Ser Val Leu Gln Glu Ile
                245                 250

<210> SEQ ID NO 68
<211> LENGTH: 252
<212> TYPE: PRT
<213> ORGANISM: Leptospira interrogans

<400> SEQUENCE: 68

His Asn Leu Lys Ile Ile Gly Ser Glu Lys Glu Thr Ile Val Phe Ser
 1               5                  10                  15

His Gly Phe Gly Cys Asp Gln Ser Thr Trp Asn Lys Leu Ile Pro Asn
            20                  25                  30

Leu Lys Asp His Tyr Arg Leu Val Leu Phe Asp Thr Ile Gly Ser Gly
        35                  40                  45

Lys Thr Asp Pro Ser Leu Phe Ser Ala Asp Arg Tyr Ser Asn Leu Tyr
    50                  55                  60

```
Ser Tyr Ala Glu Asp Leu Ile Leu Leu Met Asp Glu Leu Lys Ile Arg
 65                  70                  75                  80

Asn Ser Leu Tyr Val Gly His Ser Val Ser Gly Met Ile Gly Leu Ile
                 85                  90                  95

Thr Ser Ile Arg Arg Pro Glu Leu Phe Ser Lys Leu Ala Phe Ile Ser
            100                 105                 110

Ala Ser Pro Arg Tyr Leu Asn Asp Thr Asn Tyr Lys Gly Gly Phe Glu
        115                 120                 125

Gln Thr Asp Leu Asp Gln Leu Phe Ala Ala Met Glu Thr Asn Phe Phe
    130                 135                 140

Ser Trp Ala Gly Gly Phe Ala Pro Leu Ala Met Gly Asn Pro Asp Arg
145                 150                 155                 160

Pro Glu Leu Ala Gln Ser Phe Ala Glu Ser Leu Arg Glu Ile Arg Pro
                165                 170                 175

Asp Ile Gly Leu Thr Val Ser Arg Thr Ile Phe Gln Ser Asp His Arg
            180                 185                 190

Lys Asp Leu Asn Gln Cys Lys Gln Pro Val Leu Ile Leu Gln Pro Ser
        195                 200                 205

Ser Asp Ile Ala Val Pro Ile Glu Val Gly Lys Tyr Leu Ser Ala Asn
    210                 215                 220

Ile Pro Gln Ala Ile Phe Lys Ser Ile Pro Ala Thr Gly His Leu Pro
225                 230                 235                 240

His Phe Ser Ser Pro Glu Ser Val Leu Gln Glu Ile
                245                 250

<210> SEQ ID NO 69
<211> LENGTH: 227
<212> TYPE: PRT
<213> ORGANISM: Physcomitrella patens

<400> SEQUENCE: 69

Ala His Asn Leu Ser Val Leu Gly Asn Gly Asp Gln Val Val Val Leu
  1               5                  10                  15

Gly His Gly Phe Gly Ser Asp Gln Ser Met Trp Lys Tyr Val Val Pro
                 20                  25                  30

Ser Leu Leu Ser Asn Asn Phe Arg Val Val Leu Tyr Asp Leu Met Gly
            35                  40                  45

Ala Ser Thr Thr Asp Ala Asn Asn Phe Ser Phe Lys Arg Tyr Thr Ser
        50                  55                  60

Leu Gln Ser Phe Ala Asp Asp Leu Leu Ala Ile Leu Asp Glu Leu Glu
 65                  70                  75                  80

Ile Glu Ser Cys Val Tyr Val Gly His Ser Ile Ser Gly Met Ile Gly
                 85                  90                  95

Cys Leu Ala Ser Leu Glu Lys Pro Asp Ile Phe Gln Lys Leu Ile Leu
            100                 105                 110

Leu Gly Ala Ser Pro Arg Tyr Leu Asn Asp Thr Asn Tyr His Gly Gly
        115                 120                 125

Phe Glu Gln His Asp Leu Asp Gln Met Tyr Ala Asn Met Lys Ser Asn
    130                 135                 140

Phe Arg Thr Trp Val Ser Gly Phe Ala Pro Ala Ala Leu Gly Ala His
145                 150                 155                 160

Ile Asp Asn Arg Ala Val Thr Val Pro Cys His Ile Leu Gln Ser Met
                165                 170                 175

Lys Asp Leu Ala Val Pro Val Glu Val Ala Glu Tyr Leu Asn Ser Asn
```

```
              180                 185                 190
Leu Gly Gly Trp Thr Ser Ile Arg Ile Leu Gln Thr Glu Gly His Ile
            195                 200                 205

Pro Gln Leu Ser Ser Pro Glu Leu Val Ile Pro Val Leu Leu Arg Cys
            210                 215                 220

Ile Glu Asp
225

<210> SEQ ID NO 70
<211> LENGTH: 245
<212> TYPE: PRT
<213> ORGANISM: Picea sitchensis

<400> SEQUENCE: 70

Asn Val Lys Val Ile Gly Ser Gly Asp Arg Ile Leu Val Leu Ala His
  1               5                  10                  15

Gly Phe Gly Ala Asp Gln Ser Val Trp Gln Tyr Ile Leu Pro Tyr Leu
             20                  25                  30

Val Val His Tyr Lys Val Ile Val Phe Asp Met Val Phe Ser Gly Asn
             35                  40                  45

Val Asp Pro Lys His Phe Asp Ile Asp Arg Tyr Thr Ser Leu Tyr Ser
         50                  55                  60

Tyr Ala Ala Asp Leu Ile Ala Ile Leu Asp Glu Leu Lys Val Glu Lys
 65                  70                  75                  80

Cys Leu Phe Val Gly His Ser Val Ser Gly Met Val Gly Cys Leu Ala
             85                  90                  95

Ser Ile Lys Arg Pro Glu Leu Phe Glu Arg Leu Ile Leu Leu Cys Ala
            100                 105                 110

Ser Pro Arg Tyr Leu Asn Asp Glu Ser Tyr His Gly Gly Phe Glu Arg
            115                 120                 125

Gly Gln Val Asp Ile Leu Tyr Cys Ala Met Lys Ser Asp Tyr Ala Glu
        130                 135                 140

Trp Val Ser Gly Phe Ala Pro Leu Ala Val Gly Val Asp Ala Pro Ser
145                 150                 155                 160

Val Val Gln Glu Phe Ser Arg Thr Met Met Asn Met Lys Pro Glu Ile
            165                 170                 175

Ala Val Ala Val Ala Ser Thr Ile Phe Glu Ser Asp Met Arg Ser Ile
            180                 185                 190

Leu Cys Asp Val Met Thr Pro Val Ser Ile Ile Gln Thr Ala Arg Asp
            195                 200                 205

Ile Val Val Pro Met Thr Val Pro Tyr His Met Gln Gly Ile Leu Gly
        210                 215                 220

Gly Lys Thr Asn Ser Val Asp Ile Leu Asp Val Asp Gly His Leu Pro
225                 230                 235                 240

His Leu Thr Ser Pro
            245

<210> SEQ ID NO 71
<211> LENGTH: 220
<212> TYPE: PRT
<213> ORGANISM: Populus trichocarpa

<400> SEQUENCE: 71

Tyr Arg Val Ile Leu Phe Asp Leu Val Cys Ala Gly Ser Val Asn Pro
  1               5                  10                  15

Asp Tyr Phe Asn Phe Arg Arg Tyr Thr Asn Leu Glu Ala Tyr Val Asp
```

```
            20                  25                  30
Asp Leu Leu Asn Ile Leu Asp Thr Leu Gly Val Asp Arg Cys Phe Tyr
            35                  40                  45

Val Gly His Ser Val Ser Ala Met Ile Gly Ile Leu Ala Ser Ile Arg
        50                  55                  60

Arg Pro Glu Leu Phe Thr Lys Leu Ile Met Ile Gly Ala Ser Pro Arg
 65                  70                  75                  80

Phe Leu Asn Asp Lys Asp Tyr His Gly Gly Phe Glu Gln Glu Glu Ile
                85                  90                  95

Glu Ser Val Phe Val Ala Met Glu Ala Asn Tyr Glu Ala Trp Val Lys
            100                 105                 110

Gly Phe Ala Pro Leu Ala Val Gly Ala Asp Val Pro Ala Ala Val Arg
            115                 120                 125

Glu Phe Ser Arg Thr Leu Phe Asn Met Arg Pro Asp Ile Thr Leu Phe
            130                 135                 140

Val Ser Arg Thr Val Phe Asn Ser Asp Leu Arg Gly Ile Leu Gly Leu
145                 150                 155                 160

Val Lys Val Pro Cys Cys Val Ile Gln Thr Ser Lys Asp Val Ser Val
                165                 170                 175

Pro Ala Ser Val Ala Lys Tyr Leu Lys Asn His Leu Gly Gly Lys Ala
            180                 185                 190

Thr Val Glu Met Leu Arg Thr Glu Gly His Leu Pro His Leu Ser Ala
            195                 200                 205

Pro Ala Met Leu Ala Pro Val Ile Arg Arg Ala Leu
            210                 215                 220

<210> SEQ ID NO 72
<211> LENGTH: 226
<212> TYPE: PRT
<213> ORGANISM: Zea mays

<400> SEQUENCE: 72

Leu Thr Pro Tyr Leu Thr Arg Asp His Arg Val Val Leu Tyr Asp Leu
 1               5                  10                  15

Val Cys Ala Gly Ser Val Asn Pro Glu His Phe Asp Phe Arg Arg Tyr
            20                  25                  30

Asp Thr Leu Asp Ser Tyr Val Asp Leu Leu Ala Ile Leu Asp Ala
            35                  40                  45

Leu Arg Val Pro Arg Cys Ala Phe Val Gly His Ser Val Ser Ala Met
        50                  55                  60

Ile Gly Ile Leu Ala Ser Ile Arg Arg Pro Glu Leu Phe Ala Lys Leu
 65                  70                  75                  80

Val Leu Ile Gly Ala Ser Pro Arg Phe Leu Asn Asp His Asp Tyr His
                85                  90                  95

Gly Gly Phe Glu Leu Pro Glu Ile Gln Gln Val Phe Asp Ala Met Ala
            100                 105                 110

Ala Asn Tyr Ser Ala Trp Ala Thr Gly Tyr Ala Pro Leu Ala Val Gly
            115                 120                 125

Ala Asp Val Pro Ala Ala Val Gln Glu Phe Ser Arg Thr Leu Phe Asn
            130                 135                 140

Met Arg Pro Asp Ile Ser Leu His Val Cys Arg Thr Val Phe Asn Thr
145                 150                 155                 160

Asp Leu Arg Gly Val Leu Gly Met Val Arg Ala Pro Cys Val Val Val
                165                 170                 175
```

Gln Thr Thr Arg Asp Val Ser Val Pro Ala Ser Val Ala Ala Tyr Leu
            180                 185                 190

Lys Ala His Leu Gly Gly Arg Thr Ala Val Glu Phe Leu Gln Thr Glu
        195                 200                 205

Gly His Leu Pro His Leu Ser Ala Pro Gly Leu Leu Ala Gln Val Leu
    210                 215                 220

Arg Arg
225

<210> SEQ ID NO 73
<211> LENGTH: 252
<212> TYPE: PRT
<213> ORGANISM: Picea sitchensis

<400> SEQUENCE: 73

Gly Arg Leu Leu Glu Val Leu Asn Val Arg Val Thr Gly Ser Gly Glu
1               5                   10                  15

Arg Val Val Val Leu Ser His Gly Phe Gly Gly Asp Gln Ser Met Trp
            20                  25                  30

Lys Asp Ile Leu Pro Tyr Leu Val Pro Asp Phe Lys Val Ile Val Phe
        35                  40                  45

Asp Leu Val Phe Ala Gly Ser Val Asp Pro Lys His Phe Asp Phe Asp
    50                  55                  60

Gln Ser Ser Asn Ser Leu Ala Ala Tyr Ala Asp Asp Ile Leu Ala Ile
65                  70                  75                  80

Leu Glu Glu Leu Lys Ile Asp Arg Cys Met Tyr Val Gly His Ser Val
                85                  90                  95

Ser Gly Met Leu Gly Cys Leu Ala Ser Ile Lys Arg Pro Glu Leu Phe
            100                 105                 110

Glu Arg Leu Ile Leu Leu Gly Ala Ser Pro Arg Tyr Leu Asn Asp Glu
        115                 120                 125

Ser Tyr Glu Gly Gly Ser Glu Arg Gly Glu Ile Asp Gly Ile Leu Ser
    130                 135                 140

Thr Ile Lys Ser Asn Tyr Ser Ala Trp Val Ser Gly Phe Val Pro Leu
145                 150                 155                 160

Leu Ile Gly Val Asp Gln Pro Ser Ile Val Asp Asp Leu Ser Arg Lys
                165                 170                 175

Trp Leu Ser Ile Lys Pro Glu Ile Ala Phe Pro Val Ala Lys Ser Ile
            180                 185                 190

Phe Glu Cys Asp Leu Arg Ser Ile Leu Thr Asp Val Lys Thr Pro Cys
        195                 200                 205

Ser Ile Ile Gln Thr Arg Lys Asp Val Val Val Pro Ser Ser Val Pro
    210                 215                 220

Tyr Tyr Met Gln Arg Asn Leu Gly Gly Glu Asn Asn Ser Val His Ile
225                 230                 235                 240

Leu Asp Ile Asp Gly His Leu Pro Gln Leu Thr Ser
                245                 250

<210> SEQ ID NO 74
<211> LENGTH: 148
<212> TYPE: PRT
<213> ORGANISM: Solanum lycopersicum

<400> SEQUENCE: 74

Arg Tyr Leu Asn Asp Val Asp Tyr Gly Gly Phe Glu Gln Glu Asp
1               5                   10                  15

```
Leu Asp Gln Leu Phe Glu Ala Met Arg Ser Asn Tyr Lys Ala Trp Cys
             20                  25                  30

Ser Gly Phe Ala Pro Leu Ala Ile Gly Gly Asp Met Asp Ser Val Ala
         35                  40                  45

Val Gln Glu Phe Ser Arg Thr Leu Phe Asn Met Arg Pro Asp Met Ala
     50                  55                  60

Leu Ser Val Leu Gln Ile Ile Phe Gln Ser Asp Leu Arg His Met Leu
 65                  70                  75                  80

Pro His Val Thr Val Pro Cys His Ile Ile Gln Ser Met Lys Asp Leu
                 85                  90                  95

Ala Val Pro Val Val Val Ser Glu Tyr Leu His Gln Asn Leu Gly Gly
             100                 105                 110

Glu Ser Ile Val Glu Val Met Ser Thr Asp Gly His Leu Pro Gln Leu
         115                 120                 125

Ser Ser Pro Asp Val Val Ile Pro Val Leu Leu Arg His Ile Arg Phe
     130                 135                 140

Asp Ile Ser Val
145

<210> SEQ ID NO 75
<211> LENGTH: 148
<212> TYPE: PRT
<213> ORGANISM: Solanum lycopersicum

<400> SEQUENCE: 75

Arg Tyr Leu Asn Asp Val Asp Tyr Tyr Gly Gly Phe Glu Gln Glu Asp
 1               5                  10                  15

Leu Asp Gln Leu Phe Glu Ala Met Arg Ser Asn Tyr Lys Ala Trp Cys
             20                  25                  30

Ser Gly Phe Ala Pro Leu Ala Ile Gly Gly Asp Met Asp Ser Val Ala
         35                  40                  45

Val Gln Glu Phe Ser Arg Thr Leu Phe Asn Met Arg Pro Asp Met Ala
     50                  55                  60

Leu Ser Val Leu Gln Ile Ile Phe Gln Ser Asp Leu Arg His Met Leu
 65                  70                  75                  80

Pro His Val Thr Val Pro Cys His Ile Ile Gln Ser Met Lys Asp Leu
                 85                  90                  95

Ala Val Pro Val Val Val Ser Glu Tyr Leu His Gln Asn Leu Gly Gly
             100                 105                 110

Glu Ser Ile Val Glu Val Met Ser Thr Asp Gly His Leu Pro Gln Leu
         115                 120                 125

Ser Ser Pro Asp Val Val Ile Pro Val Leu Leu Arg His Ile Arg Phe
     130                 135                 140

Asp Ile Ser Val
145

<210> SEQ ID NO 76
<211> LENGTH: 146
<212> TYPE: PRT
<213> ORGANISM: Vitis vinifera

<400> SEQUENCE: 76

Arg Tyr Leu Asn Asp Val Asp Tyr Tyr Gly Gly Phe Glu Gln Glu Asp
 1               5                  10                  15

Leu Asp Gln Leu Phe Glu Ala Met Gly Ser Asn Tyr Lys Ala Trp Cys
             20                  25                  30
```

Ser Gly Phe Ala Pro Leu Ala Val Gly Gly Asp Met Asp Ser Val Ala
         35                  40                  45

Val Gln Glu Phe Ser Arg Thr Leu Phe Asn Met Arg Pro Asp Ile Ala
 50                  55                  60

Leu Ser Val Ala Gln Thr Ile Phe Gln Val Asp Leu Arg Gln Ile Leu
 65                  70                  75                  80

Cys His Val Thr Val Pro Cys His Ile Leu Gln Ser Ile Lys Asp Leu
                 85                  90                  95

Ala Val Pro Val Val Ser Glu Tyr Leu His Gln Asn Leu Gly Gly
             100                 105                 110

Glu Ser Ile Val Glu Val Met Thr Ser Asp Gly His Leu Pro Gln Leu
             115                 120                 125

Ser Ser Pro Asp Ile Val Val Pro Val Leu Leu Arg His Ile Arg Tyr
 130                 135                 140

Asn Ile
145

<210> SEQ ID NO 77
<211> LENGTH: 146
<212> TYPE: PRT
<213> ORGANISM: Vitis vinifera

<400> SEQUENCE: 77

Arg Tyr Leu Asn Asp Val Asp Tyr Tyr Gly Gly Phe Glu Gln Glu Asp
 1               5                  10                  15

Leu Asp Gln Leu Phe Glu Ala Met Gly Ser Asn Tyr Lys Ala Trp Cys
             20                  25                  30

Ser Gly Phe Ala Pro Leu Ala Val Gly Gly Asp Met Asp Ser Val Ala
         35                  40                  45

Val Gln Glu Phe Ser Arg Thr Leu Phe Asn Met Arg Pro Asp Ile Ala
 50                  55                  60

Leu Ser Val Ala Gln Thr Ile Phe Gln Val Asp Leu Arg Gln Ile Leu
 65                  70                  75                  80

Cys His Val Thr Val Pro Cys His Ile Leu Gln Ser Ile Lys Asp Leu
                 85                  90                  95

Ala Val Pro Val Val Ser Glu Tyr Leu His Gln Asn Leu Gly Gly
             100                 105                 110

Glu Ser Ile Val Glu Val Met Thr Ser Asp Gly His Leu Pro Gln Leu
             115                 120                 125

Ser Ser Pro Asp Ile Val Val Pro Val Leu Leu Arg His Ile Arg Tyr
 130                 135                 140

Asn Ile
145

<210> SEQ ID NO 78
<211> LENGTH: 150
<212> TYPE: PRT
<213> ORGANISM: Oryza sativa

<400> SEQUENCE: 78

Ser Asn Arg Tyr Leu Asn Asp Val Asp Tyr Tyr Gly Gly Phe Glu Gln
 1               5                  10                  15

Glu Asp Leu Asp Glu Leu Phe Glu Ala Met Gly Ser Asn Tyr Lys Ala
             20                  25                  30

Trp Cys Ser Gly Phe Ala Pro Leu Cys Val Gly Gly Asp Met Glu Ser
         35                  40                  45

Val Ala Val Gln Glu Phe Ser Arg Thr Leu Phe Asn Ile Arg Pro Asp
 50                  55                  60

Ile Ala Leu Ser Val Ala Gln Thr Ile Phe Gln Ser Asp Val Arg Ser
 65                  70                  75                  80

Leu Leu Pro Leu Val Thr Val Pro Cys His Ile Val Gln Ser Thr Lys
                 85                  90                  95

Asp Leu Ala Val Pro Val Val Ser Glu Tyr Leu His Lys His Leu
                100                 105                 110

Gly Gly Asp Ser Ile Val Glu Val Met Pro Ser Glu Gly His Leu Pro
            115                 120                 125

Gln Leu Ser Ser Pro Asp Ile Val Ile Pro Val Leu Leu Arg His Ile
    130                 135                 140

Gln His Asp Ile Ala Val
145                 150

<210> SEQ ID NO 79
<211> LENGTH: 147
<212> TYPE: PRT
<213> ORGANISM: Medicago truncatula

<400> SEQUENCE: 79

Arg Tyr Leu Asn Asp Arg Asp Tyr Phe Gly Gly Phe Glu Gln Glu Asp
  1               5                  10                  15

Leu Asp Gln Leu Phe Asp Ala Met Ala Ser Asn Tyr Lys Ser Trp Cys
                 20                  25                  30

Ser Gly Phe Ala Pro Met Ala Val Gly Gly Asp Met Glu Ser Val Ala
             35                  40                  45

Val Gln Glu Phe Ser Arg Thr Leu Phe Asn Met Arg Pro Asp Ile Ala
 50                  55                  60

Leu Ser Val Leu Gln Thr Ile Phe Lys Ser Asp Met Arg Gln Ile Leu
 65                  70                  75                  80

Cys Met Val Thr Val Pro Cys His Ile Ile Gln Ser Met Lys Asp Leu
                 85                  90                  95

Ala Val Pro Val Val Ala Glu Tyr Leu His Gln His Val Gly Ser
                100                 105                 110

Glu Ser Ile Val Glu Val Met Ser Thr Glu Gly His Leu Pro Gln Leu
            115                 120                 125

Ser Ser Pro Asp Val Val Ile Pro Val Ile Leu Lys His Ile Arg His
    130                 135                 140

Asp Ile Ala
145

<210> SEQ ID NO 80
<211> LENGTH: 146
<212> TYPE: PRT
<213> ORGANISM: Medicago truncatula

<400> SEQUENCE: 80

Arg Tyr Leu Asn Asp Val Asn Tyr Phe Gly Gly Phe Glu Gln Glu Asp
  1               5                  10                  15

Leu Asn Gln Leu Phe Asn Ala Met Ala Glu Asn Tyr Lys Ala Trp Cys
                 20                  25                  30

Tyr Gly Phe Ala Pro Leu Ala Val Gly Gly Asp Met Asp Ser Val Ala
             35                  40                  45

Val Gln Glu Phe Ser Arg Thr Leu Phe Asn Met Arg Pro Asp Ile Ala
 50                  55                  60

```
Leu Ile Val Ser Arg Thr Ile Phe Gln Ser Asp Met Arg Gln Ile Leu
 65                  70                  75                  80

Asn Leu Val Thr Val Pro Cys His Ile Ile Gln Ala Glu Lys Asp Met
                 85                  90                  95

Ala Val Pro Val Met Val Ser Glu Tyr Leu His Gln His Leu Gly Gly
            100                 105                 110

Gln Ser Ile Val Glu Val Met Thr Thr Asp Gly His Leu Pro Gln Leu
        115                 120                 125

Ser Ser Pro Asp Ile Val Ile Pro Val Leu Leu Arg His Ile Gln Leu
    130                 135                 140

Asn Ile
145

<210> SEQ ID NO 81
<211> LENGTH: 141
<212> TYPE: PRT
<213> ORGANISM: Helianthus annuus

<400> SEQUENCE: 81

Arg Tyr Leu Asn Thr Glu Asp Tyr Phe Gly Gly Phe Glu Gln Glu Asp
  1               5                  10                  15

Leu Asp Gln Leu Phe Glu Ala Met Gln Ser Asn Tyr Lys Ala Trp Cys
             20                  25                  30

Ser Gly Phe Ala Pro Leu Ala Val Gly Gly Asp Met Asp Ser Val Ala
         35                  40                  45

Val Gln Glu Phe Ser Arg Thr Leu Phe Asn Met Arg Pro Asp Ile Ala
     50                  55                  60

Leu Ser Val Ala Gln Thr Ile Phe Gln Cys Asp Met Arg His Leu Leu
 65                  70                  75                  80

Cys His Val Val Val Pro Cys His Ile Ile Gln Ser Met Lys Asp Leu
                 85                  90                  95

Ala Val Pro Val Val Val Ala Glu Tyr Leu His Gln Asn Leu Gly Gly
            100                 105                 110

Glu Ser Ile Val Glu Val Met Ser Thr Asp Gly His Leu Pro Gln Leu
        115                 120                 125

Ser Ser Pro Asp Ile Val Ile Pro Val Leu Leu Arg His
    130                 135                 140

<210> SEQ ID NO 82
<211> LENGTH: 177
<212> TYPE: PRT
<213> ORGANISM: Arabidopsis thaliana

<400> SEQUENCE: 82

Thr Gly Asp Arg Ile Leu Phe Leu Ala His Gly Phe Gly Thr Asp Gln
  1               5                  10                  15

Ala Trp His Leu Ile Leu Pro Tyr Phe Thr Gln Glu Asp Arg Val Val
             20                  25                  30

Leu Tyr Asp Leu Val Cys Ala Gly Ser Ile Asn Pro Asp Tyr Val Asp
         35                  40                  45

Phe Asp Arg Tyr Thr Thr Val Asp Pro Tyr Val Asp Asp Leu Leu Asn
     50                  55                  60

Ile Val Asp Ser Leu Gly Ile Gln Lys Cys Ala Tyr Val Gly His Ser
 65                  70                  75                  80

Val Ser Ala Met Ile Gly Met Ile Ala Ser Ile Arg Arg Pro Glu Leu
                 85                  90                  95
```

```
Phe Ser Lys Leu Met Leu Ile Gly Phe Ser Pro Arg Phe Leu Asn Asp
                100                 105                 110

Glu Asp Tyr Asp Gly Gly Phe Glu Gly Glu Ile Glu Arg Val Phe
            115                 120                 125

Ser Val Met Glu Ala Asn Tyr Glu Ala Trp Val His Gly Phe Ala Leu
        130                 135                 140

Leu Ala Val Gly Ala Asp Val Pro Ala Ala Val Arg Glu Phe Ser Arg
145                 150                 155                 160

Thr Leu Ser His Met Arg Pro Asp Ile Ser Leu Phe Val Ser Arg Thr
                165                 170                 175

Val

<210> SEQ ID NO 83
<211> LENGTH: 141
<212> TYPE: PRT
<213> ORGANISM: Helianthus annuus

<400> SEQUENCE: 83

Arg Tyr Leu Asn Thr Lys Asp Tyr Phe Gly Gly Phe Glu Gln Glu Asp
1               5                   10                  15

Leu Asp Gln Leu Phe Glu Ala Met Gln Ser Asn Tyr Lys Ala Trp Cys
            20                  25                  30

Ser Gly Phe Ala Pro Leu Ala Val Gly Gly Asp Met Asp Ser Val Ala
        35                  40                  45

Val Gln Glu Phe Ser Arg Thr Leu Phe Asn Met Arg Pro Asp Ile Ala
    50                  55                  60

Leu Ser Val Ala Gln Thr Ile Phe Gln Cys Asp Met Arg His Leu Leu
65                  70                  75                  80

Cys His Val Val Val Pro Cys His Ile Ile Gln Ser Met Lys Asp Leu
                85                  90                  95

Ala Val Pro Val Val Val Ala Glu Tyr Leu His Gln Asn Leu Gly Gly
                100                 105                 110

Glu Ser Ile Val Glu Val Met Ser Thr Asp Gly His Leu Pro Gln Leu
            115                 120                 125

Ser Ser Pro Asp Ile Val Ile Pro Val Leu Leu Arg Gln
        130                 135                 140

<210> SEQ ID NO 84
<211> LENGTH: 141
<212> TYPE: PRT
<213> ORGANISM: Helianthus annuus

<400> SEQUENCE: 84

Arg Tyr Leu Asn Thr Lys Asp Tyr Phe Gly Gly Phe Glu Gln Glu Asp
1               5                   10                  15

Leu Asp Gln Leu Phe Glu Ala Met Gln Ser Asn Tyr Lys Ala Trp Cys
            20                  25                  30

Ser Gly Phe Ala Pro Leu Ser Val Gly Gly Asp Met Asp Ser Val Ala
        35                  40                  45

Val Gln Glu Phe Ser Arg Thr Leu Phe Asn Met Arg Pro Asp Ile Ala
    50                  55                  60

Leu Ser Val Ala Gln Thr Ile Phe Gln Cys Asp Met Arg His Leu Leu
65                  70                  75                  80

Cys His Val Val Val Pro Cys His Ile Ile Gln Ser Met Lys Asp Leu
                85                  90                  95

Ala Val Pro Val Val Val Ala Glu Tyr Leu His Gln Asn Leu Gly Gly
```

```
                    100                 105                 110
Glu Ser Ile Val Glu Val Met Ser Thr Asp Gly His Leu Pro Gln Leu
            115                 120                 125

Ser Ser Pro Asp Ile Val Ile Pro Val Leu Leu Arg Gln
    130                 135                 140

<210> SEQ ID NO 85
<211> LENGTH: 165
<212> TYPE: PRT
<213> ORGANISM: Helianthus annuus

<400> SEQUENCE: 85

Asn Arg Leu Ala Leu Phe Gly Lys Phe Cys His Val Cys Leu Leu Gly
  1               5                  10                  15

Phe Val Ile Ile Leu Tyr Phe Asp Phe Phe Arg Tyr Leu Asn Thr Lys
                 20                  25                  30

Asp Tyr Phe Gly Gly Phe Glu Gln Glu Asp Leu Asp Gln Leu Phe Glu
            35                  40                  45

Ala Met Gln Ser Asn Tyr Lys Ala Trp Cys Ser Gly Phe Ala Pro Leu
     50                  55                  60

Ala Val Gly Gly Asp Met Asp Ser Val Ala Val Gln Glu Phe Ser Arg
 65                  70                  75                  80

Thr Leu Phe Asn Met Arg Pro Asp Ile Ala Leu Ser Val Ala Gln Thr
                 85                  90                  95

Ile Phe Gln Cys Asp Met Arg His Leu Leu Cys His Val Val Val Pro
            100                 105                 110

Cys His Ile Ile Gln Ser Met Lys Asp Leu Ala Val Pro Val Val Val
        115                 120                 125

Ala Glu Tyr Leu His Gln Asn Leu Gly Gly Glu Ser Ile Val Glu Val
    130                 135                 140

Met Ser Thr Asp Gly His Leu Pro Gln Leu Ser Ser Pro Asp Ile Val
145                 150                 155                 160

Ile Pro Val Leu Leu
                165

<210> SEQ ID NO 86
<211> LENGTH: 139
<212> TYPE: PRT
<213> ORGANISM: Helianthus annuus

<400> SEQUENCE: 86

Arg Tyr Leu Asn Thr Lys Asp Tyr Phe Gly Gly Phe Glu Gln Glu Asp
  1               5                  10                  15

Leu Asp Gln Leu Phe Glu Ala Met Gln Ser Asn Tyr Lys Ala Trp Cys
                 20                  25                  30

Ser Gly Phe Ala Pro Leu Ala Val Gly Gly Asp Met Asp Ser Val Ala
             35                  40                  45

Val Gln Glu Phe Ser Arg Thr Leu Phe Asn Met Arg Pro Asp Ile Ala
     50                  55                  60

Leu Ser Val Ala Gln Thr Ile Phe Gln Cys Asp Met Arg His Leu Leu
 65                  70                  75                  80

Cys His Val Val Val Pro Cys His Ile Ile Gln Ser Met Lys Asp Leu
                 85                  90                  95

Ala Val Pro Val Val Val Ala Glu Tyr Leu His Gln Asn Leu Gly Gly
            100                 105                 110

Glu Ser Ile Val Glu Val Met Ser Thr Asp Gly His Leu Pro Gln Leu
```

115                 120                 125

Ser Ser Pro Asp Ile Val Ile Pro Val Leu Leu
    130                 135

<210> SEQ ID NO 87
<211> LENGTH: 139
<212> TYPE: PRT
<213> ORGANISM: Helianthus annuus

<400> SEQUENCE: 87

Arg Tyr Leu Asn Thr Lys Asp Tyr Phe Gly Gly Phe Glu Gln Glu Asp
1               5                   10                  15

Leu Asp Gln Leu Phe Glu Ala Met Gln Ser Asn Tyr Lys Ala Trp Cys
            20                  25                  30

Ser Gly Phe Ala Pro Leu Ala Val Gly Gly Asp Met Asp Ser Val Ala
        35                  40                  45

Val Gln Glu Phe Ser Arg Thr Leu Phe Asn Met Arg Pro Asp Ile Ala
    50                  55                  60

Leu Ser Val Ala Gln Thr Ile Phe Gln Cys Asp Met Arg His Leu Leu
65                  70                  75                  80

Cys His Val Val Val Pro Cys His Ile Ile Gln Ser Met Lys Asp Leu
                85                  90                  95

Ala Val Pro Val Val Val Ala Glu Tyr Leu His Gln Asn Leu Gly Gly
            100                 105                 110

Glu Ser Ile Val Glu Val Met Ser Thr Asp Gly His Leu Pro Gln Leu
        115                 120                 125

Ser Ser Pro Asp Ile Val Ile Pro Val Leu Leu
    130                 135

<210> SEQ ID NO 88
<211> LENGTH: 139
<212> TYPE: PRT
<213> ORGANISM: Helianthus annuus

<400> SEQUENCE: 88

Arg Tyr Leu Asn Thr Lys Asp Tyr Phe Gly Gly Phe Glu Gln Glu Asp
1               5                   10                  15

Leu Asp Gln Leu Phe Glu Ala Met Gln Ser Asn Tyr Lys Ala Trp Cys
            20                  25                  30

Ser Gly Phe Ala Pro Leu Ala Val Gly Gly Asp Met Asp Ser Val Ala
        35                  40                  45

Val Gln Glu Phe Ser Arg Thr Leu Phe Asn Met Arg Pro Asp Ile Ala
    50                  55                  60

Leu Ser Val Ala Gln Thr Ile Phe Gln Cys Asp Met Arg His Leu Leu
65                  70                  75                  80

Cys His Val Val Val Pro Cys His Ile Ile Gln Ser Met Lys Asp Leu
                85                  90                  95

Ala Val Pro Val Val Val Ala Glu Tyr Leu His Gln Asn Leu Gly Gly
            100                 105                 110

Glu Ser Ile Val Glu Val Met Ser Thr Asp Gly His Leu Pro Gln Leu
        115                 120                 125

Ser Ser Pro Asp Ile Val Ile Pro Val Leu Leu
    130                 135

<210> SEQ ID NO 89
<211> LENGTH: 139
<212> TYPE: PRT

<213> ORGANISM: Helianthus annuus

<400> SEQUENCE: 89

Arg Tyr Leu Asn Thr Lys Asp Tyr Phe Gly Gly Phe Glu Gln Glu Asp
1               5                   10                  15

Leu Asp Gln Leu Phe Glu Ala Met Gln Ser Asn Tyr Lys Ala Trp Cys
            20                  25                  30

Ser Gly Phe Ala Pro Leu Ser Val Gly Gly Asp Met Asp Ser Val Ala
        35                  40                  45

Val Gln Glu Phe Ser Arg Thr Leu Phe Asn Met Arg Pro Asp Ile Ala
    50                  55                  60

Leu Ser Val Ala Gln Thr Ile Phe Gln Cys Asp Met Arg His Leu Leu
65                  70                  75                  80

Cys His Val Val Val Pro Cys His Ile Ile Gln Ser Met Lys Asp Leu
                85                  90                  95

Ala Val Pro Val Val Val Ala Glu Tyr Leu His Gln Asn Leu Gly Gly
            100                 105                 110

Glu Ser Ile Val Glu Val Met Ser Thr Asp Gly His Leu Pro Gln Leu
        115                 120                 125

Ser Ser Pro Asp Ile Val Ile Pro Val Leu Leu
    130                 135

<210> SEQ ID NO 90
<211> LENGTH: 139
<212> TYPE: PRT
<213> ORGANISM: Helianthus annuus

<400> SEQUENCE: 90

Arg Tyr Leu Asn Thr Lys Asp Tyr Phe Gly Gly Phe Glu Gln Glu Asp
1               5                   10                  15

Leu Asp Gln Leu Phe Glu Ala Met Gln Ser Asn Tyr Lys Ala Trp Cys
            20                  25                  30

Ser Gly Phe Ala Pro Leu Ala Val Gly Gly Asp Met Asp Ser Val Ala
        35                  40                  45

Val Gln Glu Ser Ser Arg Thr Leu Phe Asn Met Arg Pro Asp Ile Ala
    50                  55                  60

Leu Ser Val Ala Gln Thr Ile Phe Gln Cys Asp Met Arg His Leu Leu
65                  70                  75                  80

Cys His Val Val Val Pro Cys His Ile Ile Gln Ser Met Lys Asp Leu
                85                  90                  95

Ala Val Pro Val Val Val Ala Glu Tyr Leu His Gln Asn Leu Gly Gly
            100                 105                 110

Glu Ser Ile Val Glu Val Met Ser Thr Asp Gly His Leu Pro Gln Leu
        115                 120                 125

Ser Ser Pro Asp Ile Val Ile Pro Val Leu Leu
    130                 135

<210> SEQ ID NO 91
<211> LENGTH: 257
<212> TYPE: PRT
<213> ORGANISM: Arabidopsis thaliana

<400> SEQUENCE: 91

Ala Met Asn Ala Lys Ile Ile Gly Ser Gly Glu Arg Ser Met Val Leu
1               5                   10                  15

Ala His Gly Phe Gly Gly Asp Gln Ser Val Trp Asp Lys Ile Ile Pro
            20                  25                  30

```
Val Leu Ser Gln Ser Phe Lys Val Leu Val Phe Asp Trp Leu Phe Ser
            35                  40                  45

Gly Ala Ile Lys Asp Gln Thr Leu Tyr Asp Pro Ser Lys Tyr Asn Ser
 50                  55                  60

Leu Asp Val Phe Ser Asp Leu Ile Ala Leu Met Glu Glu Leu Lys
 65                  70                  75                  80

Phe Gly Pro Val Val Phe Val Gly His Ser Met Ser Gly Val Ile Gly
                85                  90                  95

Cys Ala Ala Ser Ile Lys Arg Pro Asp Leu Phe Thr Asn Leu Leu Leu
                100                 105                 110

Ile Ala Ala Ser Pro Arg Tyr Ile Asn Ser Glu Asp Tyr Lys Gly Gly
                115                 120                 125

Phe Glu Ser Lys Asp Ile Asp Thr Ile Ile Thr Ser Ile Gly Ser Asn
130                 135                 140

Tyr Glu Ala Trp Ala Val Asp Phe Ser Ser Phe Val Val Asp Ser Arg
145                 150                 155                 160

Asp Ser Leu Ser Val Gln Arg Phe Glu Lys Ser Leu Lys Lys Met Lys
                165                 170                 175

Pro Glu Thr Ala Leu Ala Leu Ala Lys Ile Val Phe Gly Ser Asp Glu
                180                 185                 190

Arg Glu Ile Leu Gly Gln Val Ser Val Pro Cys His Val Ile Gln Pro
                195                 200                 205

Gly Asn Asp Val Val Pro Val Ser Val Ala Tyr Phe Met Gln Glu
                210                 215                 220

Lys Ile Lys Gly Lys Ser Thr Val Glu Ile Ile Glu Asp Ala Ile Gly
225                 230                 235                 240

His Phe Pro Gln Met Thr Ser His Leu Glu Leu Leu Gly Val Met Arg
                245                 250                 255

Arg

<210> SEQ ID NO 92
<211> LENGTH: 257
<212> TYPE: PRT
<213> ORGANISM: Arabidopsis thaliana

<400> SEQUENCE: 92

Ala Met Asn Ala Lys Ile Ile Gly Ser Gly Glu Arg Ser Met Val Leu
 1               5                  10                  15

Ala His Gly Phe Gly Gly Asp Gln Ser Val Trp Asp Lys Ile Ile Pro
                20                  25                  30

Val Leu Ser Gln Ser Phe Lys Val Leu Val Phe Asp Trp Leu Phe Ser
            35                  40                  45

Gly Ala Ile Lys Asp Gln Thr Leu Tyr Asp Pro Ser Lys Tyr Asn Ser
 50                  55                  60

Leu Asp Val Phe Ser Asp Leu Ile Ala Leu Met Glu Glu Leu Lys
 65                  70                  75                  80

Phe Gly Pro Val Val Phe Val Gly His Ser Met Ser Gly Val Ile Gly
                85                  90                  95

Cys Ala Ala Ser Ile Lys Arg Pro Asp Leu Phe Thr Asn Leu Leu Leu
                100                 105                 110

Ile Ala Ala Ser Pro Arg Tyr Ile Asn Ser Glu Asp Tyr Lys Gly Gly
                115                 120                 125

Phe Glu Ser Lys Asp Ile Asp Thr Ile Ile Thr Ser Ile Gly Ser Asn
130                 135                 140
```

```
Tyr Glu Ala Trp Ala Val Asp Phe Ser Ser Phe Val Val Asp Ser Arg
145                 150                 155                 160

Asp Ser Leu Ser Val Gln Arg Phe Glu Lys Ser Leu Lys Lys Met Lys
                165                 170                 175

Pro Glu Thr Ala Leu Ala Leu Ala Lys Ile Val Phe Gly Ser Asp Glu
            180                 185                 190

Arg Glu Ile Leu Gly Gln Val Ser Val Pro Cys His Val Ile Gln Pro
        195                 200                 205

Gly Asn Asp Val Val Pro Val Ser Val Ala Tyr Phe Met Gln Glu
    210                 215                 220

Lys Ile Lys Gly Lys Ser Thr Val Glu Ile Ile Glu Asp Ala Ile Gly
225                 230                 235                 240

His Phe Pro Gln Met Thr Ser His Leu Glu Leu Leu Gly Val Met Arg
                245                 250                 255

Arg

<210> SEQ ID NO 93
<211> LENGTH: 257
<212> TYPE: PRT
<213> ORGANISM: Arabidopsis thaliana

<400> SEQUENCE: 93

Ala Met Asn Ala Lys Ile Ile Gly Ser Gly Glu Arg Ser Met Val Leu
1               5                   10                  15

Ala His Gly Phe Gly Gly Asp Gln Ser Val Trp Asp Lys Ile Ile Pro
            20                  25                  30

Val Leu Ser Gln Ser Phe Lys Val Leu Val Phe Asp Trp Leu Phe Ser
        35                  40                  45

Gly Ala Ile Lys Asp Gln Thr Leu Tyr Asp Pro Ser Lys Tyr Asn Ser
    50                  55                  60

Leu Asp Val Phe Ser Asp Asp Leu Ile Ala Leu Met Glu Glu Leu Lys
65                  70                  75                  80

Phe Gly Pro Val Val Phe Val Gly His Ser Met Ser Gly Val Ile Gly
                85                  90                  95

Cys Ala Ala Ser Ile Lys Arg Pro Asp Leu Phe Thr Asn Leu Leu Leu
            100                 105                 110

Ile Ala Ala Ser Pro Arg Tyr Ile Asn Ser Glu Asp Tyr Lys Gly Gly
        115                 120                 125

Phe Glu Ser Lys Asp Ile Asp Thr Ile Thr Ser Ile Gly Ser Asn
    130                 135                 140

Tyr Glu Ala Trp Ala Val Asp Phe Ser Ser Phe Val Val Asp Ser Arg
145                 150                 155                 160

Asp Ser Leu Ser Val Gln Arg Phe Glu Lys Ser Leu Lys Lys Met Lys
                165                 170                 175

Pro Glu Thr Ala Leu Ala Leu Ala Lys Ile Val Phe Gly Ser Asp Glu
            180                 185                 190

Arg Glu Ile Leu Gly Gln Val Ser Val Pro Cys His Val Ile Gln Pro
        195                 200                 205

Gly Asn Asp Val Val Pro Val Ser Val Ala Tyr Phe Met Gln Glu
    210                 215                 220

Lys Ile Lys Gly Lys Ser Thr Val Glu Ile Ile Glu Asp Ala Ile Gly
225                 230                 235                 240

His Phe Pro Gln Met Thr Ser His Leu Glu Leu Leu Gly Val Met Arg
                245                 250                 255
```

Arg

<210> SEQ ID NO 94
<211> LENGTH: 257
<212> TYPE: PRT
<213> ORGANISM: Arabidopsis thaliana

<400> SEQUENCE: 94

```
Ala Met Asn Ala Lys Ile Ile Gly Ser Gly Glu Arg Ser Met Val Leu
 1               5                  10                  15

Ala His Gly Phe Gly Gly Asp Gln Ser Val Trp Asp Lys Ile Ile Pro
            20                  25                  30

Val Leu Ser Gln Ser Phe Lys Val Leu Val Phe Asp Trp Leu Phe Ser
        35                  40                  45

Gly Ala Ile Lys Asp Gln Thr Leu Tyr Asp Pro Ser Lys Tyr Asn Ser
    50                  55                  60

Leu Asp Val Phe Ser Asp Leu Ile Ala Leu Met Glu Glu Leu Lys
65                  70                  75                  80

Phe Gly Pro Val Val Phe Val Gly His Ser Met Ser Gly Val Ile Gly
                85                  90                  95

Cys Ala Ala Ser Ile Lys Arg Pro Asp Leu Phe Thr Asn Leu Leu Leu
            100                 105                 110

Ile Ala Ala Ser Pro Arg Tyr Ile Asn Ser Glu Asp Tyr Lys Gly Gly
        115                 120                 125

Phe Glu Ser Lys Asp Ile Asp Thr Ile Ile Thr Ser Ile Gly Ser Asn
    130                 135                 140

Tyr Glu Ala Trp Ala Val Asp Phe Ser Ser Phe Val Val Asp Ser Arg
145                 150                 155                 160

Asp Ser Leu Ser Val Gln Arg Phe Glu Lys Ser Leu Lys Lys Met Lys
                165                 170                 175

Pro Glu Thr Ala Leu Ala Leu Ala Lys Ile Val Phe Gly Ser Asp Glu
            180                 185                 190

Arg Glu Ile Leu Gly Gln Val Ser Val Pro Cys His Val Ile Gln Pro
        195                 200                 205

Gly Asn Asp Val Val Pro Val Ser Val Ala Tyr Phe Met Gln Glu
    210                 215                 220

Lys Ile Lys Gly Lys Ser Thr Val Glu Ile Ile Glu Asp Ala Ile Gly
225                 230                 235                 240

His Phe Pro Gln Met Thr Ser His Leu Glu Leu Leu Gly Val Met Arg
                245                 250                 255

Arg
```

<210> SEQ ID NO 95
<211> LENGTH: 135
<212> TYPE: PRT
<213> ORGANISM: Helianthus annuus

<400> SEQUENCE: 95

```
Arg Tyr Leu Asn Thr Lys Asp Tyr Phe Gly Gly Phe Glu Gln Glu Asp
 1               5                  10                  15

Leu Asp Gln Leu Phe Glu Ala Met Gln Ser Asn Tyr Lys Ala Trp Cys
            20                  25                  30

Ser Gly Phe Ala Pro Leu Ala Val Gly Gly Asp Met Asp Ser Val Ala
        35                  40                  45

Val Gln Glu Phe Ser Arg Thr Leu Phe Asn Met Arg Pro Asp Ile Ala
```

-continued

```
                50                  55                  60
Leu Ser Val Ala Gln Thr Ile Phe Gln Cys Asp Met Arg His Leu Leu
 65                  70                  75                  80

Cys His Val Val Val Pro Cys His Ile Ile Gln Ser Met Lys Asp Leu
                 85                  90                  95

Ala Val Pro Val Val Ala Glu Tyr Leu His Gln Asn Leu Gly Gly
                100                 105                 110

Glu Ser Ile Val Glu Val Met Ser Thr Asp Gly His Leu Pro Gln Leu
            115                 120                 125

Ser Ser Pro Asp Ile Val Ile
            130                 135

<210> SEQ ID NO 96
<211> LENGTH: 126
<212> TYPE: PRT
<213> ORGANISM: Helianthus annuus

<400> SEQUENCE: 96

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
                 20                  25                  30

Trp Lys His Leu Val Pro His Leu Val Asp Asp Tyr Lys Val Val Leu
             35                  40                  45

Tyr Asp Asn Met Gly Ala Gly Thr Thr Asn Pro Glu Tyr Phe Asp Phe
 50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                 85                  90                  95

Ser Ala Met Val Gly Ala Val Ala Ser Ile Thr Arg Pro Asp Leu Phe
                100                 105                 110

Ser Lys Ile Val Met Ile Ser Ala Ser Pro Arg Leu Val Asp
            115                 120                 125

<210> SEQ ID NO 97
<211> LENGTH: 126
<212> TYPE: PRT
<213> ORGANISM: Helianthus annuus

<400> SEQUENCE: 97

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
                 20                  25                  30

Trp Lys His Leu Val Pro His Leu Val Asp Asp Tyr Lys Val Val Leu
             35                  40                  45

Tyr Asp Asn Met Gly Ala Gly Thr Thr Asn Pro Glu Tyr Phe Asp Phe
 50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                 85                  90                  95

Ser Ala Met Val Gly Ala Val Ala Ser Ile Thr Arg Pro Asp Leu Phe
                100                 105                 110

Ser Lys Ile Val Met Ile Ser Ala Ser Pro Arg Leu Val Glu
```

```
                    115                 120                 125

<210> SEQ ID NO 98
<211> LENGTH: 126
<212> TYPE: PRT
<213> ORGANISM: Helianthus annuus

<400> SEQUENCE: 98

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
             20                  25                  30

Trp Lys His Leu Val Pro His Leu Val Asp Asp Tyr Lys Val Val Leu
         35                  40                  45

Tyr Asp Asn Met Gly Ala Gly Thr Thr Asn Pro Glu Tyr Phe Asp Phe
     50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                 85                  90                  95

Ser Ala Met Val Gly Ala Val Ala Ser Ile Thr Arg Pro Asp Leu Phe
            100                 105                 110

Ser Lys Ile Val Met Ile Ser Ala Ser Pro Arg Leu Val Asp
        115                 120                 125

<210> SEQ ID NO 99
<211> LENGTH: 125
<212> TYPE: PRT
<213> ORGANISM: Helianthus annuus

<400> SEQUENCE: 99

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
             20                  25                  30

Trp Lys His Leu Val Pro His Leu Val Asp Asp Tyr Lys Val Val Leu
         35                  40                  45

Tyr Asp Asn Met Gly Ala Gly Thr Thr Asn Pro Glu Tyr Phe Asp Phe
     50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                 85                  90                  95

Ser Ala Met Val Gly Ala Val Ala Ser Ile Thr Arg Pro Asp Leu Phe
            100                 105                 110

Ser Lys Ile Val Met Ile Ser Ala Ser Pro Arg Leu Val
        115                 120                 125

<210> SEQ ID NO 100
<211> LENGTH: 125
<212> TYPE: PRT
<213> ORGANISM: Helianthus annuus

<400> SEQUENCE: 100

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
             20                  25                  30
```

Trp Lys His Leu Val Pro His Leu Val Asp Asp Tyr Lys Val Val Leu
            35                  40                  45

Tyr Asp Asn Met Gly Ala Gly Thr Thr Asn Pro Glu Tyr Phe Asp Phe
 50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                85                  90                  95

Ser Ala Met Val Gly Ala Val Ala Ser Ile Thr Arg Pro Asp Leu Phe
                100                 105                 110

Ser Lys Ile Val Met Ile Ser Ala Ser Pro Arg Leu Val
        115                 120                 125

<210> SEQ ID NO 101
<211> LENGTH: 126
<212> TYPE: PRT
<213> ORGANISM: Helianthus annuus

<400> SEQUENCE: 101

Met Gly Val Val Glu Ala Ala His Asn Val Lys Ile Leu Gly Ser Gly
 1               5                  10                  15

Asp Arg Thr Ile Val Leu Ala His Gly Phe Gly Thr Asp Gln Ser Val
                20                  25                  30

Trp Lys His Leu Val Pro His Leu Val Asp Asp Tyr Lys Val Val Leu
            35                  40                  45

Tyr Asp Asn Met Gly Ala Gly Thr Thr Asn Pro Glu Tyr Phe Asp Phe
 50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                85                  90                  95

Ser Ala Met Val Gly Ala Val Ala Ser Ile Thr Arg Pro Asp Leu Phe
                100                 105                 110

Ser Lys Ile Val Met Ile Ser Ala Ser Pro Arg Leu Val Glu
        115                 120                 125

<210> SEQ ID NO 102
<211> LENGTH: 126
<212> TYPE: PRT
<213> ORGANISM: Helianthus annuus

<400> SEQUENCE: 102

Met Gly Val Val Glu Ala Ala His Asn Val Lys Ile Leu Gly Ser Gly
 1               5                  10                  15

Asp Arg Thr Ile Val Leu Ala His Gly Phe Gly Thr Asp Gln Ser Val
                20                  25                  30

Trp Lys His Leu Val Pro His Leu Val Asp Asp Tyr Lys Val Val Leu
            35                  40                  45

Tyr Asp Asn Met Gly Ala Gly Thr Thr Asn Pro Glu Tyr Phe Asp Phe
 50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                85                  90                  95

Ser Ala Met Val Gly Ala Val Ala Ser Ile Thr Arg Pro Asp Leu Phe
                100                 105                 110

```
Ser Lys Ile Val Met Ile Ser Ala Ser Pro Arg Leu Val Glu
        115                 120                 125

<210> SEQ ID NO 103
<211> LENGTH: 126
<212> TYPE: PRT
<213> ORGANISM: Helianthus annuus

<400> SEQUENCE: 103

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
             20                  25                  30

Trp Lys His Leu Val Pro His Leu Val Asp Asp Tyr Lys Val Val Leu
         35                  40                  45

Tyr Asp Asn Met Gly Ala Gly Thr Thr Asn Pro Glu Tyr Phe Asp Phe
     50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                 85                  90                  95

Ser Ala Met Val Gly Ala Val Ala Ser Ile Thr Arg Pro Asp Leu Phe
            100                 105                 110

Ser Lys Ile Val Met Ile Ser Ala Ser Pro Arg Leu Val Glu
        115                 120                 125

<210> SEQ ID NO 104
<211> LENGTH: 126
<212> TYPE: PRT
<213> ORGANISM: Helianthus annuus

<400> SEQUENCE: 104

Met Gly Val Val Glu Ala Ala His Asn Val Lys Ile Leu Gly Ser Gly
  1               5                  10                  15

Asp Arg Thr Ile Val Leu Ala His Gly Phe Gly Thr Asp Gln Ser Val
             20                  25                  30

Trp Lys His Leu Val Pro His Leu Val Asp Asp Tyr Lys Val Val Leu
         35                  40                  45

Tyr Asp Asn Met Gly Ala Gly Thr Thr Asn Pro Glu Tyr Phe Asp Phe
     50                  55                  60

Gly Arg Tyr Ala Thr Leu Glu Gly Tyr Ala Tyr Asp Val Ile Ser Ile
 65                  70                  75                  80

Leu Glu Glu Leu Lys Ile Ser Ser Cys Val Phe Val Gly His Ser Val
                 85                  90                  95

Ser Ala Met Val Gly Ala Val Ala Ser Ile Thr Arg Pro Asp Leu Phe
            100                 105                 110

Ser Lys Ile Val Met Ile Ser Ala Ser Pro Arg Leu Val Glu
        115                 120                 125

<210> SEQ ID NO 105
<211> LENGTH: 125
<212> TYPE: PRT
<213> ORGANISM: Helianthus annuus

<400> SEQUENCE: 105

Met Gly Val Val Glu Ala Ala His Asn Val Lys Ile Leu Gly Ser Gly
  1               5                  10                  15
```

```
Asp Arg Thr Ile Val Leu Ala His Gly Phe Gly Thr Asp Gln Ser Val
            20                  25                  30

Trp Lys His Leu Val Pro His Leu Val Asp Asp Tyr Lys Val Val Leu
        35                  40                  45

Tyr Asp Asn Met Gly Ala Gly Thr Thr Asn Pro Glu Tyr Phe Asp Phe
    50                  55                  60

Gly Arg Tyr Ala Thr Leu Glu Gly Tyr Ala Tyr Asp Val Ile Ser Ile
65                  70                  75                  80

Leu Glu Glu Leu Lys Ile Ser Ser Cys Val Phe Val Gly His Ser Val
                85                  90                  95

Ser Ala Met Val Gly Ala Val Ala Ser Ile Thr Arg Pro Asp Leu Phe
            100                 105                 110

Ser Lys Ile Val Met Ile Ser Ala Ser Pro Arg Leu Val
        115                 120                 125
```

<210> SEQ ID NO 106
<211> LENGTH: 259
<212> TYPE: PRT
<213> ORGANISM: Lysinibacillus sphaericus

<400> SEQUENCE: 106

```
Asn His Val Lys Ile Val Gly Gln Gly Asp Gln Pro Ile Ile Phe Gly
 1               5                  10                  15

His Gly Phe Gly Cys Asp Gln Asn Met Trp Arg Tyr Ile Thr Pro Ala
            20                  25                  30

Phe Met Asp Lys Tyr Lys Ile Ile Leu Phe Asp Tyr Val Gly Ser Gly
        35                  40                  45

Arg Ser Asp Lys Asn Ala Tyr Ile Ser Glu Lys Tyr Lys Asn Leu Glu
    50                  55                  60

Gly Tyr Met Gln Asp Leu Leu Asp Ile Ile Glu Ser Leu Lys Leu Gln
65                  70                  75                  80

Gln Ser Val Phe Val Gly His Ser Ile Ser Ser Met Ile Gly Leu Leu
                85                  90                  95

Ala Ser Ile Lys Arg Pro Glu Tyr Phe Lys Lys Leu Ile Met Ile Gly
            100                 105                 110

Pro Ser Pro Cys Tyr Leu Asn Asp Gly Glu Tyr Ile Gly Gly Phe Glu
        115                 120                 125

Arg Ser Asp Ile Ser Glu Leu Leu Glu Met Met Glu Met Asn Phe Ala
    130                 135                 140

Gly Trp Ala Ser Tyr Met Ala Pro Ile Ala Met Ser Asn Pro Glu Asn
145                 150                 155                 160

Pro Ala Leu Thr Asp Glu Leu Lys Gln Thr Phe Lys Ser Ala Asp Pro
                165                 170                 175

Val Ile Ala Arg Glu Phe Ala Glu Val Thr Phe Leu Ser Asp His Arg
            180                 185                 190

Asn Glu Leu Ser Gln Val Thr Val Pro Val Leu Ile Ile Gln Cys Ser
        195                 200                 205

Glu Asp Ser Ile Val Pro Ile Ser Val Gly Asp Tyr Leu His Lys His
    210                 215                 220

Ile Lys Asp Ser Thr Phe Ser Leu Met Glu Ala Lys Gly His Tyr Pro
225                 230                 235                 240

His Ile Ser His Pro Asn Glu Thr Ile Gln Cys Ile Met Asp Phe Cys
                245                 250                 255

Arg Glu Asp
```

<210> SEQ ID NO 107
<211> LENGTH: 255
<212> TYPE: PRT
<213> ORGANISM: Populus trichocarpa

<400> SEQUENCE: 107

```
Ala Leu Asn Ala Arg Val Thr Gly Ser Gly Asn Glu Ala Ile Ile Leu
1               5                   10                  15

Ala His Gly Phe Gly Gly Asp Gln Ser Val Trp Asp Lys Ile Val Pro
            20                  25                  30

Arg Leu Ala Lys His Cys Arg Val Leu Val Phe Asp Trp Ile Phe Ser
        35                  40                  45

Gly Ala Ile Lys Asp Pro Asn Leu Phe Asp Pro Val Lys Tyr Ser Ser
    50                  55                  60

Tyr Asp Ala Phe Ala Asn Asp Leu Ile Ser Leu Met Asp Glu Leu Asp
65                  70                  75                  80

Leu Lys Ser Ser Val Leu Val Gly His Ser Met Ser Gly Met Ile Gly
                85                  90                  95

Cys Ile Ala Ser Ile Lys Arg Pro Asp Leu Phe Lys Lys Leu Ile Leu
            100                 105                 110

Val Gly Ala Ser Pro Arg Tyr Ile Asn Ala Asp Asp Tyr Glu Gly Gly
        115                 120                 125

Phe Ser Asn Ser Glu Val Glu Asp Ile Ile Ser Asn Ile Glu Ser Asn
    130                 135                 140

Tyr Tyr Asn Trp Ala Gln Ala Phe Ala Ser Ala Val Val Asp Ala Asn
145                 150                 155                 160

Asp Pro Pro Ser Val Asp Met Phe Ser Lys Cys Leu Gln Arg Met Arg
                165                 170                 175

Pro Glu Phe Ala Val Pro Val Ala Lys Thr Val Phe Tyr Cys Asp Glu
            180                 185                 190

Arg Asp Ile Leu Glu Lys Val Leu Thr Pro Cys Ile Ile Val Gln Thr
        195                 200                 205

Thr Arg Asp Ile Val Val Pro Asn Ser Val Ala Tyr Tyr Met Gln Glu
    210                 215                 220

Lys Ile Lys Gly Lys Ser Thr Val Glu Ile Ile Glu Thr Asp Gly His
225                 230                 235                 240

Phe Pro His Leu Thr Ala His Gln Gln Leu Leu Asp Val Leu Ile
                245                 250                 255
```

<210> SEQ ID NO 108
<211> LENGTH: 124
<212> TYPE: PRT
<213> ORGANISM: Arabidopsis thaliana

<400> SEQUENCE: 108

```
Met Gly Val Val Glu Glu Ala His Asn Val Lys Val Ile Gly Ser Gly
1               5                   10                  15

Glu Ala Thr Ile Val Leu Gly His Gly Phe Gly Thr Asp Gln Ser Val
            20                  25                  30

Trp Lys His Leu Val Pro His Leu Val Asp Asp Tyr Arg Val Val Leu
        35                  40                  45

Tyr Asp Asn Met Gly Ala Gly Thr Thr Asn Pro Asp Tyr Phe Asp Phe
    50                  55                  60

Asp Arg Tyr Ser Asn Leu Glu Gly Tyr Ser Phe Asp Leu Ile Ala Ile
65                  70                  75                  80
```

```
Leu Glu Asp Leu Lys Ile Glu Ser Cys Ile Phe Val Gly His Ser Val
             85                  90                  95

Ser Ala Met Ile Gly Val Leu Ala Ser Leu Asn Arg Pro Asp Leu Phe
            100                 105                 110

Ser Lys Ile Val Met Ile Ser Ala Ser Pro Arg Tyr
        115                 120

<210> SEQ ID NO 109
<211> LENGTH: 124
<212> TYPE: PRT
<213> ORGANISM: Arabidopsis thaliana

<400> SEQUENCE: 109

Met Gly Val Val Glu Ala His Asn Val Lys Val Ile Gly Ser Gly
 1               5                  10                  15

Glu Ala Thr Ile Val Leu Gly His Gly Phe Gly Thr Asp Gln Ser Val
             20                  25                  30

Trp Lys His Leu Val Pro His Leu Val Asp Asp Tyr Arg Val Val Leu
         35                  40                  45

Tyr Asp Asn Met Gly Ala Gly Thr Thr Asn Pro Asp Tyr Phe Asp Phe
 50                  55                  60

Asp Arg Tyr Ser Asn Leu Glu Gly Tyr Ser Phe Asp Leu Ile Ala Ile
 65                  70                  75                  80

Leu Glu Asp Leu Lys Ile Glu Ser Cys Ile Phe Val Gly His Ser Val
             85                  90                  95

Ser Ala Met Ile Gly Val Leu Ala Ser Leu Asn Arg Pro Asp Leu Phe
            100                 105                 110

Ser Lys Ile Val Met Ile Ser Ala Ser Pro Arg Tyr
        115                 120

<210> SEQ ID NO 110
<211> LENGTH: 141
<212> TYPE: PRT
<213> ORGANISM: Oryza sativa

<400> SEQUENCE: 110

Arg Phe Leu Asn Asp Ser Asp Tyr His Gly Gly Phe Glu Leu Glu Glu
 1               5                  10                  15

Ile Gln Gln Val Phe Asp Ala Met Gly Ala Asn Tyr Ser Ala Trp Ala
             20                  25                  30

Thr Gly Tyr Ala Pro Leu Ala Val Gly Ala Asp Val Pro Ala Ala Val
         35                  40                  45

Gln Glu Phe Ser Arg Thr Leu Phe Asn Met Arg Pro Asp Ile Ser Leu
 50                  55                  60

His Val Cys Gln Thr Val Phe Lys Thr Asp Leu Arg Gly Val Leu Gly
 65                  70                  75                  80

Met Val Arg Ala Pro Cys Val Val Gln Thr Thr Arg Asp Val Ser
             85                  90                  95

Val Pro Ala Ser Val Ala Ala Tyr Leu Lys Ala His Leu Gly Gly Arg
            100                 105                 110

Thr Thr Val Glu Phe Leu Gln Thr Glu Gly His Leu Pro His Leu Ser
        115                 120                 125

Ala Pro Ser Leu Leu Ala Gln Val Leu Arg Arg Ala Leu
        130                 135                 140

<210> SEQ ID NO 111
<211> LENGTH: 150
```

```
<212> TYPE: PRT
<213> ORGANISM: Oryza sativa

<400> SEQUENCE: 111

Ser Asn Arg Tyr Leu Asn Asp Val Asp Tyr Tyr Gly Gly Phe Glu Gln
 1               5                  10                  15

Glu Asp Leu Asp Glu Leu Phe Glu Ala Met Gly Ser Asn Tyr Lys Ala
            20                  25                  30

Trp Cys Ser Gly Phe Ala Pro Leu Cys Val Gly Asp Met Glu Ser
        35                  40                  45

Val Ala Val Gln Glu Phe Ser Arg Thr Leu Phe Asn Ile Arg Pro Asp
50                  55                  60

Ile Ala Leu Ser Val Ala Gln Thr Ile Phe Gln Ser Asp Val Arg Ser
65                  70                  75                  80

Leu Leu Pro Leu Val Thr Val Pro Cys His Ile Val Gln Ser Thr Lys
                85                  90                  95

Asp Leu Ala Val Pro Val Val Val Ser Glu Tyr Leu His Lys His Leu
            100                 105                 110

Gly Gly Asp Ser Ile Val Glu Val Met Pro Ser Glu Gly His Leu Pro
        115                 120                 125

Gln Leu Ser Ser Pro Asp Ile Val Ile Pro Val Leu Leu Arg His Ile
    130                 135                 140

Gln His Asp Ile Ala Val
145                 150

<210> SEQ ID NO 112
<211> LENGTH: 125
<212> TYPE: PRT
<213> ORGANISM: Oryza sativa

<400> SEQUENCE: 112

Met Gly Ile Val Glu Glu Ala His Asn Leu Arg Val Val Gly Glu Gly
 1               5                  10                  15

Lys Arg Gly Val Ile Val Leu Ala His Gly Phe Gly Thr Asp Gln Ser
            20                  25                  30

Val Trp Lys His Leu Val Pro His Leu Val Ala Asp Tyr Arg Val Val
        35                  40                  45

Leu Phe Asp Thr Met Gly Ala Gly Pro Thr Asn Pro Asp Tyr Phe Asp
50                  55                  60

Phe Ser Arg Tyr Ala Thr Leu Glu Gly Tyr Ala Leu Asp Leu Leu Ala
65                  70                  75                  80

Ile Leu Gln Glu Leu Arg Val Ala Ser Cys Ile Tyr Val Gly His Ser
                85                  90                  95

Val Ser Ala Val Ile Gly Ala Ile Ala Ser Ile Ser Arg Pro Asp Leu
            100                 105                 110

Phe Ser Lys Leu Val Leu Leu Ser Ala Ser Pro Arg Tyr
        115                 120                 125

<210> SEQ ID NO 113
<211> LENGTH: 141
<212> TYPE: PRT
<213> ORGANISM: Oryza sativa

<400> SEQUENCE: 113

Arg Phe Leu Asn Asp Ser Asp Tyr His Gly Gly Phe Glu Leu Glu Glu
 1               5                  10                  15

Ile Gln Gln Val Phe Asp Ala Met Gly Ala Asn Tyr Ser Ala Trp Ala
```

```
                20                  25                  30
Thr Gly Tyr Ala Pro Leu Ala Val Gly Ala Asp Val Pro Ala Val
            35                  40                  45

Gln Glu Phe Ser Arg Thr Leu Phe Asn Met Arg Pro Asp Ile Ser Leu
    50                  55                  60

His Val Cys Gln Thr Val Phe Lys Thr Asp Leu Arg Gly Val Leu Gly
65                  70                  75                  80

Met Val Arg Ala Pro Cys Val Val Gln Thr Thr Arg Asp Val Ser
                85                  90                  95

Val Pro Ala Ser Val Ala Ala Tyr Leu Lys Ala His Leu Gly Gly Arg
                100                 105                 110

Thr Thr Val Glu Phe Leu Gln Thr Glu Gly His Leu Pro His Leu Ser
            115                 120                 125

Ala Pro Ser Leu Leu Ala Gln Val Leu Arg Arg Ala Leu
        130                 135                 140

<210> SEQ ID NO 114
<211> LENGTH: 99
<212> TYPE: PRT
<213> ORGANISM: Leptospira interrogans

<400> SEQUENCE: 114

Ser Lys Ser Lys Pro Thr Ile Leu Leu Cys His Ala Asn Gly Tyr Ser
1               5                   10                  15

Ala Phe Thr Tyr Lys Phe Tyr Ile Glu Ser Leu Gln Asn Ser Tyr Arg
            20                  25                  30

Val Ile Ala Leu Asp Phe Ala Gly His Gly Glu Ser Asp Ser Thr Leu
        35                  40                  45

Asn Phe Arg Asp Trp Tyr Phe Phe Arg Asp Gln Val Leu Ser Leu Ile
    50                  55                  60

Glu Ser Glu Asn Leu Asn Asn Val Ile Gly Ile Gly His Ser Leu Gly
65                  70                  75                  80

Gly Ala Ser Leu Leu Leu Ala Ser Tyr His Ser Pro Asp Lys Phe Lys
                85                  90                  95

Lys Val Ile

<210> SEQ ID NO 115
<211> LENGTH: 237
<212> TYPE: PRT
<213> ORGANISM: Leptospira interrogans

<400> SEQUENCE: 115

Ser Ile Leu Leu Ile His Gly Leu Leu Asp Ser Ala Thr Gly Leu Arg
1               5                   10                  15

Lys Val Ala Pro Lys Ile Arg Glu Asp Tyr Arg Val Leu Ile Pro Asp
            20                  25                  30

Ile Pro Gly Phe Gly Asn Ser Lys Leu Pro Asn Leu Lys Tyr Leu Tyr
        35                  40                  45

Gln Val Asn Val Phe Ala Asp Leu Ile Tyr Glu Ser Ile Arg Lys Leu
    50                  55                  60

Asn Leu Thr Asn Thr Val Leu Gly Gly His Ser Met Gly Ala Leu Ile
65                  70                  75                  80

Ser Met His Ile Ala Leu Lys Asp Ser Glu Lys Arg Ile Ser Lys Leu
                85                  90                  95

Val Leu Met Ala Pro Gly Gly Ile Pro His Pro Lys Arg Asp Glu Met
                100                 105                 110
```

```
Lys Glu Leu Leu Phe Pro Lys Thr Glu Glu Asp Leu Leu Lys Leu Ile
            115                 120                 125

Glu Ala Leu Tyr Tyr Glu Thr Pro Thr Leu Pro Gly Lys Ile Ala Arg
130                 135                 140

Lys Ala Leu Ile Gln Ser Trp Asn Glu Leu Pro Asn Gln Phe Leu Thr
145                 150                 155                 160

Val Asn Thr Ile Glu Arg Glu Glu Ile Phe Leu Gly Lys Lys Leu
                165                 170                 175

Ser Ala Ile Gln Ile Pro Ala Leu Ile Leu Ser Gly Lys Glu Asp Pro
                180                 185                 190

Ile Thr Asp Thr Thr Met Ile Lys Lys Leu His Ser Tyr Leu Lys Arg
                195                 200                 205

Ser Lys Leu Val Leu Ile Pro Gly Ala Lys His Ala Ile His Met Glu
210                 215                 220

Lys Ser Asp Glu Leu Ser Leu Glu Ile Asn Arg Tyr Leu
225                 230                 235

<210> SEQ ID NO 116
<211> LENGTH: 99
<212> TYPE: PRT
<213> ORGANISM: Leptospira interrogans

<400> SEQUENCE: 116

Ser Lys Ser Lys Pro Thr Ile Leu Leu Cys His Ala Asn Gly Tyr Ser
1               5                   10                  15

Ala Phe Thr Tyr Lys Phe Tyr Ile Glu Ser Leu Gln Asn Ser His Arg
                20                  25                  30

Val Ile Ala Leu Asp Phe Ala Gly His Gly Glu Ser Asp Ser Thr Leu
            35                  40                  45

Asn Phe Arg Asp Trp Tyr Phe Phe Arg Asp Gln Val Leu Ser Leu Ile
50                  55                  60

Glu Asn Glu Asn Leu Asn Asn Val Ile Gly Ile Gly His Ser Leu Gly
65                  70                  75                  80

Gly Ala Ser Leu Leu Leu Ala Ser Tyr His Ser Pro Asp Lys Phe Lys
                85                  90                  95

Lys Val Ile

<210> SEQ ID NO 117
<211> LENGTH: 237
<212> TYPE: PRT
<213> ORGANISM: Leptospira interrogans

<400> SEQUENCE: 117

Ser Ile Leu Leu Ile His Gly Leu Leu Asp Ser Ala Thr Gly Leu Arg
1               5                   10                  15

Lys Val Ala Pro Lys Ile Arg Glu Asp Tyr Arg Val Leu Ile Pro Asp
                20                  25                  30

Ile Pro Gly Phe Gly Lys Ser Lys Leu Pro Asn Leu Lys Tyr Leu Tyr
            35                  40                  45

Gln Val Asn Val Phe Ala Asp Leu Ile Tyr Glu Ser Ile Arg Lys Leu
50                  55                  60

Asn Leu Thr Asn Thr Val Leu Gly Gly His Ser Met Gly Ala Leu Ile
65                  70                  75                  80

Ser Met His Ile Ala Leu Lys Asp Ser Glu Lys Arg Ile Ser Lys Leu
                85                  90                  95
```

```
Val Leu Met Ala Pro Gly Gly Ile Pro His Pro Lys Arg Asp Glu Met
            100                 105                 110

Lys Glu Leu Leu Phe Pro Lys Thr Glu Glu Asp Leu Leu Lys Leu Ile
            115                 120                 125

Glu Ala Leu Tyr Tyr Glu Thr Pro Thr Leu Pro Gly Lys Ile Ala Arg
            130                 135                 140

Lys Ala Leu Ile Gln Ser Trp Asn Glu Leu Pro Asn Gln Phe Leu Thr
145                 150                 155                 160

Val Asn Thr Ile Glu Arg Glu Glu Ile Phe Leu Gly Lys Lys Leu
                    165                 170                 175

Ser Ala Ile Gln Ile Pro Ala Leu Ile Leu Ser Gly Lys Glu Asp Pro
            180                 185                 190

Ile Thr Asp Thr Thr Met Ile Lys Lys Leu His Ser Tyr Leu Lys Arg
            195                 200                 205

Ser Lys Leu Val Leu Ile Pro Gly Ala Lys His Ala Ile His Met Glu
            210                 215                 220

Lys Ser Asp Glu Leu Ser Leu Gly Ile Asn Arg Tyr Leu
225                 230                 235

<210> SEQ ID NO 118
<211> LENGTH: 147
<212> TYPE: PRT
<213> ORGANISM: Solanum lycopersicum

<400> SEQUENCE: 118

Arg Phe Ile Asn Thr Asp Asp Tyr Tyr Gly Gly Phe Glu Ser Glu Asp
1               5                   10                  15

Ile Glu Gln Leu Cys Gln Ala Met Glu Ser Asn Tyr Lys Ala Trp Val
            20                  25                  30

Ser Gly Phe Ala Pro Leu Ala Val Gly Gly Asp Met Asn Ser Val Ala
            35                  40                  45

Val Gln Glu Phe Ser Arg Thr Leu Phe Asn Met Arg Pro Asp Ile Ala
        50                  55                  60

Leu Ser Val Phe Arg Thr Val Phe Thr Phe Asp Leu Arg His Tyr Leu
65                  70                  75                  80

Ser Arg Val Thr Val Pro Cys His Ile Ile Gln Ser Ser Met Asp Val
                85                  90                  95

Ala Met Pro Val Thr Val Ser Glu Tyr Leu His Arg Asn Leu Gly Gly
            100                 105                 110

Lys Ser Ile Val Glu Ile Ile Ser Thr Glu Gly His Leu Pro His Leu
            115                 120                 125

Ser Ala Pro Glu Ala Thr Ile Pro Val Leu Leu Arg His Ile Ser His
            130                 135                 140

Asp Ile Thr
145

<210> SEQ ID NO 119
<211> LENGTH: 123
<212> TYPE: PRT
<213> ORGANISM: Solanum lycopersicum

<400> SEQUENCE: 119

Met Gly Ile Gly Glu Glu Ala His Asn Val Lys Val Gly Ser Gly
1               5                   10                  15

Glu Lys Thr Ile Val Leu Gly His Gly Phe Gly Thr Asp Gln Ser Val
            20                  25                  30
```

```
Trp Lys Gln Leu Val Pro Tyr Leu Val Asp Glu Tyr Arg Val Val Leu
            35                  40                  45

Tyr Asp Asn Met Gly Ala Gly Pro Thr Asn Pro Asp Tyr Phe Asp Phe
 50                  55                  60

Asp Arg Tyr Ser Ser Leu Glu Gly Tyr Ala Tyr Asp Leu Ile Ser Ile
 65                  70                  75                  80

Leu Glu Glu Leu Gln Ile Asn Arg Cys Met Tyr Leu Gly His Ser Leu
                 85                  90                  95

Ser Ala Met Thr Gly Val Val Ala Ser Ile Phe Arg Pro Asp Leu Phe
                100                 105                 110

Ser Lys Leu Ile Leu Val Ser Ala Ser Pro Arg
                115                 120
```

<210> SEQ ID NO 120
<211> LENGTH: 130
<212> TYPE: PRT
<213> ORGANISM: Solanum lycopersicum

<400> SEQUENCE: 120

```
Met Gly Ile Val Glu Glu Ala His Asn Val Lys Ile Leu Gly Thr Gly
 1               5                  10                  15

Asp Arg Ser Ile Val Leu Ala His Gly Phe Gly Thr Asp Gln Ser Val
                 20                  25                  30

Trp Lys His Leu Val Pro His Leu Val Glu Asp Tyr Lys Val Val Leu
            35                  40                  45

Phe Asp Asn Met Gly Ala Gly Thr Thr Asn Pro Asp Tyr Phe Asp Phe
 50                  55                  60

Glu Arg Tyr Ser Thr Leu Glu Gly Tyr Ala Tyr Asp Val Ile Ala Ile
 65                  70                  75                  80

Leu Glu Glu Leu Gln Ile Pro Cys Cys Ile Tyr Val Gly His Ser Val
                 85                  90                  95

Ser Ala Met Ile Gly Ala Ile Ala Ser Val Ala Arg Pro Asp Leu Phe
                100                 105                 110

Thr Lys Leu Val Thr Val Ser Gly Ser Pro Arg Leu Ile Ser Ser Phe
                115                 120                 125

Thr Phe
    130
```

<210> SEQ ID NO 121
<211> LENGTH: 147
<212> TYPE: PRT
<213> ORGANISM: Solanum lycopersicum

<400> SEQUENCE: 121

```
Arg Phe Ile Asn Thr Asp Asp Tyr Tyr Gly Gly Phe Glu Ser Glu Asp
 1               5                  10                  15

Ile Glu Gln Leu Cys Gln Ala Met Glu Ser Asn Tyr Lys Ala Trp Val
                 20                  25                  30

Ser Gly Phe Ala Pro Leu Ala Val Gly Gly Asp Met Asn Ser Val Ala
            35                  40                  45

Val Gln Glu Phe Ser Arg Thr Leu Phe Asn Met Arg Pro Asp Ile Ala
 50                  55                  60

Leu Ser Val Phe Arg Thr Val Phe Thr Phe Asp Leu Arg His Tyr Leu
 65                  70                  75                  80

Ser Arg Val Thr Val Pro Cys His Ile Ile Gln Ser Met Asp Val
            85                  90                  95
```

```
Ala Met Pro Val Thr Val Ser Glu Tyr Leu His Arg Asn Leu Gly Gly
            100                 105                 110

Lys Ser Ile Val Glu Ile Ser Thr Glu Gly His Leu Pro His Leu
        115                 120                 125

Ser Ala Pro Glu Ala Thr Ile Pro Val Leu Leu Arg His Ile Ser His
    130                 135                 140

Asp Ile Thr
145

<210> SEQ ID NO 122
<211> LENGTH: 123
<212> TYPE: PRT
<213> ORGANISM: Solanum lycopersicum

<400> SEQUENCE: 122

Met Gly Ile Gly Glu Glu Ala His Asn Val Lys Val Gly Ser Gly
1               5                   10                  15

Glu Lys Thr Ile Val Leu Gly His Gly Phe Gly Thr Asp Gln Ser Val
            20                  25                  30

Trp Lys Gln Leu Val Pro Tyr Leu Val Asp Glu Tyr Arg Val Val Leu
        35                  40                  45

Tyr Asp Asn Met Gly Ala Gly Pro Thr Asn Pro Asp Tyr Phe Asp Phe
50                  55                  60

Asp Arg Tyr Ser Ser Leu Glu Gly Tyr Ala Tyr Asp Leu Ile Ser Ile
65                  70                  75                  80

Leu Glu Glu Leu Gln Ile Asn Arg Cys Met Tyr Leu Gly His Ser Leu
                85                  90                  95

Ser Ala Met Thr Gly Val Val Ala Ser Ile Phe Arg Pro Asp Leu Phe
            100                 105                 110

Ser Lys Leu Ile Leu Val Ser Ala Ser Pro Arg
        115                 120

<210> SEQ ID NO 123
<211> LENGTH: 130
<212> TYPE: PRT
<213> ORGANISM: Solanum lycopersicum

<400> SEQUENCE: 123

Met Gly Ile Val Glu Glu Ala His Asn Val Lys Ile Leu Gly Thr Gly
1               5                   10                  15

Asp Arg Ser Ile Val Leu Ala His Gly Phe Gly Thr Asp Gln Ser Val
            20                  25                  30

Trp Lys His Leu Val Pro His Leu Val Glu Asp Tyr Lys Val Val Leu
        35                  40                  45

Phe Asp Asn Met Gly Ala Gly Thr Thr Asn Pro Asp Tyr Phe Asp Phe
50                  55                  60

Glu Arg Tyr Ser Thr Leu Glu Gly Tyr Ala Tyr Asp Val Ile Ala Ile
65                  70                  75                  80

Leu Glu Glu Leu Gln Ile Pro Cys Cys Ile Tyr Val Gly His Ser Val
                85                  90                  95

Ser Ala Met Ile Gly Ala Ile Ala Ser Val Ala Arg Pro Asp Leu Phe
            100                 105                 110

Thr Lys Leu Val Thr Val Ser Gly Ser Pro Arg Leu Ile Ser Ser Phe
        115                 120                 125

Thr Phe
    130
```

<210> SEQ ID NO 124
<211> LENGTH: 123
<212> TYPE: PRT
<213> ORGANISM: Vitis vinifera

<400> SEQUENCE: 124

Met Gly Ile Val Glu Ala His Asn Leu Lys Val Val Gly Ser Gly
1               5                   10                  15

Glu Gln Ile Ile Val Leu Ala His Gly Phe Gly Thr Asp Gln Ser Leu
            20                  25                  30

Trp Lys His Leu Val Pro His Leu Val Asp Asp Tyr Arg Val Ile Leu
        35                  40                  45

Phe Asp Asn Met Gly Ala Gly Thr Thr Asn Pro Glu Tyr Phe Asp Phe
    50                  55                  60

Glu Arg Tyr Ser Asn Leu Glu Gly Tyr Ala Tyr Asp Val Leu Ala Ile
65                  70                  75                  80

Leu Glu Glu Leu Gln Val Gln Ser Cys Ile Phe Val Gly His Ser Val
                85                  90                  95

Ser Ala Met Ile Gly Ala Ile Ala Ser Ile Thr Arg Pro Asp Leu Phe
            100                 105                 110

Ser Lys Leu Ile Ser Ile Asn Gly Ser Pro Arg
        115                 120

<210> SEQ ID NO 125
<211> LENGTH: 123
<212> TYPE: PRT
<213> ORGANISM: Vitis vinifera

<400> SEQUENCE: 125

Met Gly Ile Val Glu Ala His Asn Leu Lys Val Val Gly Ser Gly
1               5                   10                  15

Glu Gln Ile Ile Val Leu Ala His Gly Phe Gly Thr Asp Gln Ser Leu
            20                  25                  30

Trp Lys His Leu Val Pro His Leu Val Asp Asp Tyr Arg Val Ile Leu
        35                  40                  45

Phe Asp Asn Met Gly Ala Gly Thr Thr Asn Pro Glu Tyr Phe Asp Phe
    50                  55                  60

Glu Arg Tyr Ser Asn Leu Glu Gly Tyr Ala Tyr Asp Val Leu Ala Ile
65                  70                  75                  80

Leu Glu Glu Leu Gln Val Gln Ser Cys Ile Phe Val Gly His Ser Val
                85                  90                  95

Ser Ala Met Ile Gly Ala Ile Ala Ser Ile Thr Arg Pro Asp Leu Phe
            100                 105                 110

Ser Lys Leu Ile Ser Ile Asn Gly Ser Pro Arg
        115                 120

<210> SEQ ID NO 126
<211> LENGTH: 150
<212> TYPE: PRT
<213> ORGANISM: Oryza sativa

<400> SEQUENCE: 126

Ser Asn Arg Tyr Leu Asn Asp Val Asp Tyr Tyr Gly Gly Phe Glu Gln
1               5                   10                  15

Glu Asp Leu Asp Glu Leu Phe Glu Ala Met Gly Ser Asn Tyr Lys Ala
            20                  25                  30

Trp Cys Ser Gly Phe Ala Pro Leu Cys Val Gly Gly Asp Met Glu Ser

```
                35                  40                  45
Val Ala Val Gln Glu Phe Ser Arg Thr Leu Phe Asn Ile Arg Pro Asp
 50                  55                  60
Ile Ala Leu Ser Val Ala Gln Thr Ile Phe Gln Ser Asp Val Arg Ser
65                  70                  75                  80
Leu Leu Pro Leu Val Thr Val Pro Cys His Ile Val Gln Ser Thr Lys
                85                  90                  95
Asp Leu Ala Val Pro Val Val Ser Glu Tyr Leu His Lys His Leu
            100                 105                 110
Gly Gly Asp Ser Ile Val Glu Val Met Pro Ser Glu Gly His Leu Pro
            115                 120                 125
Gln Leu Ser Ser Pro Asp Ile Val Ile Pro Val Leu Leu Arg His Ile
            130                 135                 140
Gln His Asp Ile Ala Val
145                 150

<210> SEQ ID NO 127
<211> LENGTH: 125
<212> TYPE: PRT
<213> ORGANISM: Oryza sativa

<400> SEQUENCE: 127

Met Gly Ile Val Glu Glu Ala His Asn Leu Arg Val Val Gly Glu Gly
 1               5                  10                  15
Lys Arg Gly Val Ile Val Leu Ala His Gly Phe Gly Thr Asp Gln Ser
                20                  25                  30
Val Trp Lys His Leu Val Pro His Leu Val Ala Asp Tyr Arg Val Val
                35                  40                  45
Leu Phe Asp Thr Met Gly Ala Gly Pro Thr Asn Pro Asp Tyr Phe Asp
 50                  55                  60
Phe Ser Arg Tyr Ala Thr Leu Glu Gly Tyr Ala Leu Asp Leu Leu Ala
65                  70                  75                  80
Ile Leu Gln Glu Leu Arg Val Ala Ser Cys Ile Tyr Val Gly His Ser
                85                  90                  95
Val Ser Ala Val Ile Gly Ala Ile Ala Ser Ile Ser Arg Pro Asp Leu
            100                 105                 110
Phe Ser Lys Leu Val Leu Leu Ser Ala Ser Pro Arg Tyr
            115                 120                 125

<210> SEQ ID NO 128
<211> LENGTH: 124
<212> TYPE: PRT
<213> ORGANISM: Medicago truncatula

<400> SEQUENCE: 128

Met Gly Ile Val Glu Glu Ala His Asn Val Lys Val Leu Gly Ser Gly
 1               5                  10                  15
Ser Arg Phe Ile Val Leu Ala His Gly Phe Gly Thr Asp Gln Ser Val
                20                  25                  30
Trp Lys His Leu Val Pro His Leu Leu Asp Glu Phe Arg Val Ile Leu
            35                  40                  45
Tyr Asp Asn Met Gly Ala Gly Thr Thr Asn Pro Asp Tyr Phe Asp Phe
 50                  55                  60
Glu Arg Tyr Ser Thr Leu Glu Gly Tyr Ala Tyr Asp Leu Leu Ala Ile
65                  70                  75                  80
Leu Glu Glu Leu Arg Val Asp Ser Cys Ile Phe Val Gly His Ser Val
```

```
                85                  90                  95

Ser Ala Met Ile Gly Thr Val Ala Ser Ile Ser Arg Pro Asp Leu Phe
            100                 105                 110

Asn Lys Ile Ile Leu Ile Ser Ala Ser Pro Arg Tyr
        115                 120

<210> SEQ ID NO 129
<211> LENGTH: 123
<212> TYPE: PRT
<213> ORGANISM: Medicago truncatula

<400> SEQUENCE: 129

Met Gly Ile Val Glu Glu Ala His Asn Val Lys Val Leu Gly Thr Gly
 1               5                  10                  15

Asn Arg Tyr Ile Val Leu Ala His Gly Phe Gly Thr Asp Gln Ser Val
            20                  25                  30

Trp Lys His Phe Val Pro Tyr Leu Val Asp Asp Phe Arg Val Val Leu
        35                  40                  45

Tyr Asp Asn Met Gly Ala Gly Thr Thr Asn Pro Glu Tyr Phe Asp Ser
    50                  55                  60

Glu Arg His Ser Ser Leu Glu Gly Tyr Ala Tyr Asp Leu Leu Ala Ile
65                  70                  75                  80

Leu Glu Glu Leu Gln Ile Asp Ser Cys Ile Phe Val Gly His Ser Val
                85                  90                  95

Ser Ala Met Ile Gly Ala Ile Ala Ser Ile Thr Arg Pro Asp Leu Phe
            100                 105                 110

Leu Lys Leu Ile Met Val Ser Ser Ser Pro Arg
        115                 120

<210> SEQ ID NO 130
<211> LENGTH: 69
<212> TYPE: PRT
<213> ORGANISM: Arabidopsis thaliana

<400> SEQUENCE: 130

Leu Asn Ser Asp Phe Arg Gly Val Leu Gly Leu Val Arg Val Pro Thr
 1               5                  10                  15

Cys Val Ile Glu Thr Ala Lys Asp Val Phe Val Pro Ala Ser Val Ala
            20                  25                  30

Glu Tyr Leu Arg Ser His Leu Gly Ala Asp Thr Thr Val His Thr Leu
        35                  40                  45

Lys Thr Glu Gly His Leu Pro Gln Leu Ser Ala Pro Ala Gln Leu Ala
    50                  55                  60

Gln Phe Leu Arg Arg
65

<210> SEQ ID NO 131
<211> LENGTH: 114
<212> TYPE: PRT
<213> ORGANISM: Lysinibacillus sphaericus

<400> SEQUENCE: 131

Glu Asn Met Asn Ile Thr Ile Gln Gly Lys Gly Thr Glu Thr Ile Val
 1               5                  10                  15

Leu Leu Pro Gly Phe Gly Thr Ala Ala Pro Thr Leu Asp Phe Gln Pro
            20                  25                  30

Leu Ile Glu Glu Leu Ala Pro Asn Tyr Lys Val Val Ser Val Glu Pro
        35                  40                  45
```

Phe Gly Tyr Gly Leu Ser Asp Asp Thr Lys Lys Glu Arg Ser Thr Glu
    50                  55                  60

Asn Ile Val Ser Glu Ile His Glu Ala Leu Gln Thr Leu Lys Ile Asp
65                  70                  75                  80

Gln Tyr Met Leu Met Gly His Ser Ile Ala Gly Ile Tyr Gly Leu Asn
                85                  90                  95

Tyr Val Asn Lys Tyr Pro Asp Glu Val Thr Ala Phe Ile Gly Ile Asp
            100                 105                 110

Ser Ser

<210> SEQ ID NO 132
<211> LENGTH: 100
<212> TYPE: PRT
<213> ORGANISM: Lysinibacillus sphaericus

<400> SEQUENCE: 132

Gly His Gly Glu Pro Leu Ile Phe Thr His Gly Ala Ser Trp Asp His
1               5                   10                  15

Gln Gln Trp Asp Lys Gln Val Asp Tyr Phe Ser Lys Tyr Tyr Gln Thr
            20                  25                  30

Ile Thr Trp Asp Val Arg Gly His Gly Ala Ser Ser Leu Pro Asn Gly
        35                  40                  45

Lys Val Asp Ala Glu Asp Phe Thr Lys Asp Leu Ile Gly Leu Met His
    50                  55                  60

His Leu Lys Ile Arg Arg Ala His Leu Cys Gly Leu Ser Met Gly Gly
65                  70                  75                  80

His Ile Ser Leu Gln Ala Ala Ile His Tyr Pro Asp Tyr Val Lys Ser
                85                  90                  95

Leu Thr Leu Ile
            100

<210> SEQ ID NO 133
<211> LENGTH: 22
<212> TYPE: DNA
<213> ORGANISM: Artificial Sequence
<220> FEATURE:
<223> OTHER INFORMATION: Synthetic sequence

<400> SEQUENCE: 133
ggttaacgaa agaattttgt cg                                          22

<210> SEQ ID NO 134
<211> LENGTH: 22
<212> TYPE: DNA
<213> ORGANISM: Artificial Sequence
<220> FEATURE:
<223> OTHER INFORMATION: Synthetic sequence

<400> SEQUENCE: 134
tggcaaaaag ttcttatttg gg                                          22

<210> SEQ ID NO 135
<211> LENGTH: 24
<212> TYPE: DNA
<213> ORGANISM: Artificial Sequence
<220> FEATURE:
<223> OTHER INFORMATION: Synthetic sequence

<400> SEQUENCE: 135
gacatcttca gggacagtgt agtc                                        24

```
<210> SEQ ID NO 136
<211> LENGTH: 28
<212> TYPE: DNA
<213> ORGANISM: Artificial Sequence
<220> FEATURE:
<223> OTHER INFORMATION: Synthetic sequence

<400> SEQUENCE: 136
tggtgagttt atatgtgatc aaagttgc                                    28

<210> SEQ ID NO 137
<211> LENGTH: 20
<212> TYPE: DNA
<213> ORGANISM: Artificial Sequence
<220> FEATURE:
<223> OTHER INFORMATION: Synthetic sequence

<400> SEQUENCE: 137
ggtcgggaaa ctagctctac                                             20

<210> SEQ ID NO 138
<211> LENGTH: 19
<212> TYPE: DNA
<213> ORGANISM: Artificial Sequence
<220> FEATURE:
<223> OTHER INFORMATION: Synthetic sequence

<400> SEQUENCE: 138
tcgtttccgt cccgcaagt                                              19

<210> SEQ ID NO 139
<211> LENGTH: 23
<212> TYPE: DNA
<213> ORGANISM: Artificial Sequence
<220> FEATURE:
<223> OTHER INFORMATION: Synthetic sequence

<400> SEQUENCE: 139
cgtttacgta tctataaacg tac                                         23

<210> SEQ ID NO 140
<211> LENGTH: 24
<212> TYPE: DNA
<213> ORGANISM: Artificial Sequence
<220> FEATURE:
<223> OTHER INFORMATION: Synthetic sequence

<400> SEQUENCE: 140
atacgtaaca ctctaaaaca acac                                        24

<210> SEQ ID NO 141
<211> LENGTH: 22
<212> TYPE: DNA
<213> ORGANISM: Artificial Sequence
<220> FEATURE:
<223> OTHER INFORMATION: Synthetic sequence

<400> SEQUENCE: 141
cacgactgca gactttattg gt                                          22

<210> SEQ ID NO 142
<211> LENGTH: 25
<212> TYPE: DNA
<213> ORGANISM: Artificial Sequence
<220> FEATURE:
```

<223> OTHER INFORMATION: Synthetic sequence

<400> SEQUENCE: 142
aatttggtaa ccatcacaat atgta       25

<210> SEQ ID NO 143
<211> LENGTH: 21
<212> TYPE: DNA
<213> ORGANISM: Artificial Sequence
<220> FEATURE:
<223> OTHER INFORMATION: Synthetic sequence

<400> SEQUENCE: 143
tagagccatg ggtgtggtag a       21

<210> SEQ ID NO 144
<211> LENGTH: 21
<212> TYPE: DNA
<213> ORGANISM: Artificial Sequence
<220> FEATURE:
<223> OTHER INFORMATION: Synthetic sequence

<400> SEQUENCE: 144
aaatcggtta ccatcacata g       21

<210> SEQ ID NO 145
<211> LENGTH: 141
<212> TYPE: PRT
<213> ORGANISM: Oryza minuta

<400> SEQUENCE: 145

Arg Phe Leu Asn Asp Ser Asp Tyr His Gly Gly Phe Glu Leu Glu Glu
1               5                   10                  15

Ile Gln Gln Val Phe Asp Ala Met Gly Ala Asn Tyr Ser Ala Trp Ala
            20                  25                  30

Thr Gly Tyr Ala Pro Leu Ala Val Gly Ala Asp Val Pro Ala Ala Val
        35                  40                  45

Gln Glu Phe Ser Arg Thr Leu Phe Asn Met Arg Pro Asp Ile Ser Leu
    50                  55                  60

His Val Cys Gln Thr Val Phe Lys Thr Asp Leu Arg Gly Val Leu Gly
65                  70                  75                  80

Met Val Arg Ala Pro Cys Val Val Val Gln Thr Thr Arg Asp Val Ser
                85                  90                  95

Val Pro Ala Ser Val Ala Ala Tyr Leu Lys Ala His Leu Gly Gly Arg
            100                 105                 110

Thr Thr Val Glu Phe Leu Gln Thr Glu Gly His Leu Pro His Leu Ser
        115                 120                 125

Ala Pro Ser Leu Leu Ala Gln Val Leu Arg Arg Ala Leu
    130                 135                 140

<210> SEQ ID NO 146
<211> LENGTH: 141
<212> TYPE: PRT
<213> ORGANISM: Oryza sativa

<400> SEQUENCE: 146

Arg Phe Leu Asn Asp Ser Asp Tyr His Gly Gly Phe Glu Leu Glu Glu
1               5                   10                  15

Ile Gln Gln Val Phe Asp Ala Met Gly Ala Asn Tyr Ser Ala Trp Ala
            20                  25                  30

Thr Gly Tyr Ala Pro Leu Ala Val Gly Ala Asp Val Pro Ala Ala Val
              35                  40                  45

Gln Glu Phe Ser Arg Thr Leu Phe Asn Met Arg Pro Asp Ile Ser Leu
 50                  55                  60

His Val Cys Gln Thr Val Phe Lys Thr Asp Leu Arg Gly Val Leu Gly
 65                  70                  75                  80

Met Val Arg Ala Pro Cys Val Val Gln Thr Thr Arg Asp Val Ser
                 85                  90                  95

Val Pro Ala Ser Val Ala Ala Tyr Leu Lys Ala His Leu Gly Gly Arg
             100                 105                 110

Thr Thr Val Glu Phe Leu Gln Thr Glu Gly His Leu Pro His Leu Ser
         115                 120                 125

Ala Pro Ser Leu Leu Ala Gln Val Leu Arg Arg Ala Leu
     130                 135                 140

<210> SEQ ID NO 147
<211> LENGTH: 1813
<212> TYPE: DNA
<213> ORGANISM: Arabidopsis thaliana

<400> SEQUENCE: 147

| | | | | | |
|---|---|---|---|---|---|
| ataaagaata | atacgtaaca | ctctaaaaca | acacaaatat | cataatttct | ccacgaactg | 60 |
| actaagagag | gtaccaagaa | gaaaaccaga | gaagaatctt | ctttagagag | atgggtgtgg | 120 |
| tagaagaagc | tcacaacgtg | aaggtgattg | gttcaggaga | agccacgatc | gtgttaggtc | 180 |
| acgggttcgg | cacggaccag | tcagtatgga | aacacttggt | tccacatctg | gtcgacgatt | 240 |
| accgcgtcgt | cctctacgac | aacatgggag | ccggtacgac | caaccctgac | tatttcgact | 300 |
| tcgatcgtta | ctcaaatctc | gaaggctact | ctttcgattt | gattgcaatc | ttggaagatc | 360 |
| tcaagattga | gtcttgtatc | tttgttggcc | actctgtttc | tgccatgatt | ggtgtcttgg | 420 |
| cttctcttaa | ccgtcctgat | ctcttctcca | aaatcgtcat | gatctctgct | tctccgagat | 480 |
| aacttttca | caagttgtac | atagaaatat | gttttgcttt | ttatctcatc | ctgacatagt | 540 |
| ttagacaaaa | gggcttctct | gttccttctc | ttgtctgatt | tcataaaaac | tattaaacat | 600 |
| tacaatttaa | ataaaaaaaa | atcatcttaa | gtccttaaat | ttacacaatt | atctattatt | 660 |
| tcgaaatatt | tatttctcat | tctgacataa | tttcgacaaa | gtgcctcttt | gtttatcctc | 720 |
| ttgtctgaat | tatcctatt | tctcaaaatca | gtgaagcatt | tcattatata | tttcaataaa | 780 |
| aatccgtaaa | ttatgaacaa | aaaatcatga | aatacccatt | tgtttatttg | tttttttta | 840 |
| tttggtttta | ctgaggtgtt | acttacactt | tttttaaaaa | aaattgttga | aacggtgctc | 900 |
| acacagtata | ttatatattt | taattttctt | ctgacaaaag | aaacatatat | aatcaaatta | 960 |
| tattgttttg | gtacgtttat | agatacgtaa | acgatgttga | ttaccaaggt | ggattcgaac | 1020 |
| aagaagactt | aaaccaacta | ttcgaagcca | tccgaagcaa | ctacaaagcg | tggtgcttag | 1080 |
| gtttcgctcc | actcgccgtc | ggtggcgaca | tggactccat | cgccgttcaa | gaattcagca | 1140 |
| gaacactctt | caatatgcgt | cccgacatag | ctctctccgt | cggccagacc | attttccaaa | 1200 |
| gtgacatgag | acagatctta | ccttttgtca | ctgttccgtg | tcacattctc | caaagtgtta | 1260 |
| aggacttagc | tgtaccagtc | gttgtctccg | agtatcttca | cgccaatctt | ggctgtgaat | 1320 |
| ccgtcgtcga | ggttattcct | tctgatggtc | atcttcctca | gcttagctca | ccagattctg | 1380 |
| ttattcctgt | catcctccgt | cacattcgta | atgacattgc | tatgtgattg | taagagattt | 1440 |
| aattagttaa | ttattaaacg | atgtaagaaa | agttgaaaaa | aaatatctga | tgtgatatgt | 1500 |

-continued

```
ctgtctagtc tattgagaac attatttcgt tgtcgtttgg ttctgattcg tttatcttga    1560
gtatcttgat ctttgttgtt cttatcttgt ttaacgaaaa gtctctgtct tttgtccaca    1620
gctttgctca gagctcatta ttgcttgatg taatagtgat gttcgtaatt gatggtccat    1680
agtgaattat tgcaactttg caagagtgct tgtgctatac tgtgtgaaga gtaattaaca    1740
tgtgatacta ggaattagca ttgagtttgc atttatggat gggtaatcca aaccataaaa    1800
catacatatt gtg                                                       1813
```